US010828059B2

(12) United States Patent
Price et al.

(10) Patent No.: US 10,828,059 B2
(45) Date of Patent: *Nov. 10, 2020

(54) ERGONOMIC SURGICAL INSTRUMENTS

(71) Applicant: Ethicon LLC, Guaynabo, PR (US)

(72) Inventors: Daniel W. Price, Loveland, OH (US);
Galen C. Robertson, Apex, NC (US);
Cory G. Kimball, Hamilton, OH (US);
Scott A. Woodruff, Boston, MA (US);
Matthew C. Miller, Cincinnati, OH
(US); Kip M. Rupp, New Richmond,
OH (US); Carrie I. Hensley, Yulee, FL
(US); Jane A. Sheetz, Cincinnati, OH
(US); Carl J. Draginoff, Jr., Mason,
OH (US)

(73) Assignee: Ethicon LLC, Guaynabo, PR (US)

( * ) Notice: Subject to any disclaimer, the term of this patent is extended or adjusted under 35 U.S.C. 154(b) by 161 days.

This patent is subject to a terminal disclaimer.

(21) Appl. No.: 15/837,241

(22) Filed: Dec. 11, 2017

(65) Prior Publication Data

US 2018/0206881 A1 Jul. 26, 2018

Related U.S. Application Data

(63) Continuation of application No. 14/172,334, filed on Feb. 4, 2014, now Pat. No. 9,848,902, which is a
(Continued)

(51) Int. Cl.
*A61B 17/32* (2006.01)
*A61B 17/29* (2006.01)
*A61B 17/00* (2006.01)

(52) U.S. Cl.
CPC ........... *A61B 17/320092* (2013.01); *A61B 2017/00424* (2013.01); *A61B 2017/00429* (2013.01);
(Continued)

(58) Field of Classification Search
CPC ............ A61B 17/29; A61B 17/320092; A61B 17/320068; A61B 2017/0042;
(Continued)

(56) References Cited

U.S. PATENT DOCUMENTS 969,528 A * 11/1910 Disbrow ................. A47L 13/08
30/169
1,570,025 A 1/1926 Young
(Continued)

FOREIGN PATENT DOCUMENTS

CA 2535467 A1 4/1993
CA 2214413 A1 9/1996
(Continued)

OTHER PUBLICATIONS

AST Products, Inc., "Principles of Video Contact Angle Analysis," 20 pages, (2006).
(Continued)

*Primary Examiner* — Tuan V Nguyen

(57) ABSTRACT

A handle assembly for a handheld surgical instrument is disclosed. The handle assembly may include a body portion extending parallel to a longitudinal axis, a fixed handle interfaced with the body portion and extending downwardly from the body portion and away from the longitudinal axis, and a detachable handle portion. The fixed handle may define a proximal contact surface. The detachable handle portion may define an internal surface configured to interface with the proximal contact surface of the fixed handle and comprise at least one attachment feature to removably couple the detachable handle portion to the fixed handle.

17 Claims, 76 Drawing Sheets

Related U.S. Application Data continuation of application No. 13/426,232, filed on Mar. 21, 2012, now Pat. No. 9,486,236, which is a continuation of application No. 12/245,158, filed on Oct. 3, 2008, now Pat. No. 8,623,027.

(60) Provisional application No. 60/997,901, filed on Oct. 5, 2007.

(52) U.S. Cl.
CPC ............... A61B 2017/2925 (2013.01); A61B 2017/2929 (2013.01); A61B 2017/320093 (2017.08); A61B 2017/320094 (2017.08); A61B 2017/320095 (2017.08)

(58) Field of Classification Search
CPC .......... A61B 2017/00424; A61B 2017/00429; A61B 2017/00442; A61B 2017/00446; A61B 2017/00455
See application file for complete search history.

(56) References Cited

U.S. PATENT DOCUMENTS

| | | | |
|---|---|---|---|
| 1,813,902 | A | 7/1931 | Bovie |
| 2,188,497 | A | 1/1940 | Calva |
| 2,366,274 | A | 1/1945 | Luth et al. |
| 2,425,245 | A | 8/1947 | Johnson |
| 2,442,966 | A | 6/1948 | Wallace |
| 2,458,152 | A | 1/1949 | Eakins |
| 2,510,693 | A | 6/1950 | Green |
| 2,597,564 | A | 5/1952 | Bugg |
| 2,704,333 | A | 3/1955 | Calosi et al. |
| 2,736,960 | A | 3/1956 | Armstrong |
| 2,743,726 | A | 5/1956 | Grieshaber |
| 2,748,967 | A | 6/1956 | Roach |
| 2,845,072 | A | 7/1958 | Shafer |
| 2,849,788 | A | 9/1958 | Creek |
| 2,867,039 | A | 1/1959 | Zach |
| 2,874,470 | A | 2/1959 | Richards |
| 2,990,616 | A | 7/1961 | Balamuth et al. |
| RE25,033 | E | 8/1961 | Balamuth et al. |
| 3,015,961 | A | 1/1962 | Roney |
| 3,033,407 | A | 5/1962 | Alfons |
| 3,053,124 | A | 9/1962 | Balamuth et al. |
| 3,082,805 | A | 3/1963 | Royce |
| 3,166,971 | A | 1/1965 | Stoecker |
| 3,322,403 | A | 5/1967 | Murphy |
| 3,432,691 | A | 3/1969 | Shoh |
| 3,433,226 | A | 3/1969 | Boyd |
| 3,489,930 | A | 1/1970 | Shoh |
| 3,503,396 | A | 3/1970 | Pierie et al. |
| 3,503,397 | A | 3/1970 | Fogarty et al. |
| 3,503,398 | A | 3/1970 | Fogarty et al. |
| 3,513,848 | A | 5/1970 | Winston et al. |
| 3,514,856 | A | 6/1970 | Camp et al. |
| 3,525,912 | A | 8/1970 | Wallin |
| 3,526,219 | A | 9/1970 | Balamuth |
| 3,554,198 | A | 1/1971 | Tatoian et al. |
| 3,580,841 | A | 5/1971 | Cadotte et al. |
| 3,606,682 | A | 9/1971 | Camp et al. |
| 3,614,484 | A | 10/1971 | Shoh |
| 3,616,375 | A | 10/1971 | Inoue |
| 3,629,726 | A | 12/1971 | Popescu |
| 3,636,943 | A | 1/1972 | Balamuth |
| 3,668,486 | A | 6/1972 | Silver |
| 3,702,948 | A | 11/1972 | Balamuth |
| 3,703,651 | A | 11/1972 | Blowers |
| 3,776,238 | A | 12/1973 | Peyman et al. |
| 3,777,760 | A | 12/1973 | Essner |
| 3,792,701 | A | 2/1974 | Kloz et al. |
| 3,805,787 | A | 4/1974 | Banko |
| 3,809,977 | A | 5/1974 | Balamuth et al. |
| 3,830,098 | A | 8/1974 | Antonevich |
| 3,832,776 | A | 9/1974 | Sawyer |
| 3,854,737 | A | 12/1974 | Gilliam, Sr. |
| 3,862,630 | A | 1/1975 | Balamuth |
| 3,875,945 | A | 4/1975 | Friedman |
| 3,885,438 | A | 5/1975 | Harris, Sr. et al. |
| 3,900,823 | A | 8/1975 | Sokal et al. |
| 3,918,442 | A | 11/1975 | Nikolaev et al. |
| 3,924,335 | A | 12/1975 | Balamuth et al. |
| 3,946,738 | A | 3/1976 | Newton et al. |
| 3,955,859 | A | 5/1976 | Stella et al. |
| 3,956,826 | A | 5/1976 | Perdreaux, Jr. |
| 3,989,952 | A | 11/1976 | Hohmann |
| 4,005,714 | A | 2/1977 | Hiltebrandt |
| 4,012,647 | A | 3/1977 | Balamuth et al. |
| 4,034,762 | A | 7/1977 | Cosens et al. |
| 4,058,126 | A | 11/1977 | Leveen |
| 4,074,719 | A | 2/1978 | Semm |
| 4,085,893 | A | 4/1978 | Durley, III |
| 4,156,187 | A | 5/1979 | Murry et al. |
| 4,167,944 | A | 9/1979 | Banko |
| 4,173,725 | A | 11/1979 | Asai et al. |
| 4,188,927 | A | 2/1980 | Harris |
| 4,193,009 | A | 3/1980 | Durley, III |
| 4,200,106 | A | 4/1980 | Douvas et al. |
| 4,203,430 | A | 5/1980 | Takahashi |
| 4,203,444 | A | 5/1980 | Bonnell et al. |
| 4,220,154 | A | 9/1980 | Semm |
| 4,237,441 | A | 12/1980 | van Konynenburg et al. |
| 4,281,785 | A | 8/1981 | Brooks |
| 4,300,083 | A | 11/1981 | Heiges |
| 4,302,728 | A | 11/1981 | Nakamura |
| 4,304,987 | A | 12/1981 | van Konynenburg |
| 4,306,570 | A | 12/1981 | Matthews |
| 4,314,559 | A | 2/1982 | Allen |
| 4,445,063 | A | 4/1984 | Smith |
| 4,463,759 | A | 8/1984 | Garito et al. |
| 4,491,132 | A | 1/1985 | Aikins |
| 4,492,231 | A | 1/1985 | Auth |
| 4,494,759 | A | 1/1985 | Kieffer |
| 4,504,264 | A | 3/1985 | Kelman |
| 4,512,344 | A | 4/1985 | Barber |
| 4,526,571 | A | 7/1985 | Wuchinich |
| 4,535,773 | A | 8/1985 | Yoon |
| 4,541,638 | A | 9/1985 | Ogawa et al. |
| 4,545,374 | A | 10/1985 | Jacobson |
| 4,545,926 | A | 10/1985 | Fouts, Jr. et al. |
| 4,550,870 | A | 11/1985 | Krumme et al. |
| 4,553,544 | A | 11/1985 | Nomoto et al. |
| 4,562,838 | A | 1/1986 | Walker |
| 4,574,615 | A | 3/1986 | Bower et al. |
| 4,582,236 | A | 4/1986 | Hirose |
| 4,617,927 | A | 10/1986 | Manes |
| 4,633,119 | A | 12/1986 | Thompson |
| 4,633,874 | A | 1/1987 | Chow et al. |
| 4,634,420 | A | 1/1987 | Spinosa et al. |
| 4,640,279 | A | 2/1987 | Beard |
| 4,641,053 | A | 2/1987 | Takeda |
| 4,646,738 | A | 3/1987 | Trott |
| 4,646,756 | A | 3/1987 | Watmough et al. |
| 4,649,919 | A | 3/1987 | Thimsen et al. |
| 4,662,068 | A | 5/1987 | Polonsky |
| 4,663,677 | A | 5/1987 | Griffith et al. |
| 4,674,502 | A | 6/1987 | Imonti |
| 4,708,127 | A | 11/1987 | Abdelghani |
| 4,712,722 | A | 12/1987 | Hood et al. |
| 4,735,603 | A | 4/1988 | Goodson et al. |
| 4,750,488 | A | 6/1988 | Wuchinich et al. |
| 4,761,871 | A | 8/1988 | O'Connor et al. |
| 4,783,997 | A | 11/1988 | Lynnworth |
| 4,808,154 | A | 2/1989 | Freeman |
| 4,819,635 | A | 4/1989 | Shapiro |
| 4,821,719 | A | 4/1989 | Fogarty |
| 4,827,911 | A | 5/1989 | Broadwin et al. |
| 4,830,462 | A | 5/1989 | Karny et al. |
| 4,832,683 | A | 5/1989 | Idemoto et al. |
| 4,836,186 | A | 6/1989 | Scholz |
| 4,838,853 | A | 6/1989 | Parisi |
| 4,844,064 | A | 7/1989 | Thimsen et al. |
| 4,849,133 | A | 7/1989 | Yoshida et al. |
| 4,850,354 | A | 7/1989 | McGurk-Burleson et al. |

(56) References Cited

U.S. PATENT DOCUMENTS

| | | |
|---|---|---|
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,869,715 A | 9/1989 | Sherburne |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 4,983,160 A | 1/1991 | Steppe et al. |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,047,043 A | 9/1991 | Kubota et al. |
| 5,059,210 A | 10/1991 | Clark et al. |
| 5,061,269 A | 10/1991 | Muller |
| 5,084,052 A | 1/1992 | Jacobs |
| 5,088,687 A | 2/1992 | Stender |
| 5,096,532 A | 3/1992 | Neuwirth et al. |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| D327,872 S | 7/1992 | McMills et al. |
| D330,253 S | 10/1992 | Burek |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,103 A | 5/1993 | Martin et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,234,428 A | 8/1993 | Kaufman |
| 5,234,436 A | 8/1993 | Eaton et al. |
| 5,241,236 A | 8/1993 | Sasaki et al. |
| 5,241,968 A | 9/1993 | Slater |
| 5,242,460 A | 9/1993 | Klein et al. |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,323,055 A | 6/1994 | Yamazaki |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,339,723 A | 8/1994 | Huitema |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A * | 10/1994 | Good ............... B25F 5/006 16/421 |
| 5,354,265 A | 10/1994 | Mackool |
| 5,357,164 A | 10/1994 | Imabayashi et al. |
| 5,357,423 A | 10/1994 | Weaver et al. |
| 5,358,506 A | 10/1994 | Green et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,387,207 A | 2/1995 | Dyer et al. |
| 5,387,215 A | 2/1995 | Fisher |
| 5,389,098 A | 2/1995 | Tsuruta et al. |
| 5,391,144 A | 2/1995 | Sakurai et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |

(56) References Cited

U.S. PATENT DOCUMENTS

| | | | |
|---|---|---|---|
| 5,409,453 | A | 4/1995 | Lundquist et al. |
| D358,887 | S | 5/1995 | Feinberg |
| 5,411,481 | A | 5/1995 | Allen et al. |
| 5,417,709 | A | 5/1995 | Slater |
| 5,419,761 | A | 5/1995 | Narayanan et al. |
| 5,421,829 | A | 6/1995 | Olichney et al. |
| 5,423,844 | A | 6/1995 | Miller |
| 5,428,504 | A | 6/1995 | Bhatla |
| 5,429,131 | A | 7/1995 | Scheinman et al. |
| 5,438,997 | A | 8/1995 | Sieben et al. |
| 5,441,499 | A | 8/1995 | Fritzsch |
| 5,443,463 | A | 8/1995 | Stern et al. |
| 5,445,638 | A | 8/1995 | Rydell et al. |
| 5,445,639 | A | 8/1995 | Kuslich et al. |
| 5,447,509 | A | 9/1995 | Mills et al. |
| 5,449,370 | A | 9/1995 | Vaitekunas |
| 5,451,220 | A | 9/1995 | Ciervo |
| 5,451,227 | A | 9/1995 | Michaelson |
| 5,456,684 | A | 10/1995 | Schmidt et al. |
| 5,458,598 | A | 10/1995 | Feinberg et al. |
| 5,462,604 | A | 10/1995 | Shibano et al. |
| 5,465,895 | A | 11/1995 | Knodel et al. |
| 5,471,988 | A | 12/1995 | Fujio et al. |
| 5,472,443 | A | 12/1995 | Cordis et al. |
| 5,476,479 | A | 12/1995 | Green et al. |
| 5,478,003 | A | 12/1995 | Green et al. |
| 5,480,409 | A | 1/1996 | Riza |
| 5,483,501 | A | 1/1996 | Park et al. |
| 5,484,436 | A | 1/1996 | Eggers et al. |
| 5,486,162 | A | 1/1996 | Brumbach |
| 5,486,189 | A | 1/1996 | Mudry et al. |
| 5,490,860 | A | 2/1996 | Middle et al. |
| 5,496,317 | A | 3/1996 | Goble et al. |
| 5,499,992 | A | 3/1996 | Meade et al. |
| 5,500,216 | A | 3/1996 | Julian et al. |
| 5,501,654 | A | 3/1996 | Failla et al. |
| 5,504,650 | A | 4/1996 | Katsui et al. |
| 5,505,693 | A | 4/1996 | Mackool |
| 5,507,738 | A | 4/1996 | Ciervo |
| 5,509,922 | A | 4/1996 | Aranyi et al. |
| 5,511,556 | A | 4/1996 | DeSantis |
| 5,520,704 | A | 5/1996 | Castro et al. |
| 5,522,832 | A | 6/1996 | Kugo et al. |
| 5,522,839 | A | 6/1996 | Pilling |
| 5,527,273 | A | 6/1996 | Manna et al. |
| 5,527,331 | A | 6/1996 | Kresch et al. |
| 5,531,744 | A | 7/1996 | Nardella et al. |
| 5,540,681 | A | 7/1996 | Strul et al. |
| 5,540,693 | A | 7/1996 | Fisher |
| 5,542,916 | A | 8/1996 | Hirsch et al. |
| 5,553,675 | A | 9/1996 | Pitzen et al. |
| 5,558,671 | A | 9/1996 | Yates |
| 5,562,609 | A | 10/1996 | Brumbach |
| 5,562,610 | A | 10/1996 | Brumbach |
| 5,562,659 | A | 10/1996 | Morris |
| 5,562,703 | A | 10/1996 | Desai |
| 5,563,179 | A | 10/1996 | Stone et al. |
| 5,569,164 | A | 10/1996 | Lurz |
| 5,571,121 | A | 11/1996 | Heifetz |
| 5,573,424 | A | 11/1996 | Poppe |
| 5,573,534 | A | 11/1996 | Stone |
| 5,577,654 | A | 11/1996 | Bishop |
| 5,582,618 | A | 12/1996 | Chin et al. |
| 5,584,830 | A | 12/1996 | Ladd et al. |
| 5,591,187 | A | 1/1997 | Dekel |
| 5,593,414 | A | 1/1997 | Shipp et al. |
| 5,599,350 | A | 2/1997 | Schulze et al. |
| 5,601,601 | A | 2/1997 | Tal et al. |
| 5,603,773 | A | 2/1997 | Campbell |
| 5,607,436 | A | 3/1997 | Pratt et al. |
| 5,607,450 | A | 3/1997 | Zvenyatsky et al. |
| 5,609,573 | A | 3/1997 | Sandock |
| 5,611,813 | A | 3/1997 | Lichtman |
| 5,618,304 | A | 4/1997 | Hart et al. |
| 5,618,307 | A | 4/1997 | Donlon et al. |
| 5,618,492 | A | 4/1997 | Auten et al. |
| 5,620,447 | A | 4/1997 | Smith et al. |
| 5,624,452 | A | 4/1997 | Yates |
| 5,626,587 | A | 5/1997 | Bishop et al. |
| 5,626,595 | A | 5/1997 | Sklar et al. |
| 5,628,760 | A | 5/1997 | Knoepfler |
| 5,630,420 | A | 5/1997 | Vaitekunas |
| 5,632,432 | A | 5/1997 | Schulze et al. |
| 5,632,717 | A | 5/1997 | Yoon |
| 5,640,741 | A * | 6/1997 | Yano ..................... B25F 5/006 16/421 |
| D381,077 | S | 7/1997 | Hunt |
| 5,643,301 | A | 7/1997 | Mollenauer |
| 5,647,871 | A | 7/1997 | Levine et al. |
| 5,649,937 | A | 7/1997 | Bito et al. |
| 5,649,955 | A | 7/1997 | Hashimoto et al. |
| 5,651,780 | A | 7/1997 | Jackson et al. |
| 5,653,713 | A | 8/1997 | Michelson |
| 5,658,281 | A | 8/1997 | Heard |
| 5,662,662 | A | 9/1997 | Bishop et al. |
| 5,662,667 | A | 9/1997 | Knodel |
| 5,665,085 | A | 9/1997 | Nardella |
| 5,665,100 | A | 9/1997 | Yoon |
| 5,669,922 | A | 9/1997 | Hood |
| 5,674,219 | A | 10/1997 | Monson et al. |
| 5,674,220 | A | 10/1997 | Fox et al. |
| 5,674,235 | A | 10/1997 | Parisi |
| 5,678,568 | A | 10/1997 | Uchikubo et al. |
| 5,688,270 | A | 11/1997 | Yates et al. |
| 5,690,269 | A | 11/1997 | Bolanos et al. |
| 5,693,051 | A | 12/1997 | Schulze et al. |
| 5,694,936 | A | 12/1997 | Fujimoto et al. |
| 5,695,510 | A | 12/1997 | Hood |
| 5,700,261 | A | 12/1997 | Brinkerhoff |
| 5,704,534 | A | 1/1998 | Huitema et al. |
| 5,704,791 | A | 1/1998 | Gillio |
| 5,709,680 | A | 1/1998 | Yates et al. |
| 5,711,472 | A | 1/1998 | Bryan |
| 5,713,896 | A | 2/1998 | Nardella |
| 5,715,817 | A | 2/1998 | Stevens-Wright et al. |
| 5,716,366 | A | 2/1998 | Yates |
| 5,717,306 | A | 2/1998 | Shipp |
| 5,720,742 | A | 2/1998 | Zacharias |
| 5,720,744 | A | 2/1998 | Eggleston et al. |
| 5,722,980 | A | 3/1998 | Schulz et al. |
| 5,728,130 | A | 3/1998 | Ishikawa et al. |
| 5,730,752 | A | 3/1998 | Alden et al. |
| 5,733,074 | A | 3/1998 | Stock et al. |
| 5,735,848 | A | 4/1998 | Yates et al. |
| 5,741,226 | A | 4/1998 | Strukel et al. |
| 5,743,906 | A | 4/1998 | Parins et al. |
| 5,752,973 | A | 5/1998 | Kieturakis |
| 5,755,717 | A | 5/1998 | Yates et al. |
| 5,762,255 | A | 6/1998 | Chrisman et al. |
| 5,766,164 | A | 6/1998 | Mueller et al. |
| 5,772,659 | A | 6/1998 | Becker et al. |
| 5,776,130 | A | 7/1998 | Buysse et al. |
| 5,776,155 | A | 7/1998 | Beaupre et al. |
| 5,779,130 | A | 7/1998 | Alesi et al. |
| 5,779,701 | A | 7/1998 | McBrayer et al. |
| 5,782,834 | A | 7/1998 | Lucey et al. |
| 5,792,135 | A | 8/1998 | Madhani et al. |
| 5,792,138 | A | 8/1998 | Shipp |
| 5,792,165 | A | 8/1998 | Klieman et al. |
| 5,796,188 | A | 8/1998 | Bays |
| 5,797,941 | A | 8/1998 | Schulze et al. |
| 5,797,959 | A | 8/1998 | Castro et al. |
| 5,800,432 | A | 9/1998 | Swanson |
| 5,800,448 | A | 9/1998 | Banko |
| 5,800,449 | A | 9/1998 | Wales |
| 5,805,140 | A | 9/1998 | Rosenberg et al. |
| 5,807,393 | A | 9/1998 | Williamson, IV et al. |
| 5,808,396 | A | 9/1998 | Boukhny |
| 5,810,811 | A | 9/1998 | Yates et al. |
| 5,810,828 | A | 9/1998 | Lightman et al. |
| 5,810,859 | A | 9/1998 | DiMatteo et al. |
| 5,817,033 | A | 10/1998 | DeSantis et al. |
| 5,817,084 | A | 10/1998 | Jensen |
| 5,817,093 | A | 10/1998 | Williamson, IV et al. |

(56) References Cited

U.S. PATENT DOCUMENTS

| | | |
|---|---|---|
| 5,817,119 A | 10/1998 | Klieman et al. |
| 5,823,197 A | 10/1998 | Edwards |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,971,949 A | 10/1999 | Levin et al. |
| 5,974,342 A | 10/1999 | Petrofsky |
| D416,089 S | 11/1999 | Barton et al. |
| 5,980,510 A | 11/1999 | Tsonton et al. |
| 5,980,546 A | 11/1999 | Hood |
| 5,984,938 A | 11/1999 | Yoon |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,001,120 A | 12/1999 | Levin |
| 6,003,517 A | 12/1999 | Sheffield et al. |
| 6,004,335 A | 12/1999 | Vaitekunas et al. |
| 6,007,552 A | 12/1999 | Fogarty et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| 6,120,519 A | 9/2000 | Weber et al. |
| H1904 H | 10/2000 | Yates et al. |
| 6,126,629 A | 10/2000 | Perkins |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,165,186 A | 12/2000 | Fogarty et al. |
| 6,165,191 A | 12/2000 | Shibata et al. |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,228,104 B1 | 5/2001 | Fogarty et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |

(56) References Cited

U.S. PATENT DOCUMENTS

| | | | |
|---|---|---|---|
| 6,258,034 | B1 | 7/2001 | Hanafy |
| 6,259,230 | B1 | 7/2001 | Chou |
| 6,267,761 | B1 | 7/2001 | Ryan |
| 6,270,831 | B2 | 8/2001 | Kumar et al. |
| 6,273,852 | B1 | 8/2001 | Lehe et al. |
| 6,273,902 | B1 | 8/2001 | Fogarty et al. |
| 6,274,963 | B1 | 8/2001 | Estabrook et al. |
| 6,277,115 | B1 | 8/2001 | Saadat |
| 6,277,117 | B1 | 8/2001 | Tetzlaff et al. |
| 6,278,218 | B1 | 8/2001 | Madan et al. |
| 6,280,407 | B1 | 8/2001 | Manna et al. |
| 6,283,981 | B1 | 9/2001 | Beaupre |
| 6,287,344 | B1 | 9/2001 | Wampler et al. |
| 6,290,575 | B1 | 9/2001 | Shipp |
| 6,292,700 | B1 | 9/2001 | Morrison et al. |
| 6,293,954 | B1 | 9/2001 | Fogarty et al. |
| 6,299,591 | B1 | 10/2001 | Banko |
| 6,299,621 | B1 | 10/2001 | Fogarty et al. |
| 6,306,131 | B1 | 10/2001 | Hareyama et al. |
| 6,306,157 | B1 | 10/2001 | Shchervinsky |
| 6,309,400 | B2 | 10/2001 | Beaupre |
| 6,311,783 | B1 | 11/2001 | Harpell |
| 6,312,445 | B1 | 11/2001 | Fogarty et al. |
| 6,319,221 | B1 | 11/2001 | Savage et al. |
| 6,325,795 | B1 | 12/2001 | Lindemann et al. |
| 6,325,799 | B1 | 12/2001 | Goble |
| 6,325,811 | B1 | 12/2001 | Messerly |
| 6,328,751 | B1 | 12/2001 | Beaupre |
| 6,332,891 | B1 | 12/2001 | Himes |
| 6,333,488 | B1 | 12/2001 | Lawrence et al. |
| 6,338,657 | B1 | 1/2002 | Harper et al. |
| 6,340,352 | B1 | 1/2002 | Okada et al. |
| 6,340,878 | B1 | 1/2002 | Oglesbee |
| 6,350,269 | B1 | 2/2002 | Shipp et al. |
| 6,352,532 | B1 | 3/2002 | Kramer et al. |
| 6,358,264 | B2 | 3/2002 | Banko |
| 6,364,888 | B1 | 4/2002 | Niemeyer et al. |
| 6,379,320 | B1 | 4/2002 | Lafon et al. |
| D457,958 | S | 5/2002 | Dycus et al. |
| 6,383,194 | B1 | 5/2002 | Pothula |
| 6,384,690 | B1 | 5/2002 | Wilhelmsson et al. |
| 6,387,094 | B1 | 5/2002 | Eitenmuller |
| 6,387,109 | B1 | 5/2002 | Davison et al. |
| 6,387,112 | B1 | 5/2002 | Fogarty et al. |
| 6,388,657 | B1 | 5/2002 | Natoli |
| 6,391,026 | B1 | 5/2002 | Hung et al. |
| 6,391,042 | B1 | 5/2002 | Cimino |
| 6,398,779 | B1 | 6/2002 | Buysse et al. |
| 6,402,743 | B1 | 6/2002 | Orszulak et al. |
| 6,402,748 | B1 | 6/2002 | Schoenman et al. |
| 6,405,733 | B1 | 6/2002 | Fogarty et al. |
| 6,409,722 | B1 | 6/2002 | Hoey et al. |
| H2037 | H | 7/2002 | Yates et al. |
| 6,416,469 | B1 | 7/2002 | Phung et al. |
| 6,416,486 | B1 | 7/2002 | Wampler |
| 6,416,525 | B1 | 7/2002 | Shibata |
| 6,419,675 | B1 | 7/2002 | Gallo, Sr. |
| 6,423,073 | B2 | 7/2002 | Bowman |
| 6,423,082 | B1 | 7/2002 | Houser et al. |
| 6,425,906 | B1 | 7/2002 | Young et al. |
| 6,425,907 | B1 | 7/2002 | Shibata et al. |
| 6,428,538 | B1 | 8/2002 | Blewett et al. |
| 6,428,539 | B1 | 8/2002 | Baxter et al. |
| 6,430,446 | B1 | 8/2002 | Knowlton |
| 6,432,118 | B1 | 8/2002 | Messerly |
| 6,436,114 | B1 | 8/2002 | Novak et al. |
| 6,436,115 | B1 | 8/2002 | Beaupre |
| 6,440,062 | B1 | 8/2002 | Ouchi |
| 6,443,968 | B1 | 9/2002 | Holthaus et al. |
| 6,443,969 | B1 | 9/2002 | Novak et al. |
| 6,449,006 | B1 | 9/2002 | Shipp |
| 6,454,781 | B1 | 9/2002 | Witt et al. |
| 6,454,782 | B1 | 9/2002 | Schwemberger |
| 6,458,128 | B1 | 10/2002 | Schulze |
| 6,458,130 | B1 | 10/2002 | Frazier et al. |
| 6,458,142 | B1 | 10/2002 | Faller et al. |
| 6,461,363 | B1 | 10/2002 | Gadberry et al. |
| 6,464,689 | B1 | 10/2002 | Qin et al. |
| 6,464,702 | B2 | 10/2002 | Schulze et al. |
| 6,468,286 | B2 | 10/2002 | Mastri et al. |
| 6,475,211 | B2 | 11/2002 | Chess et al. |
| 6,475,215 | B1 | 11/2002 | Tanrisever |
| 6,480,796 | B2 | 11/2002 | Wiener |
| 6,485,490 | B2 | 11/2002 | Wampler et al. |
| 6,491,690 | B1 | 12/2002 | Goble et al. |
| 6,491,701 | B2 | 12/2002 | Tierney et al. |
| 6,491,708 | B2 | 12/2002 | Madan et al. |
| 6,497,715 | B2 | 12/2002 | Satou |
| 6,500,112 | B1 | 12/2002 | Khouri |
| 6,500,176 | B1 | 12/2002 | Truckai et al. |
| 6,500,188 | B2 | 12/2002 | Harper et al. |
| 6,500,312 | B2 | 12/2002 | Wedekamp |
| 6,503,248 | B1 | 1/2003 | Levine |
| 6,506,208 | B2 | 1/2003 | Hunt et al. |
| 6,511,478 | B1 | 1/2003 | Burnside et al. |
| 6,511,480 | B1 | 1/2003 | Tetzlaff et al. |
| 6,511,493 | B1 | 1/2003 | Moutafis et al. |
| 6,514,252 | B2 | 2/2003 | Nezhat et al. |
| 6,514,267 | B2 | 2/2003 | Jewett |
| 6,517,565 | B1 | 2/2003 | Whitman et al. |
| 6,524,251 | B2 | 2/2003 | Rabiner et al. |
| 6,524,316 | B1 | 2/2003 | Nicholson et al. |
| 6,527,736 | B1 | 3/2003 | Attinger et al. |
| 6,531,846 | B1 | 3/2003 | Smith |
| 6,533,784 | B2 | 3/2003 | Truckai et al. |
| 6,537,272 | B2 | 3/2003 | Christopherson et al. |
| 6,537,291 | B2 | 3/2003 | Friedman et al. |
| 6,543,452 | B1 | 4/2003 | Lavigne |
| 6,543,456 | B1 | 4/2003 | Freeman |
| 6,544,260 | B1 | 4/2003 | Markel et al. |
| 6,551,309 | B1 | 4/2003 | LePivert |
| 6,554,829 | B2 | 4/2003 | Schulze et al. |
| 6,558,376 | B2 | 5/2003 | Bishop |
| 6,561,983 | B2 | 5/2003 | Cronin et al. |
| 6,562,035 | B1 | 5/2003 | Levin |
| 6,562,037 | B2 | 5/2003 | Paton et al. |
| 6,565,558 | B1 | 5/2003 | Lindenmeier et al. |
| 6,569,178 | B1 | 5/2003 | Miyawaki et al. |
| 6,572,563 | B2 | 6/2003 | Ouchi |
| 6,572,632 | B2 | 6/2003 | Zisterer et al. |
| 6,572,639 | B1 | 6/2003 | Ingle et al. |
| 6,575,969 | B1 | 6/2003 | Rittman, III et al. |
| 6,582,427 | B1 | 6/2003 | Goble et al. |
| 6,582,451 | B1 | 6/2003 | Marucci et al. |
| 6,584,360 | B2 | 6/2003 | Francischelli et al. |
| D477,408 | S | 7/2003 | Bromley |
| 6,585,735 | B1 | 7/2003 | Frazier et al. |
| 6,588,277 | B2 | 7/2003 | Giordano et al. |
| 6,589,200 | B1 | 7/2003 | Schwemberger et al. |
| 6,589,239 | B2 | 7/2003 | Khandkar et al. |
| 6,599,288 | B2 | 7/2003 | Maguire et al. |
| 6,602,252 | B2 | 8/2003 | Mollenauer |
| 6,607,540 | B1 | 8/2003 | Shipp |
| 6,610,059 | B1 | 8/2003 | West, Jr. |
| 6,610,060 | B2 | 8/2003 | Mulier et al. |
| 6,616,450 | B2 | 9/2003 | Mossle et al. |
| 6,619,529 | B2 | 9/2003 | Green et al. |
| 6,620,161 | B2 | 9/2003 | Schulze et al. |
| 6,622,731 | B2 | 9/2003 | Daniel et al. |
| 6,623,482 | B2 | 9/2003 | Pendekanti et al. |
| 6,623,500 | B1 | 9/2003 | Cook et al. |
| 6,623,501 | B2 | 9/2003 | Heller et al. |
| 6,626,848 | B2 | 9/2003 | Neuenfeldt |
| 6,626,926 | B2 | 9/2003 | Friedman et al. |
| 6,629,974 | B2 | 10/2003 | Penny et al. |
| 6,633,234 | B2 | 10/2003 | Wiener et al. |
| 6,635,057 | B2 | 10/2003 | Harano et al. |
| 6,644,532 | B2 | 11/2003 | Green et al. |
| 6,648,883 | B2 | 11/2003 | Francischelli et al. |
| 6,651,669 | B1 | 11/2003 | Burnside |
| 6,652,513 | B2 | 11/2003 | Panescu et al. |
| 6,652,539 | B2 | 11/2003 | Shipp et al. |
| 6,652,545 | B2 | 11/2003 | Shipp et al. |
| 6,656,132 | B1 | 12/2003 | Ouchi |

(56) References Cited

U.S. PATENT DOCUMENTS

| | | |
|---|---|---|
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,696 B2 | 12/2003 | Bacher et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,766 B1 | 4/2004 | Buelna et al. |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,154 B2 | 6/2004 | Fogarty et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,676 B2 | 9/2005 | Buelna |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,002,283 B2 | 2/2006 | Li et al. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,618 B2 | 8/2006 | Couture et al. |

(56) References Cited

U.S. PATENT DOCUMENTS

| | | |
|---|---|---|
| 7,083,619 B2 | 8/2006 | Truckai et al. |
| 7,087,054 B2 | 8/2006 | Truckai et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,201 B1 | 1/2007 | Peshkovskiy et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,282,836 B2 | 10/2007 | Kwon et al. |
| 7,285,895 B2 | 10/2007 | Beaupre |
| 7,287,682 B1 | 10/2007 | Ezzat et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,413,123 B2 | 8/2008 | Ortenzi |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,435,582 B2 | 10/2008 | Zimmermann et al. |
| 7,441,684 B2 | 10/2008 | Shelton, IV et al. |
| 7,442,168 B2 | 10/2008 | Novak et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,472,815 B2 | 1/2009 | Shelton, IV et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |

(56) References Cited

U.S. PATENT DOCUMENTS

| | | |
|---|---|---|
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,559,450 B2 | 7/2009 | Wales et al. |
| 7,559,452 B2 | 7/2009 | Wales et al. |
| 7,563,259 B2 | 7/2009 | Takahashi |
| 7,563,269 B2 | 7/2009 | Hashiguchi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,166 B2 | 8/2009 | Ethridge et al. |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,604,150 B2 | 10/2009 | Boudreaux |
| 7,607,557 B2 | 10/2009 | Shelton, IV et al. |
| 7,608,054 B2 | 10/2009 | Soring et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,245 B2 | 1/2010 | Sekino et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,654,431 B2 | 2/2010 | Hueil et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,734,476 B2 | 6/2010 | Wildman et al. |
| 7,738,969 B2 | 6/2010 | Bleich |
| 7,740,594 B2 | 6/2010 | Hibner |
| 7,749,240 B2 | 7/2010 | Takahashi et al. |
| 7,749,273 B2 | 7/2010 | Cauthen, III et al. |
| 7,751,115 B2 | 7/2010 | Song |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,762,979 B2 | 7/2010 | Wuchinich |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |

(56) References Cited

U.S. PATENT DOCUMENTS

| | | |
|---|---|---|
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,878,991 B2 | 2/2011 | Babaev |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,465 B2 | 2/2011 | Donofrio et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,329 B2 | 7/2011 | Refior et al. |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,020,743 B2 | 9/2011 | Shelton, IV |
| 8,025,630 B2 | 9/2011 | Murakami et al. |
| 8,028,885 B2 | 10/2011 | Smith et al. |
| 8,033,173 B2 | 10/2011 | Ehlert et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,056,720 B2 | 11/2011 | Hawkes |
| 8,057,467 B2 | 11/2011 | Faller et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,128,624 B2 | 3/2012 | Couture et al. |
| 8,133,218 B2 | 3/2012 | Daw et al. |
| 8,136,712 B2 | 3/2012 | Zingman |
| 8,137,263 B2 | 3/2012 | Marescaux et al. |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,501 B2 | 5/2012 | Houser et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,221,306 B2 | 7/2012 | Okada et al. |
| 8,221,415 B2 | 7/2012 | Francischelli |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,298,223 B2 | 10/2012 | Wham et al. |
| 8,298,225 B2 | 10/2012 | Gilbert |
| 8,298,232 B2 | 10/2012 | Unger |

(56) References Cited

U.S. PATENT DOCUMENTS

| | | |
|---|---|---|
| 8,298,233 B2 | 10/2012 | Mueller |
| 8,303,576 B2 | 11/2012 | Brock |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,158 B2 | 1/2013 | McKenna et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisel |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,394,096 B2 | 3/2013 | Moses et al. |
| 8,394,115 B2 | 3/2013 | Houser et al. |
| 8,397,971 B2 | 3/2013 | Yates et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,161 B2 | 4/2013 | Nagaya et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,460,288 B2 | 6/2013 | Tamai et al. |
| 8,460,292 B2 | 6/2013 | Truckai et al. |
| 8,460,326 B2 | 6/2013 | Houser et al. |
| 8,461,744 B2 | 6/2013 | Wiener et al. |
| 8,469,981 B2 | 6/2013 | Robertson et al. |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,562,592 B2 | 10/2013 | Conlon et al. |
| 8,562,598 B2 | 10/2013 | Falkenstein et al. |
| 8,562,604 B2 | 10/2013 | Nishimura |
| 8,568,390 B2 | 10/2013 | Mueller |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,597,193 B2 | 12/2013 | Grunwald et al. |
| 8,602,031 B2 | 12/2013 | Reis et al. |
| 8,602,288 B2 | 12/2013 | Shelton, IV et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,651,230 B2 | 2/2014 | Peshkovsky et al. |
| 8,652,120 B2 | 2/2014 | Giordano et al. |

(56) References Cited

U.S. PATENT DOCUMENTS

| | | |
|---|---|---|
| 8,652,132 B2 | 2/2014 | Tsuchiya et al. |
| 8,652,155 B2 | 2/2014 | Houser et al. |
| 8,659,208 B1 | 2/2014 | Rose et al. |
| 8,663,220 B2 | 3/2014 | Wiener et al. |
| 8,663,222 B2 | 3/2014 | Anderson et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,715,306 B2 | 5/2014 | Faller et al. |
| 8,721,640 B2 | 5/2014 | Taylor et al. |
| 8,721,657 B2 | 5/2014 | Kondoh et al. |
| 8,734,443 B2 | 5/2014 | Hixson et al. |
| 8,734,476 B2 | 5/2014 | Rhee et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,773,001 B2 | 7/2014 | Wiener et al. |
| 8,777,944 B2 | 7/2014 | Frankhouser et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,709 B2 | 10/2014 | Akagane et al. |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,870,867 B2 | 10/2014 | Walberg et al. |
| 8,882,766 B2 | 11/2014 | Couture et al. |
| 8,882,791 B2 | 11/2014 | Stulen |
| 8,882,792 B2 | 11/2014 | Dietz et al. |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,071 B2 | 5/2015 | Miller et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,039,705 B2 | 5/2015 | Takashino |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |

(56) References Cited

U.S. PATENT DOCUMENTS

| | | |
|---|---|---|
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,084,878 B2 | 7/2015 | Kawaguchi et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,114,245 B2 | 8/2015 | Dietz et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,125,722 B2 | 9/2015 | Schwartz |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,055 B2 | 10/2015 | Houser et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,237,923 B2 | 1/2016 | Worrell et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,301,772 B2 | 4/2016 | Kimball et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanai et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,445,833 B2 | 9/2016 | Akagane |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,236 B2 | 11/2016 | Price et al. |
| 9,492,187 B2 | 11/2016 | Ravikumar et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,729 B2 | 4/2017 | Dewaele et al. |
| 9,623,237 B2 | 4/2017 | Turner et al. |
| 9,636,135 B2 | 5/2017 | Stulen |
| 9,638,770 B2 | 5/2017 | Dietz et al. |

(56) References Cited

U.S. PATENT DOCUMENTS

| | | |
|---|---|---|
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanai et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,901,359 B2 | 2/2018 | Faller et al. |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,182,837 B2 | 1/2019 | Isola et al. |
| 10,188,385 B2 | 1/2019 | Kerr et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,245,064 B2 | 4/2019 | Rhee et al. |
| 10,245,065 B2 | 4/2019 | Witt et al. |
| 10,245,095 B2 | 4/2019 | Boudreaux |
| 10,251,664 B2 | 4/2019 | Shelton, IV et al. |
| 10,263,171 B2 | 4/2019 | Wiener et al. |
| 10,265,094 B2 | 4/2019 | Witt et al. |
| 10,265,117 B2 | 4/2019 | Wiener et al. |
| 10,265,118 B2 | 4/2019 | Gerhardt |
| D847,990 S | 5/2019 | Kimball |
| 10,278,721 B2 | 5/2019 | Dietz et al. |
| 10,285,723 B2 | 5/2019 | Conlon et al. |
| 10,285,724 B2 | 5/2019 | Faller et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,614 B2 | 7/2019 | Messerly et al. |
| 10,342,602 B2 | 7/2019 | Strobl et al. |
| 10,357,303 B2 | 7/2019 | Conlon et al. |
| 10,368,892 B2 | 8/2019 | Stulen et al. |
| 10,368,894 B2 | 8/2019 | Madan et al. |
| 10,368,957 B2 | 8/2019 | Denzinger et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,580 B2 | 9/2019 | Messerly et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,463,421 B2 | 11/2019 | Boudreaux et al. |
| 10,463,887 B2 | 11/2019 | Witt et al. |
| 10,470,788 B2 | 11/2019 | Sinelnikov |
| 10,512,795 B2 | 12/2019 | Voegele et al. |
| 10,517,627 B2 | 12/2019 | Timm et al. |
| 10,524,854 B2 | 1/2020 | Woodruff et al. |
| 10,531,910 B2 | 1/2020 | Houser et al. |
| 10,537,351 B2 | 1/2020 | Shelton, IV et al. |
| 10,537,352 B2 | 1/2020 | Faller et al. |
| 10,537,667 B2 | 1/2020 | Anim |
| 10,543,008 B2 | 1/2020 | Vakharia et al. |
| 10,555,750 B2 | 2/2020 | Conlon et al. |
| 10,555,769 B2 | 2/2020 | Worrell et al. |
| 10,575,892 B2 | 3/2020 | Danziger et al. |

(56) References Cited

U.S. PATENT DOCUMENTS

| | | |
|---|---|---|
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002378 A1 | 1/2002 | Messerly |
| 2002/0016603 A1* | 2/2002 | Wells .......... A61B 17/2841 606/153 |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052595 A1 | 5/2002 | Witt et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckai et al. |
| 2003/0114874 A1 | 6/2003 | Craig et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0160698 A1 | 8/2003 | Andreasson et al. |
| 2003/0171747 A1 | 9/2003 | Kanehira et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0147946 A1 | 7/2004 | Mastri et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0199194 A1 | 10/2004 | Witt et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0131390 A1 | 6/2005 | Heinrich et al. |
| 2005/0143759 A1 | 6/2005 | Kelly |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0267464 A1 | 12/2005 | Truckai et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0095046 A1 | 5/2006 | Trieu et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0032704 A1 | 2/2007 | Gandini et al. |
| 2007/0055228 A1* | 3/2007 | Berg .......... A61B 17/320092 606/41 |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208340 A1 | 9/2007 | Ganz et al. |

(56) References Cited

U.S. PATENT DOCUMENTS

| | | |
|---|---|---|
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0282333 A1 | 12/2007 | Fortson et al. |
| 2007/0287933 A1 | 12/2007 | Phan et al. |
| 2007/0288055 A1 | 12/2007 | Lee |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0281200 A1 | 11/2008 | Voic et al. |
| 2008/0281315 A1 | 11/2008 | Gines |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1 | 3/2009 | Mulvihill et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0118751 A1 | 5/2009 | Wiener et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0299141 A1 | 12/2009 | Downey et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228191 A1 | 9/2010 | Alvarez et al. |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0312186 A1 | 12/2010 | Suchdev et al. |
| 2010/0331742 A1 | 12/2010 | Masuda |
| 2010/0331873 A1 | 12/2010 | Dannaher et al. |
| 2011/0004233 A1 | 1/2011 | Muir et al. |
| 2011/0028964 A1 | 2/2011 | Edwards |
| 2011/0106141 A1 | 5/2011 | Nakamura |
| 2011/0125151 A1 | 5/2011 | Strauss et al. |
| 2011/0278343 A1 | 11/2011 | Knodel et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0143211 A1 | 6/2012 | Kishi |
| 2012/0172904 A1 | 7/2012 | Muir et al. |
| 2012/0265241 A1 | 10/2012 | Hart et al. |
| 2012/0296371 A1 | 11/2012 | Kappus et al. |
| 2013/0023925 A1 | 1/2013 | Mueller |
| 2013/0035685 A1 | 2/2013 | Fischer et al. |
| 2013/0090576 A1 | 4/2013 | Stulen et al. |
| 2013/0116717 A1 | 5/2013 | Balek et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0253256 A1 | 9/2013 | Griffith et al. |
| 2013/0277410 A1 | 10/2013 | Fernandez et al. |
| 2013/0296843 A1 | 11/2013 | Boudreaux et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |

(56) References Cited

U.S. PATENT DOCUMENTS

| | | |
|---|---|---|
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0081299 A1 | 3/2014 | Dietz et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh, II et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0323926 A1 | 10/2014 | Akagane |
| 2014/0371735 A1 | 12/2014 | Long |
| 2015/0011889 A1 | 1/2015 | Lee |
| 2015/0080876 A1 | 3/2015 | Worrell et al. |
| 2015/0112335 A1 | 4/2015 | Boudreaux et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0257780 A1 | 9/2015 | Houser |
| 2015/0272659 A1 | 10/2015 | Boudreaux et al. |
| 2015/0289854 A1 | 10/2015 | Cho et al. |
| 2016/0045248 A1 | 2/2016 | Unger et al. |
| 2016/0051316 A1 | 2/2016 | Boudreaux |
| 2016/0114355 A1 | 4/2016 | Sakai et al. |
| 2016/0121143 A1 | 5/2016 | Mumaw et al. |
| 2016/0128769 A1 | 5/2016 | Rontal et al. |
| 2016/0157927 A1 | 6/2016 | Corbett et al. |
| 2016/0175029 A1 | 6/2016 | Witt et al. |
| 2016/0199125 A1 | 7/2016 | Jones |
| 2016/0206342 A1 | 7/2016 | Robertson et al. |
| 2016/0240768 A1 | 8/2016 | Fujii et al. |
| 2016/0262786 A1 | 9/2016 | Madan et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0367281 A1 | 12/2016 | Gee et al. |
| 2017/0000541 A1 | 1/2017 | Yates et al. |
| 2017/0014152 A1 | 1/2017 | Noui et al. |
| 2017/0027624 A1 | 2/2017 | Wilson et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0105757 A1 | 4/2017 | Weir et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0189095 A1 | 7/2017 | Danziger et al. |
| 2017/0196586 A1 | 7/2017 | Witt et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0245875 A1 | 8/2017 | Timm et al. |
| 2017/0360468 A1 | 12/2017 | Eichmann et al. |
| 2018/0014845 A1 | 1/2018 | Dannaher |
| 2018/0014848 A1 | 1/2018 | Messerly et al. |
| 2018/0049767 A1 | 2/2018 | Gee et al. |
| 2018/0055529 A1 | 3/2018 | Messerly et al. |
| 2018/0055531 A1 | 3/2018 | Messerly et al. |
| 2018/0055532 A1 | 3/2018 | Messerly et al. |
| 2018/0056095 A1 | 3/2018 | Messerly et al. |
| 2018/0078268 A1 | 3/2018 | Messerly et al. |
| 2018/0125523 A1 | 5/2018 | Johnson |
| 2018/0146975 A1 | 5/2018 | Zhang |
| 2018/0168680 A1 | 6/2018 | Houser et al. |
| 2018/0177521 A1 | 6/2018 | Faller et al. |
| 2018/0199957 A1 | 7/2018 | Robertson et al. |
| 2019/0008543 A1 | 1/2019 | Scoggins et al. |
| 2019/0053822 A1 | 2/2019 | Robertson et al. |
| 2019/0090900 A1 | 3/2019 | Rhee et al. |
| 2019/0133633 A1 | 5/2019 | Neurohr et al. |
| 2019/0239919 A1 | 8/2019 | Witt et al. |
| 2019/0262029 A1 | 8/2019 | Messerly et al. |
| 2019/0350615 A1 | 11/2019 | Messerly et al. |
| 2019/0380733 A1 | 12/2019 | Stulen et al. |
| 2019/0381339 A1 | 12/2019 | Voegele et al. |
| 2019/0381340 A1 | 12/2019 | Voegele et al. |
| 2020/0008857 A1 | 1/2020 | Conlon et al. |
| 2020/0015798 A1 | 1/2020 | Wiener et al. |
| 2020/0015838 A1 | 1/2020 | Robertson |
| 2020/0046401 A1 | 2/2020 | Witt et al. |
| 2020/0054386 A1 | 2/2020 | Houser et al. |
| 2020/0054899 A1 | 2/2020 | Wiener et al. |

FOREIGN PATENT DOCUMENTS

| | | |
|---|---|---|
| CN | 2460047 Y | 11/2001 |
| CN | 1634601 A | 7/2005 |
| CN | 1775323 A | 5/2006 |
| CN | 1922563 A | 2/2007 |
| CN | 2868227 Y | 2/2007 |
| CN | 202027624 U | 11/2011 |
| CN | 102335778 A | 2/2012 |
| CN | 103668171 A | 3/2014 |
| CN | 103921215 A | 7/2014 |
| CN | 106077718 A | 11/2016 |
| DE | 2065681 A1 | 3/1975 |
| DE | 3904558 A1 | 8/1990 |
| DE | 9210327 U1 | 11/1992 |
| DE | 4300307 A1 | 7/1994 |
| DE | 4434938 C1 | 2/1996 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2510891 B1 | 6/2016 |
| FR | 2454351 A1 | 11/1980 |
| FR | 2964554 A1 | 3/2012 |
| GB | 2032221 A | 4/1980 |
| GB | 2317566 A | 4/1998 |
| GB | 2318298 A | 4/1998 |

(56) References Cited

FOREIGN PATENT DOCUMENTS

| | | |
|---|---|---|
| GB | 2425480 A | 11/2006 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H0595955 A | 4/1993 |
| JP | H05115490 A | 5/1993 |
| JP | H0647048 A | 2/1994 |
| JP | H0670938 A | 3/1994 |
| JP | H06104503 A | 4/1994 |
| JP | H0824266 A | 1/1996 |
| JP | H08229050 A | 9/1996 |
| JP | H08275950 A | 10/1996 |
| JP | H08275951 A | 10/1996 |
| JP | H08299351 A | 11/1996 |
| JP | H08336545 A | 12/1996 |
| JP | H09135553 A | 5/1997 |
| JP | H09140722 A | 6/1997 |
| JP | H105236 A | 1/1998 |
| JP | H105237 A | 1/1998 |
| JP | H10295700 A | 11/1998 |
| JP | H11128238 A | 5/1999 |
| JP | 2000139943 A | 5/2000 |
| JP | 2000210299 A | 8/2000 |
| JP | 2000271145 A | 10/2000 |
| JP | 2000287987 A | 10/2000 |
| JP | 2000312682 A | 11/2000 |
| JP | 2001029353 A | 2/2001 |
| JP | 2001057985 A | 3/2001 |
| JP | 2001170066 A | 6/2001 |
| JP | 2002186901 A | 7/2002 |
| JP | 2002233533 A | 8/2002 |
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2004209043 A | 7/2004 |
| JP | 2005027026 A | 1/2005 |
| JP | 2005074088 A | 3/2005 |
| JP | 2005094552 A | 4/2005 |
| JP | 2005253674 A | 9/2005 |
| JP | 2006217716 A | 8/2006 |
| JP | 2006288431 A | 10/2006 |
| JP | D1339835 S | 8/2008 |
| JP | 2009297352 A | 12/2009 |
| JP | 2010009686 A | 1/2010 |
| JP | 2010121865 A | 6/2010 |
| JP | 2011160586 A | 8/2011 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9816157 A1 | 4/1998 |
| WO | WO-9920213 A1 | 4/1999 |
| WO | WO-9923960 A1 | 5/1999 |
| WO | WO-0024322 A1 | 5/2000 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0195810 A2 | 12/2001 |
| WO | WO-02080799 A1 | 10/2002 |
| WO | WO-2004037095 A2 | 5/2004 |
| WO | WO-2004078051 A2 | 9/2004 |
| WO | WO-2004098426 A1 | 11/2004 |
| WO | WO-2005084250 A2 | 9/2005 |
| WO | WO-2007008710 A2 | 1/2007 |
| WO | WO-2008118709 A1 | 10/2008 |
| WO | WO-2008130793 A1 | 10/2008 |
| WO | WO-2010104755 A1 | 9/2010 |
| WO | WO-2011008672 A2 | 1/2011 |
| WO | WO-2011052939 A2 | 5/2011 |
| WO | WO-2011060031 A1 | 5/2011 |
| WO | WO-2012044606 A2 | 4/2012 |
| WO | WO-2012066983 A1 | 5/2012 |
| WO | WO-2013048963 A2 | 4/2013 |

OTHER PUBLICATIONS

Lim et al., "A Review of Mechanism Used in Laparoscopic Surgical Instruments," Mechanism and Machine Theory, vol. 38, pp. 1133-1147, (2003).
F. A. Duck, "Optical Properties of Tissue Including Ultraviolet and Infrared Radiation," pp. 43-71 in Physical Properties of Tissue (1990).
Sullivan, "Optimal Choice for Number of Strands in a Litz-Wire Transformer Winding," IEEE Transactions on Power Electronics, vol. 14, No. 2, Mar. 1999, pp. 283-291.
Walsh, S. J., White, R. G., "Vibrational Power Transmission in Curved Beams," Journal of Sound and Vibration, 233(3), 455-488 (2000).
http://www.apicalinstr.com/generators.htm.
http://www.medicalexpo.com/medical-manufacturer/electrosurgical-generator-6951.html.
Covidien 501(k) Summary Sonicision, dated Feb. 24, 2011 (7 pages).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
http:/www.ethicon.com/gb-en/healthcare-professionals/products/energy-devices/capital//ge . . . .
http://www.megadyne.com/es_generator.php.
Campbell et al, "Thermal Imaging in Surgery," p. 19-3, in Medical Infrared Imaging, N. A. Diakides and J. D. Bronzino, Eds. (2008).
Incropera et al., Fundamentals of Heat and Mass Transfer, Wiley, New York (1990). (Book—not attached).
Graff, K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).

(56) References Cited

OTHER PUBLICATIONS http://www.dotmed.com/listing/electrosurical-unit/ethicon/ultracision-g110-/1466724.

http://www.valleylab.com/product/es/generators/index.html.

Technology Overview, printed from www.harmonicscalpel.com, Internet site, website accessed on Jun. 13, 2007, (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Orr et al., "Overview of Bioheat Transfer," pp. 367-384 in Optical-Thermal Response of Laser-Irradiated Tissue, A. J. Welch and M. J. C. van Gernert, eds., Plenum, New York (1995).

LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.

http://www.4-traders.com/JOHNSON-JOHNSON-4832/news/Johnson-Johnson-Ethicon-E . . . .

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Henriques. F.C., "Studies in thermal injury V. The predictability and the significance of thermally induced rate processes leading to irreversible epidermal injury." Archives of Pathology, 434, pp. 489-502 (1947).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wall et al., "Thermal modification of collagen," J Shoulder Elbow Surg, No. 8, pp. 339-344 (Jul./Aug. 1999).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

National Semiconductors Temperature Sensor Handbook—http://www.national.com/appinfo/tempsensors/files/temphb.pdf; accessed online: Apr. 1, 2011.

Chen et al., "Heat-induced changes in the mechanics of a collagenous tissue: pseudoelastic behavior at 37° C.," Journal of Biomechanics, 31, pp. 211-216 (1998).

Kurt Gieck & Reiner Gieck, *Engineering Formulas* § Z.7 (7th ed. 1997).

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, [Value Analysis Brief], LigaSure Advance™ Pistol Grip, dated Rev. Apr. 2010 (7 pages).

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

Douglas, S.C. "Introduction to Adaptive Filter". Digital Signal Processing Handbook. Ed. Vijay K. Madisetti and Douglas B. Williams. Boca Raton: CRC Press LLC, 1999.

Leonard I. Malis, M.D., "The Value of Irrigation During Bipolar Coagulation," 1989.

Covidien Brochure, The LigaSure Precise™ Instrument, dated Mar. 2011 (2 pages).

Glaser and Subak-Sharpe,lntegrated Circuit Engineering, Addison-Wesley Publishing, Reading, MA (1979). (book—not attached).

Jang, J. et al. "Neuro-fuzzy and Soft Computing." Prentice Hall, 1997, pp. 13-89, 199-293, 335-393, 453-496, 535-549.

Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.

Sadiq Muhammad et al: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.

Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news_events/article20030224.html.

* cited by examiner

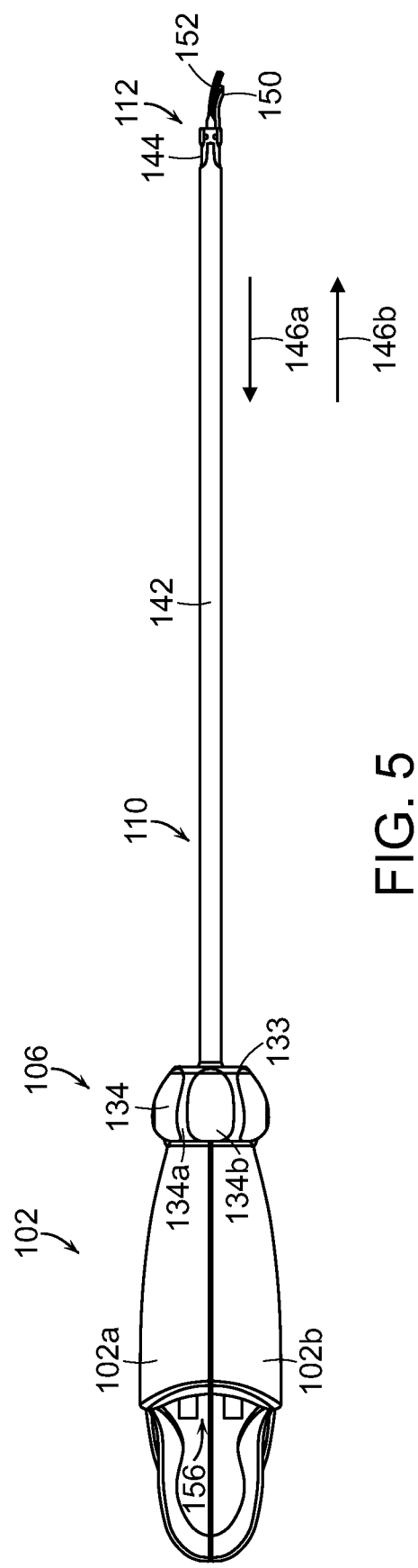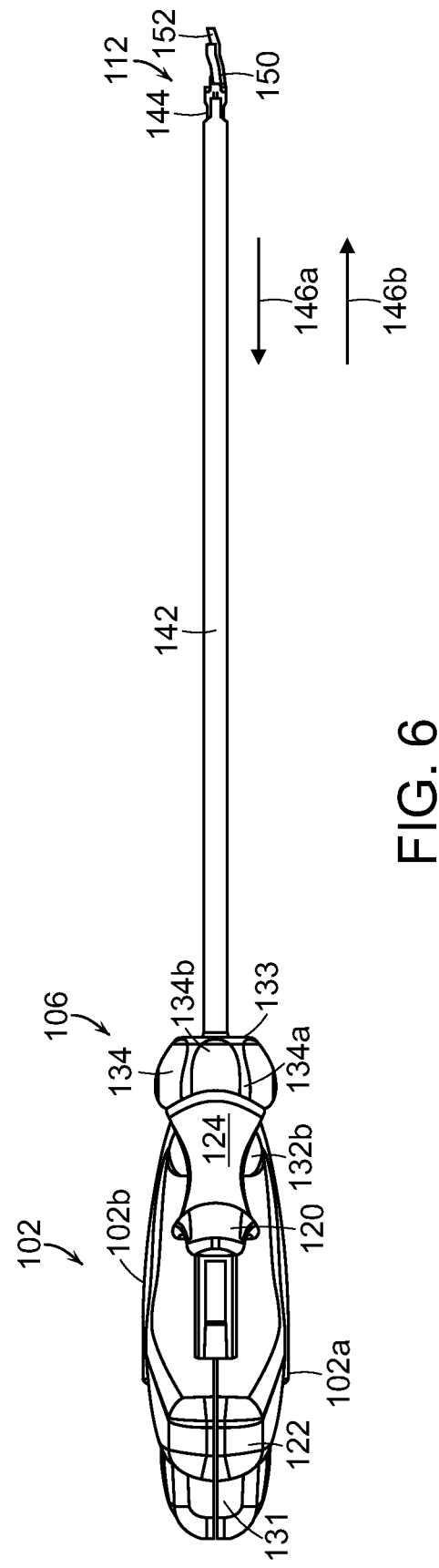

ERGONOMIC SURGICAL INSTRUMENTS

CROSS REFERENCE TO RELATED APPLICATION

This application is a continuation application claiming priority under 35 U.S.C. § 120 to U.S. patent application Ser. No. 14/172,334, filed Feb. 4, 2014, entitled ERGONOMIC SURGICAL INSTRUMENTS, which issued on Dec. 26, 2017 as U.S. Pat. No. 9,848,902, which is a continuation application claiming priority under 35 U.S.C. § 120 to U.S. patent application Ser. No. 13/426,232, filed Mar. 21, 2012, entitled ERGONOMIC SURGICAL INSTRUMENTS, which issued on Nov. 8, 2016 as U.S. Pat. No. 9,486,236, which is a continuation application claiming priority under 35 U.S.C. § 120 to U.S. patent application Ser. No. 12/245,158, filed Oct. 3, 2008, entitled ERGONOMIC SURGICAL INSTRUMENTS, which issued on Jan. 7, 2014 as U.S. Pat. No. 8,623,027, which claims the benefit under Title 35, United States Code § 119(e), of U.S. Patent Provisional Application Ser. No. 60/997,901, filed Oct. 5, 2007, entitled ERGONOMIC ULTRASONIC SURGICAL INSTRUMENTS, the entire disclosures of which are hereby incorporated by reference herein.

BACKGROUND

Ultrasonic surgical instruments, including both hollow core and solid core instruments, are used for the safe and effective treatment of many medical conditions. Ultrasonic surgical instruments, and particularly solid core ultrasonic surgical instruments, are advantageous because they may be used to cut and/or coagulate tissue using energy in the form of mechanical vibrations transmitted to a surgical end effector at ultrasonic frequencies. Ultrasonic vibrations, when transmitted to tissue at suitable energy levels and using a suitable end effector, may be used to cut, dissect, coagulate, elevate or separate tissue. Ultrasonic surgical instruments utilizing solid core technology are particularly advantageous because of the amount of ultrasonic energy that may be transmitted from the ultrasonic transducer, through an ultrasonic transmission waveguide, to the surgical end effector. Such instruments may be used for open procedures or minimally invasive procedures, such as endoscopic or laparoscopic procedures, wherein the end effector is passed through a trocar to reach the surgical site.

Activating or exciting the end effector (e.g., cutting blade, ball coagulator) of such instruments at ultrasonic frequencies induces longitudinal vibratory movement that generates localized heat within adjacent tissue, facilitating both cutting and coagulating. Because of the nature of ultrasonic surgical instruments, a particular ultrasonically actuated end effector may be designed to perform numerous functions, including, for example, cutting and coagulating.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are designed to resonate at the same frequency as the transducer. When an end effector is attached to a transducer the overall system frequency may be the same frequency as the transducer itself. The transducer and the end effector may be designed to resonate at two different frequencies and when joined or coupled may resonate at a third frequency. The zero-to-peak amplitude of the longitudinal ultrasonic vibration at the tip, d, of the end effector behaves as a simple sinusoid at the resonant frequency as given by:

$$d = A\ \sin(\omega t)$$

where: $\omega$=the radian frequency which equals a times the cyclic frequency, f; and
A=the zero-to-peak amplitude.
The longitudinal excursion is defined as the peak-to-peak (p-t-p) amplitude, which is just twice the amplitude of the sine wave or 2 A.

Solid core ultrasonic surgical instruments may be divided into two types, single element end effector devices and multiple-element end effectors. Single element end effector devices include a variety of blade types such as ball, hooked, curved, and coagulating shears. Single-element end effector instruments have limited ability to apply blade-to-tissue pressure when the tissue is soft and loosely supported. Substantial pressure may be necessary to effectively couple ultrasonic energy to the tissue. The inability of a single-element end effector to grasp the tissue results in a further inability to fully coapt tissue surfaces while applying ultrasonic energy, leading to less-than-desired hemostasis and tissue joining. Multiple-element end effectors include a clamping mechanism comprising a clamp arm that works in conjunction with the vibrating blade to form a jaw like structure. Ultrasonic clamping coagulators provide an improved ultrasonic surgical instrument for cutting/coagulating tissue, particularly loose and unsupported tissue. The clamping mechanism presses the tissue against the vibrating ultrasonic blade and applies a compressive or biasing force against the tissue to achieve faster cutting and hemostasis (e.g., coagulation) of the tissue with less attenuation of blade motion.

As an alternative to open surgical procedures, many modern surgeons use endoscopes and endoscopic instruments to remotely access organs through smaller, puncture-like incisions. As a direct result thereof, patients tend to benefit from less scarring and reduced healing time. Endoscopic instruments are inserted into the patient through a cannula, or port, which has been made with a trocar. Typical sizes for cannulas range from three millimeters to twelve millimeters. Smaller cannulas are usually preferred. However, the smaller cannulas in turn present additional challenges in the design of the endoscopic instruments that fit through the smaller cannulas. Many endoscopic surgical procedures require cutting or ligating blood vessels or vascular tissue as well as grasping, cutting, dissecting, coagulating, elevating, manipulating, and/or separating tissue.

For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure. Tissue welding is a technique for closing wounds and vessels and is applied in many surgical specialties. Tissue welding is a technique for closing wounds by creating a hemostatic seal in the wounds or vessels as well as creating strong anastomoses in the tissue. Ultrasonic surgical instruments may be employed to achieve hemostasis with minimal lateral thermal damage to the tissue. The hemostasis or anastomoses occurs through the transfer of mechanical energy to the tissue. Internal cellular friction breaks hydrogen bonds resulting in protein denaturization. As the proteins are denatured at temperatures below 100° C., a sticky coagulum forms and seals small vessels. Anastomoses occurs when the effects are prolonged. Thus, the ultrasonic energy in the vibrating blade may be employed to create hemostatic seals in vessels and adjacent tissues in wounds and to create strong anastomoses in tissue. Ultrasonic vibrating single or multiple end effectors, either alone or in combination with clamping mechanisms, produce adequate mechanical energy to seal vessels regardless of the temperature of the end effector and/or the tissue. To create strong anastomoses of the tissue, the temperature of the end effector and the tissue should be maintained below approximately 50° C. to allow for the creation of a coagulum to seal the tissues together without desiccating the tissues.

In the design of medical instruments, several factors may be applied to assess the viability of the ergonomics of a particular design. One factor of ergonomics is comfort. Comfort may be characterized by the ability to manipulate and control the device without undue muscle strain, pressure points, or other harmful ergonomic effects. Comfort is created from properly sized features located to fit the anatomy of the user, and adequate distribution of force against the user's body. The ability to use an instrument over an extended period without fatigue, pain, or loss of precision is a measure of comfort. Another factor of ergonomics is the ability to use an instrument over an extended time period without fatigue, pain, or loss of precision is a measure of comfort. Aside from comfort, one objective factor is the ability to control the working end of the device with the degree of control needed to accomplish the surgical task with ease. The extent that this control may be achieved emanates first from the inherent stability of the instrument in the hand of the user, and second from the ability to perform finer motions in order to manipulate the specific instrument controls. Design efforts balance the ability to achieve overall stability in the hand while facilitating appropriate access and mobility to utilize the fine controls. The stability of the surgical instrument in the hand may be accomplished via a variety of grips. Common grips include ring handles, in-line scissors, and pistol configurations, among others. Pistol grips generally provide points of fixation on the hand:

(1) A point between the thumb and index finger resting in the web of the joint;

(2) A grasping force between the thumb and index finger; and (3) A gripping force between the fingers and the palm when activating a trigger, power switch, knob, lever, or other feature.

Due to the inherent spatial considerations of the surgical cavity, surgeons often have difficulty performing traditional surgical methods using endoscopic instruments inserted into the patient through a cannula. The spatial limitations, coupled with the multi-function capability of many endoscopic instruments, particularly laparoscopic ultrasonic surgical instruments, create ergonomic challenges for the surgeon to easily access and operate the multiple functions and controls of the instrument. Many ultrasonic surgical instruments with multiple-element end effectors require a high force of the jaws of the clamping mechanism, which in turn requires higher input forces at the handle/trigger. This creates challenges in providing a comfortable handle/trigger interface for the user. Just as important is to enable the surgeon to finely control the opening motion of the jaws to facilitate fine dissection without creating fatigue or pressure points on the surgeon's hands. Activating electrical power switches on the ultrasonic instrument housing also presents a challenge. A surgeon needs to easily access any of the switches at any point while also avoiding inadvertent or unintentional activation at any time. Other functions that a surgeon may need to perform include rotating the shaft, or selecting power levels. In addition, the user should be able to operate any of these functions without looking, allowing them to focus entirely on the monitor view during a laparoscopic procedure. In addition, it may be desirable for the user not to have to reposition their grip in order to operate any of these key functions the power switches, and be able to easily manipulate the clamp force or power levels while opening the jaws of the clamping mechanism of the end effector.

Other ergonomic challenges presented by conventional laparoscopic ultrasonic surgical instruments include the ability of the user to easily access and operate multiple functions, sometimes simultaneously. Typically the index finger is used to operate a rotation knob located at the distal end of the device handle to rotate the shaft. However, controlling the power buttons/switches also employs the use of the index finger, creating an inherent challenge for locating the rotation knob and the switches on the housing such that they both may be reached by the index finger. Ultrasonic devices include multiple controls such as shaft rotation, power settings, and trigger closure that must be accessible in various hand positions and for many hand sizes.

Traditional laparoscopic ultrasonic surgical instruments usually have a rotation control knob located at the distal end of the instrument that can be accessed with the index finger to rotate the shaft. However, controlling the power buttons/ switches also employs the use of the index finger, creating an inherent challenge for locating the rotation knob and the switches on the housing such that they both may be reached by the index finger. The finger tip rotation control often may be difficult to reach for a surgeon with small hands especially when the instrument is oriented in positions at extreme angles or orientations that may be necessary to position the tip of the instrument in proximity to the anatomy to be treated.

With respect to hand size, it has long been a challenge to create laparoscopic ultrasonic surgical instruments with a handle design in terms of size, shape, and location of control interfaces that is "ideal" for everyone. The very large disparity of anthropometrics from small females to large males traditionally creates challenges for users at the extreme ends of the spectrum. Although instruments having various different sized handles to accommodate the disparity in hand sizes have been considered, purchasers generally desire to carry fewer inventories, and thus multiple variations have not been accepted. In addition, there is always the risk that a certain sized handle may not be available to a particular doctor at a particular hospital.

The multi-function capability of many ultrasonic surgical instruments, particularly laparoscopic ultrasonic surgical instruments, create ergonomic challenges in the ability of the user to comfortably access and operate the multiple functions and controls of the instrument. This include, for example, the ability to comfortably actuate the jaws of the clamping mechanism and activate the hand control buttons/ switches, sometimes simultaneously. The user should be able to control the opening motion of the end effectors to facilitate spreading dissection. Laparoscopic handle interface designs traditionally incorporate a "scissor" type ring to allow for this outward motion, using outward movement of the thumb to oppose the "anchored" fingers. However, this does not provide optimal control of the tip. Some conventional ultrasonic surgical instruments may comprise a pistol grip that incorporates a trigger that is pushed outward with the index and middle fingers of the user while maintaining a grip on the handle stock, however, this may create fatigue and hand strain. This outward motion, however, may be necessary when doing fine dissection during a laparoscopic procedure. The pistol grip style handle provides comfort, ease, and stability to the surgeon. The conventional pistol grip style handle may not be optimum, however, for dissection, where many surgeons prefer a scissor grip style design instead.

Accordingly, there is a need for an ergonomic handle assembly for an ultrasonic surgical instrument that provides the ability of the user to comfortably access and operate multiple functions. In addition, there is a need for a handle assembly for an ultrasonic surgical instrument that enables a user to comfortably actuate the jaws of the clamping mechanism and activate the hand control buttons/switches. There is also a need to optimize the handle assemblies in terms of ergonomic comfort, stability, and controllability for a large range of hand sizes.

SUMMARY

One aspect of the present disclosure includes a handle assembly for a handheld surgical instrument. The handle assembly may comprise a body portion extending parallel to a longitudinal axis, a fixed handle interfaced with the body portion and extending downwardly from the body portion and away from the longitudinal axis, and a detachable handle portion. In such an aspect, the fixed handle may define a proximal contact surface. Further in such an aspect, the detachable handle portion may (i) define an internal surface configured to interface with the proximal contact surface of the fixed handle, and (ii) comprise at least one attachment feature to removably couple the detachable handle portion to the fixed handle.

Another aspect of the present disclosure includes a handheld surgical instrument comprising a handle assembly, a shaft extending distally from the handle assembly along a longitudinal axis, and a trigger movably coupled to the handle assembly. The handle assembly may comprise a body portion, a fixed handle coupled to the body portion, and a detachable handle portion. In such an aspect, the fixed handle may define a proximal contact surface. Further in such an aspect the detachable handle portion may (i) define an internal surface configured to interface with the proximal contact surface of the fixed handle, and (ii) comprise at least one attachment feature to removably couple the detachable handle portion to the fixed handle. Yet further in such an aspect, the at least one attachment feature may comprise the internal surface defined by the detachable handle portion.

FIGURES

FIG. 5 is a top view of one embodiment of the ultrasonic surgical instrument shown in FIG. 3.

FIG. 6 is a bottom view of one embodiment of the ultrasonic surgical instrument shown in FIG. 3.

DESCRIPTION

Figure 1:
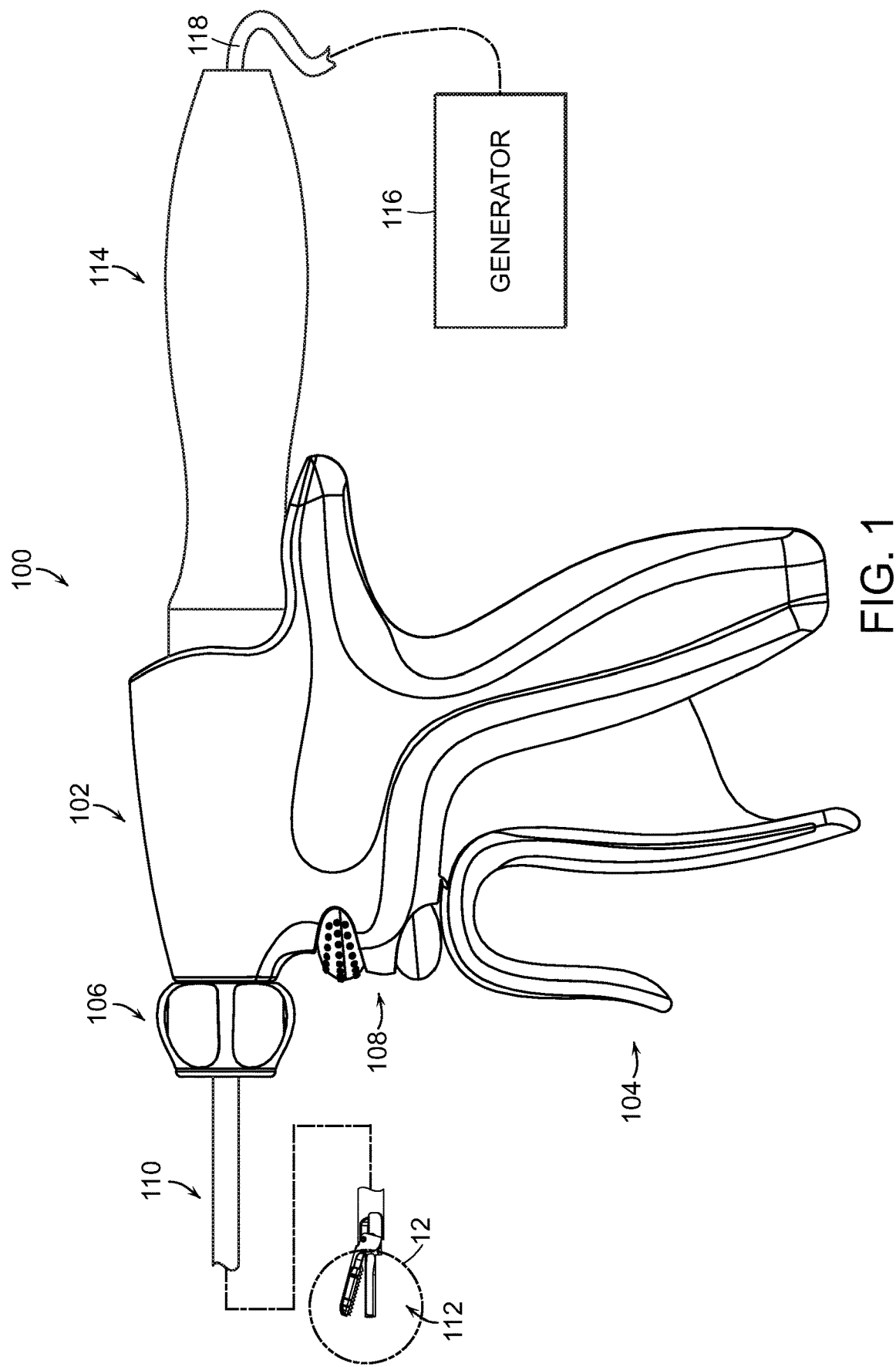
FIG. 1 is a right side view of one embodiment of an ultrasonic surgical instrument.

Before explaining the various embodiments in detail, it should be noted that the embodiments are not limited in its application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments, handle assemblies, handle adapters, and other components associated therewith disclosed below are illustrative only and not meant to limit the scope or application thereof. Furthermore, unless otherwise indicated, the terms and expressions employed herein have been chosen for the purpose of describing the illustrative embodiments for the convenience of the reader and are not to limit the scope thereof.

It will be appreciated that the terms "proximal" and "distal" are used herein with reference to a clinician gripping a handle portion of the handle assembly of an ultrasonic surgical instrument. Thus, the end effector is distal with respect to the more proximal handle portion. It will be further appreciated that, for convenience and clarity, spatial terms such as "top" and "bottom" also are used herein with respect to the clinician gripping the hand portion. However, surgical instruments may be used in many orientations and positions, and these terms are not intended to be limiting and absolute. The term "right" refers to the right side of the instrument from the perspective of a user looking toward the "front" of the instrument from the distal end towards the proximal end. The term "left" refers to the left side of the instrument from the perspective of a user looking toward the "front" of the instrument from the distal end toward the proximal end. The term "rear" refers to the user rear of the instrument from the perspective of the user looking from the proximal end towards the distal end of the instrument.

The various embodiments relate, in general, to ultrasonic surgical instruments with improved multi-function capabilities and ergonomic control features for use in laparoscopic and/or traditional open surgical procedures. The ergonomic features described with respect to the various embodiments of the ultrasonic surgical instruments enhance the ability of the user to easily and comfortably access and operate multiple functions of the instruments located in multiple places on the instruments, in order to maximize the level of precision and control the surgeon has when performing a clinical task.

Various embodiments of ultrasonic surgical instruments described herein comprise comfortable and ergonomic control features associated with the handle and trigger interfaces for the user. This may alleviate stresses and fatigue in applications that require very high clamping forces between the jaws of the end effector. The ergonomic features provide ease of control of the opening motion of the jaws to facilitate various surgical procedures, such as fine dissection. Electrical power switches are provided to activate an ultrasonic transducer assembly. These switches may be hand operated such that the user may easily access one or more of the power switches at any point while avoiding inadvertent or unintentional activation at any time. The switches include features that enable to user to select the proper switch without looking. Similarly, rotational control of the shaft is easily accessed. This allows the user to focus entirely on the monitor view during a laparoscopic procedure, for example. The switches may be activated without the user repositioning the grip on the instrument. The user can easily control power application while simultaneously opening the jaws of the end effector. In one embodiment, the power switches may be implemented as a MIN/MAX rocker-style or "toggle" style switch. In a forward position, the MIN/MAX toggle switch provides an easily accessible contact surface projection for power activation without repositioning of the hand grip, making it suitable to maintain control and keep attention focused on the surgical site (e.g., a monitor in a laparoscopic procedure).

There has been a long sought need to provide surgical instrument handles in terms of size, shape, and location of control interfaces that suitably accommodate the large disparity of anthropometrics from small females to large males and of various ethnicities. Users at these extreme ends of the spectrum traditionally have difficulty using conventionally sized instrument handles as intended. Thus, various embodiments provide a handle assembly for a surgical instrument that suitably accommodates a substantially larger range of hand sizes. Various embodiments provide more optimally designed ergonomic features for comfortably controlling the surgical instrument during use. Various embodiments provide multiple ergonomic hand adaptors are provided.

Certain embodiments will now be described to provide an overall understanding of the principles of the structure, function, manufacture, and use of the devices and methods disclosed herein. One or more examples of these embodiments are illustrated in the accompanying-drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

FIGS. 1-25 illustrate one embodiment of an ultrasonic surgical instrument suitable for endoscopic or traditional open surgical procedures. In the embodiment illustrated in FIGS. 1-25, a surgical instrument comprises improved multi-functional capabilities and ergonomic features for use in laparoscopic and/or traditional open surgical procedures.

The ergonomic features of the surgical instrument enhance the ability of the user to easily access and operate the multiple functions and controls of the surgical instrument. The ergonomic features of the multi-functional ultrasonic surgical instrument enable the user to easily access and operate the multiple functions and controls of the instrument.

In one embodiment, the instrument comprises a handle assembly comprising a rotation knob located at a distal end of the handle assembly. The user may use a finger to operate the distal rotation knob. The rotation knob is mechanically engaged to an ultrasonic transmission waveguide shaft, which is coupled to the clamping mechanism of the end effector assembly. Thus, the user may employ a finger to rotate the distal rotation knob to suitably orient the jaws of the clamping mechanism of the end effector assembly.

In one embodiment, the handle assembly comprises a rocker switch to control the power for energizing the ultrasonic transducer. In one embodiment, the rocker switch pivots between a maximum (MAX) power setting and a minimum (MIN) power setting. The MIN/MAX rocker switch is suitably located on a fixed handle portion of the handle assembly so that the rocker switch may be operated with the same finger that operates the distal rotation knob. However, a button switch may located on a moving part of the instrument, such as the trigger. Accordingly, the same finger can be used both for rotation of the shaft and operation of the power activation. The rocker switch may comprise identifying tactile features.

In one embodiment, a pivotably moveable trigger comprising a hook feature may be employed to actuate the jaws or clamping mechanism of the end effector assembly. A series of linkages translate the pivotal rotation of the trigger to axial movement of a yoke coupled to an actuation mechanism, which controls the opening and closing of the jaws of the clamping mechanism of the end effector assembly located at the distal end of the ultrasonic surgical instrument. In one embodiment, multiple links may be employed to provide mechanical advantage in a relatively short pivotal rotation span. The trigger may be operated by a finger other than the finger used to control the distal rotation knob or the toggle switch. The trigger activation finger(s) also may be employed to engage the hook feature to restore the jaws of the clamping mechanism of the end effector assembly to a predetermined state.

In one embodiment, a rotation knob may be located at a proximal end of the ultrasonic surgical instrument. The proximal rotation knob may be easily accessed with the thumb or finger and substantially reduces any obstructions or "reaching" that may be associated with a distally located rotation knob.

In one embodiment, rotation knobs may be located at distal and proximal ends of the ultrasonic surgical instrument. The distal and proximal rotation knobs may be easily accessed with either the thumb or fingers for convenience. Furthermore, the opposing nature of the thumb and finger actions used alternately substantially reduces winding of the electrical cord supplying power to the ultrasonic transducer. The natural tendency of the user is to rotate in only a downward direction because it is easier to push down than to push upward. With rotation knobs both distal and proximal, the a right-handed user uses the proximal knob to push down to rotate to the left, and uses the distal knob to push down to rotate to the right, thereby reducing or eliminating the "cord wind" of rotating only in one direction. The distal and proximal rotation knobs may be operated in conjunction with each other or may be rotated independently.

In various embodiments, multiple adapters may be provided to accommodate different sized hands. Adapters may comprise on open proximal end and can be removably attached to a fixed handle of a handle assembly either frictionally or by snap buttons. Adapters may comprise a closed proximal end to form a loop for receiving a thumb therethrough. Various embodiments of the loop adapter comprise a pliable polymeric element for added comfort.

In one embodiment, a handle assembly may comprise a projection formed on a fixed handle portion of the handle assembly. In another embodiment, the hand assembly may comprise protrusions formed on either side of the fixed handle of the hand assembly. These projections and protrusions reduce or minimize fatigue and increase control when using certain ultrasonic surgical instruments while operating the instrument.

FIG. 1 is a right side view of one embodiment of an ultrasonic surgical instrument 100. In the illustrated embodiment, the ultrasonic surgical instrument 100 may be employed in various surgical procedures including endoscopic or traditional open surgical procedures. In one embodiment, the ultrasonic surgical instrument 100 comprises a handle assembly 102, an elongated endoscopic shaft assembly 110, and an ultrasonic transducer 114. The handle assembly 102 comprises a trigger assembly 104, a distal rotation assembly 106, and a switch assembly 108. The elongated endoscopic shaft assembly 110 comprises an end effector assembly 112, which comprises elements to dissect tissue or mutually grasp, cut, and coagulate vessels and/or tissue, and actuating elements to actuate the end effector assembly 112. The handle assembly 102 is adapted to receive the ultrasonic transducer 114 at the proximal end. The ultrasonic transducer 114 is mechanically engaged to the elongated endoscopic shaft assembly 110 and portions of the end effector assembly 112. The ultrasonic transducer 114 is electrically coupled to a generator 116 via a cable 118. Although the majority of the figure drawings depict a multiple end effector assembly 112 for use in connection with endoscopic surgical procedures, the ultrasonic surgical instrument 100 may be employed in more traditional open surgical procedures. For the purposes herein, the ultrasonic surgical instrument 100 is described in terms of an endoscopic instrument; however, it is contemplated that an open version of the ultrasonic surgical instrument 100 also may include the same or similar operating components and features as described herein.

Figure 2:
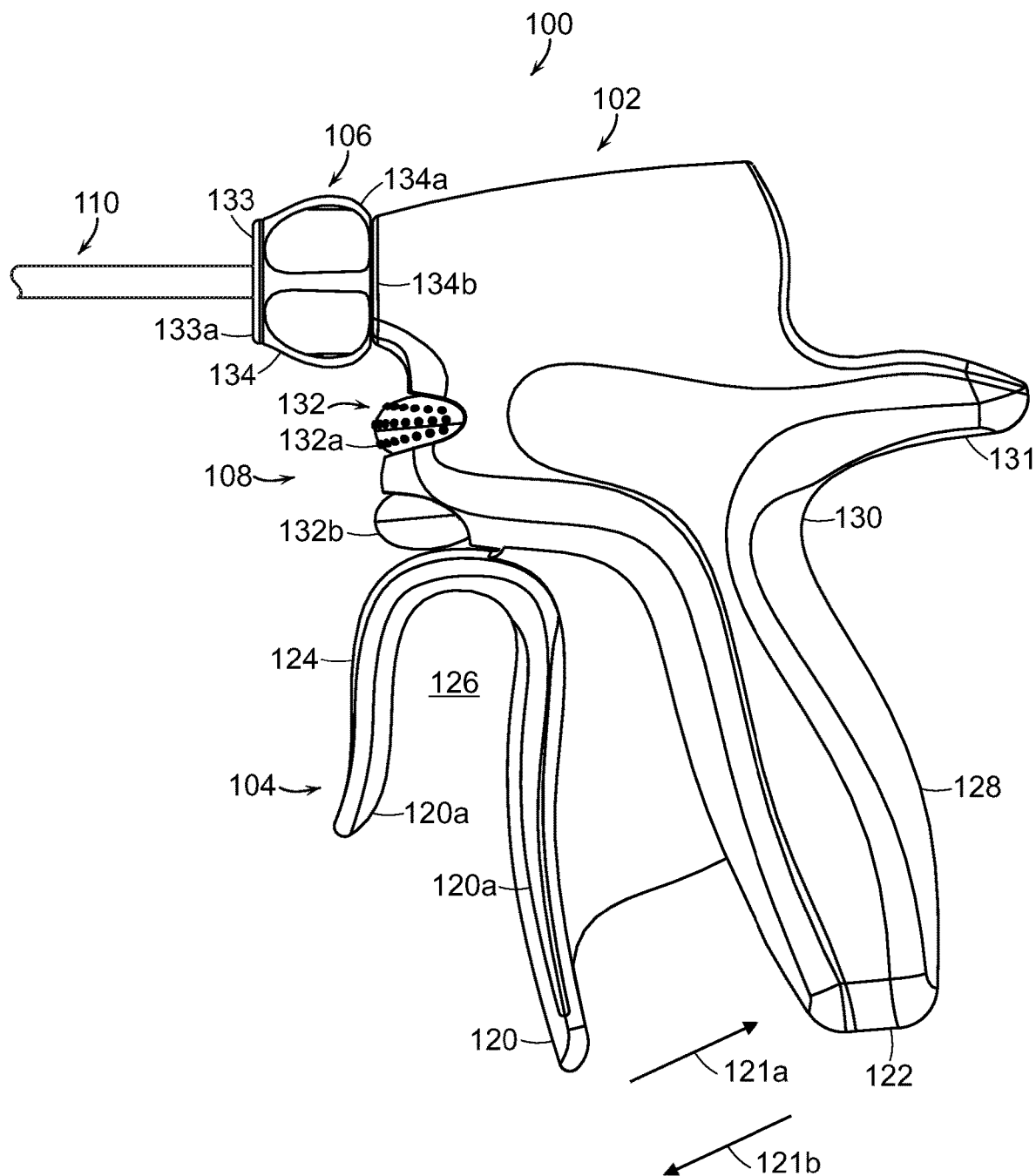
FIG. 2 is a right side view of one embodiment of the ultrasonic surgical instrument shown in FIG. 1 without the ultrasonic transducer.

FIG. 2 is a right side view of one embodiment of the ultrasonic surgical instrument 100 shown in FIG. 1 without the ultrasonic transducer 114. In the illustrated embodiment, the trigger assembly 104 comprises a trigger 120 that works in conjunction with a fixed handle 122. The fixed handle 122 and the trigger 120 are ergonomically formed and adapted to interface comfortably with the user. The fixed handle 122 is integrally associated with the handle assembly 102. The trigger 120 is pivotally movable relative to the fixed handle 122 as explained in more detail below with respect to the operation of the ultrasonic surgical instrument 100. The trigger 120 is pivotally movable in direction 121A toward the fixed handle 122 when the user applies a squeezing force against the trigger 120. A spring element 175 (FIG. 14) causes the trigger 120 to pivotally move in direction 121B when the user releases the squeezing force against the trigger 120.

In one embodiment, the trigger 120 comprises an elongated trigger hook 124, which defines an aperture 126 between the elongated trigger hook 124 and the trigger 120. The aperture 126 is suitably sized to receive one or multiple fingers of the user therethrough. The trigger 120 also may comprise a resilient portion 120a molded over the trigger 120 substrate. The overmolded resilient portion 120a is formed to provide a more comfortable contact surface for control of the trigger 120 in outward direction 121B. In one embodiment, the overmolded resilient portion 120a may be provided over a portion of the elongated trigger hook 124. For example, in the illustrated embodiment, the overmolded resilient portion 120a is provided over the distal and top surfaces of the inner portion of the elongated trigger hook 120 to cushion the contact surface between the finger and the elongated trigger hook 124. The proximal surface of the elongated trigger hook 120 remains uncoated or coated with a non-resilient substrate to enable the user to easily slide their fingers in and out of the aperture 126. In other embodiments, the elongated trigger hook 124 may incorporate an overmolded component formed of pliable, resilient, flexible polymeric materials including Versaflex® TPE alloys made by GLS Corporation, for example. The overmolded resilient portion 120a of the elongated trigger hook 124 may provide added comfort or form a more secure grip for the user. The overmolded resilient portion 120a on the top portion of the interior portion of the elongated trigger hook 124 may be contoured to alleviate edge pressure points against the fingers as they enter the aperture 126. In another embodiment, the geometry of the trigger forms a fully closed loop which defines an aperture suitably sized to receive one or multiple fingers of the user therethrough. The fully closed loop trigger also may comprise a resilient portion molded over the trigger substrate. The overmolded resilient portion is formed to provide a more comfortable contact surface for control of the trigger in outward direction.

In one embodiment, the fixed handle 122 comprises a proximal contact surface 128 and a grip anchor or saddle surface 130. The saddle surface 130 rests on the web where the thumb and the index finger are joined on the hand. The proximal contact surface 128 has a pistol grip contour that receives the palm of the hand in a normal pistol grip with no rings or apertures. The profile curve of the proximal contact surface 128 may be contoured to accommodate or receive the palm of the hand. To provide comfort and control while using the ultrasonic instrument 100, the profile of the proximal contact surface 128 is optimized to fit the natural anatomical contours in the valley of the center of the palm and base of the thumb. The saddle surface 130 provides a primary point of stability of the grip, which is the basis of the stability of control of the handle assembly 102. The saddle surface 130 is the reference point that determines a range of motion of the fingers and thumb relative to the proximal contact surface 128 of the fixed handle 122, the elongated trigger hook 124, the distal rotation assembly 106, and the toggle switch 132. A stabilization tail 131 is located towards a more proximal portion of the handle assembly 102. The stabilization tail 131 may be in contact with the uppermost web portion of the hand located between the thumb and the index finger to stabilize the handle assembly 102 and make the handle assembly 102 more controllable. The stabilization tail 131 provides an area extending in the proximal direction to allow the proximal weight of the ultrasonic surgical instrument 100 to be distributed to the top of the hand without restriction motion. The configuration of the saddle surface 130 and the stabilization tail 131 provides a greater sense of stability, comfort, and control for the user while manipulating the handle assembly 102.

Figure 36:
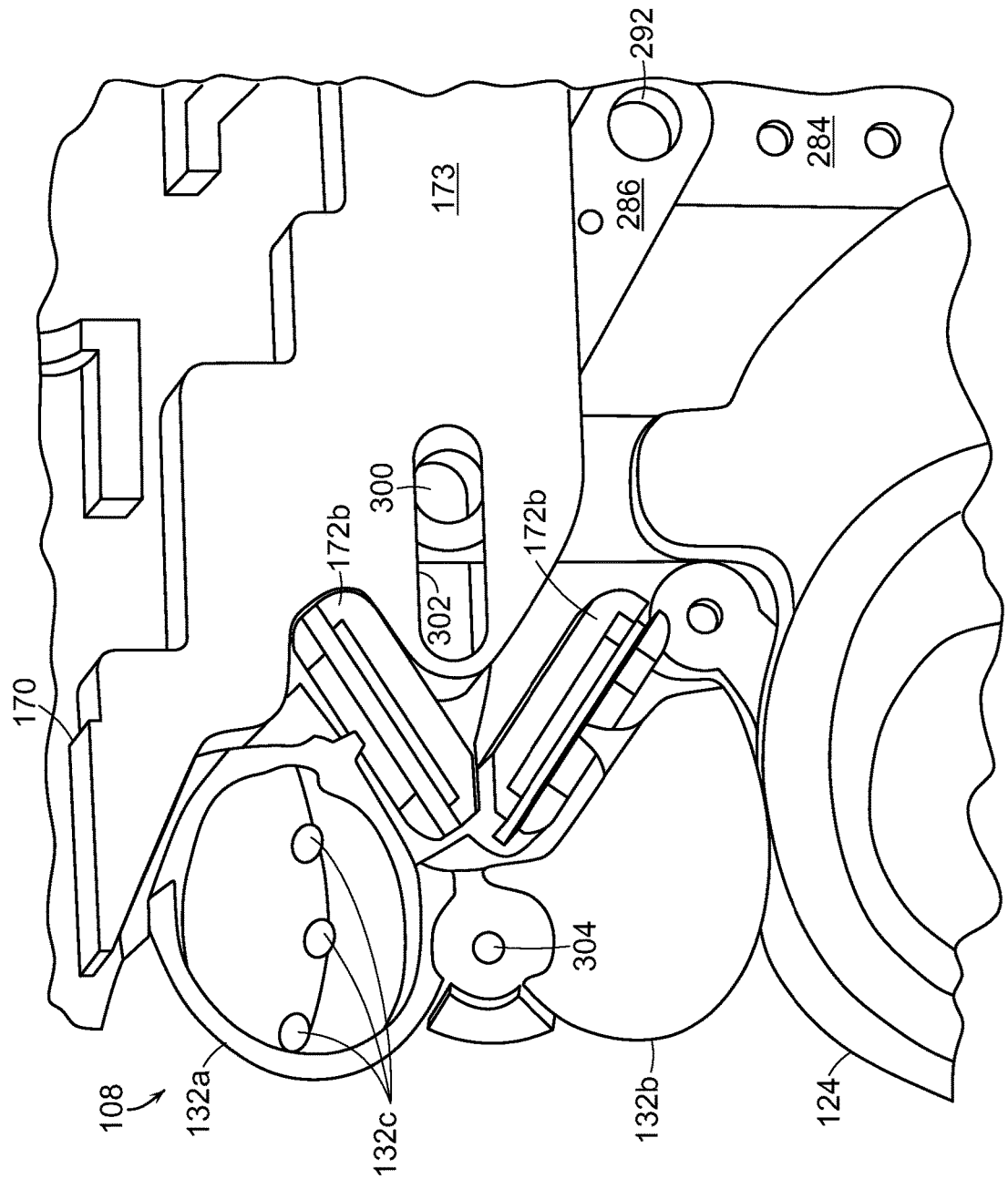
FIG. 36 is an enlarged partial view of one embodiment of the rocker switch and the reciprocating yoke assembly within the housing of the handle assembly shown in FIG. 35.
Figure 37:
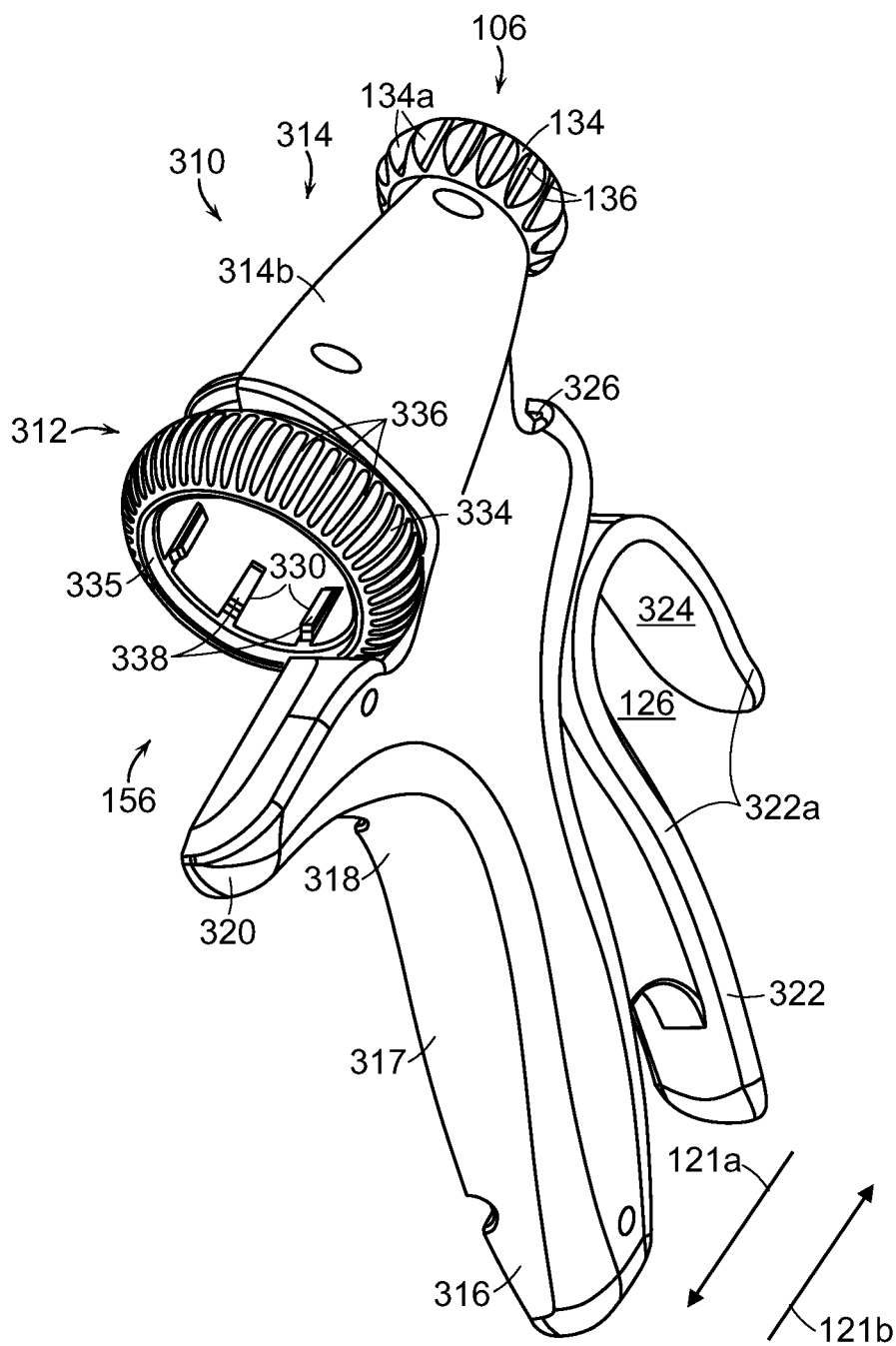
FIG. 37 is a right perspective view of a right housing portion of one embodiment of a handle assembly for an ultrasonic instrument comprising both proximal and distal rotation assemblies with the left housing portion of the housing removed.

In one embodiment, the switch assembly 108 may comprise a toggle switch 132. The toggle switch 132 may be implemented as a single component with a central pivot 304 (FIG. 34) located within inside the handle assembly 102 to eliminate the possibility of simultaneous activation. In one embodiment, the toggle switch 132 comprises a first projecting knob 132a and a second projecting knob 132b to set the power setting of the ultrasonic transducer 114 between a minimum power level (e.g., MIN) and a maximum power level (e.g., MAX). The toggle switch 132 rotates about the central pivot 304 as the first projecting knob 132a and the second projecting knob 132b are actuated. The one or more projecting knobs 132a, b are coupled to one or more arms that move through a small arc and cause electrical contacts (e.g., electrical elements 172b as shown in FIG. 36) to close or open an electric circuit to electrically energize or de-energize the ultrasonic transducer 114 in accordance with the activation of the first or second projecting knobs 132a,b. The toggle switch 132 is coupled to the generator 116 to control the activation of the ultrasonic transducer 114. The toggle switch 132 comprises one or more electrical power setting switches to activate the ultrasonic transducer 114 to set one or more power settings for the ultrasonic transducer 114. The forces required to activate the toggle switch 132 are directed substantially toward the saddle point 130, thus avoiding any tendency of the instrument to rotate in the hand when the toggle switch 132 is activated.

In one embodiment, the first and second projecting knobs 132a,b are located on the distal end of the handle assembly 102 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 132. The projecting knobs 132a,b may be configured to wrap around the side of the handle assembly 102 to some extent to be more easily accessible by variable finger lengths and to allow greater freedom of access to activation in awkward positions or for shorter fingers.

In one embodiment, the first and second projecting knobs 132a,b may be overmolded with pliable, resilient, flexible polymeric materials including Versaflex® TPE alloys made by GLS Corporation, for example. The overmolded material may be selected to withstand sterilization and to be biocompatible. Furthermore, the material may be selected to give a proper level of resilience and to provide adequate frictional resistance to surgical gloves. The overmolded portion may comprise projections with identifying tactile features useful for tactile identification or differentiation of the projecting knobs 132a,b or the rest of the handle assembly 102. As previously discussed, one of the projecting knobs 132a,b may comprises a texture or tactile surface that enables the user to differentiate between the first projecting knob 132a and the second projecting knob 132b. In the illustrated embodiment, the first projecting knob 132a comprises a plurality of tactile elements 132c, e.g., textured projections or "bumps" in the illustrated embodiment, to allow the user to differentiate the first projecting knob 132a (MAX) from the second projecting knob 132b (MIN).

In one embodiment, the toggle switch 132 may be operated by the hand of the user. The user may easily access the first and second projecting knobs 132a,b at any point while also avoiding inadvertent or unintentional activation at any time. The toggle switch 132 may readily operated with a finger to control the power to the ultrasonic assembly 114 and/or to the ultrasonic assembly 114. For example, the index finger may be employed to activate the first contact portion 132a to turn on the ultrasonic assembly 114 to a maximum (MAX) power level. The index finger may be employed to activate the second contact portion 132b to turn on the ultrasonic assembly 114 to a minimum (MIN) power level. The toggle switch 132 may be operated without the user having to look at the first or second projecting knob 132a,b. This allows the user to focus entirely on the monitor view during a laparoscopic procedure. Accordingly, the first projecting knob 132a or the second projecting knob 132b may comprise a texture or projections to tactilely differentiate between the first and second projecting knobs 132a,b without looking. For example, in the illustrated embodiment, the first projecting knob 132a comprises a plurality of tactile elements 132c to allow the user to tactilely differentiate between the first projecting knob 132a (MAX) and the second projecting knob 132b (MIN). Other tactile textures or elements may be formed on either of the first or second projecting knobs 132a,b to for purposes of differentiation therebetween. The user does not have to reposition their grip in order to operate the toggle switch 132 and can easily control power levels while opening the jaws of the end effector 112.

Figure 13:
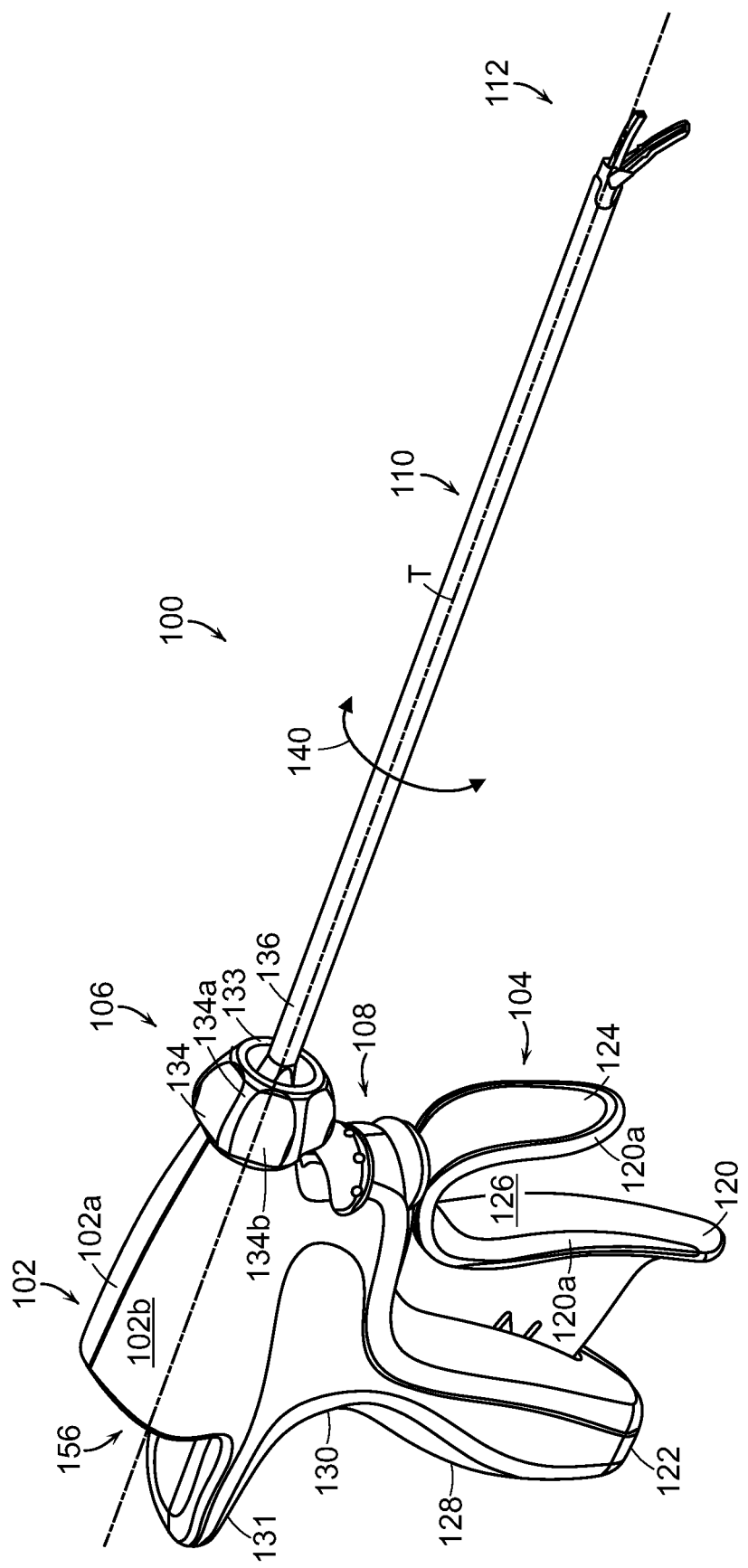
FIG. 13 is a left perspective view of one embodiment of the ultrasonic surgical instrument shown in FIG. 3 showing a central axis "T".

In one embodiment, the distal rotation assembly 106 is rotatable without limitation in either direction about a longitudinal axis "T" (FIG. 13). The distal rotation assembly 106 is mechanically engaged to the elongated endoscopic shaft assembly 110. The distal rotation assembly 106 is located on a distal end of the handle assembly 102. The distal rotation assembly 106 comprises a cylindrical hub 133 and a rotation knob 134 formed over the hub 133. The hub 133 mechanically engages the elongated endoscopic shaft assembly 110. The rotation knob 134 may comprise fluted polymeric features and may be engaged by a finger (e.g., an index finger) to rotate the elongated endoscopic shaft assembly 110. The hub 133 may comprise a material molded over the primary structure to form the rotation knob 134. The rotation knob 134 may be overmolded over the hub 133. The hub 133 comprises an end cap portion 133a that is exposed at the distal end. The end cap portion 133a of the hub 133 may contact the surface of a trocar during laparoscopic procedures. The hub 133 may be formed of a hard durable plastic such as polycarbonate to alleviate any friction that may occur between the end cap portion 133a and the trocar. The rotation knob 134 may comprise "scallops" or flutes formed of raised ribs 134a and concave portions 134b located between the ribs 134a to provide a more precise rotational grip. In one embodiment, the rotation knob 134 may comprise a plurality of flutes (e.g., three or more flutes). In other embodiments, any suitable number of flutes may be employed. The rotation knob 134 may be formed of a softer polymeric material overmolded onto the hard plastic material. For example, the rotation knob 134 may be formed of pliable, resilient, flexible polymeric materials including Versaflex® TPE alloys made by GLS Corporation, for example. This softer overmolded material may provide a greater grip and more precise control of the movement of the rotation knob 134. It will be appreciated that any materials that provide adequate resistance to sterilization, are biocompatible, and provide adequate frictional resistance to surgical gloves may be employed to form the rotation knob 134.

In one embodiment, the handle assembly 102 may comprise and may be configured with ergonomic features to enable the user to easily access and operate the multiple functions and controls of the ultrasonic surgical instrument 100. Accordingly, a finger may be used to operate the distal rotation knob 134 located at the distal portion of the handle assembly 102. The rotation knob 134 is coupled to the elongated endoscopic shaft assembly 110 of the ultrasonic transmission waveguide shaft by the hub 133. Thus, the finger can be used to rotate the ultrasonic transmission waveguide elongated endoscopic shaft assembly 110 by rotating the rotation knob 134. The MIN/MAX power buttons of the toggle switch 132 are suitably located on a distal end of the handle assembly 122 of the instrument 100 so that they may be operated with the index finger, for example. Accordingly, the index finger may be used to rotate the shaft of the elongated endoscopic shaft assembly 110 to orient the jaws of the clamping mechanism of the end effector assembly 112 in a desired position and to activate the ultrasonic transducer 114 to a suitable power level.

Figure 3:
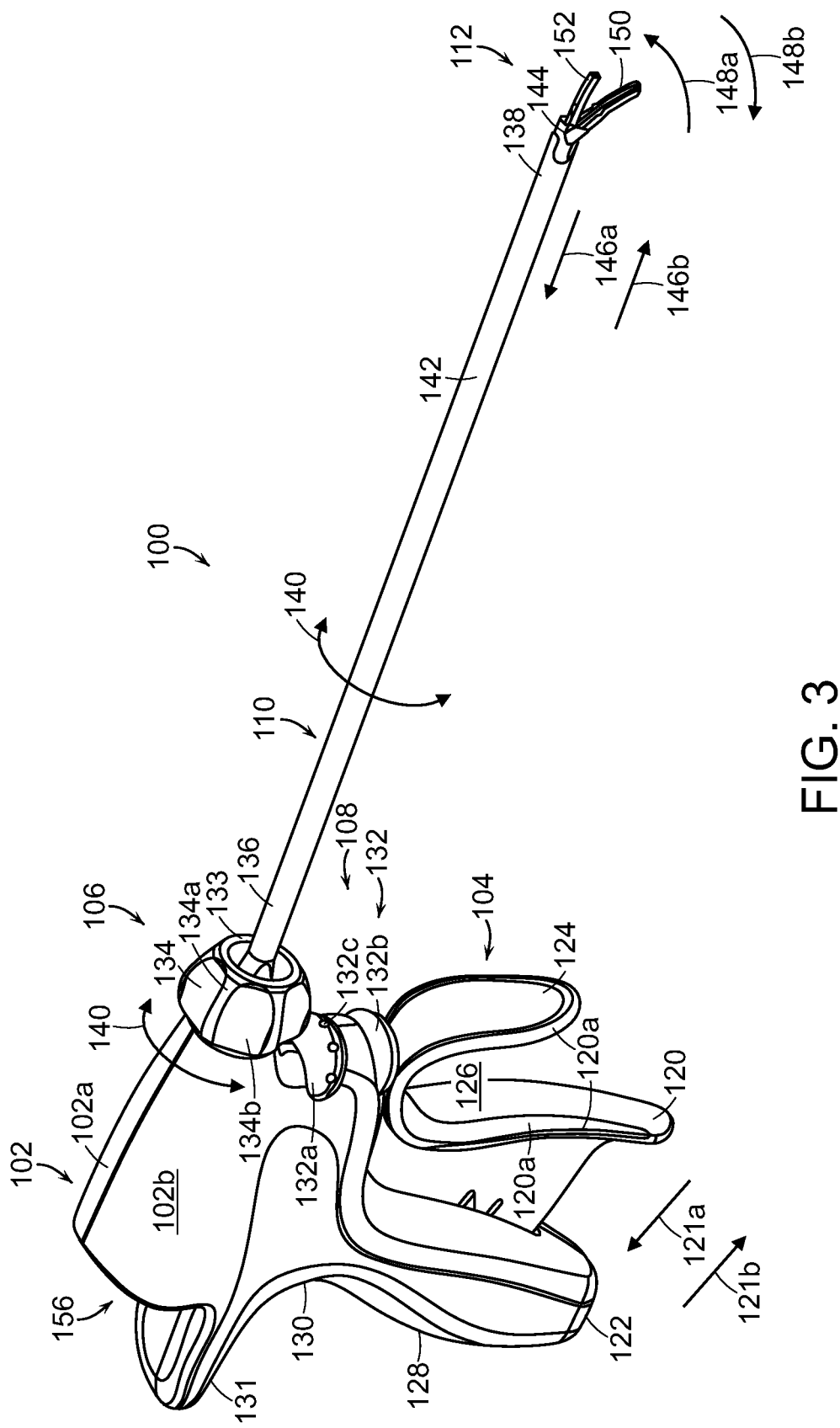
FIG. 3 is a left perspective view of one embodiment of an ultrasonic surgical instrument showing a housing, a distal rotation assembly, an elongated endoscopic shaft assembly, and an end effector assembly.
Figure 4:
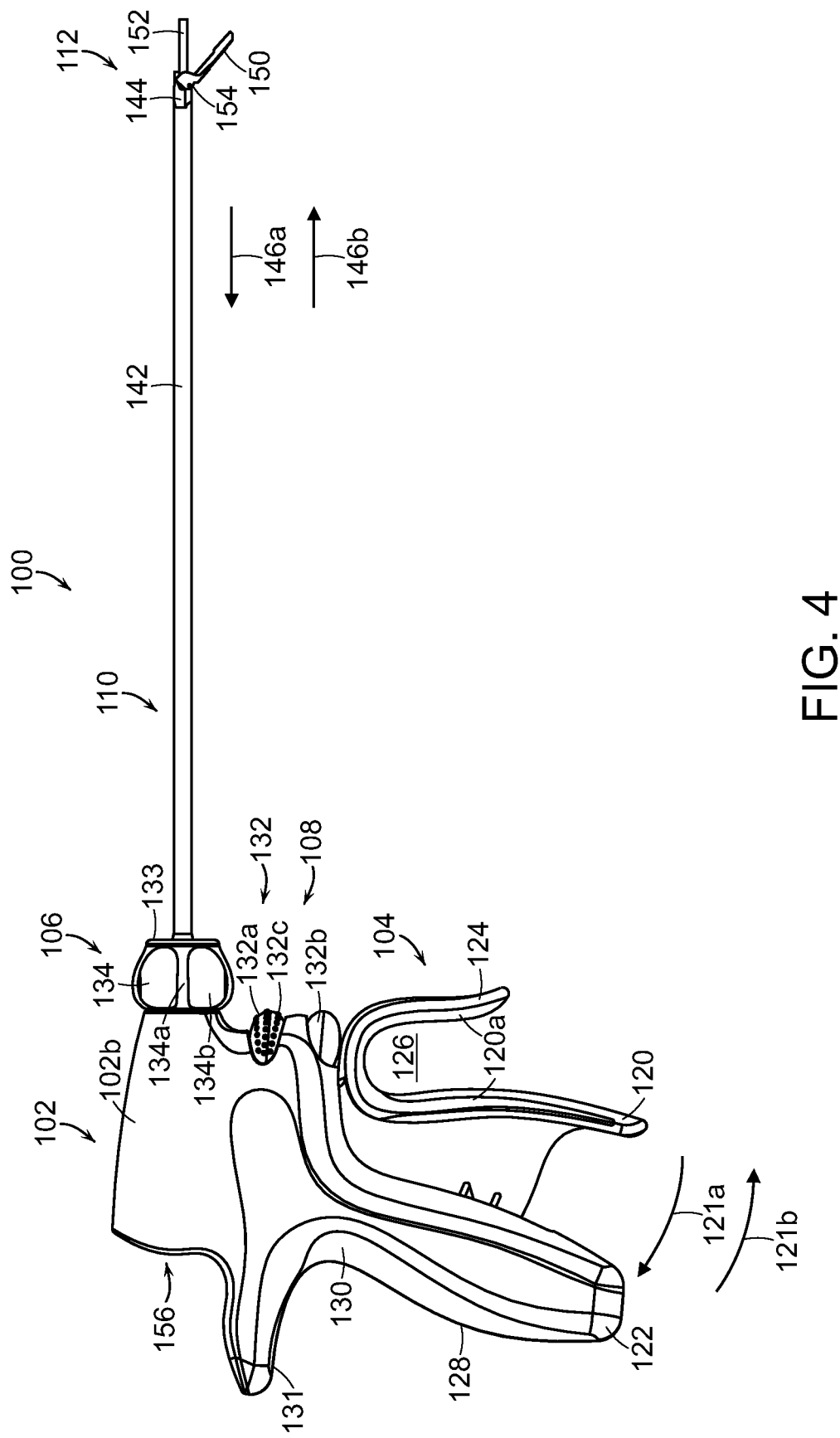
FIG. 4 is a left side view of the ultrasonic surgical instrument shown in FIG. 3.
Figure 7:
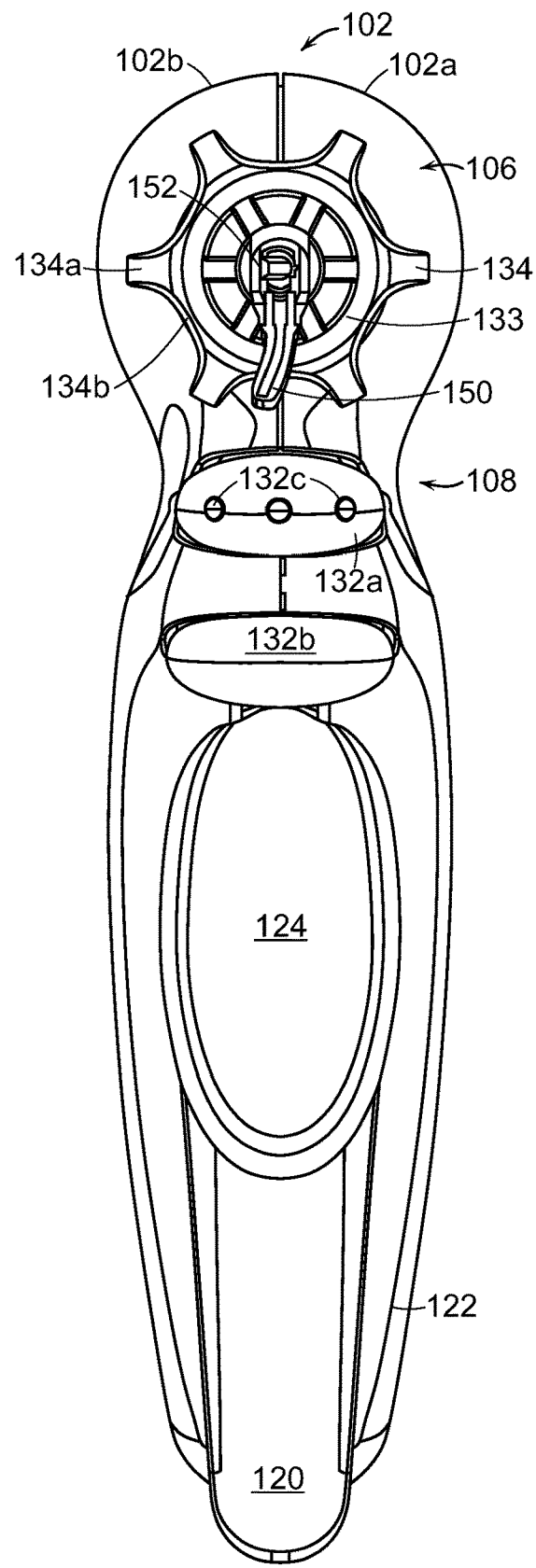
FIG. 7 is a front view of one embodiment of the ultrasonic surgical instrument shown in FIG. 3.
Figure 8:
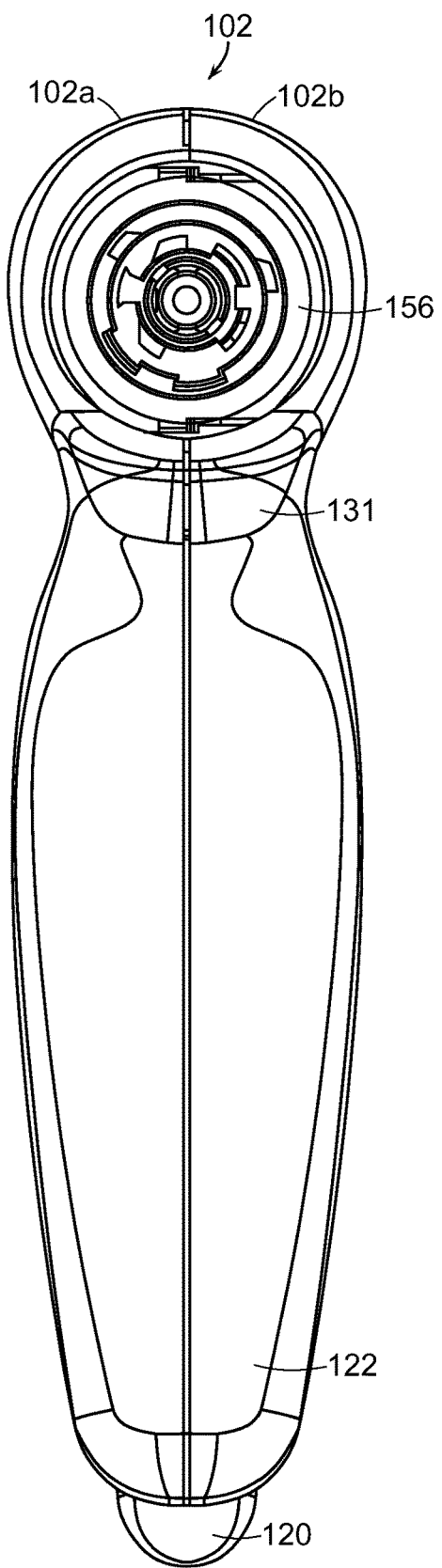
FIG. 8 is a rear view of one embodiment of the ultrasonic surgical instrument shown in FIG. 3.
Figure 9:
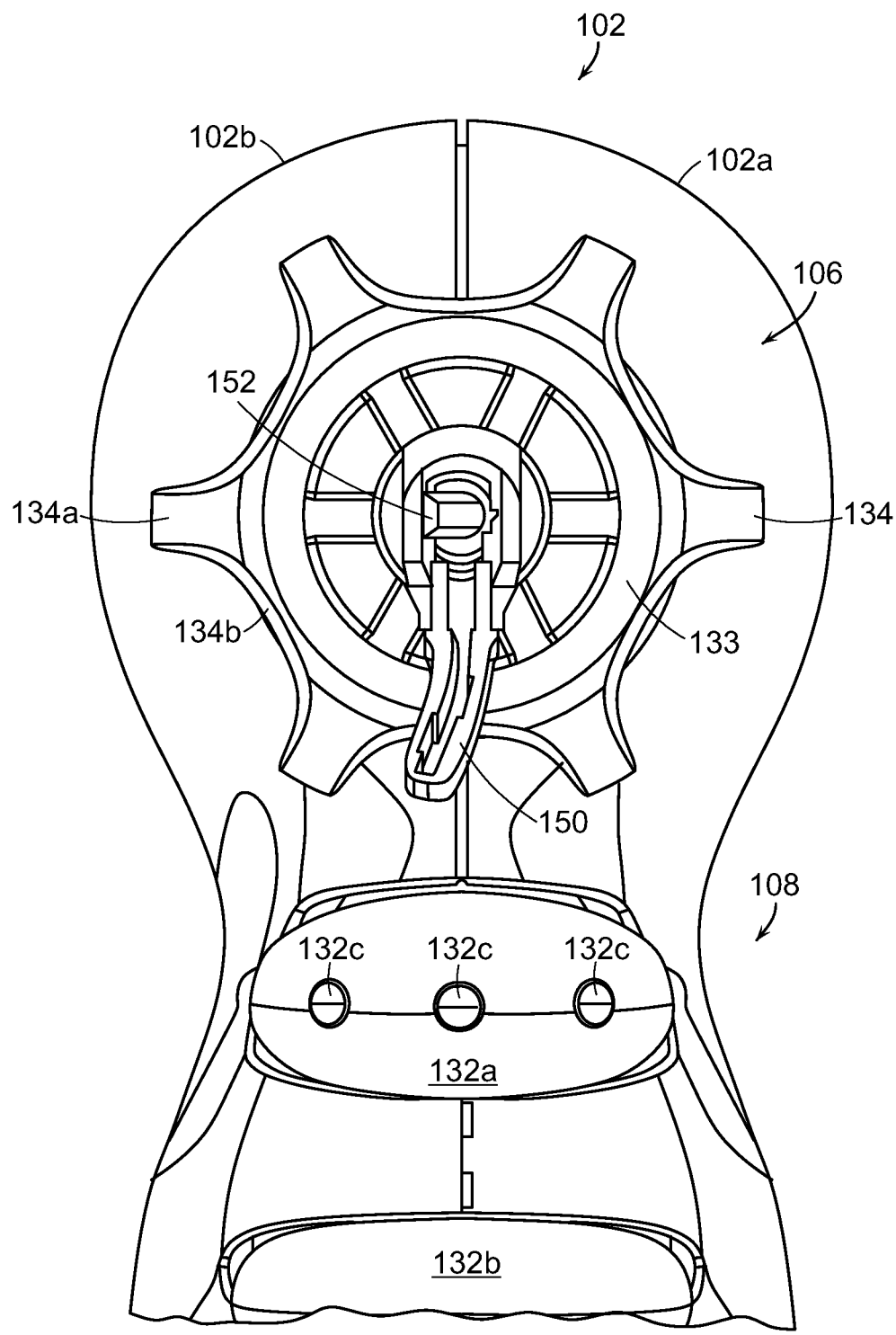
FIG. 9 is an enlarged front view of one embodiment of the ultrasonic surgical instrument shown in FIG. 3.

FIG. 3 is a left perspective view of one embodiment of the ultrasonic surgical instrument 100 showing the handle assembly 102, the distal rotation assembly 106, the elongated endoscopic shaft assembly 110, and the end effector assembly 112. With reference to FIGS. 3-9, in the illustrated embodiment the elongated endoscopic shaft assembly 110 comprises a distal end 138 dimensioned to mechanically engage the end effector assembly 112 and a proximal end 136 that mechanically engages the handle assembly 102 and the distal rotation assembly 106. The proximal end 136 of the elongated endoscopic shaft assembly 110 is received within the handle assembly 102 and the distal rotation assembly 106. More details relating to the connections between the elongated endoscopic shaft assembly 110, the handle assembly 102, and the distal rotation assembly 106 are provided in the description of FIGS. 14 and 24.

In one embodiment, the handle assembly 102 is formed from two (2) housing portions or shrouds comprising a first portion 102a and a second portion 102b. From the perspective of a user viewing the handle assembly 102 from the distal end towards the proximal end, the first portion 102a is considered the right portion and the second portion 102b is considered the left portion. Each of the first and second portions 102a,b includes a plurality of interfaces 158 (FIG. 14) dimensioned to mechanically align and engage each another to form the handle assembly 102 and enclosing the internal working components thereof. The fixed handle 122, which is integrally associated with the handle assembly 102, takes shape upon the assembly of the first and second portions 102a and 102b of the handle assembly 102. A plurality of additional interfaces (not shown) may be disposed at various points around the periphery of the first and second portions 102a and 102b of the handle assembly 102 for ultrasonic welding purposes, e.g., energy direction/deflection points. The first and second portions 102a and 102b (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

In one embodiment, the elongated endoscopic shaft assembly 110 comprises a proximal end 136 adapted to mechanically engage the handle assembly 102 and the distal rotation assembly 106; and a distal end 138 adapted to mechanically engage the end effector assembly 112. The elongated endoscopic shaft assembly 110 comprises an outer tubular sheath 142 and a reciprocating tubular actuating member 144 located within the outer tubular sheath 142. The proximal end of the tubular reciprocating tubular actuating member 144 is mechanically engaged to the trigger 120 of the handle assembly 102 to move in either direction 146A or 146B in response to the actuation and/or release of the trigger 120. The pivotably moveable trigger 120 may be employed to actuate the jaws or clamping mechanism of the end effector assembly 112. A series of linkages translate the pivotal rotation of the trigger 120 to axial movement of a yoke coupled to an actuation mechanism, which controls the opening and closing of the jaws of the clamping mechanism of the end effector assembly 112. The distal end of the tubular reciprocating tubular actuating member 144 is mechanically engaged to the end effector assembly 112. In the illustrated embodiment, the distal end of the tubular reciprocating tubular actuating member 144 is mechanically engaged to a clamp arm assembly 150, which is pivotable about a pivot point 154, to open and close the clamp arm assembly 150 in response to the actuation and/or release of the trigger 120. For example, in the illustrated embodiment, the clamp arm assembly 150 is movable in direction 148A from an open position to a closed position about a pivot point 154 when the trigger 120 is squeezed in direction 121A. The clamp arm assembly 150 is movable in direction 148B from a closed position to an open position about the pivot point 154 when the trigger 120 is released or outwardly contacted in direction 121B.

In one embodiment, the end effector assembly 112 is attached at the distal end 138 of the elongated endoscopic shaft assembly 110 and includes a clamp arm assembly 150 and a blade 152. The jaws of the clamping mechanism of the end effector assembly 112 are formed by clamp arm assembly 150 and the blade 152. The blade 152 is ultrasonically actuatable and is acoustically coupled to the ultrasonic transducer 114. The trigger 120 on the handle assembly 102 is ultimately connected to a drive assembly, which together, mechanically cooperate to effect movement of the clamp arm assembly 150. Squeezing the trigger 120 in direction 121A moves the clamp arm assembly 150 in direction 148A from an open position, wherein the clamp arm assembly 150 and the blade 152 are disposed in a spaced relation relative to one another, to a clamped or closed position, wherein the clamp arm assembly 150 and the blade 152 cooperate to grasp tissue therebetween. The clamp arm assembly 150 may comprise a clamp pad 158 to engage tissue between the blade 152 and the clamp arm 150. Releasing the trigger 120 in direction 121B moves the clamp arm assembly 150 in direction 148B from a closed relationship, to an open position, wherein the clamp arm assembly 150 and the blade 152 are disposed in a spaced relation relative to one another.

The proximal portion of the handle assembly 102 comprises a proximal opening 156 to receive the distal end of the ultrasonic assembly 114. The ultrasonic assembly 114 is inserted in the proximal opening 156 and is mechanically engaged to the elongated endoscopic shaft assembly 110.

In one embodiment, the elongated trigger hook 124 portion of the trigger 120 provides a longer trigger lever with a shorter span and rotation travel. The longer lever of the elongated trigger hook 124 allows the user to employ multiple fingers within the aperture 126 to operate the elongated trigger hook 124 and cause the trigger 120 to pivot in direction 121B to open the jaws of the end effector assembly 112. For example, the user may insert three fingers (e.g., the middle, ring, and little fingers) in the aperture 126. Multiple fingers allows the surgeon to exert higher input forces on the trigger 120 and the elongated trigger hook 124 to activate the end effector assembly 112. The shorter span and rotation travel creates a more comfortable grip when closing or squeezing the trigger 120 in direction 121A or when opening the trigger 120 in the outward opening motion in direction 121B lessening the need to extend the fingers further outward. This substantially lessens hand fatigue and strain associated with the outward opening motion of the trigger 120 in direction 121B. The outward opening motion of the trigger may be spring-assisted by spring element 175 (FIG. 14) to help alleviate fatigue. The opening spring force is sufficient to assist the ease of opening, but not strong enough to adversely impact the tactile feedback of tissue tension during spreading dissection.

For example, during a surgical procedure either the index finger may be used to control the rotation of the elongated endoscopic shaft assembly 110 to locate the jaws of the end effector assembly 112 in a suitable orientation. The middle and/or the other lower fingers may be used to squeeze the trigger 120 and grasp tissue within the jaws. Once the jaws are located in the desired position and the jaws are clamped against the tissue, the index finger can be used to activate the toggle switch 132 to adjust the power level of the ultrasonic transducer 114 to treat the tissue. Once the tissue has been treated, the user the may release the trigger 120 by pushing outwardly in the distal direction against the elongated trigger hook 124 with the middle and/or lower fingers to open the jaws of the end effector assembly 112. This basic procedure may be performed without the user having to adjust their grip of the handle assembly 102.

Figure 10:
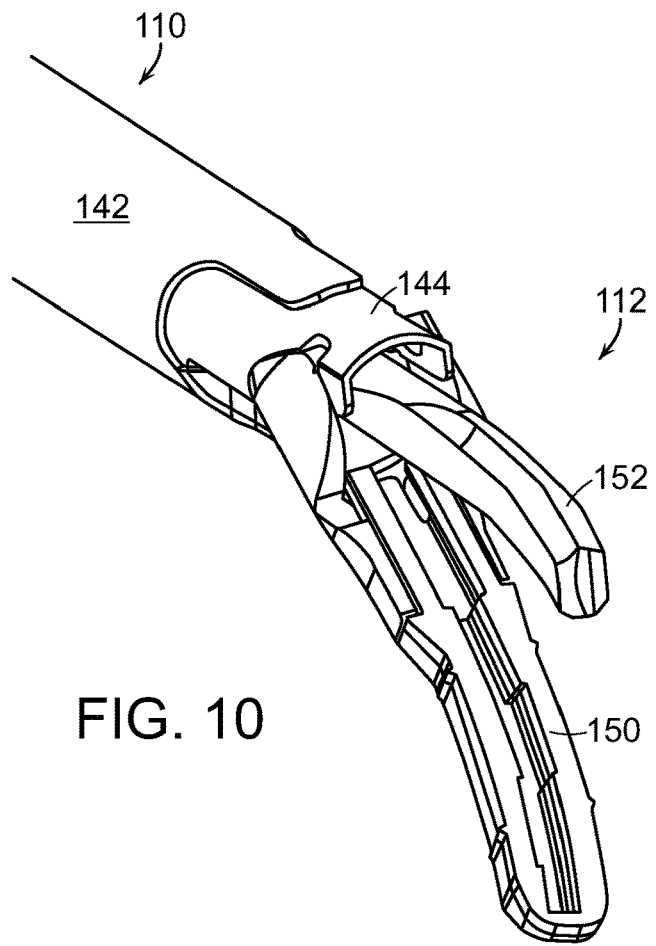
FIG. 10 is a left perspective view of one embodiment of the end effector assembly portion of the ultrasonic surgical instrument shown in FIG. 3.
Figure 11:
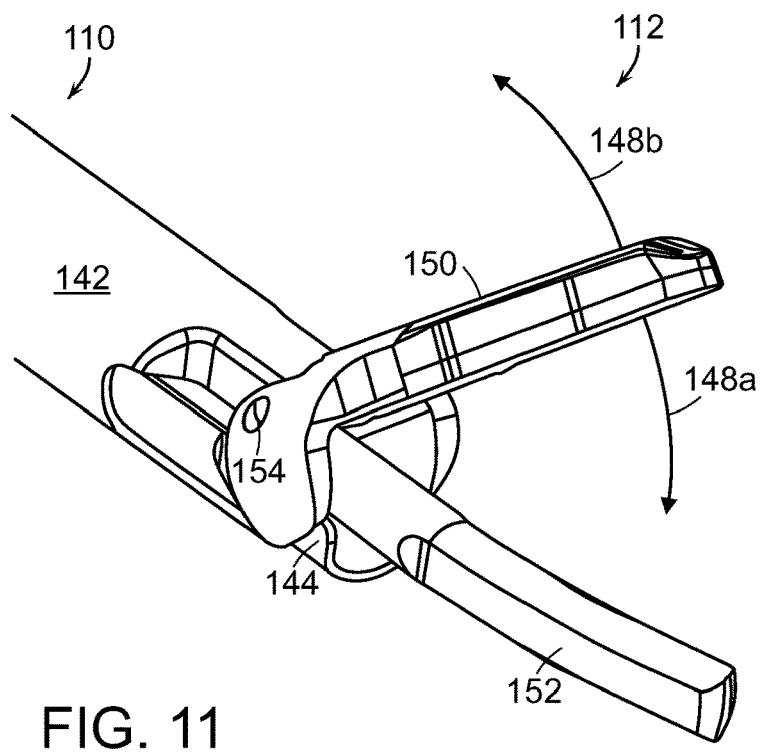
FIG. 11 is a left perspective view of one embodiment of the end effector assembly portion of the ultrasonic surgical instrument shown in FIG. 3.
Figure 12:
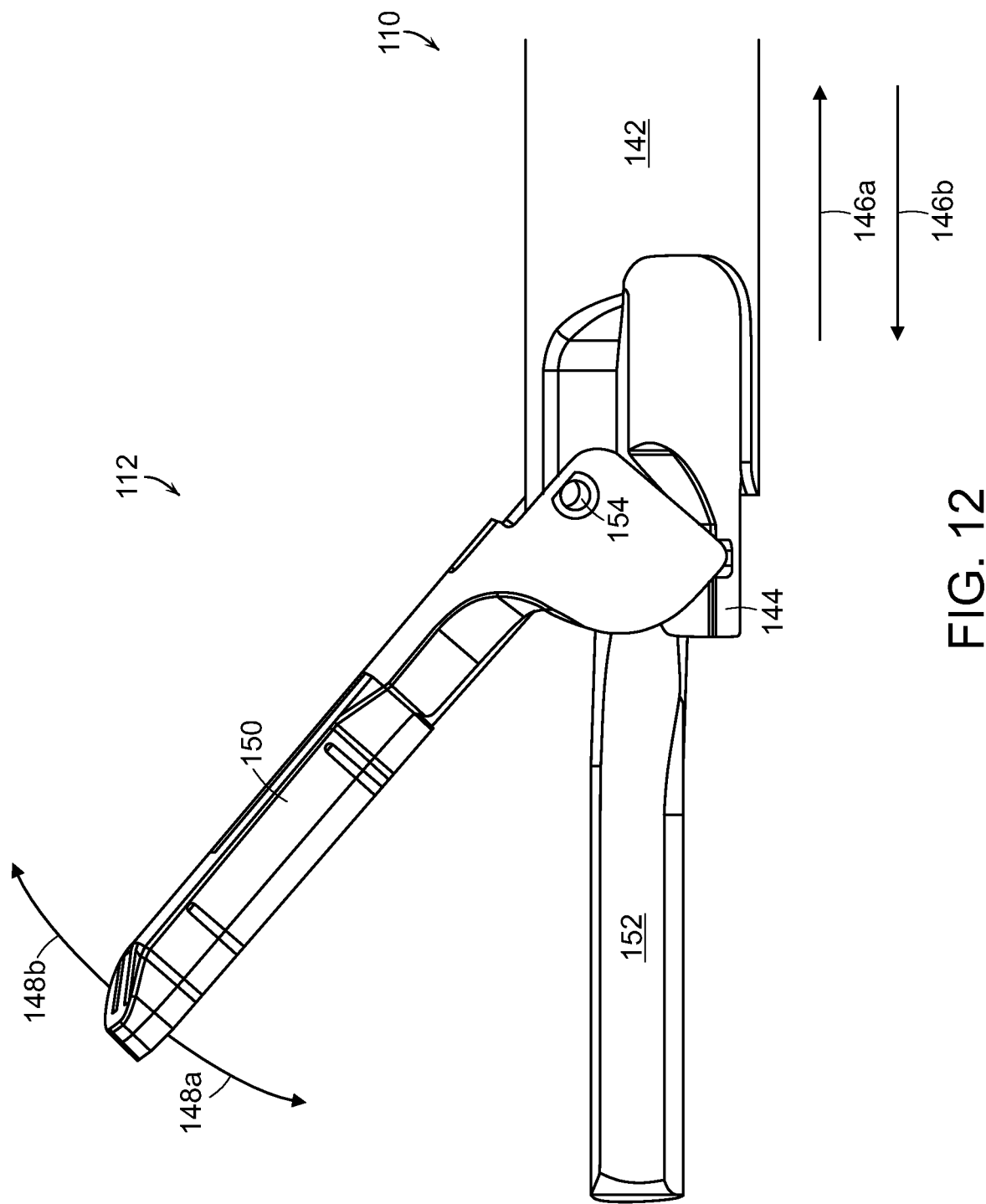
FIG. 12 is a right side view of one embodiment of the end effector assembly portion of the ultrasonic surgical instrument shown in FIG. 3.

FIGS. 10-12 illustrate the connection of the elongated endoscopic shaft assembly 110 relative to the end effector assembly 112. As previously described, in the illustrated embodiment, the end effector assembly 112 comprises a clamp arm assembly 150 and a blade 152 to form the jaws of the clamping mechanism. The blade 152 may be an ultrasonically actuatable blade acoustically coupled to the ultrasonic transducer 114. The trigger 120 is mechanically connected to a drive assembly. Together, the trigger 120 and the drive assembly mechanically cooperate to move the clamp arm assembly 150 to an open position in direction 148B wherein the clamp arm assembly 150 and the blade 152 are disposed in spaced relation relative to one another, to a clamped or closed position in direction 148A wherein the clamp arm assembly 150 and the blade 152 cooperate to grasp tissue therebetween. The clamp arm assembly 150 may comprise a clamp pad 158 to engage tissue between the blade 152 and the clamp arm 150. The distal end of the tubular reciprocating tubular actuating member 144 is mechanically engaged to the end effector assembly 112. In the illustrated embodiment, the distal end of the tubular reciprocating tubular actuating member 144 is mechanically engaged to the clamp arm assembly 150, which is pivotable about the pivot point 154, to open and close the clamp arm assembly 150 in response to the actuation and/or release of the trigger 120. For example, in the illustrated embodiment, the clamp arm assembly 150 is movable from an open position to a closed position in direction 148A about a pivot point 154 when the trigger 120 is squeezed in direction 121A. The clamp arm assembly 150 is movable from a closed position to an open position in direction 148B about the pivot point 154 when the trigger 120 is released or outwardly contacted in direction 121B.

FIG. 13 is a left perspective view of one embodiment of the ultrasonic surgical instrument shown in FIG. 3 showing a central longitudinal axis "T".

Figure 14:
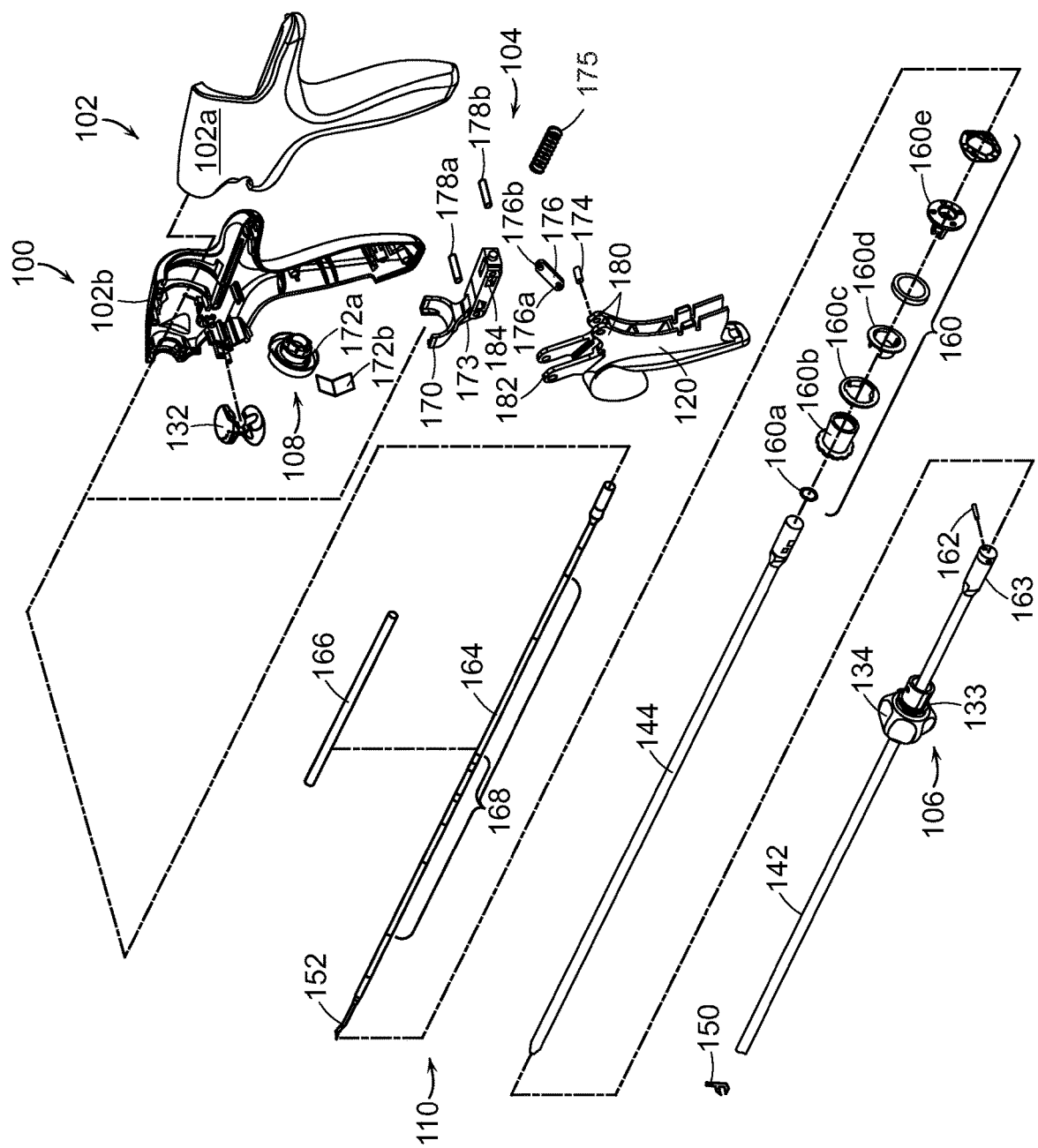
FIG. 14 is an exploded view of the ultrasonic surgical instrument shown in FIG. 3.
Figure 15:
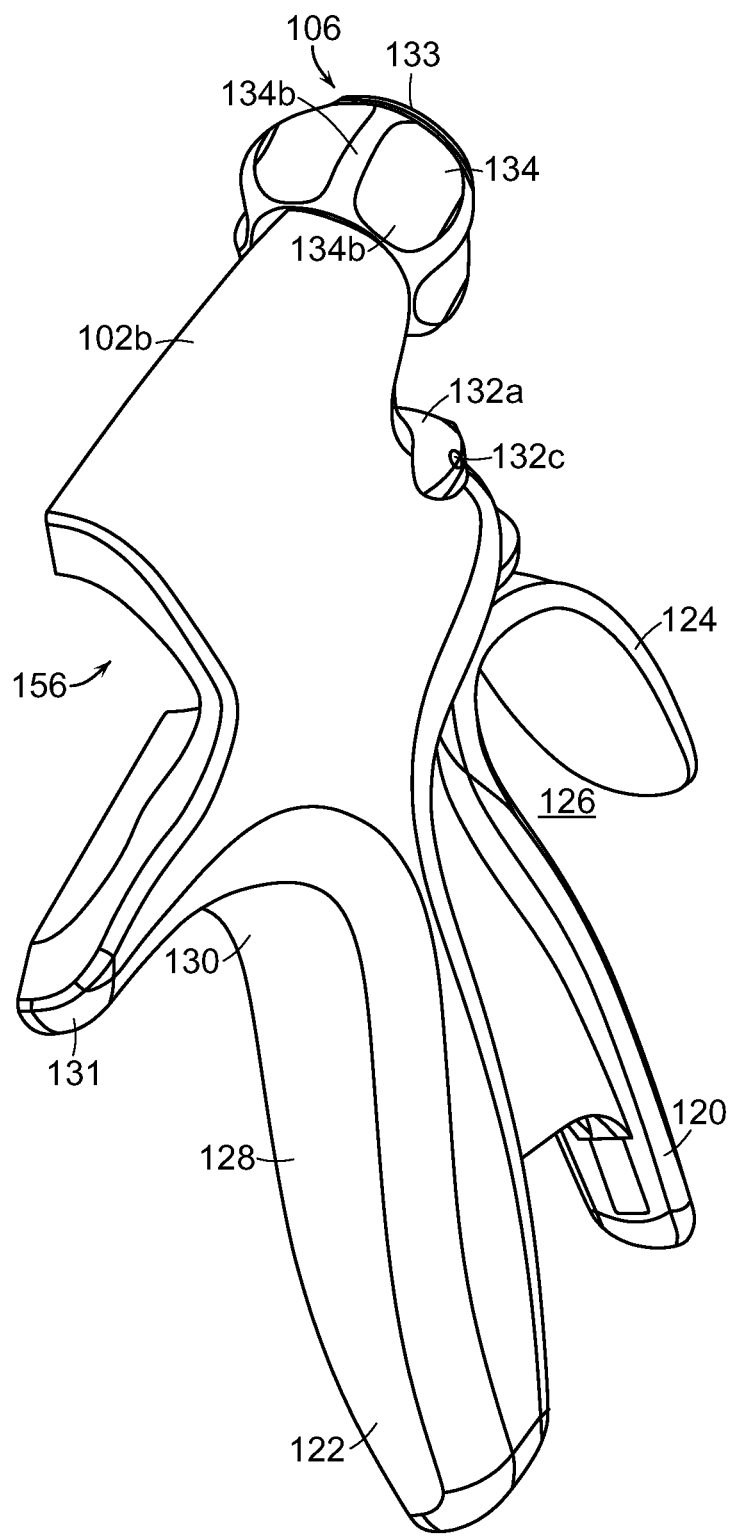
FIG. 15 is a left perspective view of a right half portion of one embodiment of the handle assembly shown in FIG. 3.
Figure 16:
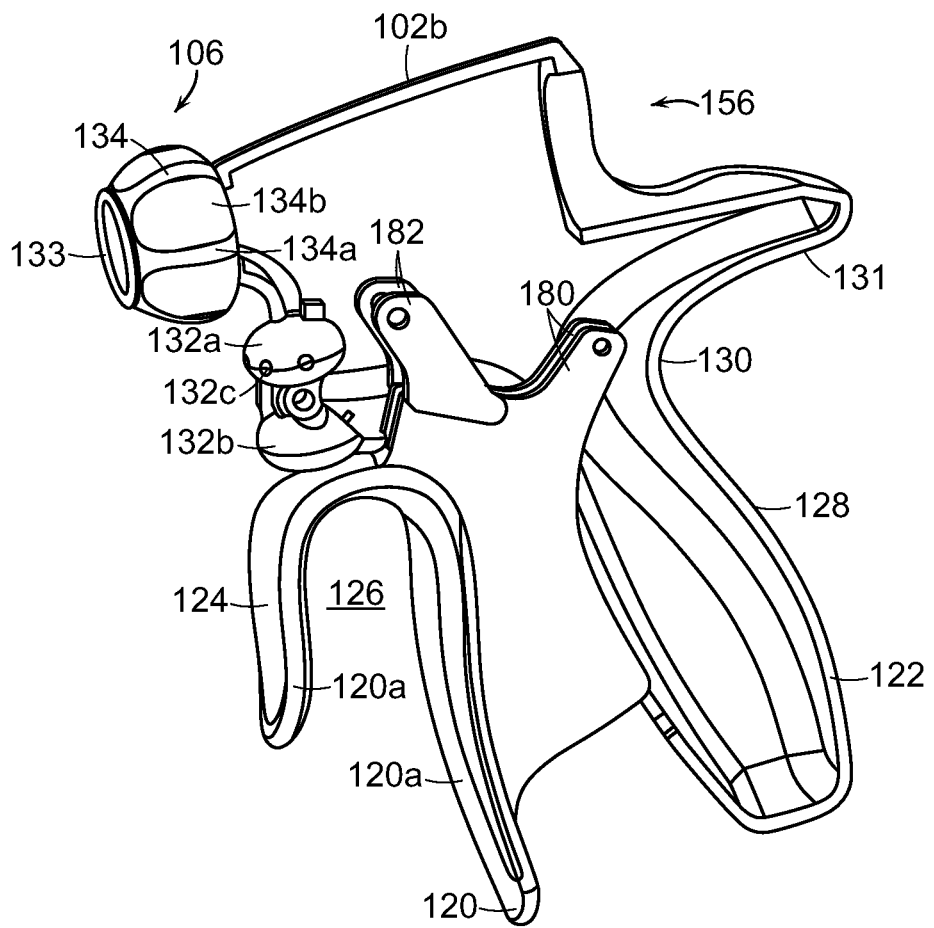
FIG. 16 is a right perspective view of the right half portion of one embodiment of the handle assembly shown in FIG. 3.
Figure 17:
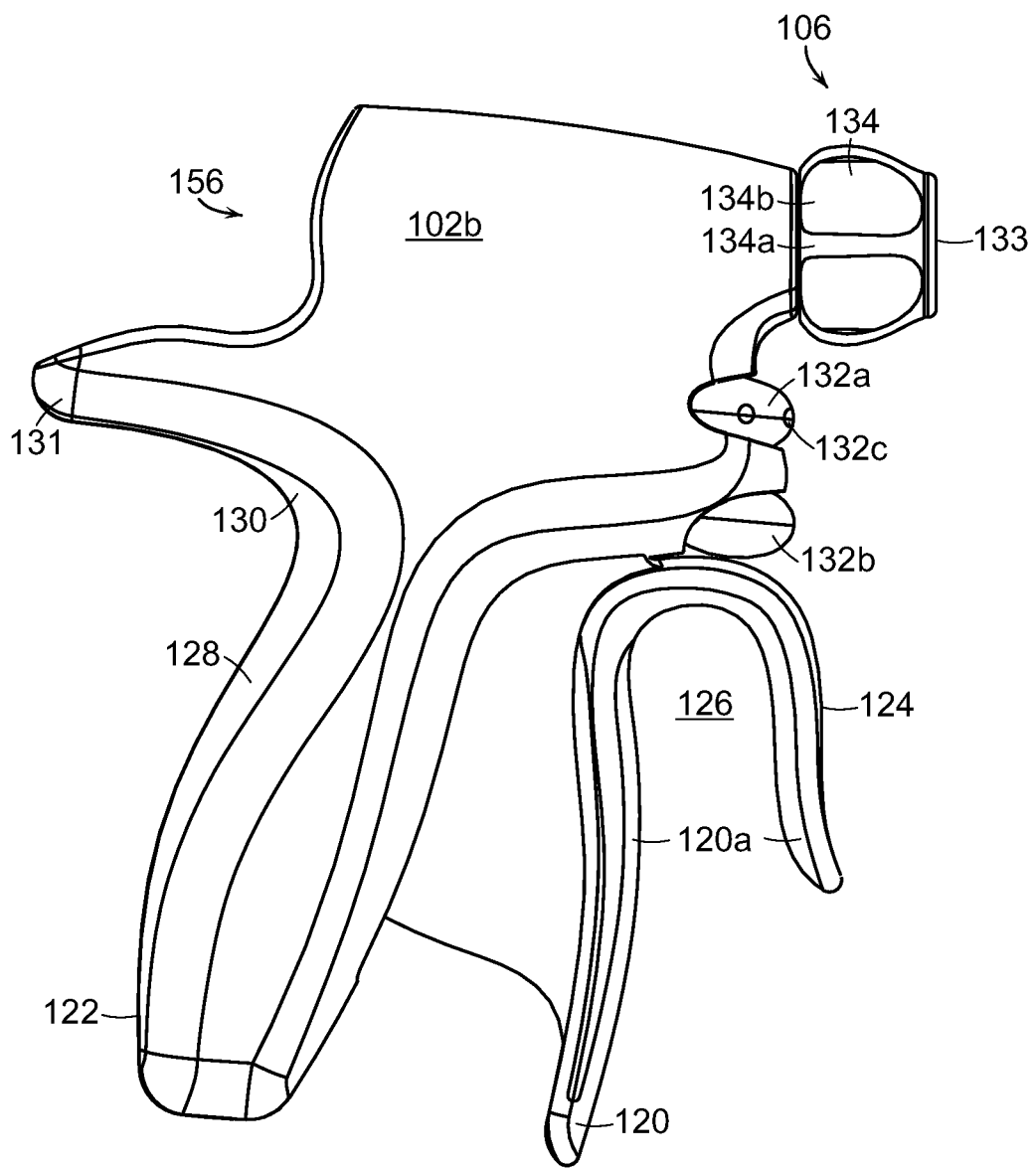
FIG. 17 is a left side view of the right half portion of one embodiment of the handle assembly shown in FIG. 3.
Figure 18:
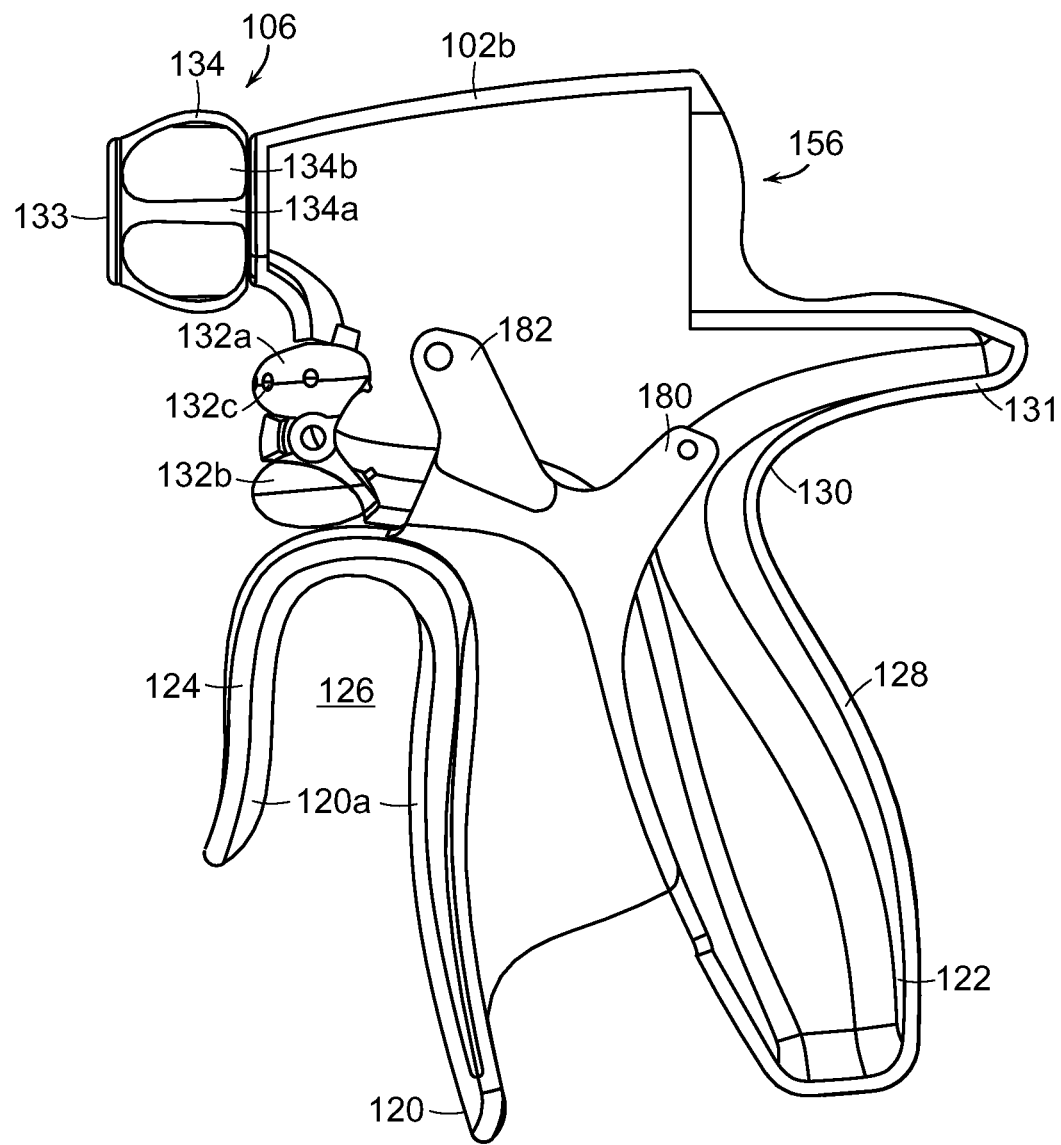
FIG. 18 is a right side view of the right half portion of one embodiment of the handle assembly shown in FIG. 3.
Figure 19:
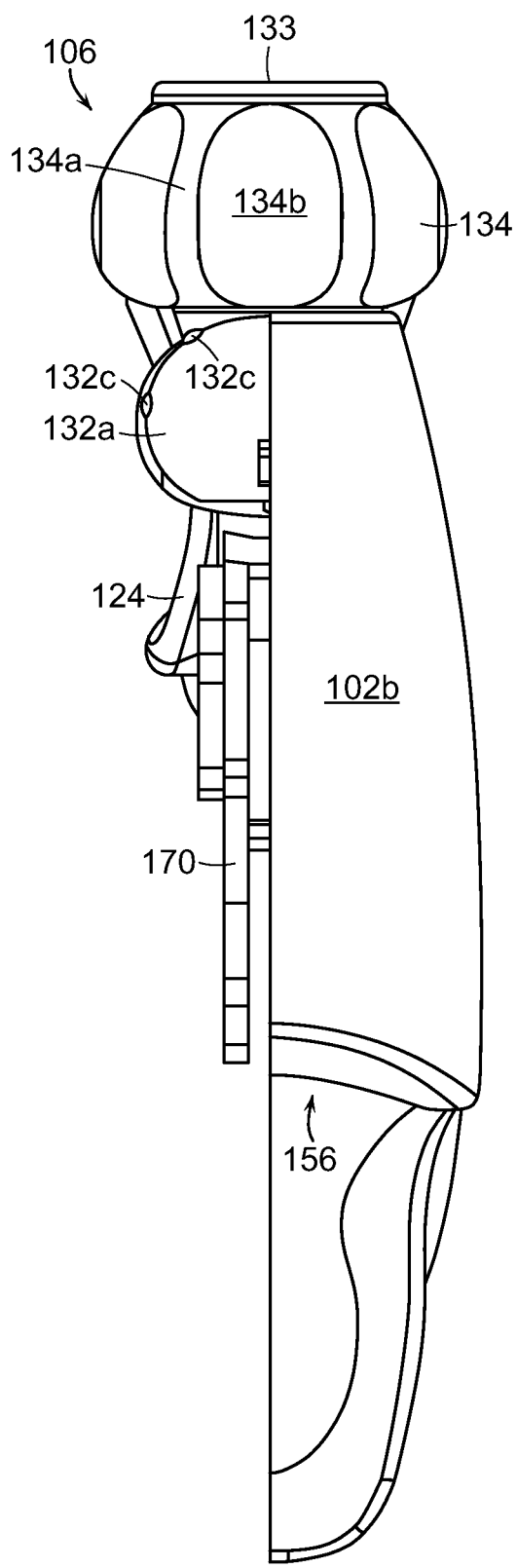
FIG. 19 is a partial cutaway top view of the right half portion of one embodiment of the handle assembly of the handle assembly shown in FIG. 3.
Figure 20:
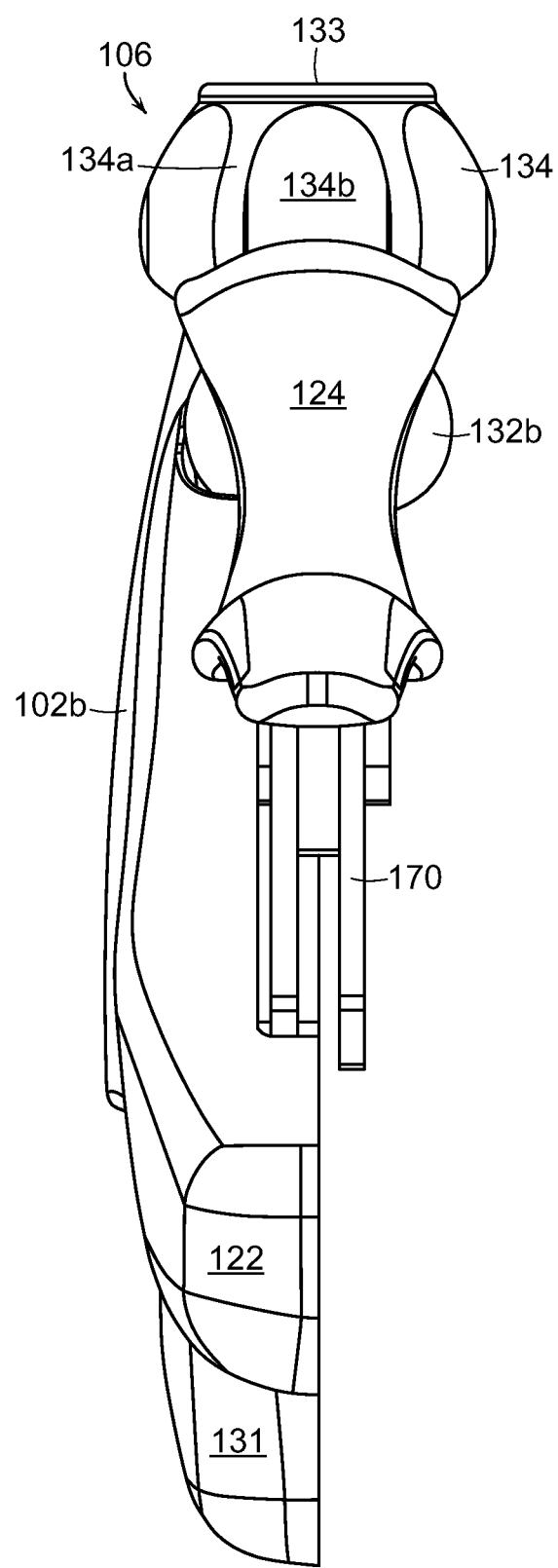
FIG. 20 is a partial cutaway bottom view of the right half portion of one embodiment of the handle assembly shown in FIG. 3.
Figure 21:
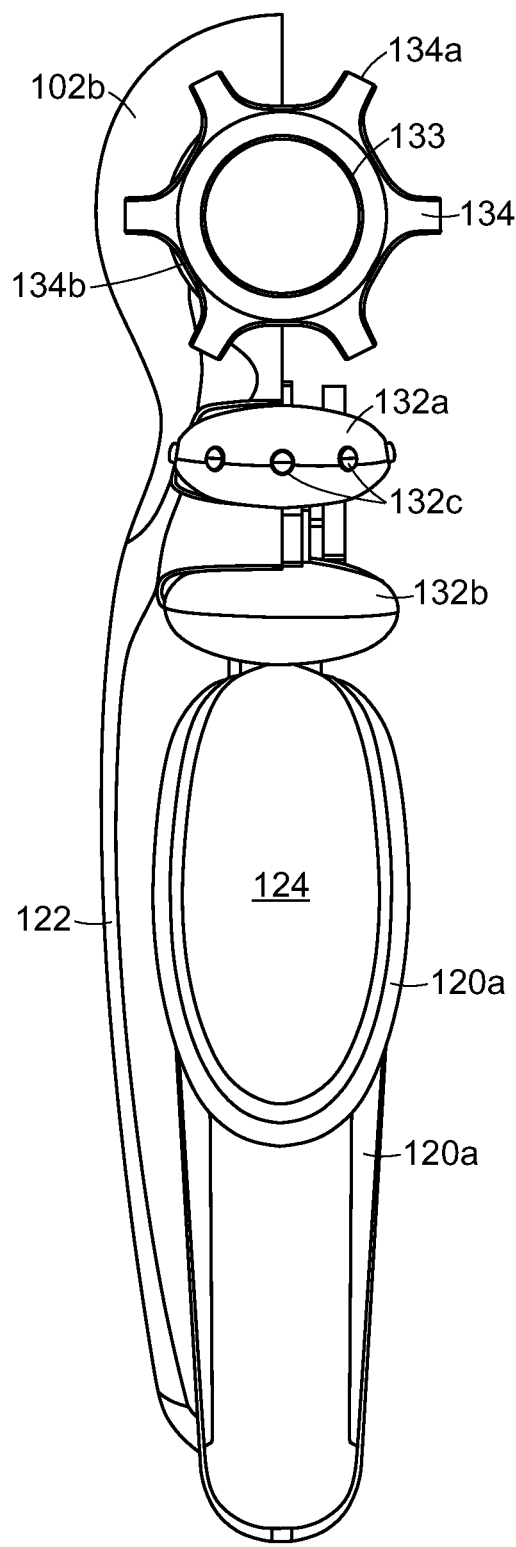
FIG. 21 is a partial cutaway front view of the right half portion of one embodiment of the handle assembly shown in FIG. 3.
Figure 22:
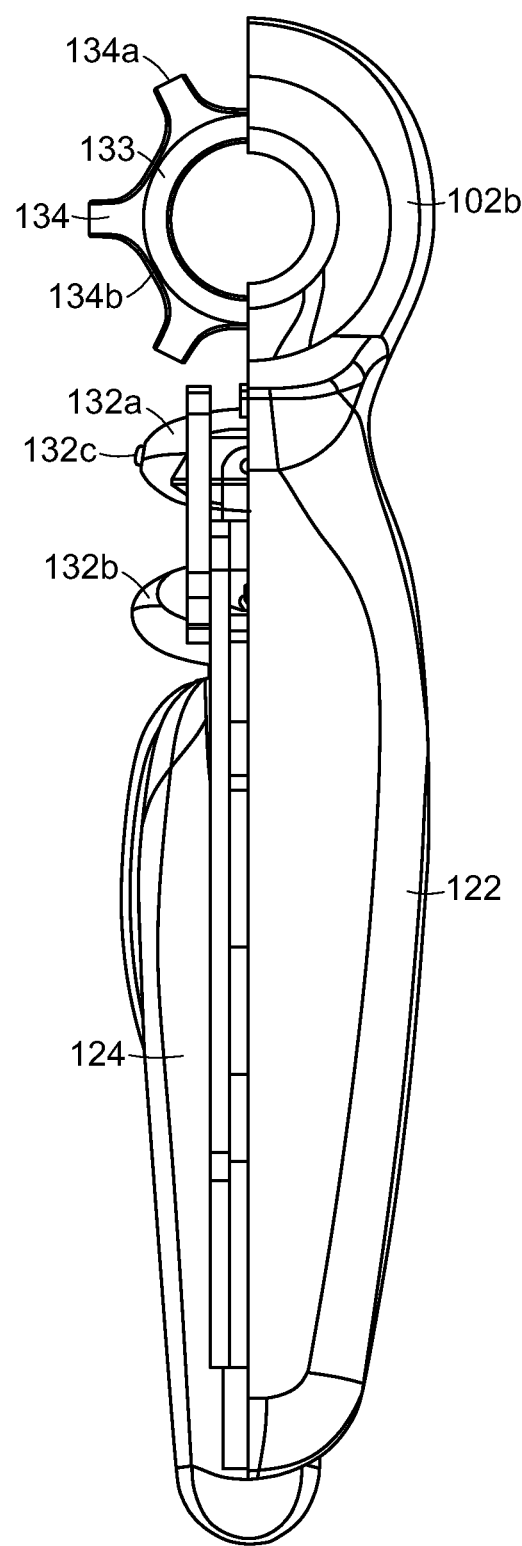
FIG. 22 is a partial cutaway bottom view of the right half portion of one embodiment of the handle assembly shown in FIG. 3.
Figure 23:
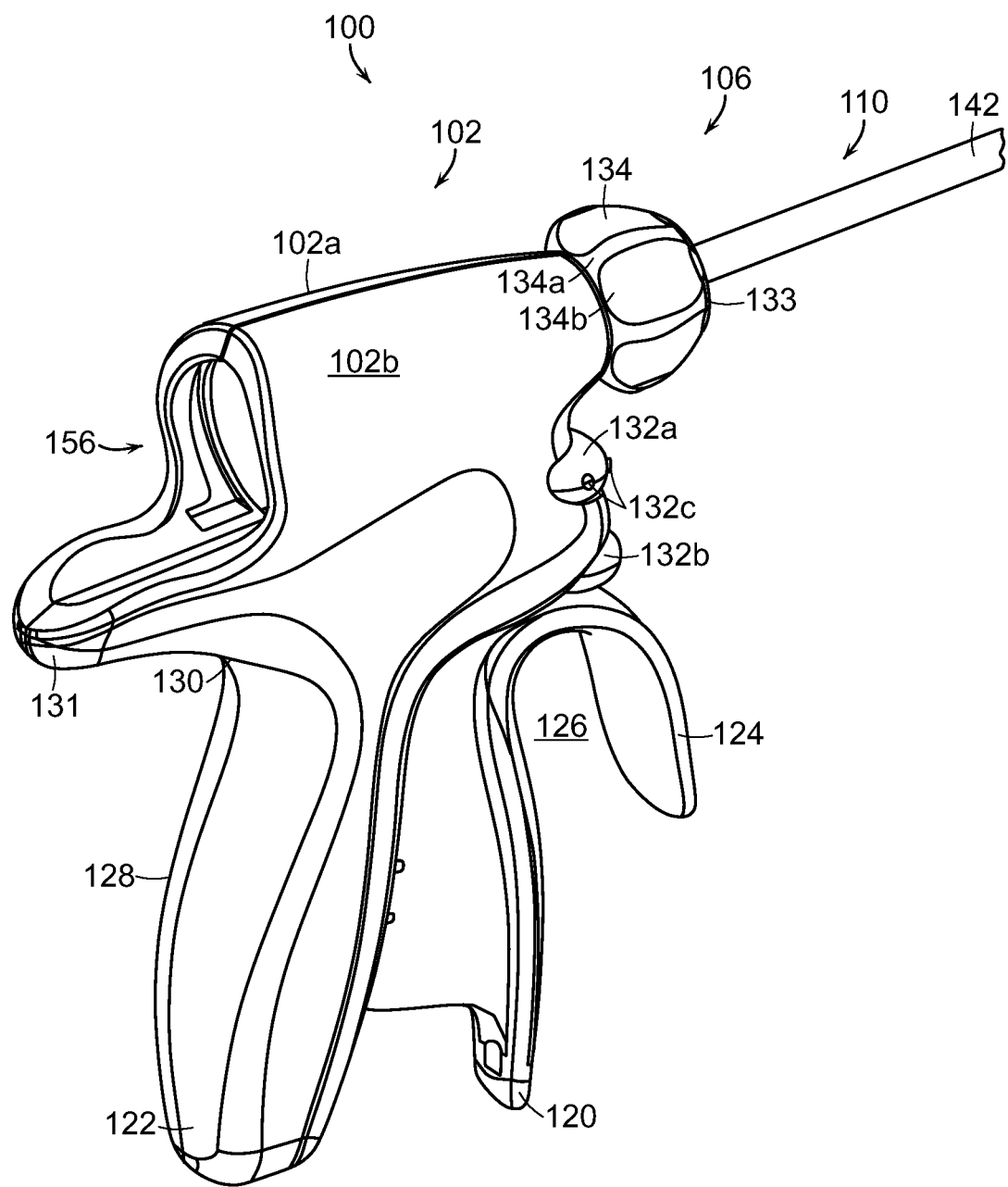
FIG. 23 is a left perspective view of one embodiment of the ultrasonic surgical instrument shown in FIG. 3.
Figure 24:
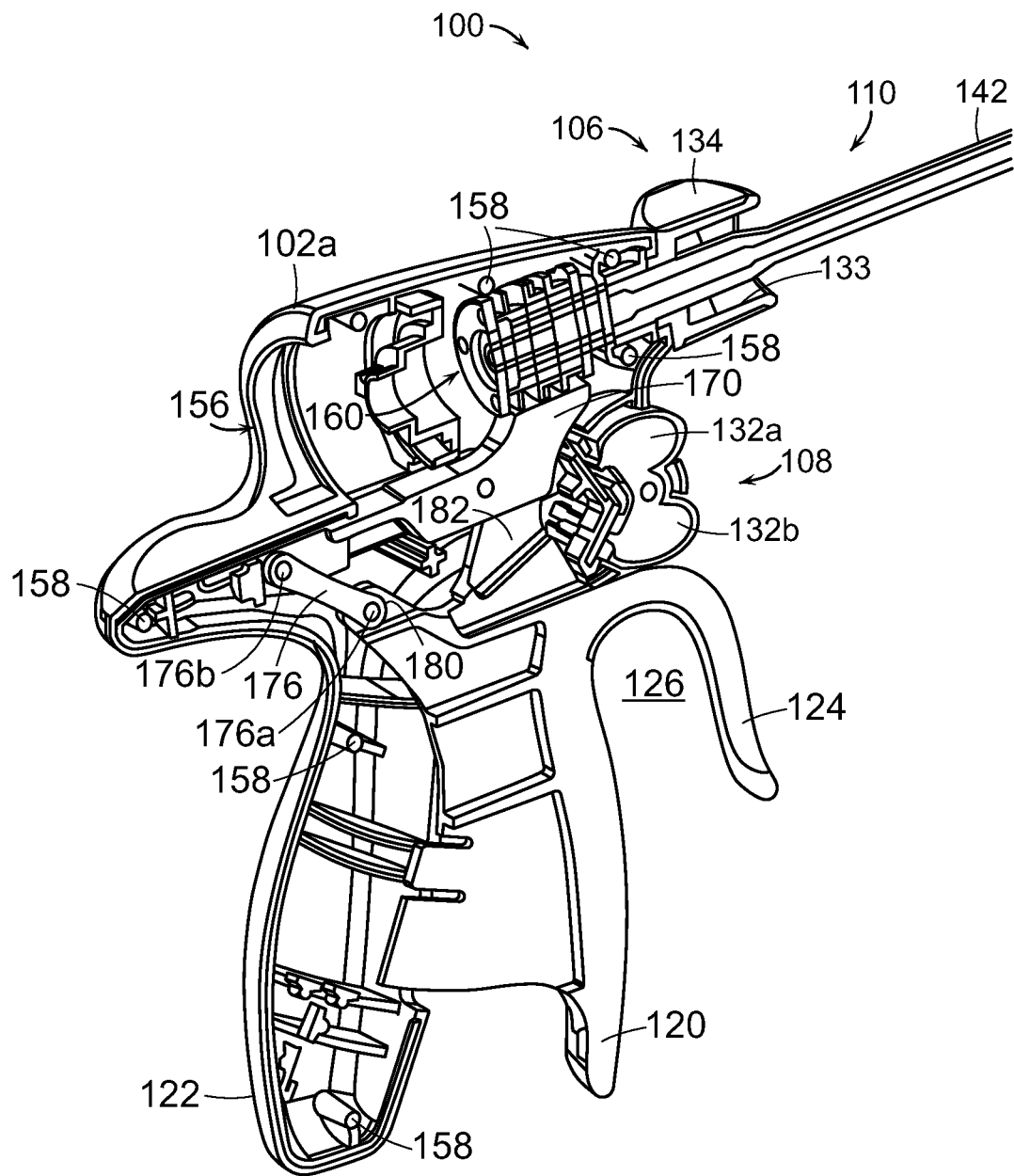
FIG. 24 is a cutaway left perspective view of the one embodiment of the ultrasonic surgical instrument shown in FIG. 3.

FIG. 14 is an exploded view of the ultrasonic surgical instrument 100 shown in FIG. 3. In the illustrated embodiment, the exploded view shows the internal elements of the handle assembly 102, the handle assembly 102, the distal rotation assembly 106, the switch assembly 108, and the elongated endoscopic shaft assembly 110. With reference now to FIGS. 14-24, in the illustrated embodiment, the first and second portions 102*a,b* mate to form the handle assembly 102. The first and second portions 102*a,b* each comprises a plurality of interfaces 158 dimensioned to mechanically align and engage one another to form the handle assembly 102 and enclose the internal working components of the ultrasonic surgical instrument 100. The rotation knob 134 is mechanically engaged to the outer tubular sheath 142 so that it may be rotated in circular direction 140 up to 360°. The outer tubular sheath 142 is located over the reciprocating tubular actuating member 144, which is mechanically engaged to and retained within the handle assembly 102 via a plurality of coupling elements 160. The coupling elements 160 may comprise an O-ring 160a, a tube collar cap 160b, a distal washer 160c, a proximal washer 160d, and a thread tube collar 160e. The reciprocating tubular actuating member 144 is located within a reciprocating yoke 170, which is retained between the first and second portions 102a,b of the handle assembly 102. The yoke 170 is part of a reciprocating yoke assembly 173. A series of linkages translate the pivotal rotation of the elongated trigger hook 120 to the axial movement of the reciprocating yoke 170, which controls the opening and closing of the jaws of the clamping mechanism of the end effector assembly 112 at the distal end of the ultrasonic surgical instrument 100. In one embodiment, a four-link design provides mechanical advantage in a relatively short rotation span, for example.

In one embodiment, an ultrasonic transmission waveguide 164 is disposed inside the reciprocating tubular actuating member 144. The distal end 138 of the ultrasonic transmission waveguide 164 is acoustically coupled to the blade 152 and the proximal end 136 of the ultrasonic transmission waveguide 164 is received within the handle assembly 102. The proximal end 136 of the ultrasonic transmission waveguide 164 is adapted to acoustically couple to the distal end of the ultrasonic transducer 114 as discussed in more detail below. The ultrasonic transmission waveguide 164 is isolated from the other elements of the elongated endoscopic shaft assembly 110 by a protective sheath 166 and a plurality of isolation elements 168, such as silicone rings. The outer tubular sheath 142, the reciprocating tubular actuating member 144, and the ultrasonic transmission waveguide 164 are mechanically engaged by a pin 162. The switch assembly 108 comprises the toggle switch 132 and electrical elements 172a,b to electrically energize the ultrasonic transducer 114 in accordance with the activation of the first or second projecting knobs 132a,b.

Figure 27:
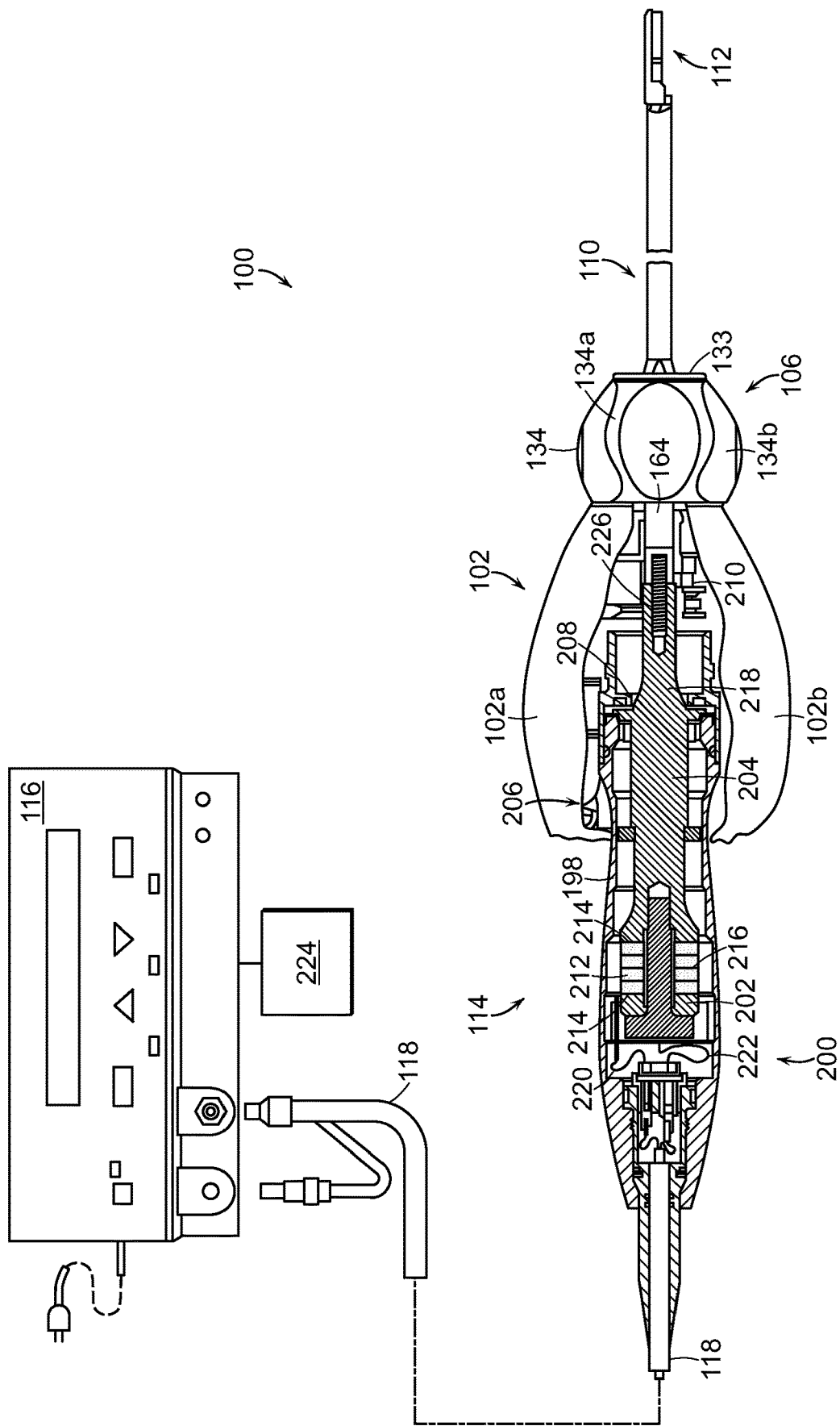
FIG. 27 illustrates one embodiment of an ultrasonic surgical instrument.

In one embodiment, the outer tubular sheath 142 isolates the user or the patient from the ultrasonic vibrations of the ultrasonic transmission waveguide 164. The outer tubular sheath 142 generally includes a hub 163. The outer tubular sheath 142 is threaded onto the distal end of the handle assembly 102. The ultrasonic transmission waveguide 164 extends through the opening of the outer tubular sheath 142 and the isolation elements 168 isolate the ultrasonic transmission waveguide 104 from the outer tubular sheath 142. The outer tubular sheath 142 may be attached to the waveguide 164 with the pin 162. The hole to receive the pin 162 in the waveguide 164 may occur nominally at a displacement node. The waveguide 164 may screw or snap into the hand piece handle assembly 102 by a stud 226 (FIG. 27). Flat portions on the hub 163 may allow the assembly to be torqued to a required level.

In one embodiment, the hub 163 portion of the outer tubular sheath 142 is preferably constructed from plastic and the tubular elongated portion of the outer tubular sheath 142 is fabricated from stainless steel. Alternatively, the ultrasonic transmission waveguide 164 may comprise polymeric material surrounding it to isolate it from outside contact.

In one embodiment, the distal end of the ultrasonic transmission waveguide 164 may be coupled to the proximal end of the blade 152 by an internal threaded connection, preferably at or near an antinode. It is contemplated that the blade 152 may be attached to the ultrasonic transmission waveguide 164 by any suitable means, such as a welded joint or the like. Although the blade 152 may be detachable from the ultrasonic transmission waveguide 164, it is also contemplated that the single element end effector (e.g., the blade 152) and the ultrasonic transmission waveguide 164 may be formed as a single unitary piece.

In one embodiment, the trigger 120 is coupled to a linkage mechanism to translate the rotational motion of the trigger 120 in directions 121A and 121B to the linear motion of the reciprocating tubular actuating member 144 in corresponding directions 146A and 146B. The trigger 120 comprises a first set of flanges 182 with openings formed therein to receive a first yoke pin 178a. The first yoke pin 178a is also located through a set of openings formed at the distal end of the yoke 170. The trigger 120 also comprises a second set of flanges 180 to receive a first end 176a of a link 176. A trigger pin 174 is received in openings formed in the link 176 and the second set of flanges 180. The trigger pin 174 is received in the openings formed in the link 176 and the second set of flanges 180 and is adapted to couple to the first and second portions 102a,b of the handle assembly 102 to form a trigger pivot point 190 (FIGS. 25, 26) for the trigger 120. A second end 176b of the link 176 is received in a slot 184 formed in a proximal end of the yoke 170 and is retained therein by a second yoke pin 178b. As the trigger 120 is pivotally rotated about the pivot point 190 formed by the trigger pin 174, the yoke translates horizontally along longitudinal axis "T" in a direction indicated by arrows 146A,B.

Figure 25:
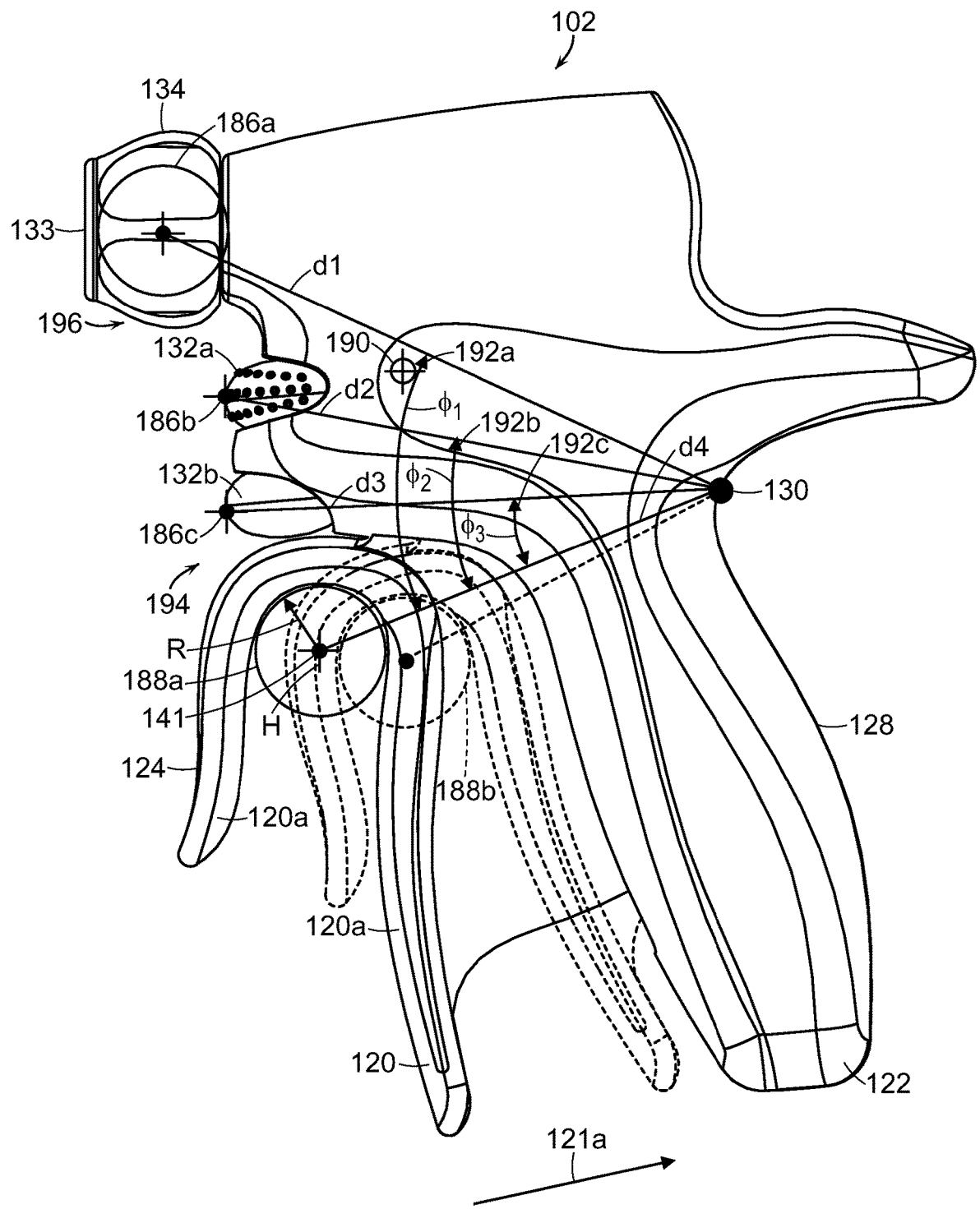
FIG. 25 illustrates relationships between various user interfaces of one embodiment of the handle assembly shown in FIG. 3.
Figure 26:
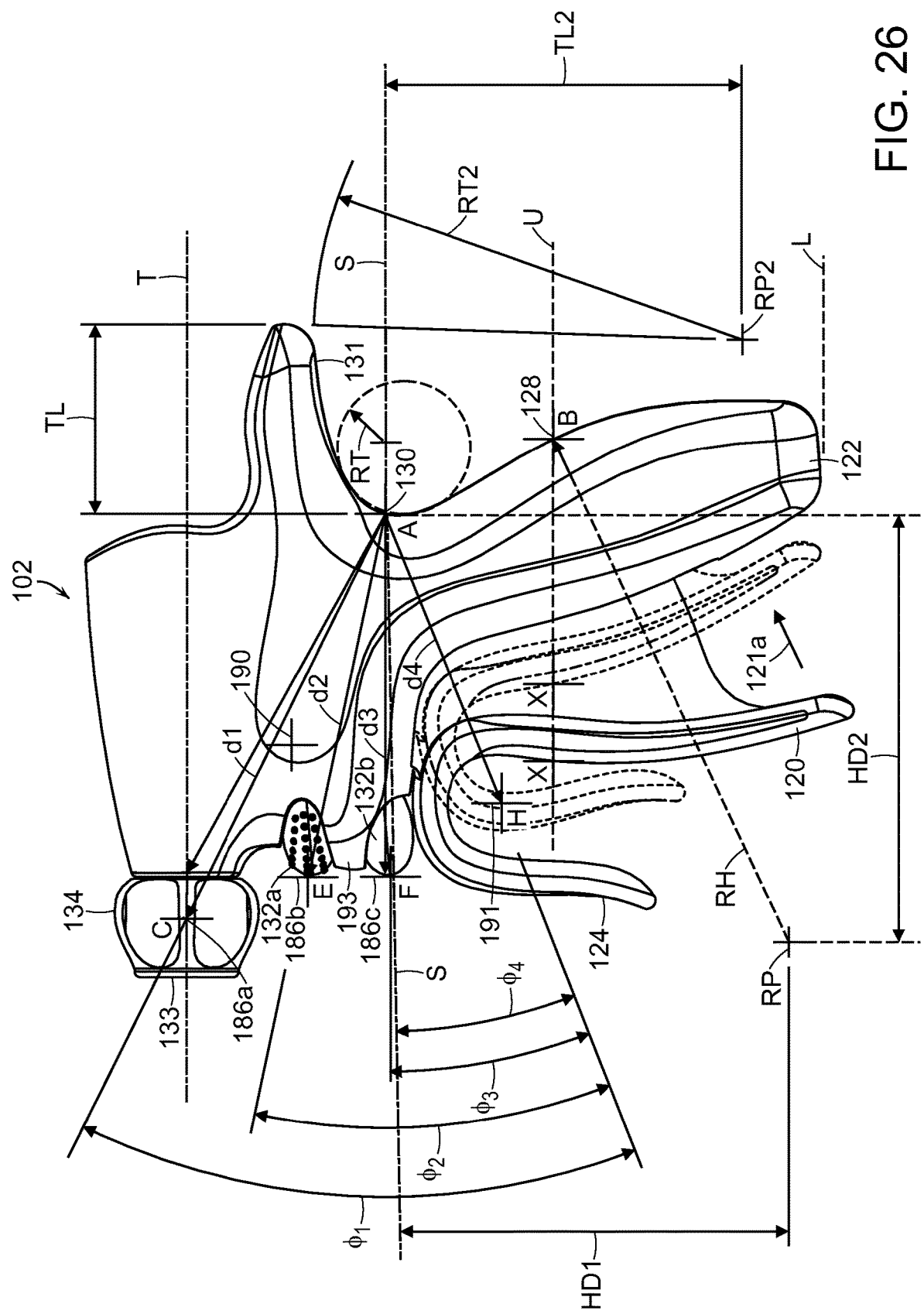
FIG. 26 illustrates relationships between various user interfaces of one embodiment of the handle assembly shown in FIG. 3.

FIGS. 25 and 26 illustrate relationships between various user interfaces of one embodiment of the handle assembly 102. In the illustrated embodiment, the user may employ a control finger to activate the power buttons of the toggle switch 132 and to control the rotation of the rotation knob 134 and precisely control the rotation of the end effector assembly 112. The control finger may be the index finger; however, the embodiments are not limited in this context. As illustrated, a control finger location 186a is used to operate (e.g., rotate) the distal rotation knob 134. The distance between the control finger location 186a and the saddle surface 130 is "d1". In one embodiment, for example, d1 may be approximately 3.17 inches. Without changing the grip relative to the fixed handle 122 the user also may operate the first projecting knob 132a by locating a finger in control finger location 186b to set the power to a first level (e.g., MAX) and may operate the second projecting knob 132b by locating the finger at control finger location 186c to set the power to a second level (e.g., MIN). The distance between the control finger location 186b and the saddle surface 130 is "d2" and the distance between the control finger location 186c and the saddle surface 130 is "d3". In one embodiment, for example, d2 may be approximately 2.55 inches and d3 may be approximately 2.46 inches. Accordingly, the user may easily and readily locate the control finger at three control finger locations 186a, 186b, and 186c without re-gripping the handle assembly 102 to operate the respective distal rotation knob 134, the first projecting knob 132a, and the second projecting knob 132b. Each of the rotation and power controls are readily accessible with the control finger without being too crowded together and resulting in a balanced access of all three.

In one embodiment, a trigger finger of the user may be located in a first position 188a within the aperture 126 to operate the trigger 120. The distance between the first position 188a and the saddle surface 130 is "d4". In one embodiment for example, d4 may be approximately 2.11 inches. The trigger finger may be the middle finger. As illustrated, the trigger finger may be contacted with the molded resilient portion 120a of the trigger 120. As the trigger 120 is squeezed in direction 121A, it pivots about the pivot point 190 from a fully open to a fully closed position, shown in phantom in FIG. 26. As the trigger 120 pivots about the pivot point 190 from a fully open position to a fully closed position, the trigger finger location moves from the trigger finger location 188a to the trigger finger location 188b, shown in phantom.

The spread angles $\varphi_1$-$\varphi_3$ are defined as the angles formed between the trigger finger location 188a with the trigger 120 in a fully open position and a control finger located on a control element. A first angle $\varphi_1$ is defined as the angle formed between the trigger finger location 188a and the control finger location 186a in contact with the distal rotation knob 134. In one embodiment, for example, $\varphi_1$ may be approximately forty-six degrees. A second angle $\varphi_2$ is defined as the angle formed between the trigger finger location 188a and the control finger location 186b in contact with the first projecting knob 132a. In one embodiment, for example, $\varphi_2$ may be approximately thirty-three degrees. A third angle $\varphi_3$ is defined as the angle formed between the trigger finger location 188a and the control finger location 186c in contact with the second projecting knob 132b. In one embodiment, angle $\varphi_3$ may be approximately twenty degrees and the angle $\varphi_4$ between the control finger location 188a and the axis S may be approximately nineteen degrees. The access spread is a combination of the distance "d" between the saddle surface 130 and the control finger location 186a, 186b, or 186c and the spread angle $\varphi$ between the control finger location and the trigger finger location. The distances $d_1$, $d_2$, and $d_3$ and the spread angles $\varphi_1$, $\varphi_2$, and $\varphi_3$ are optimized for ergonomic purposes. For example, the spread angles may be selected such that:

$$\varphi_3 < \varphi_2 < \varphi_1; \text{ and}$$

$$d_3 < d_2 < d_1.$$

The spread angle $\varphi_1$ represents the spread between the control finger location 186a on the distal rotation knob 134 and the trigger finger location 188a. The access spread 192a between the control finger position 186a and the trigger finger position 188a is the largest of the three access spreads 192a, 192b, and 192c. Operation of the distal rotation knob 134 requires the most finger spread of all the other controls. Further, the distal rotation knob 134 requires a different force vector (e.g., downward) to actuate than the first projecting knob 132a or the second projecting knob 132b, which requires less strain on the finger. The distal rotation knob 134 can be configured to deactivate and lock-out when the trigger 120 is in the fully closed position, shown in phantom, which also alleviates the "worst case" finger spread angle $\varphi_1$. In general, the spacing 196 between the distal rotation knob 134 and the first projecting knob 132a may be selected to minimize crowding therebetween and to minimize difficulty of access for larger fingers.

The spread angle $\varphi_2$ represents the spread between the control finger location 186b at the first projecting knob 132a and the trigger finger location 188a. The access spread 192b between the control finger location 186b and the trigger finger location 188a is slightly greater than the access spread 192c between the control finger location 186c and the trigger finger location 188a and requires more finger spread to access the first projecting knob 132a than the second projecting knob 132b. The first projecting knob 132a is located sufficiently apart from the second projecting knob 132b to minimize any perceived risk of inadvertent activation. In addition, the first projecting knob 132a is spaced sufficiently apart from the distal rotation knob 134 to minimize crowding and any difficulty of access for larger fingers. The spacing 196 between the distal rotation knob 134 and the first projecting knob 132a may be selected such that it is minimized to keep the distal rotation knob 134 within reach of the control finger location 186a and is maximized to avoid crowding between the distal rotation knob 134 and the first projecting knob 132a.

The spread angle $\varphi_3$ represents the spread between the control finger location 186c at the second projecting knob 132b and the trigger finger location 188a. The access spread 192c between the control finger location 186c and the trigger finger position 188a is the least spread required between the middle and control fingers and accordingly results in the lowest finger strain. Access to the second projecting knob 132b requires the least finger spread of all the controls and therefore tends to be the easiest to activate. In the fully open position, the second projecting knob 132b is located as low as possible without being too crowded against the trigger 120 and thus avoiding "crossing" the trigger finger. The spacing 194 between the second projecting knob 132b and the trigger 120a may be selected to minimize the finger spread angle required to reach the first projecting knob 132a when the trigger 120 is in the fully closed position, shown in phantom, and the trigger finger is at position 188b, also shown in phantom.

In one embodiment, the location of the trigger pivot 190 may be selected to control and optimize the arc of motion of the trigger 120 as it pivots from a fully open position, shown in solid line, to a fully closed position, shown in phantom, especially as it relates to the relative trigger finger location at each end of the span. The ideal motion arc is slightly upward moving from closed to open, to relate to the natural opening motion of the fingers. The fully closed position slightly increases the angle of the finger spread required to access controls, but is acceptable in balance to the natural motion arc of the trigger 120. When the trigger 120 is in the fully closed position, the trigger finger location 188b slightly increases the angle of the finger spread angle $\varphi$ required to access the various controls (i.e., the angle $\varphi$ formed between the middle and the control fingers). The increase, however, is minimized to be within an acceptable balance to the natural motion arc of the trigger 120.

FIG. 26 illustrates relationships between various user interfaces of one embodiment of the handle assembly 102. In the illustrated embodiment, the handle assembly 102 may be defined as having four separate axis. A longitudinal axis "T" that coincides with the longitudinal axis of the elongated endoscopic shaft assembly 110, a saddle surface axis "S", a user input axis "U", a base axis "L", the trigger 120 pivot point 190, a center point 191 of the elongated trigger hook 124, the saddle surface 130, the control finger locations 186a, 186b, 186c, and the trigger finger locations 188a, 188b. The trigger hook 124 defines an arcuate portion defined by radius "$r_1$" and center point 191. The handle assembly 102 provides suitable spacing between the trigger 120 and the fixed handle 122 at full closure. The spacing/contouring of the second projecting knob 132b (e.g., MIN button) and the top of the elongated trigger hook 124 pushes out the trigger finger when opening the trigger 120 while activating the second projecting knob 132b.

In one embodiment, the activation user input force "$f_1$" is the force necessary to activate the first projecting knob 132a or the second projecting knob 132b. In one embodiment, the force $f_1$ is approximately 400 g+/−80 g. The activation user input force $f_1$ is a balance between minimizing user fatigue (not too hard) and minimizing risk of inadvertent activation (not too light). The activation user input force $f_1$ is measured along the A-E vector (the vector from the saddle surface 130 to the finger location 186b) to activate the first projecting knob 132a and the A-F vector (the vector from the saddle surface 130 to the finger location 186c) to activate the second projecting knob 132b.

In one embodiment, a control (e.g., index) finger "rest area" 193 is defined as the space between the first projecting knob 132a and the second projecting knob 132b (e.g., MIN/MAX button spacing). A user can apply up to approximately 1.5 lbf of force on the rest area 193 between the first projecting knob 132a and the second projecting knob 132b with the control finger without activating power.

In one embodiment, the first projecting knob 132a and the second projecting knob 132b may be activated with a directional pressure vector from 0° to 30° to either side relative to the medial center plane of the hand assembly 102. This provides greater access to the first projecting knob 132a and the second projecting knob 132b when the wrist is in an extreme position with shorter fingers.

In one embodiment, the center line between the second projecting knob 132b and the highest finger located within the aperture 126 defined by the elongated trigger hook 124 is approximately at least 0.650" to maximize comfort and minimize a feeling of "crossing" two adjacent fingers.

In one embodiment, the finger clearance within the aperture 126 of the elongated trigger hook 124 is approximately at least 0.650" to avoid finger entrapment.

In one embodiment, the user input axis (U) is defined as the axis U directly between the middle and ring finger positions on the trigger 120. The trigger 120 closing force applied by the user is defined as the force $f_2$ measured along the U-X vector (the vector from the proximal contact surface 128 to the first position 188a within the aperture 126). In one embodiment, the force required to close the trigger 120 to a fully closed position, as measured along U-X vector, may be approximately less than 6.14 lbs, based upon the following:
140.8 lbs=maximum full-hand grip force for 5% small female;
40.8 lbs×0.33=13.64 lbs (67% reduction for comfortable grip force);
13.64 lbs×0.60=8.18 lbs (40% reduction for poor posture); and
8.18 lbs×0.75=6.14 lbs (25% reduction for removing index from the full grip: relative finger strengths: Index: 25%, Middle: 35%, Ring: 25%, little: 14%, source: NCBI Pub Med, 07/04).

In one embodiment, a trigger 120 abuse closing force is defined as the closing force generated when the trigger is closed by applying pressure on the distal surface of the elongated trigger hook 124. In one embodiment, the reasonable abuse force that the trigger 120 can withstand is approximately 15.00 lbs, based upon that the high end of the actual closing force manufacturing variation is 5 lbs. and it would be rare to expect that the user will exert more that three-times the required force.

In one embodiment, the trigger 120 opening force is defined as the force $f_3$ required by the user to fully open trigger 120, as measured along the U-X vector. In one embodiment, the force $f_3$ is approximately 0.0+0.5/−1.5 lbf. In one embodiment, the handle assembly 102 incorporates some means of spring-assisted opening to overcome the friction in the system such as spring element 175 (FIG. 14). In one embodiment, the jaws of the end effector assembly 112 should become fully open on their own with minimal force required. The "automatic" full opening suitably enhances ease of use when applying multiple closure "bites" in succession. Minimizing the force required for the jaws of the end effector assembly 112 to open reduces risk of losing tactile feedback during spreading dissection (surgeons want to feel the tissue tension being applied as much as possible, not the spring), for example.

In one embodiment, the contact surface width of the trigger 120 may be approximately 0.760"+/−0.200" as measured at the user input axis "U" to provide maximum comfort and avoid pressure points.

In one embodiment, the length of the elongated trigger hook 124 as measured from the elongated trigger hook center 191 to the end of the forward hook loop may be approximately 1.090"+/−0.080" to facilitate two-finger contact for an outward opening stroke of the trigger 120.

In one embodiment, the length of the trigger 120 as measured from the elongated trigger hook center 191 to the lowermost end of the trigger 120 should be approximately 2.480"+/−0.080" to facilitate three-finger contact for closing stroke.

In one embodiment, the longitudinal center of gravity may be located approximately 0.700"+/−0.150" proximal to the origin of the elongated endoscopic shaft assembly 110 at point as defined by the location of the insulated pin. The total weight of the device defined as the handle assembly fully assembled the cable 118 cut off at a proximal termination of strain relief. In one embodiment, the center of gravity may be kept closer to the center of the palm of the user for maximum feeling of control and stability.

In one embodiment, the palm surface length of the fixed handle 122 may be approximately 2.900"+/−0.125" as measured vertically from A-L (from the saddle surface 130 to the base of the fixed handle 122). This distance may be determined by balancing maximizing size for larger hand comfort and stability and minimizing potential interference of the handle assembly 102 with a patient (usually happens if legs are raised) or table.

In one embodiment, the palm surface width does not exceed approximately 1.320". This distance may be determined by balancing comfort against the palm of the user when closing pressure is applied to the trigger 120, access around the back surface area of the fixed handle 122 to the front controls for smaller hands, and overall "fit" in the hand of the user. The side surfaces of the fixed handle 122 may be curved and contoured to naturally fit the palm of a hand and provide stability for the thumb and index finger grip locations.

In one embodiment, the fully closed grip span as measured from U-X' may be greater than approximately 1.600". The fully open grip span as measured from U-X may be less than a maximum of approximately 2.300".

In one embodiment, the distal rotation knob 134 user interface may comprise a multi-flute design, with a finger-contact radius of approximately 0.250"+/−0.050" for each flute 134a. In one embodiment, the flutes 134a may be overmolded to increase gripping ability on the distal rotation knob 134.

In one embodiment, the rotation force is defined as the frictional force of the distal rotation knob 134 when it is connected to the handle assembly 112. The rotation force should provide a torque resistance of approximately 3.5-12.5 in-oz. This value may be determined by balancing suitable resistance at the low end to overcome reversal of the shaft due to winding of the cord and minimizing user input force at the high end to minimize fatigue.

In one embodiment, the overmolding compliance of the molded resilient portion 120a of the trigger 120 surface may be less than approximately 0.040" at any point of contact in the loaded trigger motion to maximize tactile feedback. This value may be determined by balancing providing increased user comfort during repetitive trigger actuation (especially outward finger extension) and not losing tactile feedback of forces being applied to tissue.

In one embodiment, the overall configuration of the handle assembly 102 may be based upon a pistol-grip design, with an optimal palm proximal contact surface 128 (P) as described and illustrated in the embodiments herein. In one embodiment, the optimization of the proximal contact surface 128 may comprise a contact surface that is best defined by an organic curve that naturally fits the palm of the hand, rather than a specified angle of the grip. This ideal curve provides maximum grip comfort, control, and stability. Locating the saddle surface 130 directly below the location of the stabilization tail 131 provides added feeling of control and stability in the nook or web defined between the thumb and index finger.

As can also be seen in FIG. 26, the contact surface 128 may have a radius RH that is measured from reference point RP. Reference point RP may be located a first distance HD1 from axis S and a second distance HD2 from point A. In one embodiment, for example, radius RH may be approximately 2.99 inches, distance HD1 may be approximately 2.27 inches and distance HD2 may be approximately 2.20 inches. Also in various embodiments, the stabilization tail 131 may have a first radius portion RT of approximately 0.40 inches and a second radius RT2 measured from a second reference point RP2 that may be approximately 2.91 inches. The second reference point RP2 may be located a distance TL from point A, wherein TL may be approximately 1.31 inches and a distance TL2 from axis S which may be approximately 2.33 inches.

In one embodiment, the edges of the handle assembly 102 contacting the palm or fingers of the user have a minimum radius of approximately 0.040", unless the material has a durometer of 70A or less.

FIG. 27 illustrates one embodiment of an ultrasonic surgical instrument 100. In the illustrated embodiment, a cross-sectional view of the ultrasonic transducer 114 is shown within a partial cutaway view of the handle assembly 102. One embodiment of the ultrasonic surgical instrument 100 comprises the ultrasonic signal generator 116 coupled to the ultrasonic transducer 114, comprising a hand piece housing 198, and an ultrasonically actuatable single or multiple element end effector assembly 112. As previously discussed, the end effector assembly 112 comprises the ultrasonically actuatable blade 152 and the clamp arm 150. The ultrasonic transducer 114, which is known as a "Langevin stack", generally includes a transduction portion 200, a first resonator portion or end-bell 202, and a second resonator portion or fore-bell 204, and ancillary components. The total construction of these components is a resonator. The ultrasonic transducer 114 is preferably an integral number of one-half system wavelengths (nλ/2; where "n" is any positive integer; e.g., n=1, 2, 3 . . . ) in length as will be described in more detail later. An acoustic assembly 206 includes the ultrasonic transducer 114, a nose cone 208, a velocity transformer 218, and a surface 210.

It will be appreciated that the terms "proximal" and "distal" are used herein with reference to a clinician gripping the handle assembly 102 of the handle assembly 102. Thus, the end effector assembly 112 is distal with respect to the more proximal handle assembly 102 of the handle assembly 102. It will be further appreciated that, for convenience and clarity, spatial terms such as "top" and "bottom" also are used herein with respect to the clinician gripping the handle assembly 102. However, surgical instruments are used in many orientations and positions, and these terms are not intended to be limiting and absolute.

In one embodiment, the distal end of the end-bell 202 is connected to the proximal end of the transduction portion 200, and the proximal end of the fore-bell 204 is connected to the distal end of the transduction portion 200. The fore-bell 204 and the end-bell 202 have a length determined by a number of variables, including the thickness of the transduction portion 200, the density and modulus of elasticity of the material used to manufacture the end-bell 202 and the fore-bell 22, and the resonant frequency of the ultrasonic transducer 114. The fore-bell 204 may be tapered inwardly from its proximal end to its distal end to amplify the ultrasonic vibration amplitude as the velocity transformer 218, or alternately may have no amplification. A suitable vibrational frequency range may be about 20 Hz to 120 kHz and a well-suited vibrational frequency range may be about 30-100 kHz. A suitable operational vibrational frequency may be approximately 55.5 kHz, for example.

In one embodiment, the piezoelectric elements 212 may be fabricated from any suitable material, such as, for example, lead zirconate-titanate, lead meta-niobate, lead titanate, barium titanate, or other piezoelectric ceramic material. Each of positive electrodes 214, negative electrodes 216, and the piezoelectric elements 212 has a bore extending through the center. The positive and negative electrodes 214 and 216 are electrically coupled to wires 220 and 222, respectively. The wires 220 and 222 are encased within the cable 118 and electrically connectable to the ultrasonic signal generator 116.

The ultrasonic transducer 114 of the acoustic assembly 206 converts the electrical signal from the ultrasonic signal generator 116 into mechanical energy that results in primarily a standing acoustic wave of longitudinal vibratory motion of the ultrasonic transducer 114 and the blade 152 portion of the end effector assembly 112 at ultrasonic frequencies. In another embodiment, the vibratory motion of the ultrasonic transducer may act in a different direction. For example, the vibratory motion may comprise a local longitudinal component of a more complicated motion of the tip of the elongated endoscopic shaft assembly 110. A suitable generator is available as model number GEN04, from Ethicon Endo-Surgery, Inc., Cincinnati, Ohio. When the acoustic assembly 206 is energized, a vibratory motion standing wave is generated through the acoustic assembly 206. The ultrasonic surgical instrument 100 is designed to operate at a resonance such that an acoustic standing wave pattern of predetermined amplitude is produced. The amplitude of the vibratory motion at any point along the acoustic assembly 206 depends upon the location along the acoustic assembly 206 at which the vibratory motion is measured. A minimum or zero crossing in the vibratory motion standing wave is generally referred to as a node (i.e., where motion is minimal), and a local absolute value maximum or peak in the standing wave is generally referred to as an anti-node (i.e., where local motion is maximal). The distance between an anti-node and its nearest node is one-quarter wavelength (λ/4).

The wires 220 and 222 transmit an electrical signal from the ultrasonic signal generator 116 to the positive electrodes 214 and the negative electrodes 216. The piezoelectric elements 212 are energized by the electrical signal supplied from the ultrasonic signal generator 116 in response to an actuator 224, such as a foot switch, for example, to produce an acoustic standing wave in the acoustic assembly 206. The electrical signal causes disturbances in the piezoelectric elements 212 in the form of repeated small displacements resulting in large alternating compression and tension forces within the material. The repeated small displacements cause the piezoelectric elements 212 to expand and contract in a continuous manner along the axis of the voltage gradient, producing longitudinal waves of ultrasonic energy. The ultrasonic energy is transmitted through the acoustic assembly 206 to the blade 152 portion of the end effector assembly 112 via a transmission component or an ultrasonic transmission waveguide portion 164 of the elongated endoscopic shaft assembly 110.

In one embodiment, in order for the acoustic assembly 206 to deliver energy to the blade 152 portion of the end effector assembly 112, all components of the acoustic assembly 206 must be acoustically coupled to the blade 152. The distal end of the ultrasonic transducer 114 may be acoustically coupled at the surface 210 to the proximal end of the ultrasonic transmission waveguide 164 by a threaded connection such as a stud 226.

In one embodiment, the components of the acoustic assembly 206 are preferably acoustically tuned such that the length of any assembly is an integral number of one-half wavelengths (n$\lambda$/2), where the wavelength $\lambda$ is the wavelength of a pre-selected or operating longitudinal vibration drive frequency $f_d$ of the acoustic assembly 206. It is also contemplated that the acoustic assembly 206 may incorporate any suitable arrangement of acoustic elements.

In one embodiment, the blade 152 may have a length substantially equal to an integral multiple of one-half system wavelengths (n$\lambda$/2). A distal end of the blade 152 may be disposed near an antinode in order to provide the maximum longitudinal excursion of the distal end. When the transducer assembly is energized, the distal end of the blade 152 may be configured to move in the range of, for example, approximately 10 to 500 microns peak-to-peak, and preferably in the range of about 30 to 150 microns at a predetermined vibrational frequency of 55 kHz, for example.

In one embodiment, the blade 152 may be coupled to the ultrasonic transmission waveguide 164. The blade 152 and the ultrasonic transmission waveguide 164 as illustrated are formed as a single unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the blade 152 may be separable (and of differing composition) from the ultrasonic transmission waveguide 164, and coupled by, for example, a stud, weld, glue, quick connect, or other suitable known methods. The length of the ultrasonic transmission waveguide 164 may be substantially equal to an integral number of one-half wavelengths (n$\lambda$/2), for example. The ultrasonic transmission waveguide 164 may be preferably fabricated from a solid core shaft constructed out of material suitable to propagate ultrasonic energy efficiently, such as the titanium alloy discussed above (i.e., Ti6Al4V) or any suitable aluminum alloy, or other alloys, for example.

In one embodiment, the ultrasonic transmission waveguide 164 comprises a longitudinally projecting attachment post at a proximal end to couple to the surface 210 of the ultrasonic transmission waveguide 164 by a threaded connection such as the stud 226. The ultrasonic transmission waveguide 164 may include a plurality of stabilizing silicone rings or compliant supports 168 (FIG. 14) positioned at a plurality of nodes. The silicone rings 168 dampen undesirable vibration and isolate the ultrasonic energy from an outer protective sheath 166 (FIG. 14) assuring the flow of ultrasonic energy in a longitudinal direction to the distal end of the blade 152 with maximum efficiency.

In various embodiments a rotation knob may be located in a proximal end of the ultrasonic surgical instrument housing. The proximal rotation knob may be accessed easily with the thumb or index finger and substantially reduces any obstructions or "reach" issues that may be associated with a distally located rotation know. Several embodiments of ultrasonic surgical instruments comprising a proximal rotation knob are described with reference to FIGS. 28-32.

Figure 28:
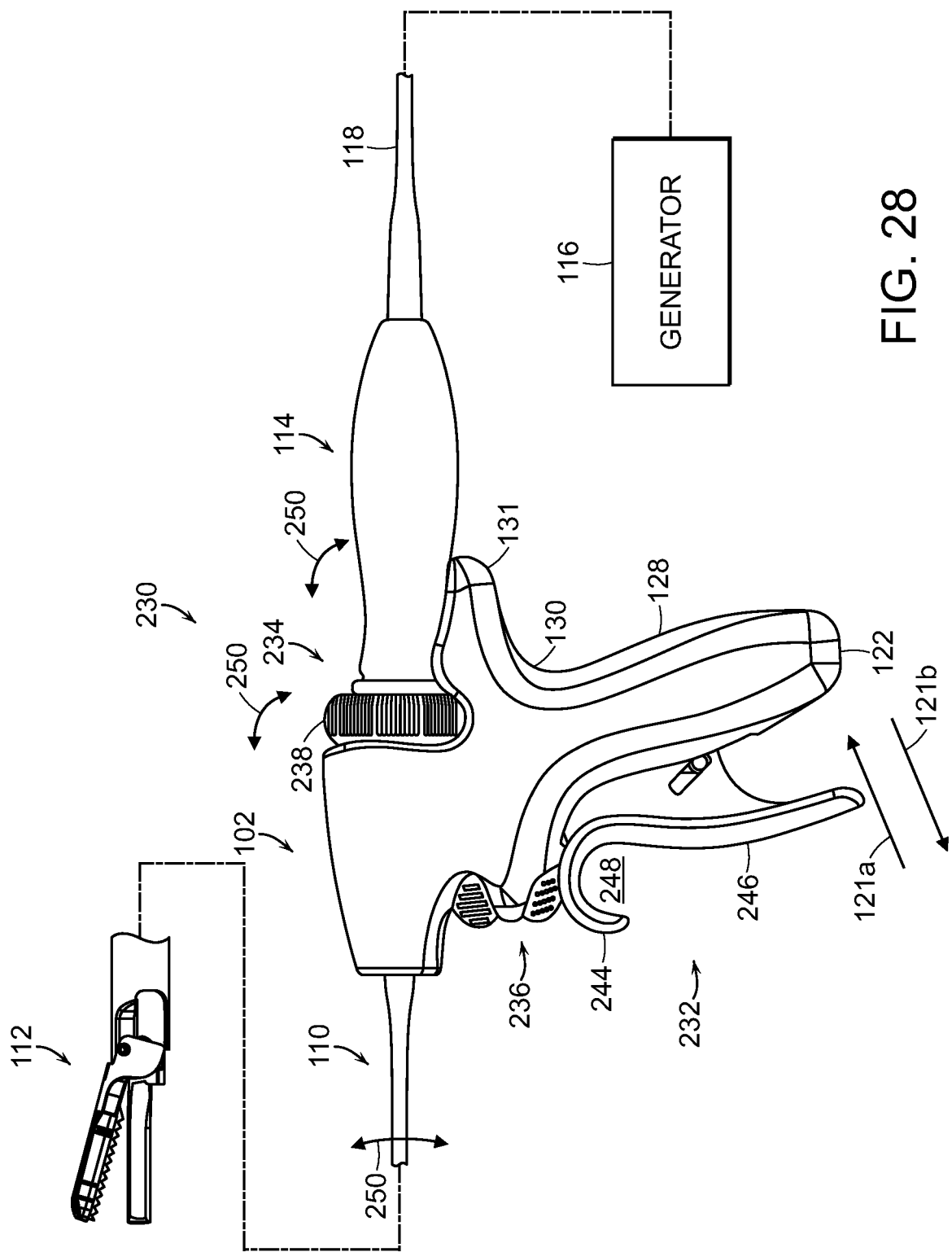
FIG. 28 is a right side view of one embodiment of an ultrasonic surgical instrument comprising a proximal rotation knob.

FIG. 28 is a right side view of one embodiment of an ultrasonic surgical instrument 230 comprising a proximal rotation knob 238. In the illustrated embodiment, the proximal rotation knob 238 may be located at a proximal end of the handle assembly 102. The proximal rotation knob 238 may be accessed easily with the thumb or index finger and substantially reduces any obstructions or "reach" issues that may be associated with a distally located rotation knob. The ultrasonic surgical instrument 230 may be employed in various surgical procedures including endoscopic or traditional open surgical procedures. The ultrasonic surgical instrument 230 comprises the handle assembly 102, a handle assembly 232, a proximal rotation assembly 234, a switch assembly 236, the elongated endoscopic shaft assembly 110, and the end effector assembly 112 comprising elements to mutually grasp, cut, and coagulate tubular vessels and/or tissue. The proximal rotation assembly 234 comprises a proximal rotation knob 238 that mechanically engages the ultrasonic transducer 114 housing. The ultrasonic surgical instrument 230 is adapted to receive an ultrasonic transducer 114 that is mechanically engaged to the elongated endoscopic shaft assembly 110 and portions of the end effector assembly 112. The ultrasonic transducer 114 is electrically coupled to a generator 116 via a cable 118. Although the majority of the figure drawings depict a multiple end effector assembly 112 for use in connection with endoscopic surgical procedures, the ultrasonic apparatus may be employed in more traditional open surgical procedures. For purposes herein, the ultrasonic surgical instrument 100 is described in terms of an endoscopic instrument; however, it is contemplated that an open version of the ultrasonic surgical instrument 230 also may include the same or similar operating components and features as described herein.

In one embodiment, the handle assembly 232 comprises a trigger 246 and the fixed handle 122 previously described. The fixed handle 122 is integrally associated with the handle assembly 102 and the trigger 246 is movable relative to the fixed handle 122 as explained in more detail below with respect to the operation of the ultrasonic surgical instrument 230. The fixed handle 122 and the trigger 246 comfortably interface with the user. The trigger 246 moves in direction 121A toward the fixed handle 122 when the user applies a squeezing force against the trigger 246. A spring element 175 (FIG. 14) causes the trigger 246 to move in direction 121B when the user releases the squeezing force against the trigger 246. The trigger 246 comprises an elongated trigger hook 244, which defines an aperture 248 between the elongated trigger hook 244 and the fixed handle 122. The aperture 248 is suitably sized to receive one or multiple fingers of the user therethrough. The trigger 246 also may comprise a contact portion (not shown), which may be molded over portions of the trigger 246. The overmolded contact portion provides a more comfortable contact surface for outward control of the trigger 246 in direction 121B. In one embodiment, the overmolded contact portion may be provided over a portion of the elongated trigger hook 244. For example, the overmolded contact portion may be provided over the distal and top surfaces of the inner portion of the elongated trigger hook 244 to provide cushion where it is needed by the user. The proximal surface of the elongated trigger hook 244 is not coated and remains bare substrate (e.g., polycarbonate) to enable the fingers to slide in and out of the aperture 248 more easily. In other embodiments, the elongated trigger hook 244 may incorporate overmolded contact surfaces comprising pliable, resilient, flexible polymeric materials such as polyurea elastomers made by VersaFlex, Inc., for example. The elongated trigger hook 244 may incorporate the overmolded contact surface portion to provide added comfort or a more secure grip to the user. The overmolded contact surface portion on the top portion of the interior portion of the elongated trigger hook 244 alleviates an edge pressure point on the user's finger as it enters the aperture 248. The fixed handle 122 comprises proximal contact surface 128 and a grip anchor or saddle surface 130 as previously discussed with reference to FIGS. 1-25.

In use, the proximal rotation knob 238 allows users to rotate the elongated endoscopic shaft assembly 110, control the jaws of the clamping mechanism of the end effector assembly 112, and activate the rocker switches 132 simultaneously, which creates new uses for the device for experienced users.

Figure 29:
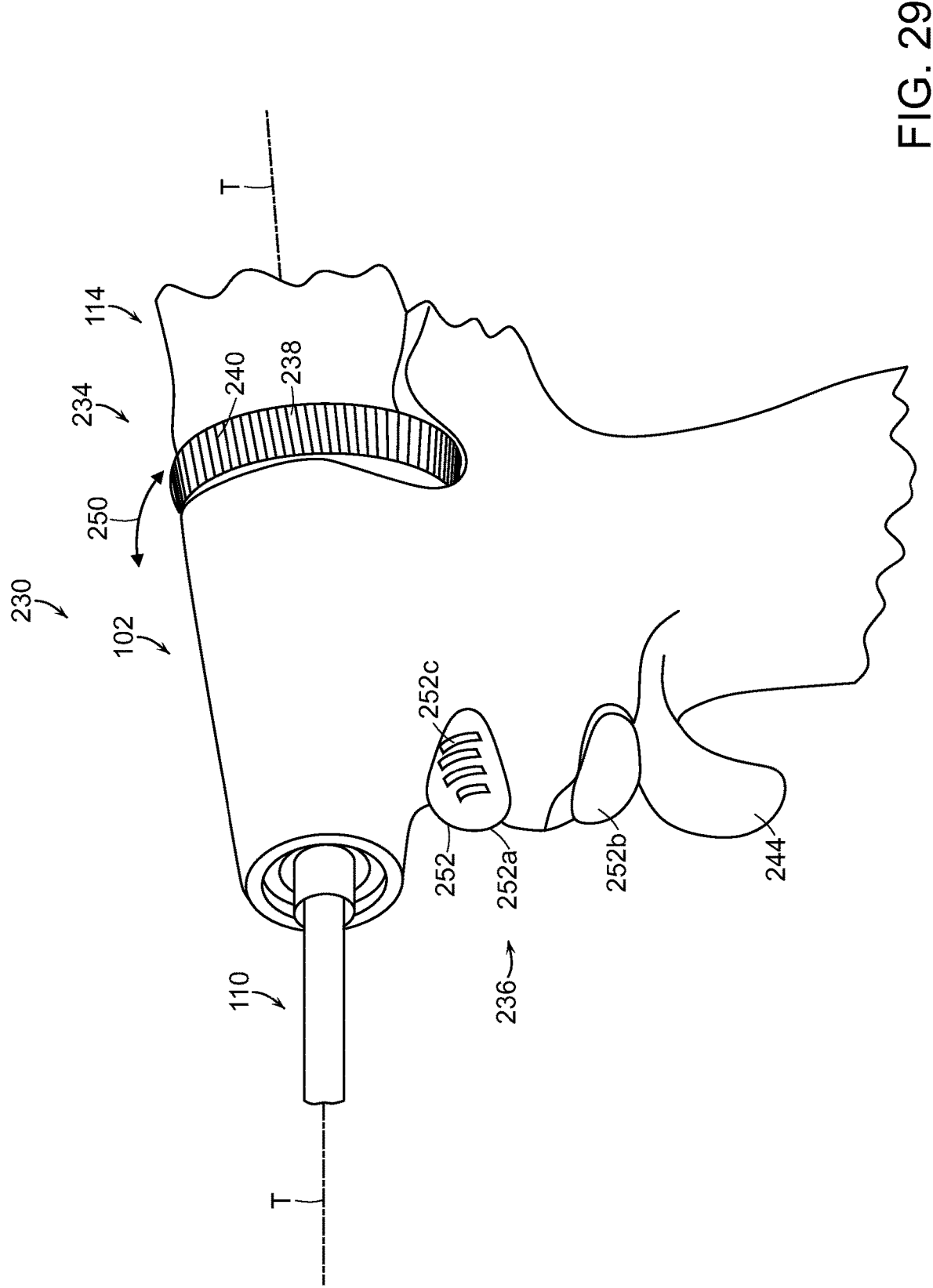
FIG. 29 is an enlarged right perspective view of one embodiment of the ultrasonic surgical instrument shown in FIG. 28

FIG. 29 is an enlarged right perspective view of one embodiment of the ultrasonic surgical instrument 230 shown in FIG. 28. In illustrated embodiment, the proximal rotation assembly 234 comprises a rotation knob 238 or ring formed of pliable, resilient, flexible polymeric materials including Versaflex® TPE alloys made by GLS Corporation, for example. In one embodiment, the proximal rotation knob 238 may be located on a proximal portion of the handle assembly 102. The user may operate the proximal rotation knob 238 with either the thumb or the index finger. Using the thumb frees up the index finger to more easily and effectively access the toggle switch 252 located on the distal end of the handle assembly 102. The proximal rotation knob 238 may be constructed in multiple elements. One element may comprise a siliconized polycarbonate component overmolded with a resilient layer formed of elastomeric materials, thermoplastic rubber known as Santoprene®, other thermoplastic vulcanizates (TPVs), or elastomers, for example. The elastomeric layer provides a secure grip for the user on the outer edge of the proximal rotation knob 238, and also protrudes through an inner polycarbonate ring (not shown) to form "gripper" ribs that firmly grip the exterior housing of the ultrasonic transducer 114. Therefore, the proximal rotation knob 238 securely grips the ultrasonic transducer 114. The ultrasonic transducer 114 is securely mechanically engaged to the elongated endoscopic shaft assembly 110, such that the entire elongated endoscopic shaft assembly 110 can be rotated when the proximal knob 238 is rotated. The proximal rotation assembly 234 comprising the proximal rotation knob 238 provides a smoother, easier rotation for better control and ease of use. The proximal rotation knob 238 stabilizes the interior mechanism located in front of the ultrasonic transducer 114 to reduce any potential "rattles." The proximal rotation knob 238 is configured to mechanically engage the housing of the ultrasonic transducer 114 such that rotation of the proximal rotation knob 238 results in rotation of the ultrasonic transducer 114 and the elongated endoscopic shaft assembly 110 in the same direction 250. The proximal rotation knob 238 comprises a plurality of flutes 240 or ribs. These flutes 240 may be engaged by a finger to rotate the rotation knob 238. The proximal rotation knob 238 may comprise "scallops" or flutes formed of flutes 240 to provide a more precise rotational grip. In one embodiment, the proximal rotation knob 238 may comprise six flutes. In other embodiments, any suitable number of flutes may be employed. The proximal rotation knob 238 may be formed of a softer polymeric material overmolded onto the hard plastic material.

The ultrasonic transducer 114 may be inserted through the proximal rotation knob 238 until the distal end of the ultrasonic transducer 114 screws in or is snapped onto the ultrasonic transmission waveguide 164 by the stud 226 (FIG. 27), for example. The elastomeric gripper ribs of the proximal rotation knob 238 provide a snug fit during insertion between the elastomeric gripper ribs and the outer diameter of the ultrasonic transducer 114. The gripper grip, however, is not tight enough to create difficulty in assembling the components. When the ultrasonic transducer 114 is threaded into the female portion of the handle 102 within the proximal opening 156, the proximal rotation knob 238 is free to rotate along with the ultrasonic transducer 114 and also is free to slide longitudinally along the longitudinal axis A along the outer surface of the ultrasonic transducer 114 as the final threads pull the ultrasonic transducer 114 forward into the elongated endoscopic shaft assembly 110. After the ultrasonic transducer 114 is completely assembled with a torque wrench, the proximal rotation knob 238 remains free to spin, gripping the ultrasonic transducer 114 and thereby rotating the entire elongated endoscopic shaft assembly 110. The gripper ribs secure the outer surface of the ultrasonic transducer 114 enough to facilitate rotation even under surgical conditions in which the assembly or the user's gloves may be wet, for example.

In one embodiment, the switch assembly 236 may be implemented as a MIN/MAX rocker-style or "toggle" switch 252. In one position, the MIN/MAX rocker-style switch (or "toggle" style) buttons create an easily accessible location for power activation with minimal (or almost no) repositioning of the hand grip, making it suitable to maintain control and keep attention focused on the surgical site (e.g., a monitor in a laparoscopic procedure). The switch assembly 236 comprises a toggle switch 252 partially located within the handle assembly 102. The switch assembly 236 comprises a rocker switch 252 implemented as a single component with a central pivot located inside the handle assembly 102, to eliminate the possibility of simultaneous activation. The rocker switch 252 may wrap around the side of the fixed handle 122 slightly to be easily accessible by variable finger lengths. The toggle switch 252 is coupled to the generator 116 to control the activation of the ultrasonic transducer 114. The toggle switch 252 comprises one or more electrical power setting switches to activate the ultrasonic transducer 114 to set one or more power settings for the ultrasonic transducer 114. In one embodiment, the toggle switch 252 comprises a first electrical contact portion 252a and a second electrical contact portion 252b to set the power setting of the ultrasonic transducer 114 between a minimum power level (e.g., MIN) and maximum power level (e.g., MAX). The first and second contact portions 252a,b of the toggle switch 252 may be overmolded with a soft polymeric material including Versaflex® TPE alloys made by GLS Corporation, for example. The overmolding portion may be useful for tactile identification or differentiation of the toggle switch 252 contact portions 252a,b from the rest of the handle assembly 102. The contact portions 252a,b may be configured to wrap around the fixed handle 122 to some extent to allow greater freedom of access to activation in awkward positions or for shorter fingers. As previously discussed, on of the contact portions 252a,b may comprise a texture or tactile surface that enables the user to differentiate between the first contact portion 252a and the second contact portion 252b. Either the first contact portion 252a or the second contact portion 252b may comprise a plurality of textured ribs 252c to allow the user to differentiate the first contact portion 252a (MAX) from the second contact portion 252b (MIN).

The toggle switch 252 may be operated by the hand of the user. The user may easily access the first and second electrical contact portions 252a,b at any point while also avoiding inadvertent or unintentional activation at any time. The toggle switch 252 may be operated by the index finger of the user to activate power to the ultrasonic assembly 114 and/or control the power level of the ultrasonic assembly 114. The index finger may be employed to activate the first contact portion 252a to turn on the ultrasonic assembly 114 to a maximum (MAX) power level. The index finger may be employed to activate the second contact portion 252b to turn on the ultrasonic assembly 114 to a minimum (MIN) power level. The first contact portion 252a or the second contact portion 252b may comprise a texture to assist the user to differentiate between them using tactile feel without looking. For example, in the illustrated embodiment, the first contact portion 252a comprises a plurality of textured ribs 252c to enable the user to differentiate the first contact portion 252a (MAX) from the second contact portion 252b (MIN). Other textures or elements may be formed on either of the first or second contact portions 252a,b to enable the user to differentiate therebetween. The toggle switch 252 may be operated without the user having to look at the first or second contact portions 252a,b. This allows the user to focus entirely on the monitor view during a laparoscopic procedure. The user does not have to reposition their grip in order to operate the toggle switch 252 and can easily adjust the power ON/OFF or MIN/MAX while opening the jaws of the end effector assembly 112.

In one embodiment, the proximal rotation assembly 234 is rotatable without limitation in either direction 250 about a longitudinal axis "T" (FIG. 13). The proximal rotation assembly 234 is mechanically engaged to the housing of the ultrasonic transducer 114, which is mechanically engaged to the elongated endoscopic shaft assembly 110. The proximal rotation assembly 234 is located at a proximal portion of the handle assembly 102. The proximal rotation assembly 234 comprises internal protrusions to mechanically engage the housing of the ultrasonic transducer 114, which is mechanically engaged to the elongated endoscopic shaft assembly 110. The rotation knob 238 may be engaged by the index finger to rotate the elongated endoscopic shaft assembly 110 360° in direction 250.

In one embodiment, the ultrasonic surgical instrument 230 may be configured with ergonomic features to enable the user to easily access and operate the multiple functions and controls of the instrument. Accordingly, the index finger may be used to operate the distal rotation knob 238 located at the proximal end of the handle assembly 102. The rotation knob 238 is mechanically engaged to the hosing of the ultrasonic transducer 114, which is mechanically engaged and acoustically coupled to the ultrasonic transmission waveguide 164 (FIG. 14). Thus, the index finer can be used to rotate the rotation knob 238 to rotate shaft of the ultrasonic transmission waveguide 164 to locate the end effector assembly 112 in the proper orientation during a surgical procedure. The MIN/MAX power buttons of the rocker switch 252 are suitably located on the fixed handle 122 of the instrument 230 so that they may be operated with the index finger. Accordingly, the index finger can be used to rotate the shaft of the endoscopic portion 110 to orient the jaws of the end effector assembly 112 in a desired position and to activate the power level of the ultrasonic transducer 114.

Figure 30:
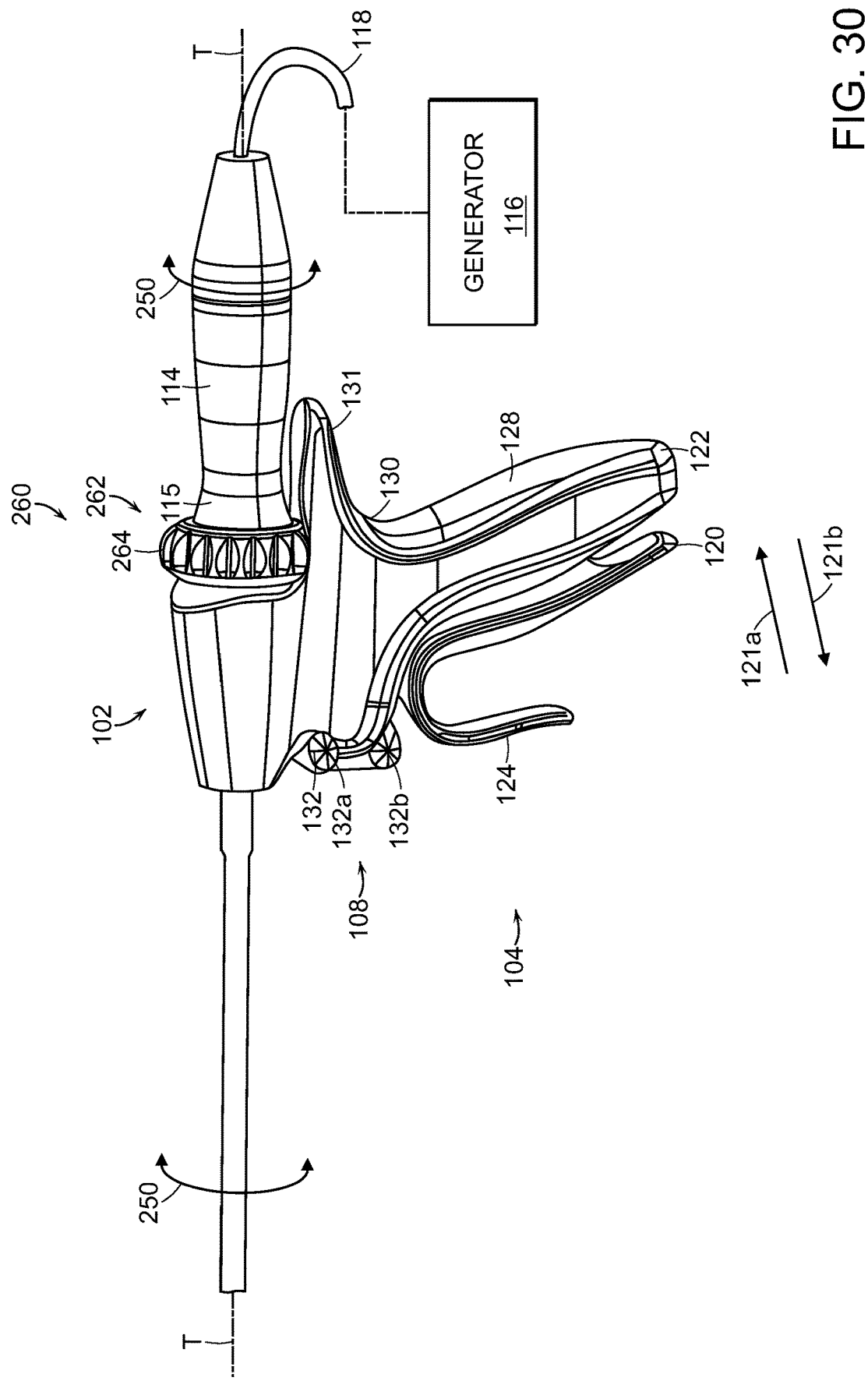
FIG. 30 is a right side view of one embodiment of an ultrasonic surgical instrument comprising a proximal rotation assembly.
Figure 31:
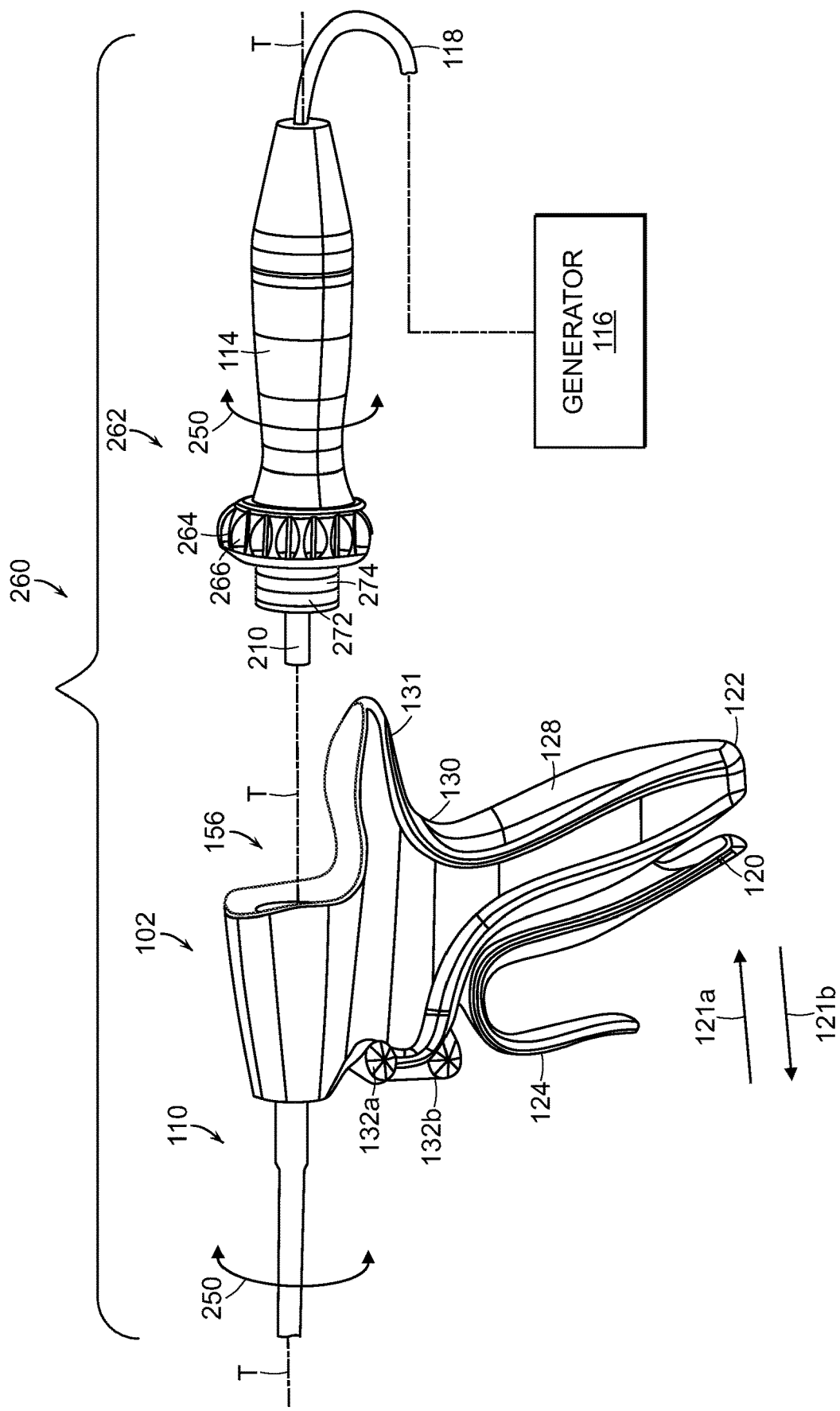
FIG. 31 is a right side view of one embodiment of the ultrasonic surgical instrument shown in FIG. 30 with the proximal rotation assembly and the ultrasonic transducer detached from the housing.
Figure 32:
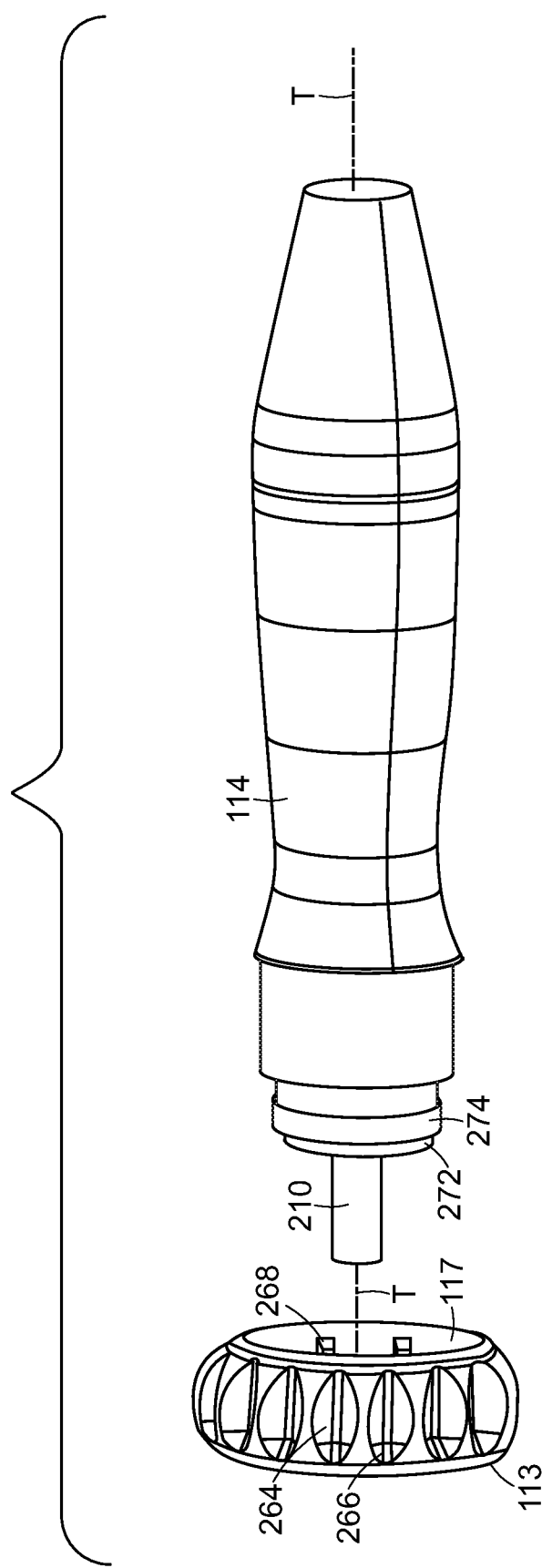
FIG. 32 is a right side view of the proximal rotation assembly shown in FIGS. 30 and 31 detached from the ultrasonic transducer.

FIGS. 30-32 illustrate one embodiment of an ultrasonic surgical instrument 260 comprising a proximal rotation assembly 262. In the illustrated embodiment, the ultrasonic surgical instrument 260 comprising the proximal rotation assembly 262 may be employed in various surgical procedures including endoscopic or traditional open surgical procedures. In one embodiment, the ultrasonic surgical instrument 260 may be configured with ergonomic features to enable the user to easily access and operate the multiple functions and controls of the instrument. The proximal rotation assembly 262 may be located on a proximal end of the handle assembly 102 and may be accessed easily with the thumb or finger (e.g., the index finger). This substantially reduces any obstructions or "reach" issues that may be associated with a rotation knob located at the distal end of the handle assembly 102. In addition, use of the thumb frees up the index finger, for example, to more easily and effectively access the toggle switch 132 located at the distal end of the handle assembly 102.

In one embodiment, the proximal rotation assembly 262 comprises a ring shaped proximal rotation knob 264. The proximal rotation knob 264 is configured to mechanically or frictionally engage the outer surface 115 of the ultrasonic transducer 114. As previously discussed, the ultrasonic transducer 114 is mechanically engaged to the elongated endoscopic shaft assembly 110. Thus, rotating the rotation knob 264 rotates the ultrasonic transducer 114 and the elongated endoscopic shaft assembly 110 in the same direction 250. The proximal rotation knob 264 comprises a plurality of flutes 266 (e.g., ribs or scallops) formed on an exterior portion 113 thereof. The flutes 266 may be engaged by the thumb or finger of the user to rotate the proximal rotation knob 264 360° in either direction 250 about the longitudinal axis "T". The flutes 266 of the proximal rotation knob 264 also provide a precise rotational grip. In one embodiment, the rotation knob 264 may comprise any suitable number of flutes 226 to provide a precise rotational grip. The proximal rotation knob 264 also comprises a plurality of radial projections 268 formed on an interior portion 117 thereof. The radial projections 268 may be formed of or may coated with a pliable, resilient polymeric material to securely frictionally engage the outer surface 115 of the ultrasonic transducer 114. The radial projections 268 are dimensioned to form a snug or tight fit between the outer surface 115 of the ultrasonic transducer 114 and the proximal rotation knob 264. The ultrasonic transducer 114 is securely mechanically engaged to the ultrasonic transmission waveguide 164 portion of the elongated endoscopic shaft assembly 110 by the surface 210 and the stud 266 (FIG. 27). Accordingly, as the securely gripped proximal rotation knob 264 is rotated in direction 250 so are the ultrasonic transducer 114 and the entire elongated endoscopic shaft assembly 110. The proximal rotation knob 264 provides a smooth, easy rotation of the ultrasonic transducer 114 and the elongated endoscopic shaft assembly 110 using the thumb or finger, providing increased control to the surgeon. The ultrasonic transducer 114 comprises a distal rim portion 272 with a circumferential ridge 274 to engage a groove (not shown) formed within the inner wall of the proximal opening 156.

As previously discussed, in one embodiment, the proximal rotation knob 264 is securely mechanically or frictionally engaged to the outer housing of the ultrasonic transducer 114, which is mechanically engaged and acoustically coupled to the ultrasonic transmission waveguide 164 (FIG. 14). For example, during a surgical procedure either the thumb or index finger may be used to control the rotation of the ultrasonic transmission waveguide 164 shaft to locate the jaws of the end effector assembly 112 in a suitable orientation. The middle and/or the other lower fingers may be used to squeeze the trigger 120 and grasp tissue within the jaws. Once the jaws are located in the desired position and the jaws are clamped against the tissue, the index finger can be used to activate the toggle switch 132 to adjust the power level of the ultrasonic transducer 114 and treat the tissue. Once the tissue has been treated, the user the may release the trigger 120 and push outwardly in the distal direction against the elongated trigger hook with the middle and/or lower fingers to open the jaws of the end effector assembly 112. This basic procedure may be performed without the user having to adjust their grip on the handle assembly 102.

In one embodiment, the proximal rotation knob 264 may be formed of pliable, resilient, flexible polymeric materials including Versaflex® TPE alloys made by GLS Corporation, for example. Pliable, resilient, and flexible polymeric materials provide a secure and comfortable grip for the user on the outer exterior portion of the proximal rotation knob 264.

The proximal rotation knob 264 may be provided separately as an accessory that may be packaged with the ultrasonic surgical instrument 260 but not attached thereto. The proximal rotation knob 264 may be a doughnut or ring shaped single component formed of a substantially pliable, resilient, and flexible polymeric material. The proximal rotation knob 264 may be inserted over the outer surface 115 of the ultrasonic transducer 114, e.g., handpiece HP054 or HPBLUE, both manufactured by Ethicon Endo-Surgery. The radial projections 268 or "gripper ribs" formed on the interior portion 117 of the proximal rotation knob 264 securely engage the outer surface 115 diameter of the ultrasonic transducer 114. The radial projections 268 may be formed of the same pliable, resilient, flexible polymeric material as the proximal rotation knob and define a diameter that is undersized relative to the outer surface 115 diameter of the ultrasonic transducer 114 to create a friction interference fit. The radial projections 268, however, do not engage the outer surface 115 diameter of the ultrasonic transducer 114 so tightly as to make it difficult to assemble the components.

Once the proximal rotation knob 264 is located on the outside surface 115 of the ultrasonic transducer 114, the transducer 114 is inserted through the proximal opening 156 of the instrument handle assembly 102 the surface 210 is attached to the ultrasonic transmission waveguide 164 by the stud 226 (FIG. 27). In other embodiments, the distal end of the ultrasonic transducer 114 may be snapped onto the proximal end of the ultrasonic transmission waveguide 164. Once the distal end of the ultrasonic transducer 114 is located within the proximal opening 156 of the instrument handle assembly 102, the proximal rotation knob 264 is free to rotate along with the ultrasonic transducer 114 and also is free to slide longitudinally along the longitudinal axis T along the outer surface of the ultrasonic transducer 114 as the final threads of the stud 226 pull the ultrasonic transducer 114 forward in the proximal direction towards the elongated endoscopic shaft assembly 110. After the ultrasonic transducer 114 is completely assembled with a torque wrench, the proximal rotation knob 264 remains free to rotate, gripping the ultrasonic transducer 114 and thereby rotating the entire elongated endoscopic shaft assembly 110. The radial projections 268 frictionally secure the outer surface of the ultrasonic transducer 114 with adequate force to facilitate rotation of the elongated endoscopic shaft assembly 110 even surgical conditions in which the exterior of the assembly or the surgeon's gloves may be wet. After use the proximal rotation knob 264 may be removed from the ultrasonic transducer 114 and either discarded or sterilized as described below.

Figure 33:
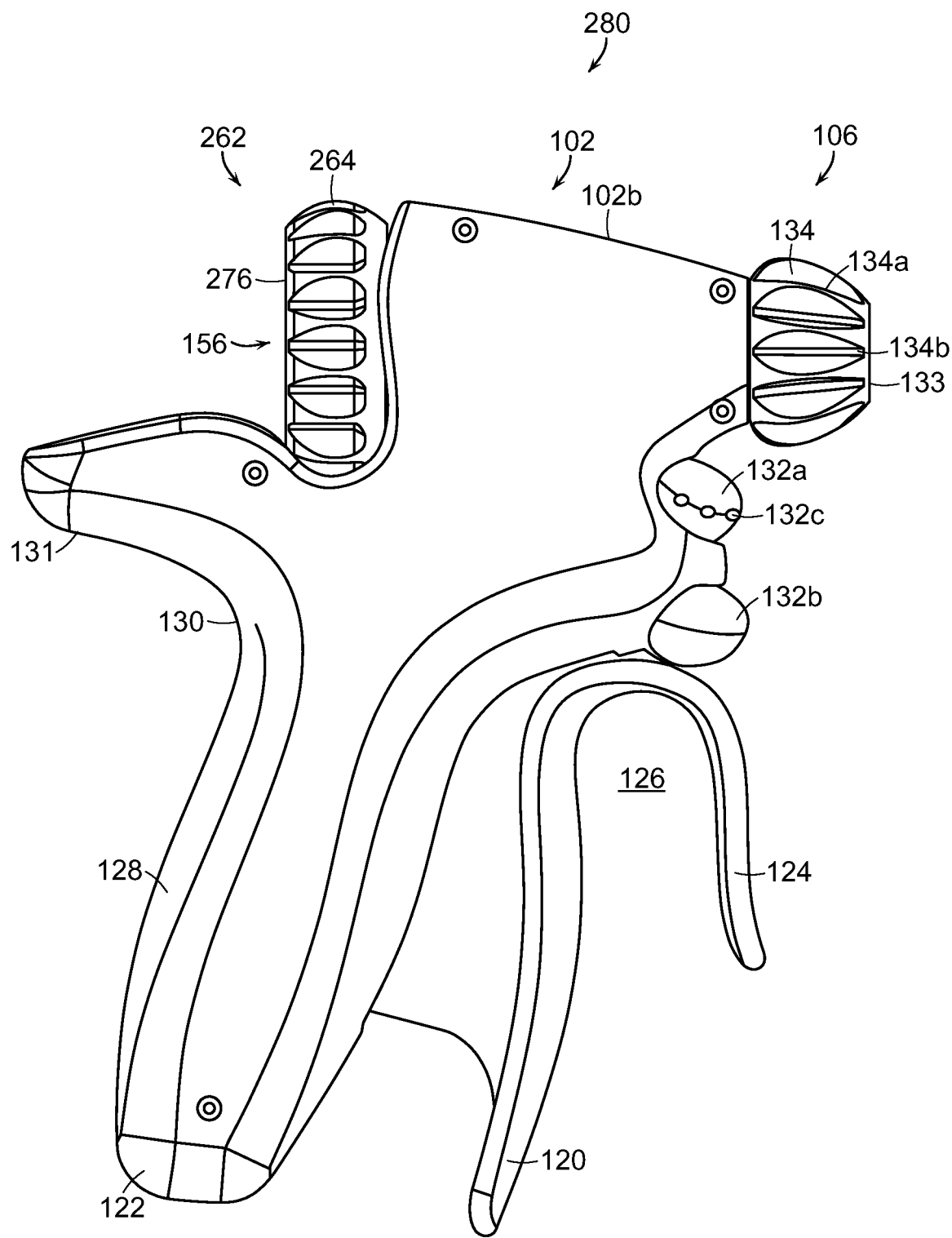
FIG. 33 is a left side view of one embodiment of handle assembly for an ultrasonic surgical instrument comprising both proximal and distal rotation assemblies.

FIG. 33 is a left side view of one embodiment of handle assembly 280 for an ultrasonic surgical instrument comprising both proximal and distal rotation assemblies. In one embodiment, the handle assembly 280 comprises multiple rotation controls that may be accessible in a multitude of hand positions and suitable for a multitude of hand sizes. In one embodiment, the handle assembly 280 comprises dual rotation controls comprising the distal rotation control knob 134 and the proximal rotation control knob 264, as previously described. In one embodiment, the handle assembly 280 comprises the distal rotation assembly 106 comprising the distal rotation knob 134 as previously described. In addition, the handle assembly 280 comprises the proximal rotation assembly 262 comprising the proximal rotation knob 264, as previously described.

Figure 34:
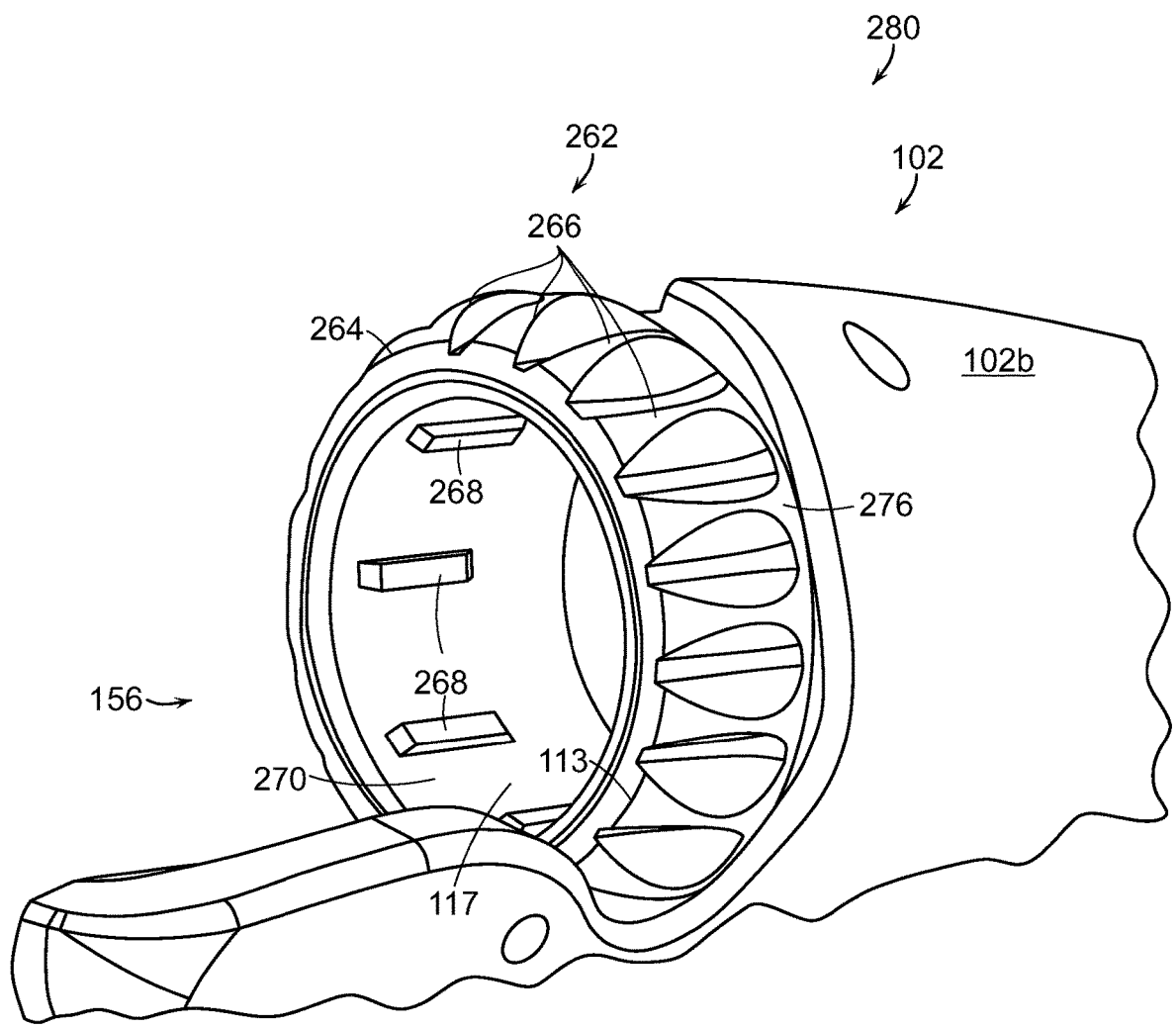
FIG. 34 is an enlarged partial left perspective view of one embodiment of the handle assembly shown in FIG. 33.

FIG. 34 is an enlarged partial left perspective view of one embodiment of the handle assembly 280. As shown in FIG. 34, in one embodiment the proximal rotation knob 264 is ring-shaped and comprises an external portion 113 and an interior portion 117. A plurality of flutes 266 are formed on an exterior surface 276 thereof. An internal surface 270 of the proximal rotation knob 264 comprises a plurality of radial projections 268 to frictionally engage the outer contours of the handpiece assembly of the ultrasonic transducer 114. As previously discussed, the proximal rotation knob 264 may be formed of pliable, resilient, flexible polymeric materials, for example.

With reference to both FIGS. 33 and 34, the combination of dual rotation controls such as the proximal rotation assembly 262 and the distal rotation assembly 106 provide several benefits. The dual rotation controls render the handle assembly 280 better suited for users with small hands and reduce fatigue because it employs a natural movement of the thumb and/or fingers. If the finger tip rotation control of the distal rotation knob 134 is difficult for a user with small hands to reach or the hand is located in an awkward position, the proximal rotation knob 264 provides the user with the option of using the proximal rotation knob 264 with their thumb to control the rotation of the elongated endoscopic shaft assembly 110.

The proximal rotation knob 264 and the distal rotation knob 134 may be used in combination to rotate the elongated endoscopic shaft assembly 110 in opposite directions to ease stress and fatigue and also to prevent the cable 118 (FIGS. 1, 27, 28, 30) from winding around the handpiece during use when only rotating in one direction. A right handed user, for example, may employ the index finger to rotate the distal rotation knob 134 clockwise and employ the thumb to rotate the proximal rotation knob 264 counter clockwise to ease finger fatigue and prevent the cable 118 from tangling. Thus, as the user may readily switch between clockwise and counter clockwise rotation methods the cable 118 becomes less tangled.

Additional benefits of the combination of the proximal rotation assembly 262 and the distal rotation assembly 106 include simultaneous multi-function use and ease of use in multiple hand positions. The proximal rotation knob 264 enables rotation control of the end effector assembly 112 with the thumb. This may be more comfortable and may allow finer rotation control for small handed users. As previously discussed, in use, the proximal rotation knob 264 allows users to rotate the elongated endoscopic shaft assembly 110, control the jaws of the clamping mechanism of the end effector assembly 112, and activate the rocker switches 132 simultaneously, which creates new uses for the device for experienced users. Providing the combination of distal and proximal rotation control lets the user select the most suitable rotation control depending on the position of the hand, e.g., neutral, supinated, pronated, awkward. Dual rotation is also less fatiguing because the natural movement of the finger and thumb are moved in a downward motion to effect rotation of control knobs. For example, the index finger may apply a downward force against the distal rotation knob 134 to rotate the elongated endoscopic shaft assembly 110 clockwise. Counter clockwise rotation of the distal rotation knob 134 requires an upward motion of the index finger, which may be awkward and slightly more fatiguing. The thumb may apply a downward force against the proximal rotation knob 264 to rotate the elongated endoscopic shaft assembly 110 counter clockwise. Thus, counter clockwise rotation of the elongated endoscopic shaft assembly 110 now requires a less awkward and fatiguing downward motion of the thumb motion. The dual rotation control configuration gives the user the option of selecting between a finger and a thumb to apply rotation to the elongated endoscopic shaft assembly 110, which causes less compounding fatigue on one muscle group. In either case, the user has the option of selecting the control configuration that is best suited for their physical attributes and styles.

Figure 35:
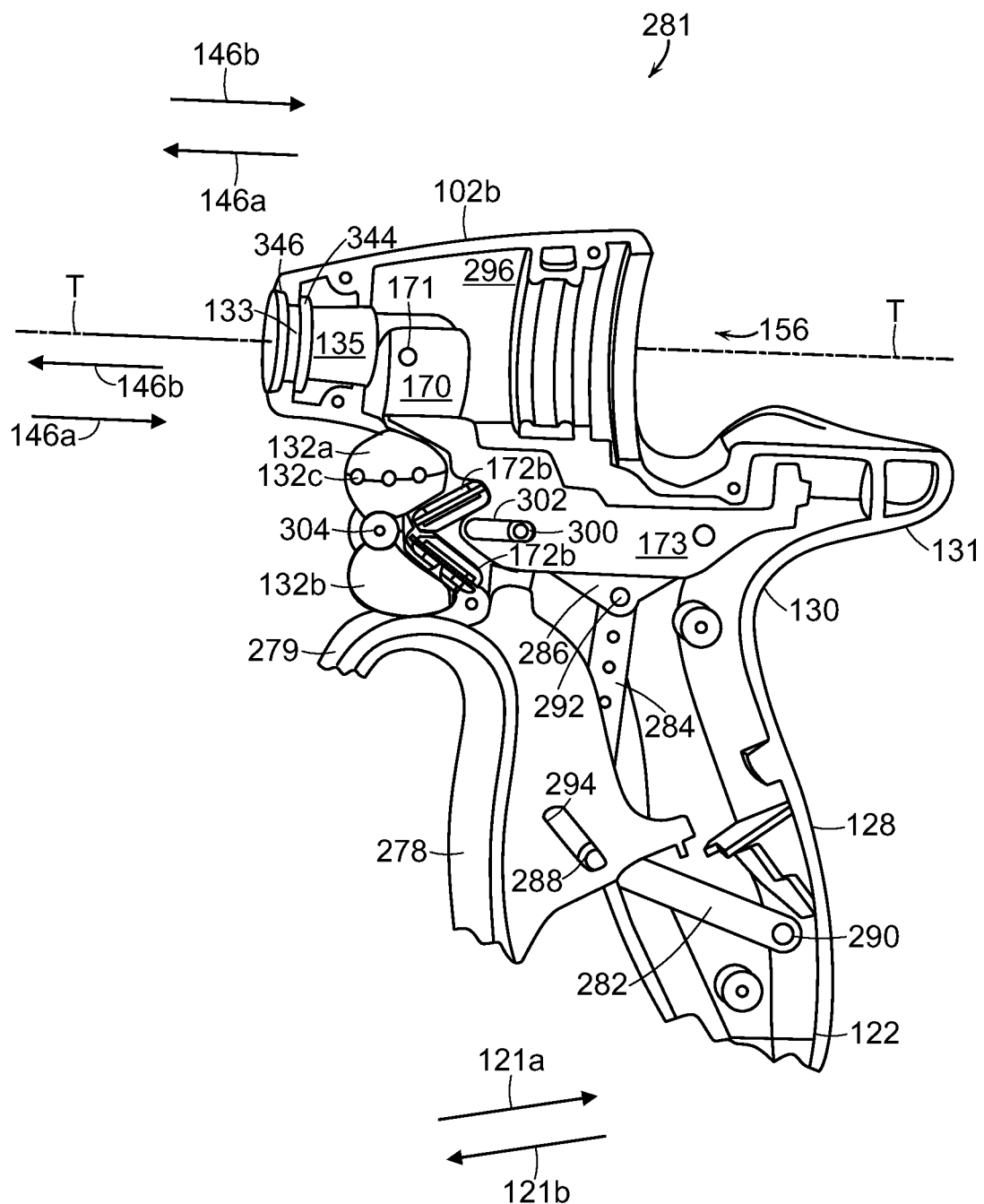
FIG. 35 illustrates a partial cut away view of one embodiment of a handle assembly for an ultrasonic surgical instrument.

FIG. 35 illustrates a partial cut away view of one embodiment of a handle assembly 281 for an ultrasonic surgical instrument. With reference now to FIG. 35 and FIGS. 10-12 and 14, in one embodiment, a trigger 278 actuates the yoke 170, which is mechanically engaged to the coupling elements 160 (FIG. 14) through various link members and the yoke 170. The coupling elements 160 are seated in the yoke 170 and locked in place with the pin 162 (FIG. 14) provided through an opening 171 in the yoke 170. The elongated endoscopic shaft assembly 110 is coupled to the yoke 170 by way of the coupling elements 160. The coupling elements 160 mechanically engage the hub 163 located at the proximal end of the outer tubular sheath 142. For example, the hub 163 of the outer tubular sheath 142 is retained in the yoke 170 by the pin 162. The proximal end of the reciprocating tubular actuating member 144 is mechanically engaged to the outer tubular sheath 142. Once locked into place, the yoke 170, the coupling elements 160 reciprocate within opening 296 in directions 146A,B along the longitudinal axis T to effect motion of the elongated endoscopic shaft assembly 110 in the same directions. The motion is in response to the trigger 278. Accordingly, as the trigger moves in directions 121A,B the yoke 170, the coupling elements 160, and the elongated endoscopic shaft assembly 110 move in corresponding directions 146A,B. Thus, when the trigger 278 is squeezed in direction 121A the reciprocating tubular actuating member 144 moves in direction 146A to close the jaw elements of the end effector assembly 112 in direction 148A as shown in FIGS. 10-12. The spring element 175 restores the movable trigger in direction 121B when the squeezing force is released. Accordingly, the yoke 170 and the reciprocating tubular actuating member 144 moves in direction 146B to open the jaws of the end effector assembly 112 in direction 148B as shown in FIGS. 10-12.

In the illustrated embodiment, the hub 133 is located within the first and second portions 102a,b of the handle assembly 102. A circumferential lip 344 is formed on a cylindrical sleeve portion 135 and is received within a circumferential groove 346 formed in the distal end of the handle assembly 102. The circumferential lip 344 and the circumferential groove 346 are dimensioned such that the cylindrical sleeve portion 135 is free to rotate within the circumferential groove 346. The hub 133 is free to rotate within the circumferential groove 346 when the first and second portions 102a,b of the handle assembly 102 are mated. The hub 133 is dimensioned and configured to receive the distal rotation knob 134.

In one embodiment, the trigger 278 is mechanically engaged to first and second link members 282, 284 at a movable first pivot point 288. The movable pivot point 288 is captured and moves within a first slot 294. At one end the first and second link members 282, 284 are pivotable at the first pivot point 288. At the other end of the first link member 282, the first link member is coupled to and is rotatable about a second pivot point 290. At the other end of the second link member 284, the second link member 284 is coupled to and is pivotable about a third pivot point 292. At one end the third link member 286 is coupled to the second link member 284 at the third pivot point 292. At the other end the third link member 286 is coupled to a fourth pivot 300, which is captured in and movable within a second slot 302. The yoke 170 is coupled to the third link member 286 at the fourth pivot 300. The yoke 170 is coupled to the coupling elements 160 and is part of the reciprocating yoke assembly 173. Accordingly, as the trigger 120 is squeezed in direction 121A, the first pivot point 288 moves downwardly within the first slot 294 pulling the second link member 284 and the third link member 286 downwardly. As the third link member 286 is pulled downwardly the yoke 170 is forced in direction directions 146A along the longitudinal axis T closing the jaw elements of the end effector assembly 112 in direction 148A. As the moveable trigger 120 is released, the spring element 182 forces the trigger 278 to move in direction 121B, which in turn forces the yoke to move in direction 146B along the longitudinal axis A opening the jaw elements of the end effector assembly 112 in direction 148B.

FIG. 36 is an enlarged partial view of one embodiment of the toggle switch 132 and the yoke assembly 173 within a housing portion of the handle assembly 281. The switch assembly 108 comprises the toggle switch 132 implemented as a single component with a central pivot 304 inside the handle assembly 102, to eliminate the possibility of simultaneous activation. The toggle switch 132 rotates about the central pivot 304 as the first projecting knob 132a and the second projecting knob 132b are actuated. The electrical element 172b electrically energizes the ultrasonic transducer 114 in accordance with the activation of the first or second projecting knobs 132a,b.

FIGS. 37-44 illustrate one embodiment of a handle assembly 310 for an ultrasonic surgical instrument comprising both proximal and distal rotation assemblies. In the illustrated embodiment, the handle assembly 310 comprises multiple rotation controls that may be accessible in a multitude of hand positions and for a multitude of hand sizes. In one embodiment, the handle assembly 310 comprises a housing 314 formed of a first portion 314a (not shown) and a second portion 314b. The handle assembly 310 comprises a proximal rotation assembly 312 and the distal rotation assembly 106 previously descried. The proximal rotation assembly 312 comprises a proximal rotation knob 334 and the distal rotation assembly 106 comprises the distal rotation knob 134.

In one embodiment, the handle assembly 310 comprises the distal rotation assembly 106 comprising the distal rotation knob 134 with the hub 133 and the flutes 134b as previously described. In addition, the handle assembly 310 comprises the proximal rotation assembly 312. The proximal rotation assembly 312 comprises the proximal rotation knob 334 attached to a cylindrical hub 335 and a plurality of flutes 336 formed on an exterior portion thereof. The cylindrical hub 335 comprises a circumferential lip 332 adapted and configured to engage a corresponding circumferential groove 328 formed in the housing 314. The circumferential lip 332 and the corresponding circumferential groove 328 are dimensioned to enable the cylindrical hub 335 to rotate freely within the circumferential groove 328. The cylindrical hub 335 comprises a plurality of slots 330 formed around a circumference thereof. The proximal rotation knob 334 comprises a plurality of radial projections 338 formed around a circumference thereof that correspond to the slots 330. The proximal rotation knob 334 may be formed of pliable, resilient, flexible materials. A portion of the plurality of radial projections 338 protrudes radially through the slots 330 to securely frictionally engage the outer surface of the ultrasonic transducer 114.

In one embodiment, the handle assembly 310 comprises a trigger 322 and a fixed handle 316. The fixed handle 316 is integrally associated with the handle housing 314 and the trigger 322 is movable relative to the fixed handle 316 as previously explained in detail in FIGS. 1-9 with respect to the operation of the ultrasonic surgical instrument 100. The fixed handle 316 and the trigger 322 comfortably interface with the user. The trigger 322 moves in direction 121A toward the fixed handle 316 when a squeezing force is applied against the trigger 322. A spring element 175 (FIG. 14) causes the trigger 322 to move in direction 121B and return to an original state when the user releases the squeezing force against the trigger 322.

In one embodiment, the trigger 322 comprises an elongated trigger hook 324 portion, which defines an aperture 126 between the elongated trigger hook 279 and the fixed handle 122. The aperture 126 is suitably sized to receive one or multiple fingers therethrough.

In one embodiment, the trigger 322 also may comprise a contact portion 322a molded over the substrate of the trigger 322. The overmolded portion 322a provides a more comfortable contact surface for outward control of the trigger 322 in direction 121B. In one embodiment, the overmolded portion 322a may be provided over a portion of the elongated trigger hook 324. For example, in the illustrated embodiment, the overmolded portion 322a contact surface is provided over the distal and top surfaces of the inner portion of the elongated trigger hook 324 to provide cushion where it is needed by the user. The proximal surface of the elongated trigger hook 324 is not coated and remains bare substrate (e.g., polycarbonate) to enable the fingers to slide in and out of the aperture 126 more easily.

In other embodiments, the elongated trigger hook 324 may incorporate an overmolded component formed of pliable, resilient, flexible polymeric materials including Versaflex® TPE alloys made by GLS Corporation, for example. The elongated trigger hook 324 may incorporate the overmolded portion 322a to provide added comfort or a more secure grip to the user. The overmolded contact portion 322a formed on a top portion of the interior portion of the elongated trigger hook 324 alleviates edge pressure points on the fingers as they enters the aperture 126. The top portion of the trigger hook 324 may comprise a concave region 325 to allow additional clearance for the second projecting knob 132b (not shown).

In one embodiment, the fixed handle 322 comprises a proximal contact surface 317 and a grip anchor or saddle surface 318. The proximal contact surface 317 is a normal pistol grip handle with no rings or apertures to be received in the palm of the user. The profile curve of the proximal contact surface 317 is contoured to accommodate or receive the palm of the hand. To provide comfort and control while using the ultrasonic instrument, the profile of the proximal contact surface 317 is optimized to fit the natural anatomical contours in the valley of the center of the palm and base of the thumb. In one embodiment, the saddle surface 318 provides a grip anchor, which contributes to the stability of control of the handle assembly 310. The location of the saddle surface 318 determines the range of motion for the fingers and thumb to access the proximal rotation knob 334, the distal rotation knob 134, the elongated trigger hook 324, and the power activation toggle switch from the proximal contact surface 317 of the fixed handle 316.

A stabilization tail 320 that may be in contact with the portion of the hand located between the thumb and the index finger adds stability when the handle provides added control to the handle assembly 310. The stabilization tail 320 provides an extended return area to allow proximal weight of the ultrasonic surgical instrument to rest on top of the hand of the user. This provides a greater sense of stability, comfort, and control in the saddle surface 318 of the handle assembly 310.

FIGS. 45-52 illustrate one embodiment of the proximal rotation assembly 312 shown in FIGS. 37-44. In the illustrated embodiment, the proximal rotation assembly 312 comprises the proximal rotation knob 334 inserted over the cylindrical hub 335. The proximal rotation knob 334 comprises a plurality of radial projections 338 that are received in corresponding slots 330 formed on a proximal end of the cylindrical hub 335. The proximal rotation knob 334 defines an opening 348 to receive the distal end of the ultrasonic transducer 114. The radial projections 338 are formed of a soft polymeric material and define a diameter that is undersized relative to the outside diameter of the ultrasonic transducer 114 to create a friction interference fit when the distal end of the ultrasonic transducer 114. The polymeric radial projections 338 protrude radially into the opening 348 to form "gripper" ribs that firmly grip the exterior housing of the ultrasonic transducer 114. Therefore, the proximal rotation knob 334 securely grips the ultrasonic transducer 114.

Figure 38:
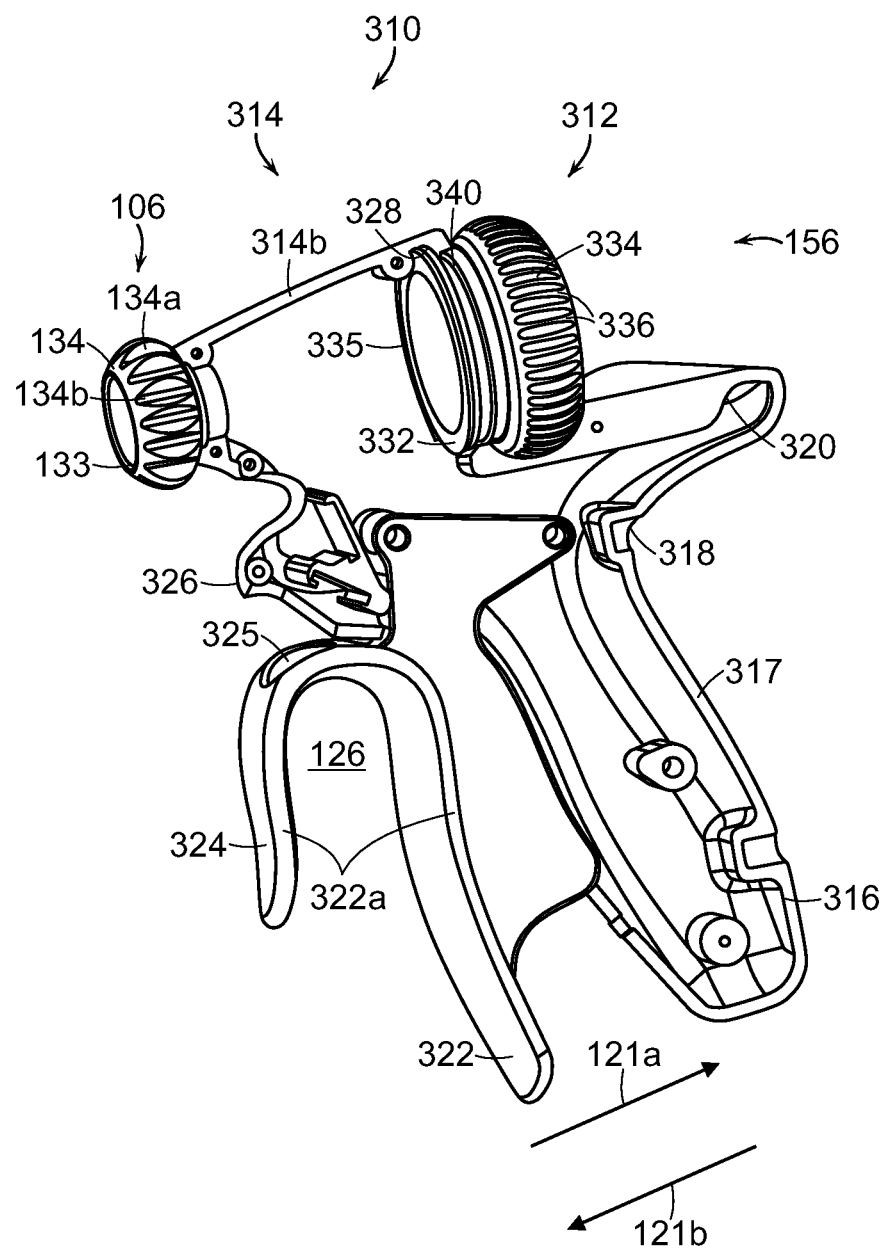
FIG. 38 is a left perspective view of the right housing portion of one embodiment of a handle assembly shown in FIG. 37 with the left housing portion of the housing removed.
Figure 39:
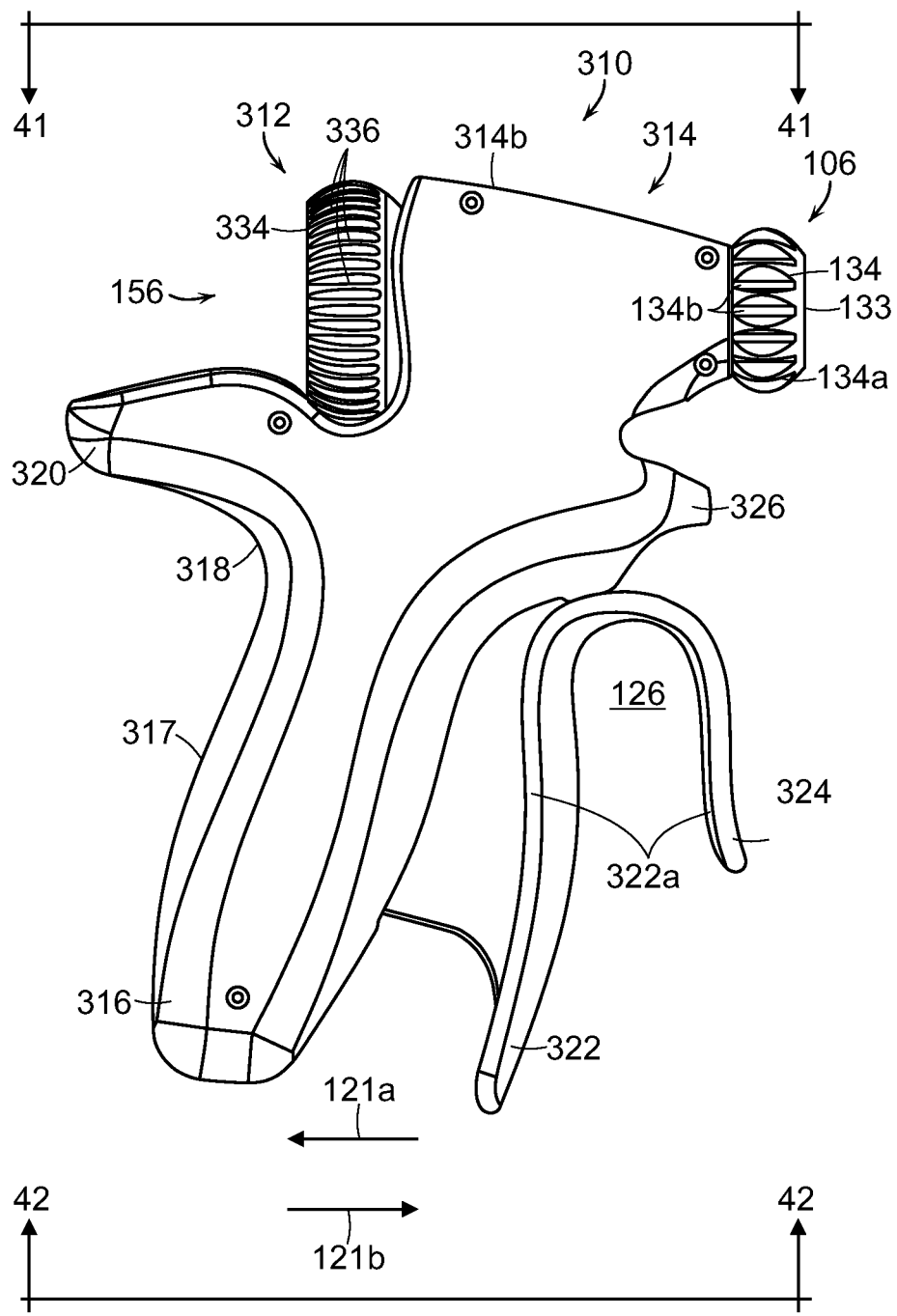
FIG. 39 is a left side view of the right housing portion of one embodiment of the handle assembly shown in FIG. 37 with the left housing portion of the housing removed.
Figure 40:
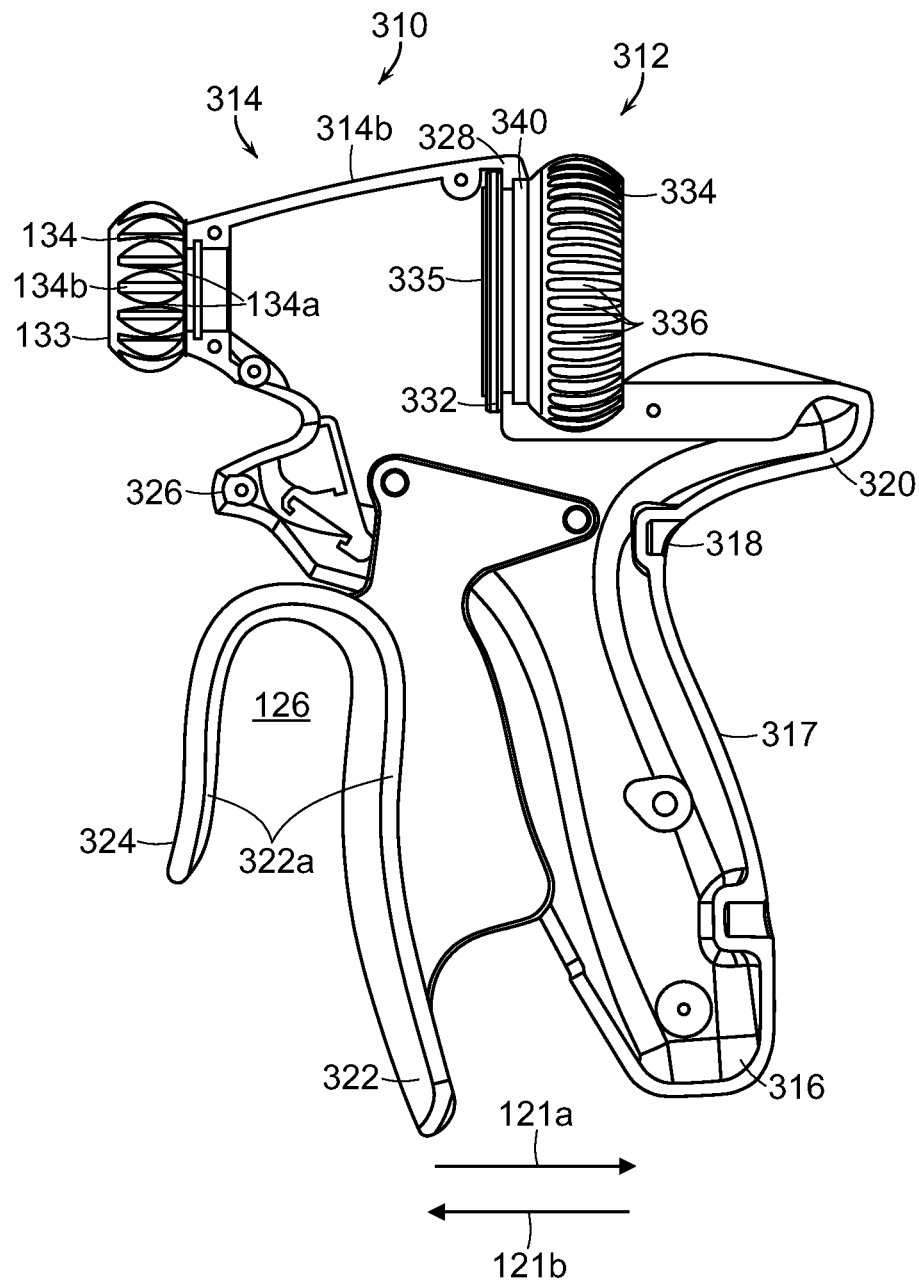
FIG. 40 is a side view of the right housing portion of one embodiment of the handle assembly shown in FIG. 37 with the left housing portion removed.
Figure 41:
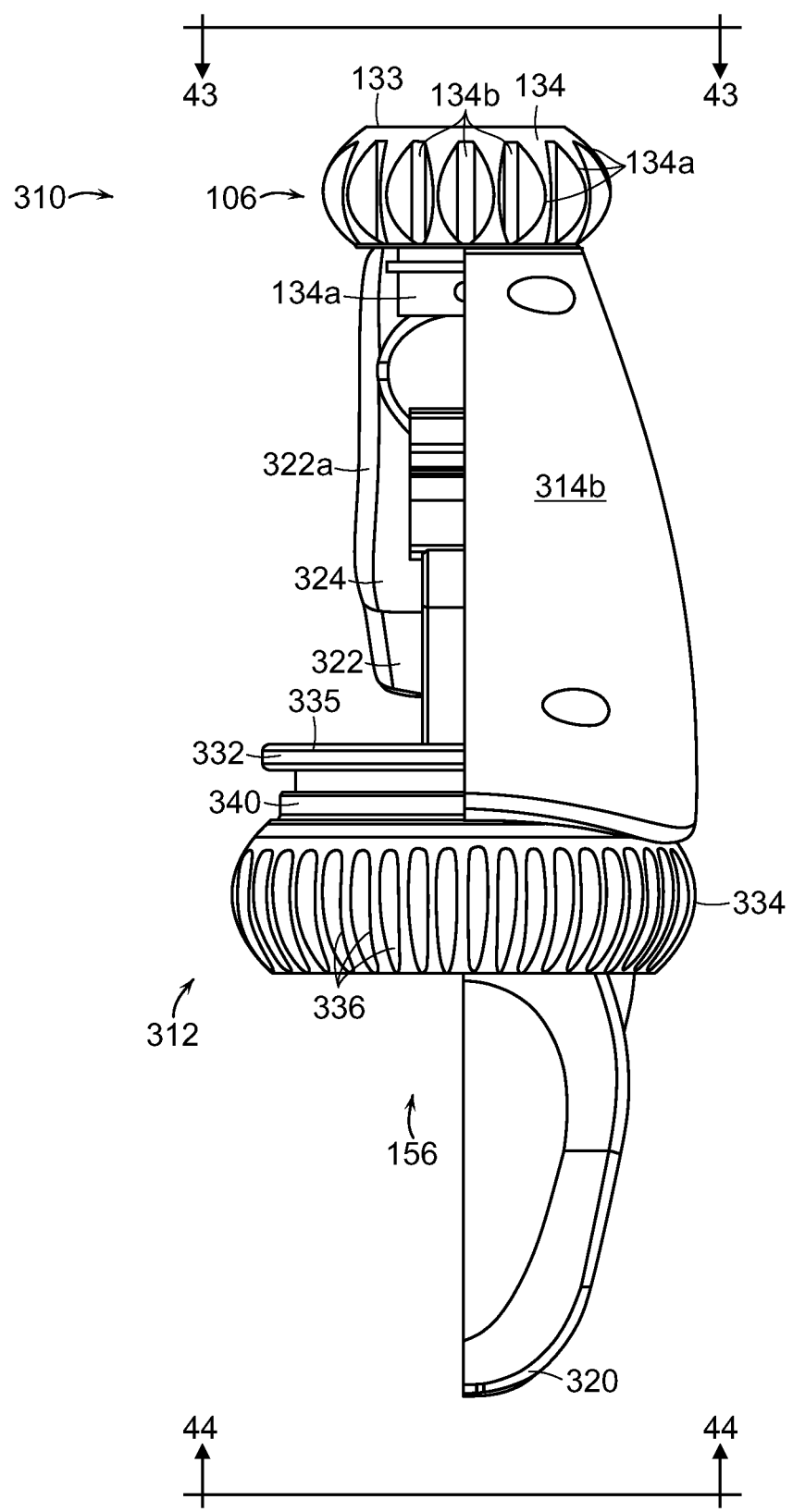
FIG. 41 is a top view of the right housing portion of one embodiment of the handle assembly shown in FIG. 39 taken along line 41-41.
Figure 42:
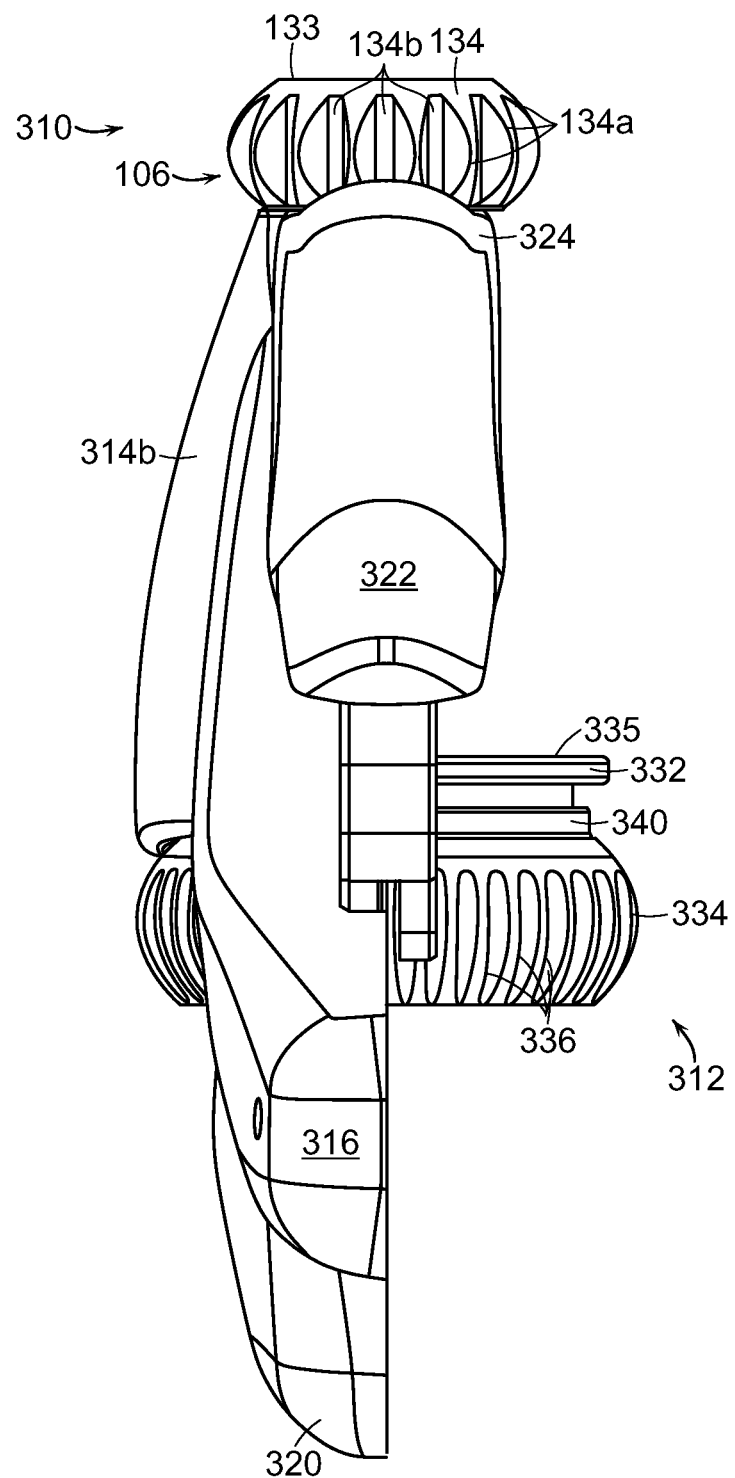
FIG. 42 is a bottom view of the right housing portion of one embodiment of the handle assembly shown in FIG. 39 taken along line 42-42.
Figure 43:
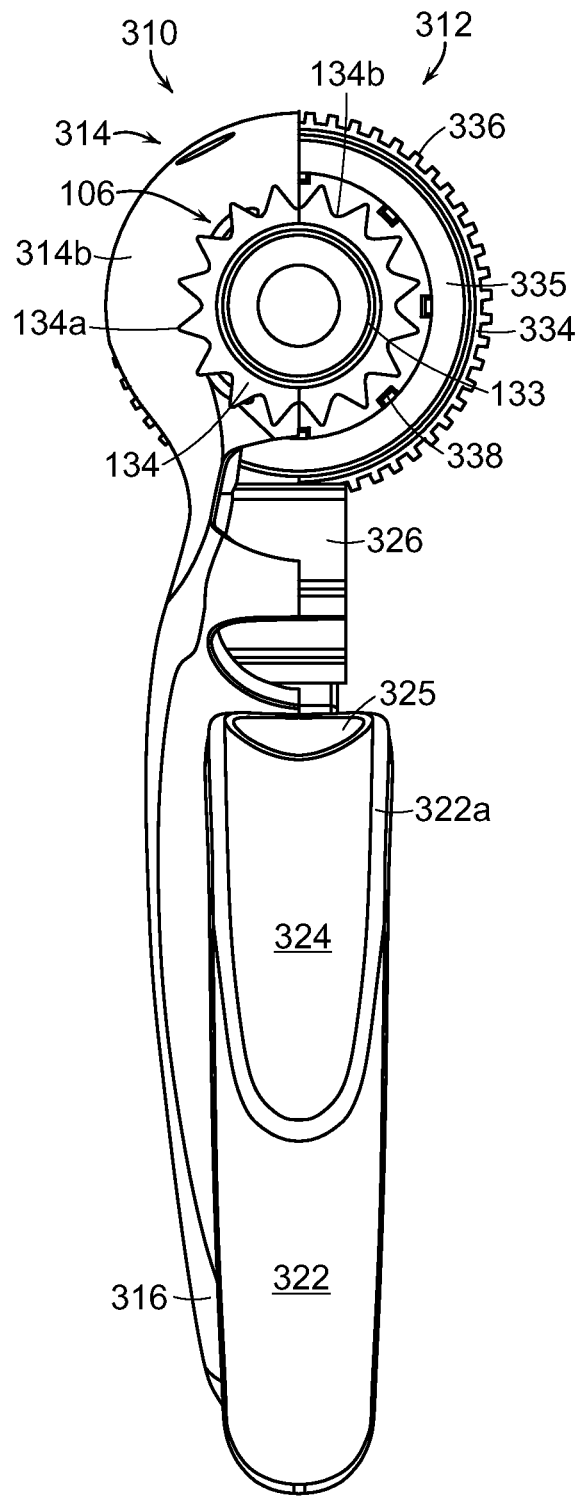
FIG. 43 is a front view of the right housing portion of one embodiment of the handle assembly shown in FIG. 41 taken along line 43-43.
Figure 44:
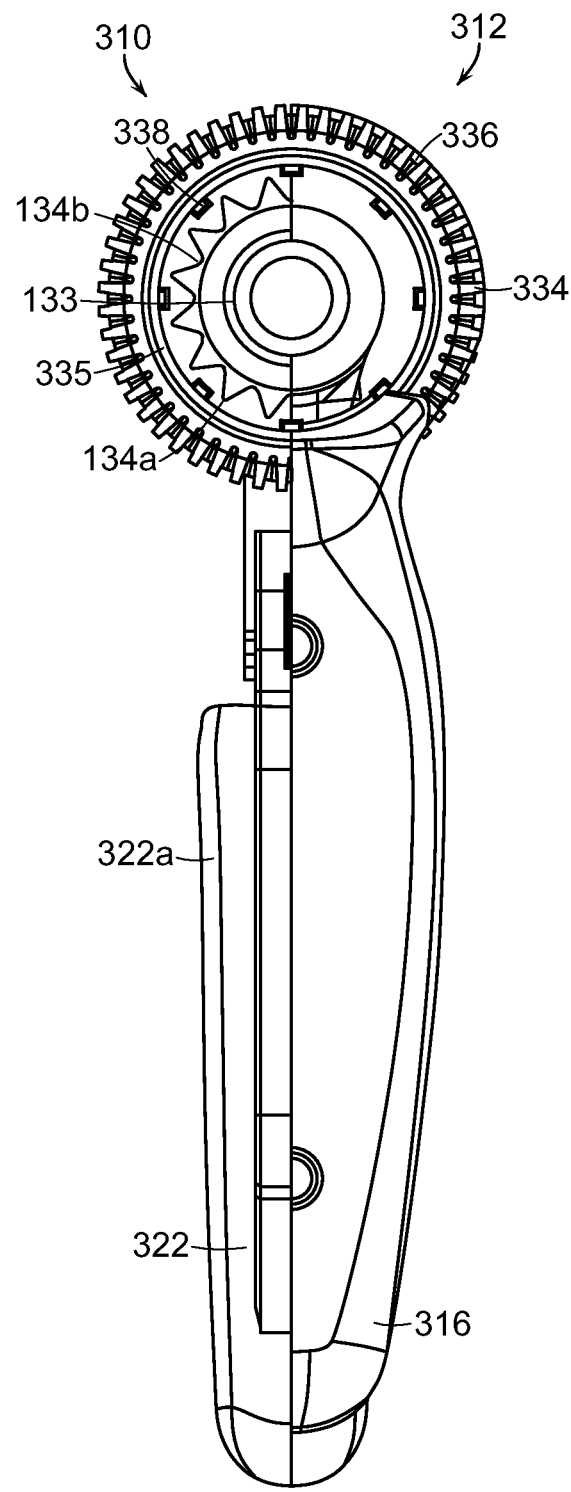
FIG. 44 is a rear view of the right housing portion of one embodiment of the handle assembly shown in FIG. 41 taken along line 44-44.
Figure 45:
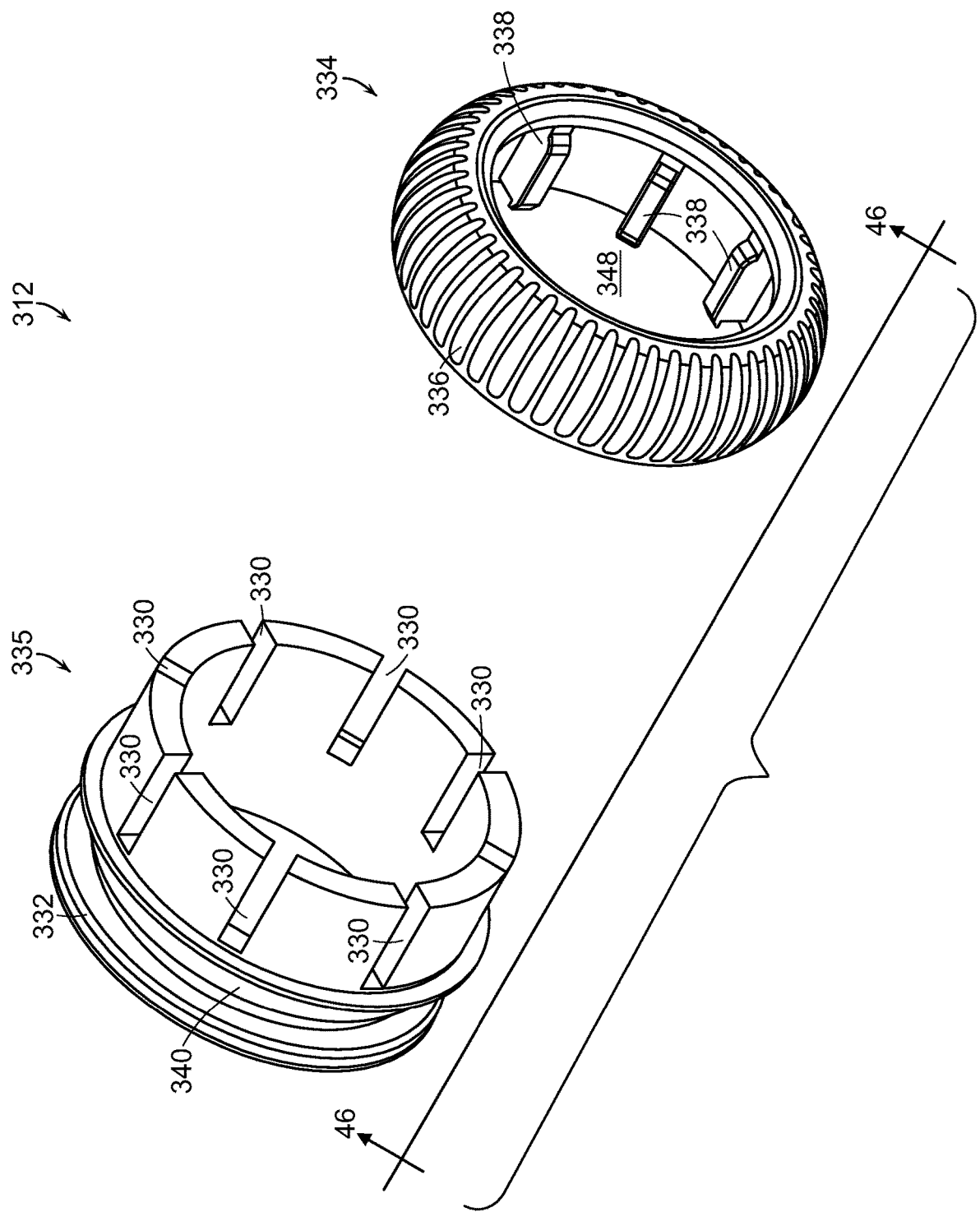
FIG. 45 illustrates an exploded view of one embodiment of the proximal rotation assembly shown in FIGS. 37-44.
Figure 46:
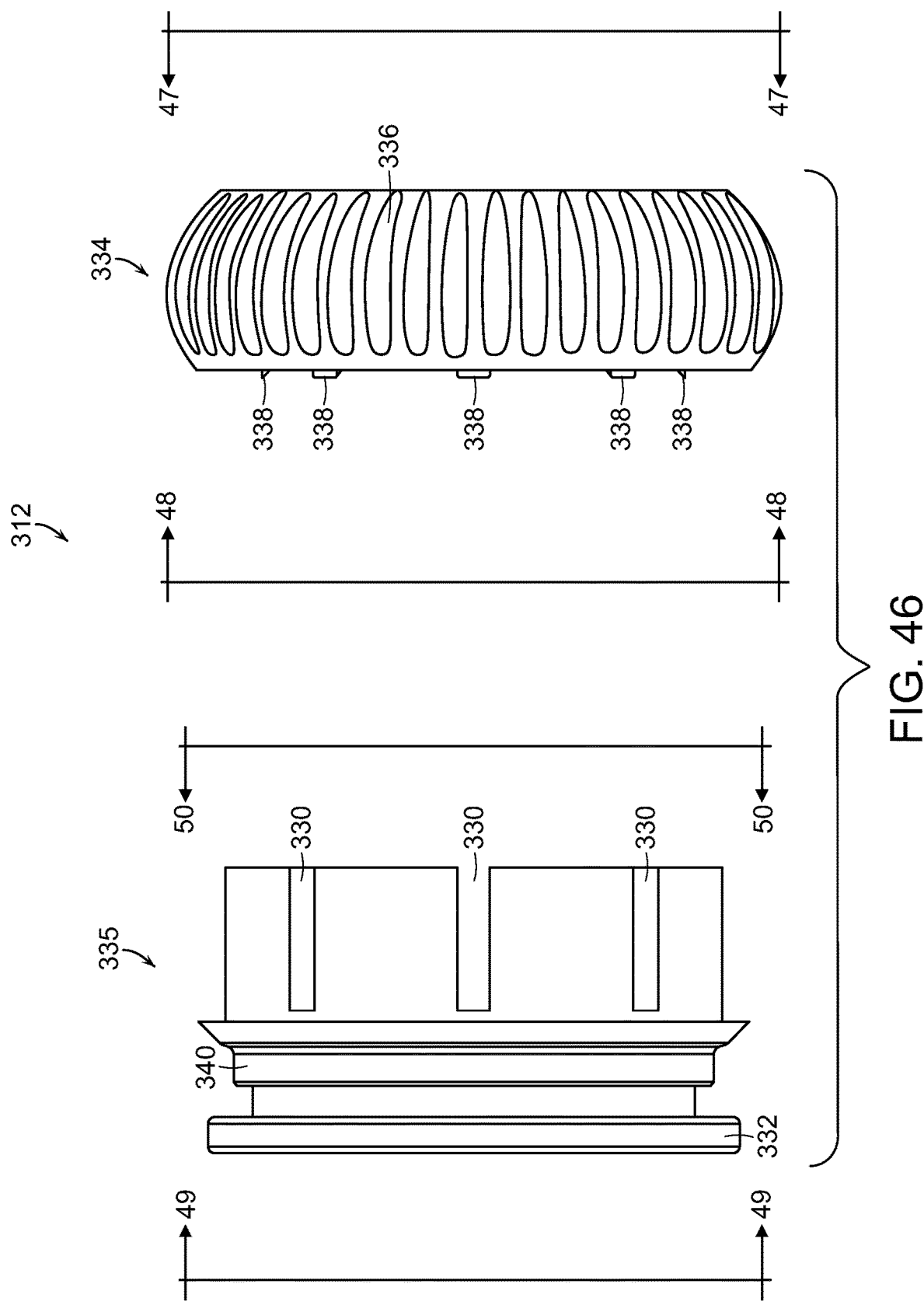
FIG. 46 is a side view of one embodiment of the proximal rotation assembly shown in FIG. 45.
Figure 47:
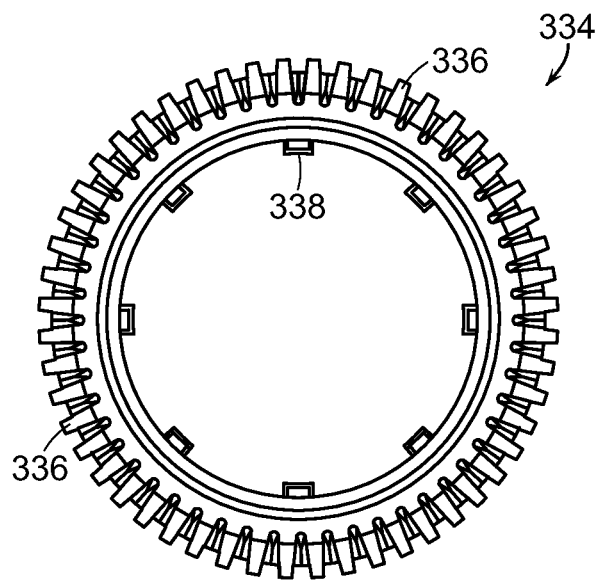
FIG. 47 is a rear view of one embodiment of the proximal rotation knob shown ion FIG. 46 taken along line 47-47.
Figure 48:
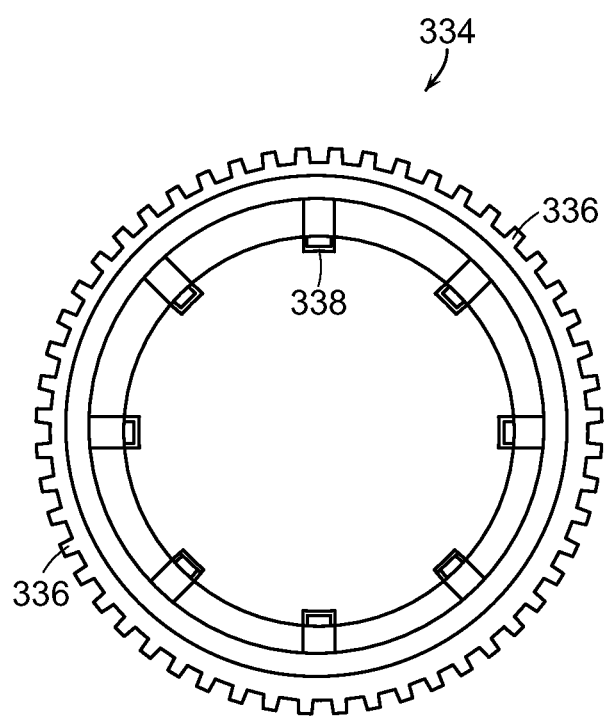
FIG. 48 is a front view of one embodiment of the proximal rotation knob shown in FIG. 46 taken along line 48-48.
Figure 49:
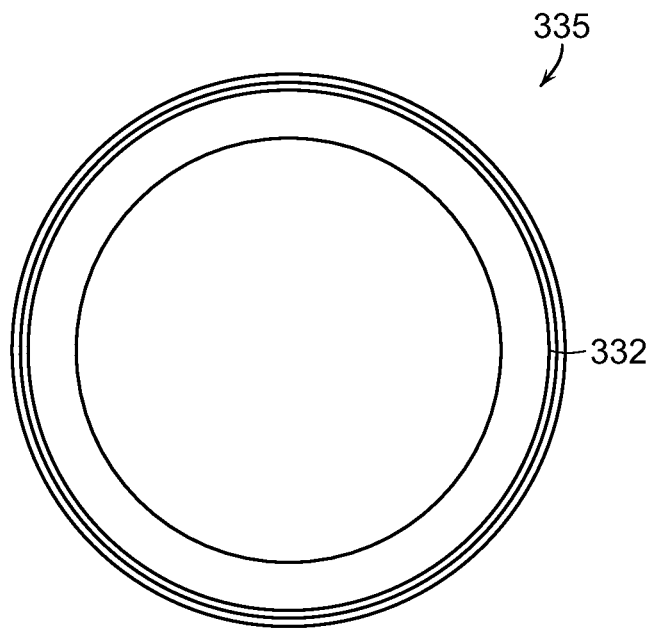
FIG. 49 is a front view of one embodiment of a cylindrical substrate shown in FIG. 46 taken along line 49-49.
Figure 50:
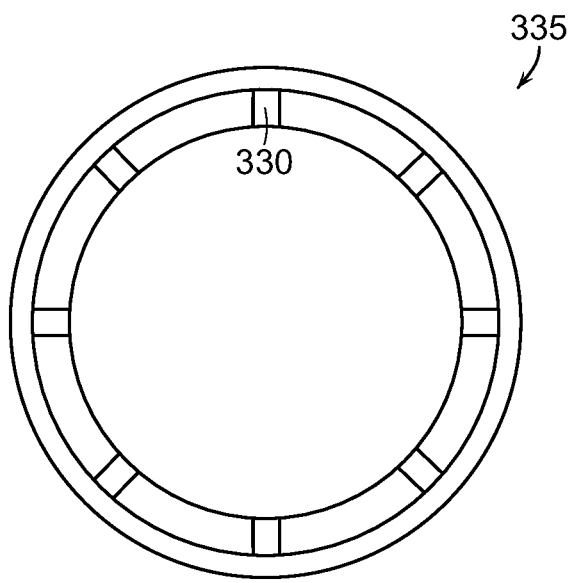
FIG. 50 is a rear view of one embodiment of the cylindrical substrate shown in FIG. 46 taken along line 50-50.
Figure 51:
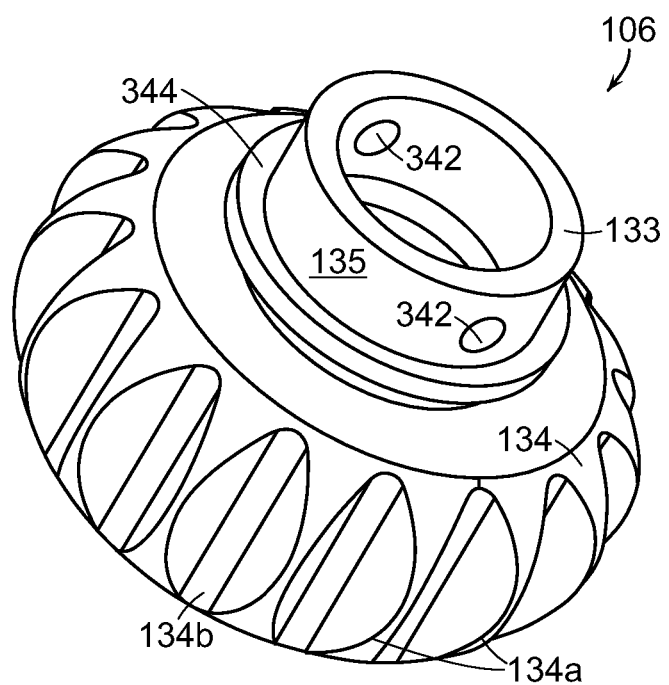
FIG. 51 is a perspective view of one embodiment of the distal rotation assembly shown in FIGS. 37-44.
Figure 52:
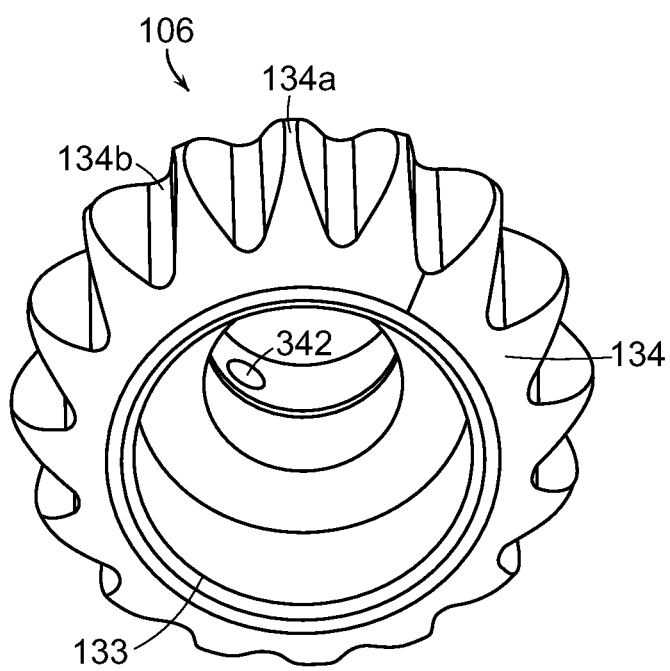
FIG. 52 is a perspective view of one embodiment of the distal rotation assembly shown in FIG. 51.
Figure 53:
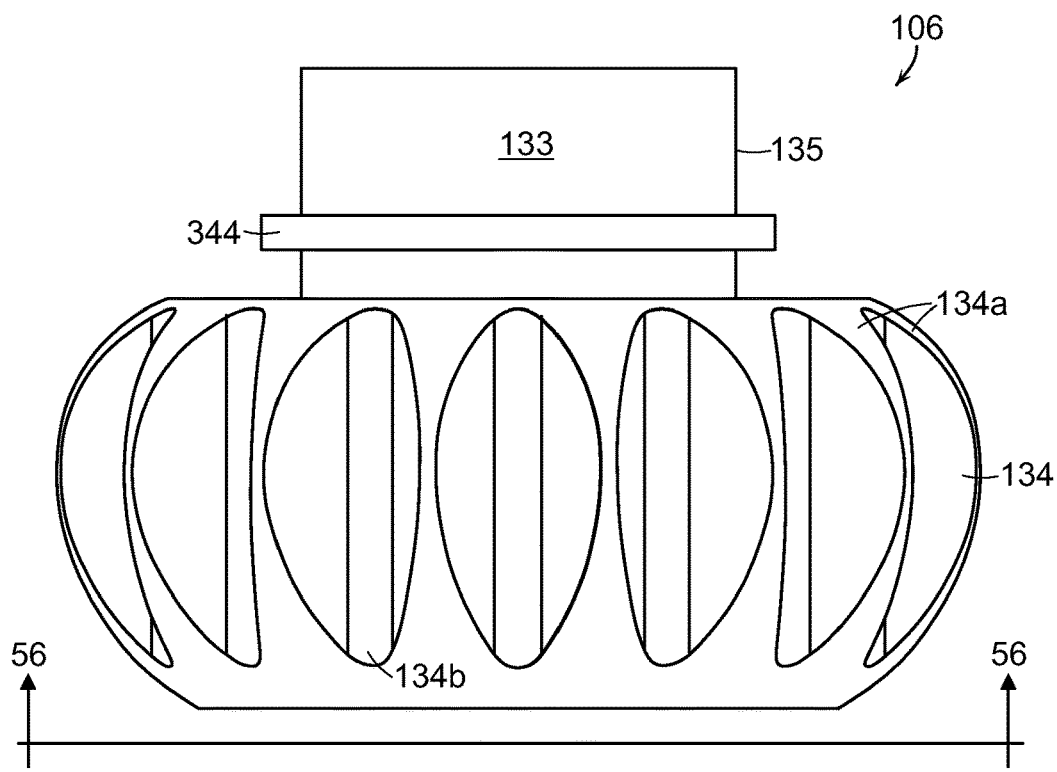
FIG. 53 is a first top view of one embodiment of the distal rotation assembly shown in FIG. 51.
Figure 54:
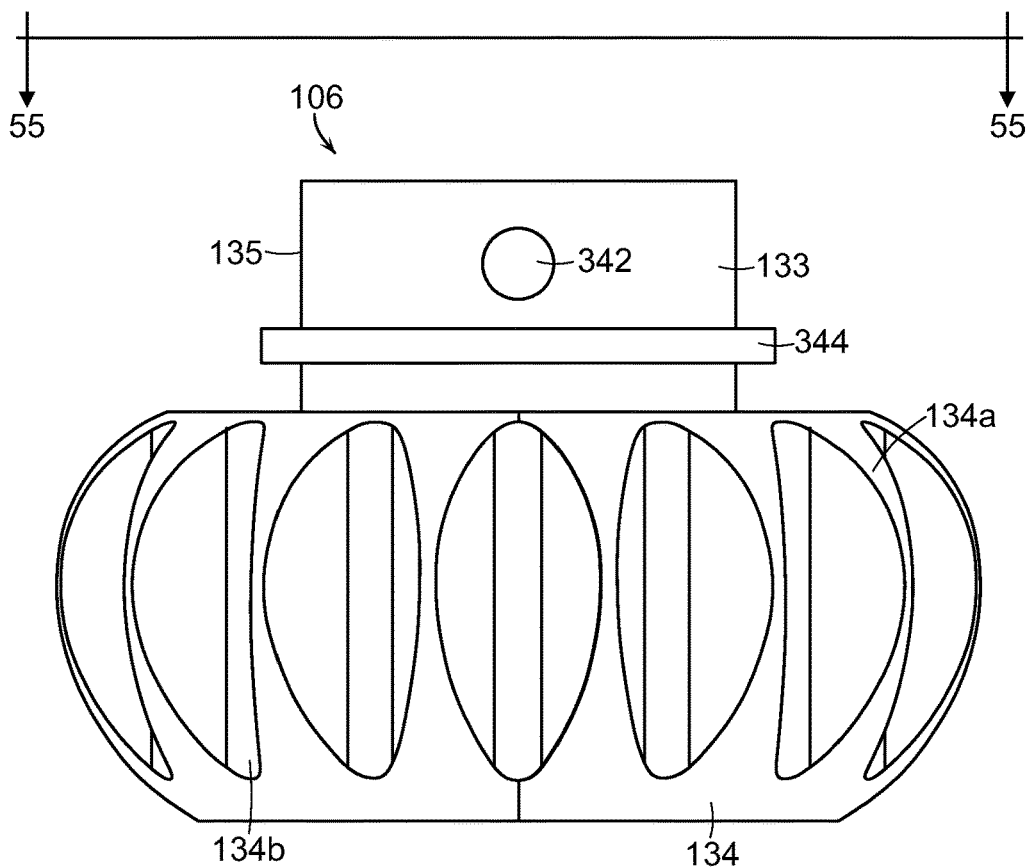
FIG. 54 is a second top view of one embodiment of the distal rotation assembly shown in FIG. 53 rotated 45°.
Figure 55:
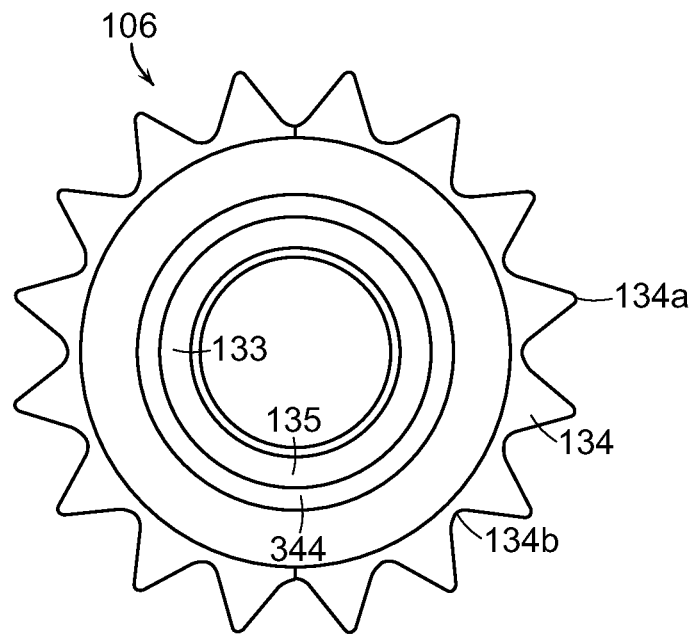
FIG. 55 is a rear view of one embodiment of the distal rotation assembly shown in FIG. 54 taken along line 55-55.
Figure 56:
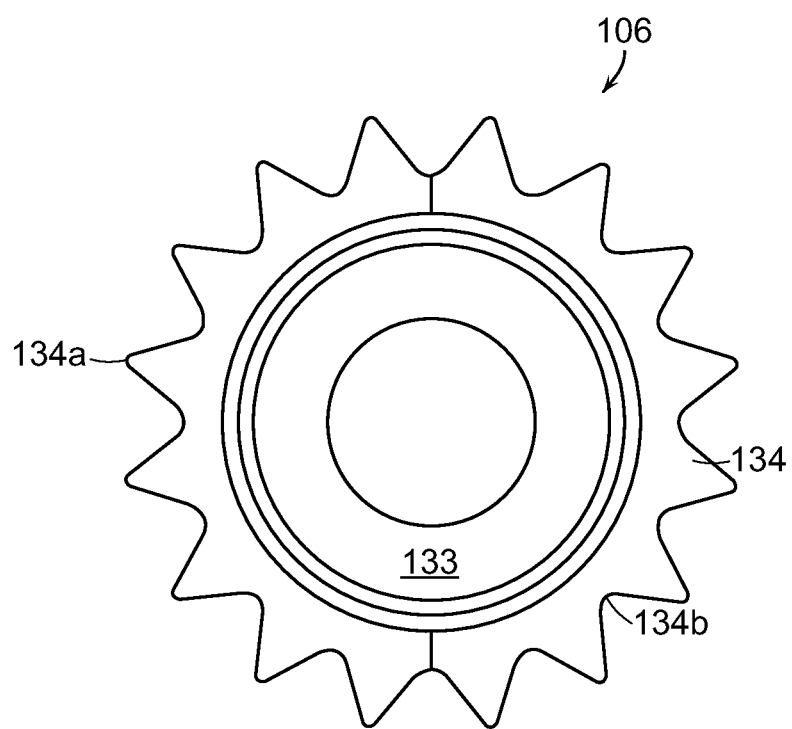
FIG. 56 is a front view of one embodiment of the distal rotation assembly shown in FIG. 53 taken along line 56-56.
Figure 57:
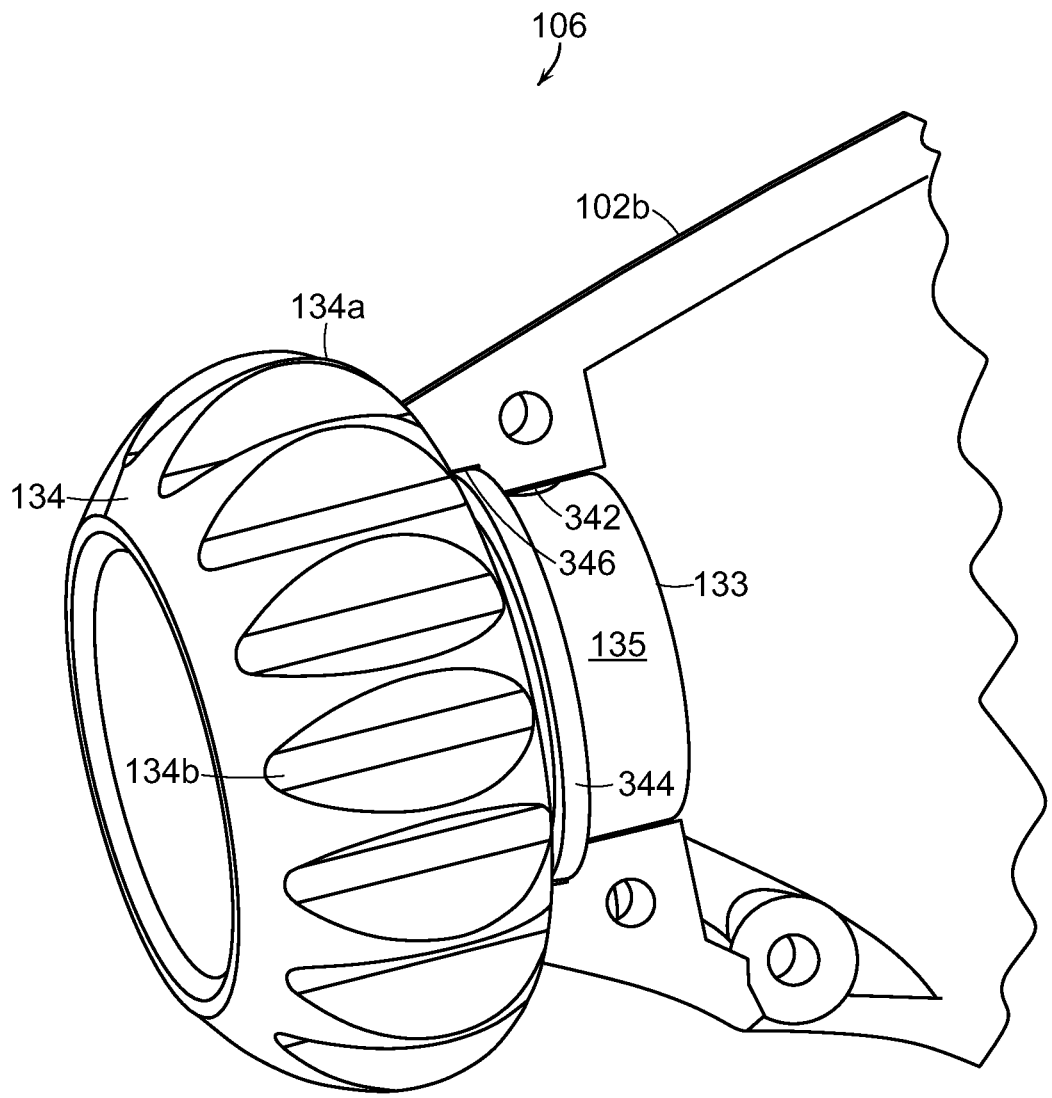
FIG. 57 is a partial right perspective view of one embodiment of the distal rotation assembly shown in FIGS. 37-44 mechanically engaged to the distal end of the left housing portion.

The distal end of the cylindrical hub 335 comprises a circumferential lip 332 and a circumferential bearing surface 340. The circumferential lip engages the groove 328 formed in the housing 314 and the circumferential bearing surface 340 engages the housing 314, as shown in FIGS. 38 and 40, for example. Thus, the cylindrical hub 335 is mechanically retained within the two housing portions 314a (not shown) and 314b of the housing 314 as shown in FIGS. 37-44. The circumferential lip 332 of the cylindrical hub 335 is located or "trapped" between the first and second housing portions 314a,b and is free to rotate in place within the groove 328. The circumferential bearing surface 340 bears against interior portions of the housing 314 to assist proper rotation. Thus, the cylindrical hub 335 is free to rotate in place within the housing 314. The user engages the flutes 336 formed on the proximal rotation knob 334 with either the finger or the thumb to rotate the cylindrical hub 335 within the housing 314.

In one embodiment, the cylindrical hub 335 may be formed of a durable plastic such as polycarbonate. In one embodiment, the cylindrical hub 335 may be formed of a siliconized polycarbonate material. In one embodiment, the proximal rotation knob 334 may be formed of pliable, resilient, flexible polymeric materials including Versaflex®

TPE alloys made by GLS Corporation, for example. The proximal rotation knob 334 may be formed of elastomeric materials, thermoplastic rubber known as Santoprene®, other thermoplastic vulcanizates (TPVs), or elastomers, for example. The embodiments, however, are not limited in this context.

FIGS. 53-57 illustrate one embodiment of the distal rotation assembly 106 shown in FIGS. 37-44. In the illustrated embodiment, the distal rotation assembly 106 is formed of a hub 133 comprising a fluted rotation knob 134 formed thereon. The hub 133 comprises a cylindrical sleeve portion 135, which is received within the distal housing portion (e.g., first and second housing portions 102a,b and first and second housing portions 314a,b). A pair of openings 342 are formed in the cylindrical sleeve portion 135 to receive the pin 162 to retain the hub portion 163 of the outer tubular sheath 142 (FIG. 14). A circumferential lip 344 is formed on the cylindrical sleeve portion 135 and is received within a corresponding groove 346 formed in the distal end of the handle assembly 102. The circumferential lip 344 and the circumferential groove 346 are dimensioned such that the cylindrical sleeve portion 135 is free to rotate within the circumferential groove 346 when the first and second portions 102a,b of the handle assembly 102 are mated.

The hub 133 is located or rotatably "trapped" between the left and right housing portions 102a,b and is free to rotate in place within the groove 346. The fluted rotation knob 134 is formed over the hub 133 employing using well known overmolding techniques or other techniques. The fluted rotation knob 134 also may be mechanically or frictionally engaged with the hub 133. The flutes are defined by raised ridges or ribs 134b and concave regions 134b formed therebetween. The hub 133 may be formed of a durable plastic such as polycarbonate. In one embodiment, the hub 133 may be formed of a siliconized polycarbonate material. The fluted rotation knob 134 may be formed of a resilient, pliable polymeric material such as Santoprene or Versaflex, for example. The embodiments are not limited in this context.

Turning now to FIGS. 58-69, it has long been a challenge to create a handle design in terms of size, shape, and location of control interfaces that is "ideal" for everyone. The very large disparity of anthropometrics from 5th percentile small female to 95th percentile large male surgeon from traditionally creates ergonomic challenges for users at the extreme ends of the spectrum. Although provision of multiple different handle sizes has been considered for some time, there is a general within the hospital community to carry fewer inventories, thus there still would exist the risk that a certain size handle would not be available for a particular individual at a particular hospital. Thus, various embodiments provide a handle design for multiple instruments to more optimally ergonomically interface in terms of comfort and control for a large variety of hand sizes.

Figure 58:
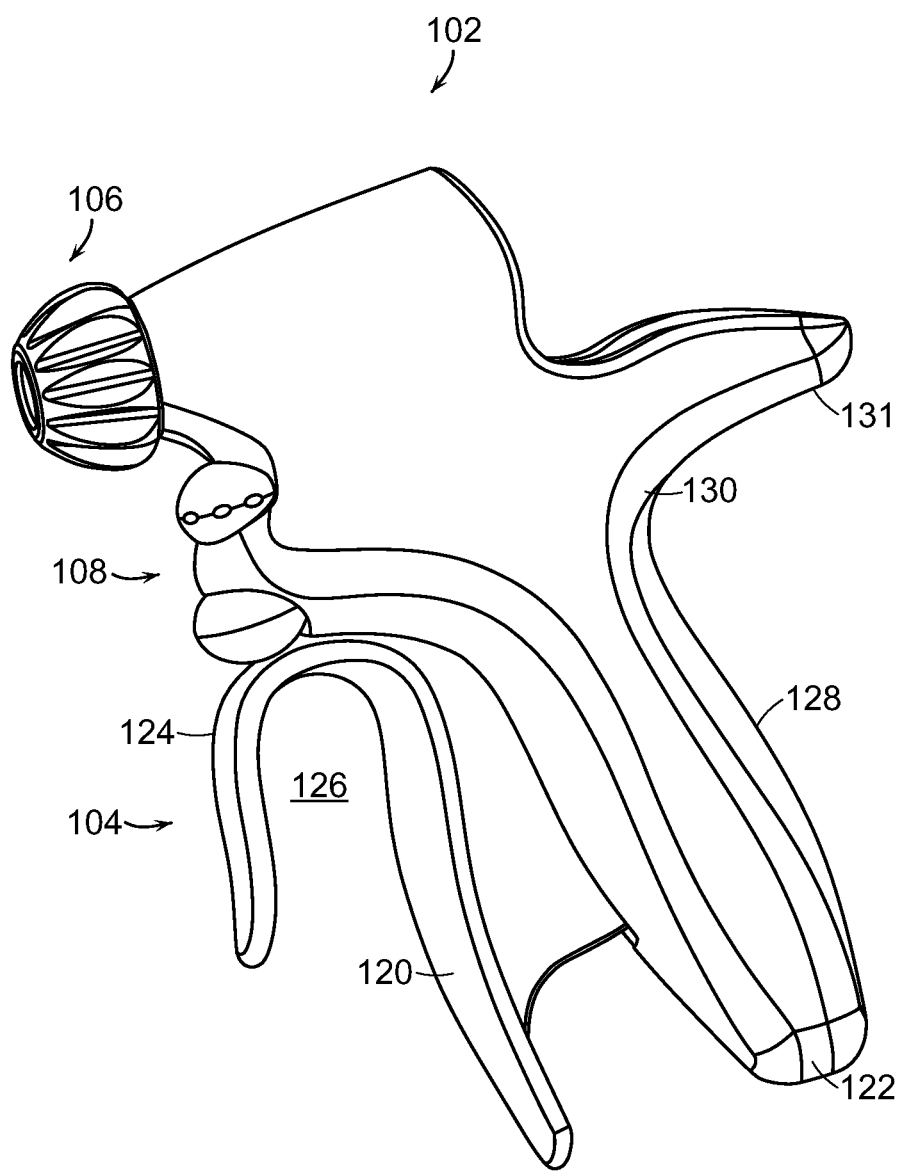
FIG. 58 is a right side perspective view of one embodiment of a handle assembly for an ultrasonic surgical instrument suitable to receive a handle adapter.

FIG. 58 is a right side perspective view of one embodiment of the handle assembly 102 for an ultrasonic surgical instrument suitable to receive a handle adapter. The handle assembly 102 comprises a trigger assembly 104, a distal rotation assembly 106, and a switch assembly 108. The handle assembly 102 comprises a trigger 120 and a fixed handle 122. The fixed handle 122 is integrally associated with the handle assembly 102 and the trigger 120 is movable relative to the fixed handle 122 as explained in more detail below with respect to the operation of the ultrasonic surgical instrument 100. The fixed handle 122 and the trigger 120 comfortably interface with the user. The fixed handle 122 comprises proximal contact surface 128 and a grip anchor or saddle surface 130. The stabilization tail 131 may be in contact with the portion of the hand located between the thumb and the index finger and adds stability to the handle assembly 102. The trigger 120 comprises the elongated trigger hook 124, which defines the aperture 126 between the elongated trigger hook 124 and the fixed handle 122. The handle assembly 102 is suitable to receive a handle adapter as described below.

Figure 59:
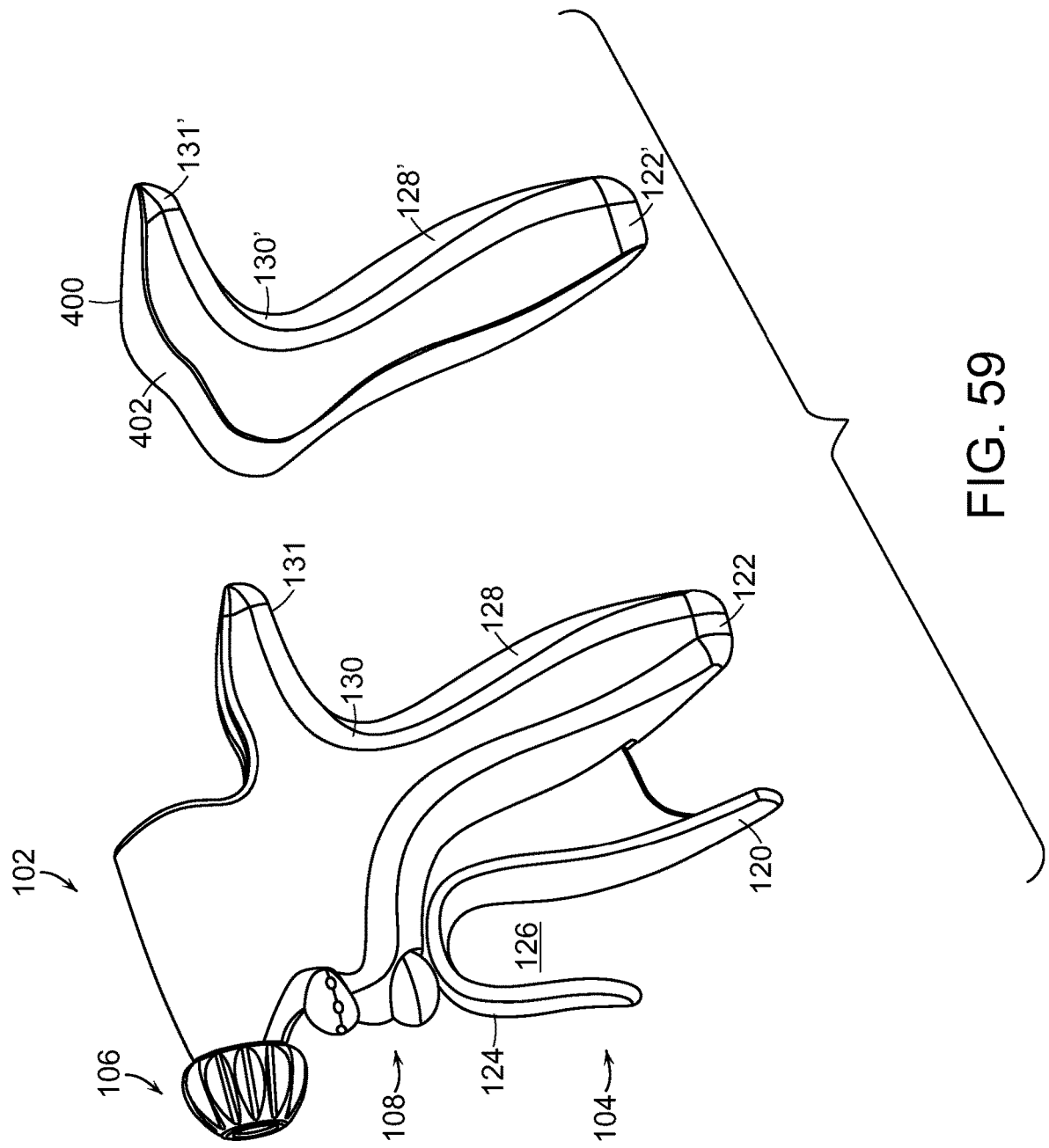
FIG. 59 is a right side perspective view of one embodiment of the handle assembly shown in FIG. 58 and one embodiment of a handle adapter.

FIG. 59 is a right side perspective view of one embodiment of the handle assembly 102 and one embodiment of a handle adapter 400. The handle adapter 400 comprises a body that defines an opening 402 to receive the fixed handle 122, the proximal contact surface 128, the saddle surface 130, and the stabilization tail 131. The interior of the opening 402 defines a contour that is the inverse shape of the proximal contact surface 128, the saddle surface 130, and the stabilization tail 131 such that the adapter fits snugly against the proximal contact surface 128, the saddle surface 130, and the stabilization tail 131. An external contour of the opening 402 defines a new fixed handle 122', a proximal contact surface 128', a saddle surface 130', and a stabilization tail 131' portion that is substantially similar to the proximal contact surface 128, the saddle surface 130, and the stabilization tail 131 originally formed on the fixed handle 122. The thickness or width of the handle adapter 400 is ergonomically adapted to the size of the hand of the user. The handle adapter 400 may be formed of a single-piece component and may be packaged to be used in conjunction with an ultrasonic surgical instrument that may be sized for average-to-smaller hands. The handle adapter 400 may easily be removably attached to the handle assembly 102 of the ultrasonic surgical instrument 100 to expand or enlarge the size of the grip to accommodate larger hands. Prominent graphics may be provided on the instrument package and on the handle adaptor 400 to communicate the intended use of the handle adapter 400. The overall appearance of the handle adaptor 400 makes its function readily understandable.

Figure 60:
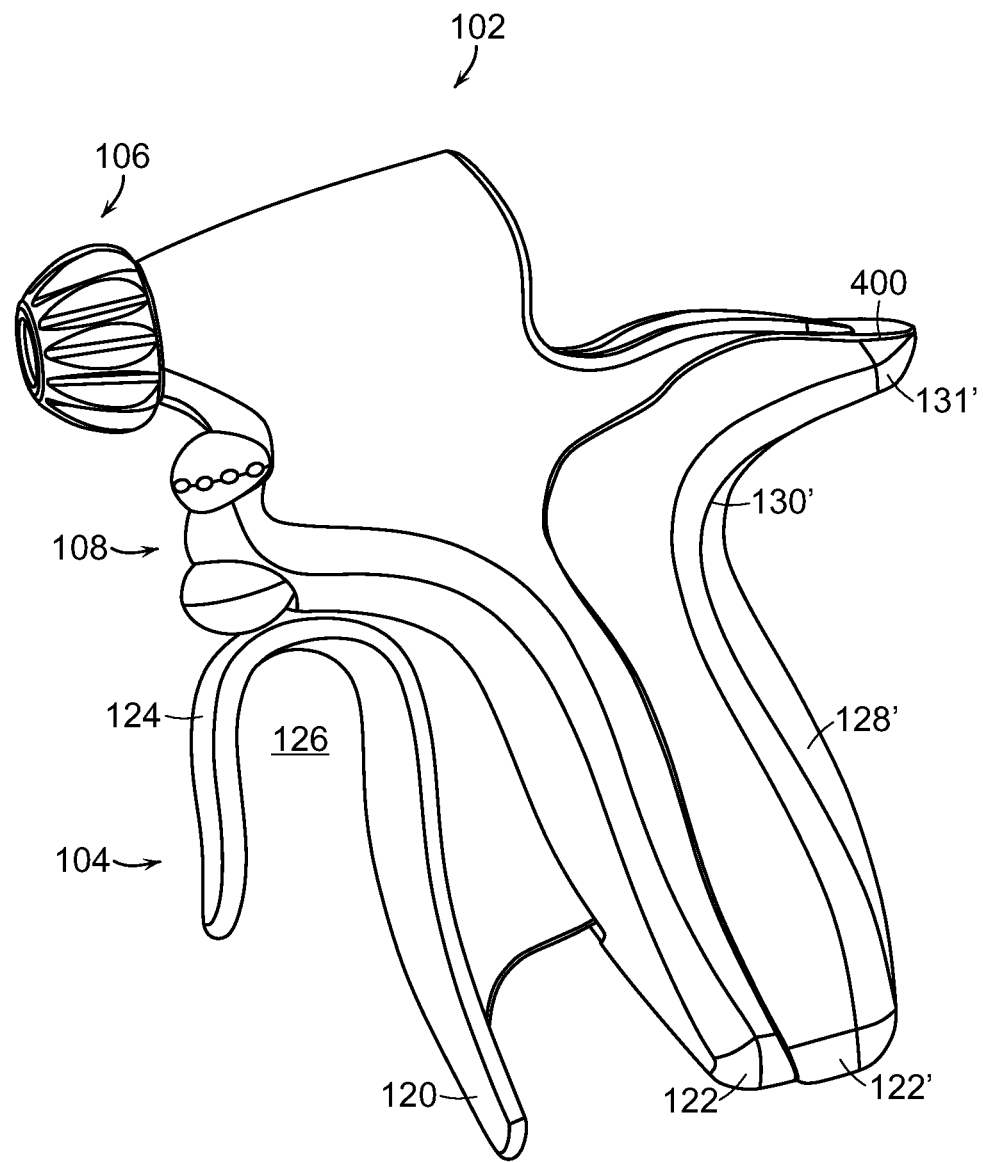
FIG. 60 is a right side perspective view of one embodiment of the handle assembly shown in FIGS. 58-59 comprising the handle adapter shown in FIG. 59 attached thereto.
Figure 62:
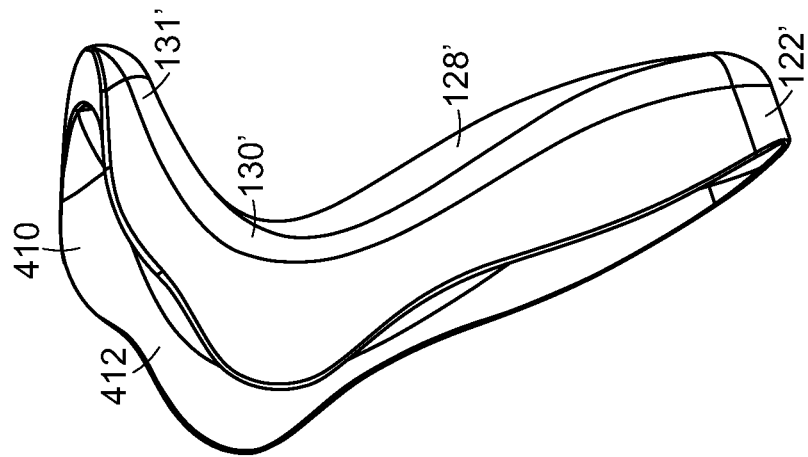
FIG. 62 is a left perspective view of one embodiment of the handle adapter comprising snap-button features shown in FIG. 61.
Figure 61:
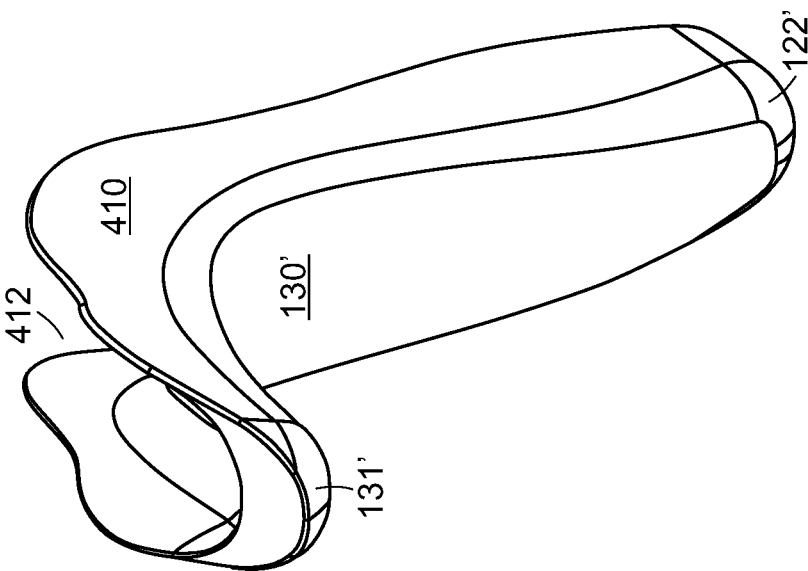
FIG. 61 is right perspective view of one embodiment of a handle adapter comprising snap-button features suitable for attaching to a handle assembly of an ultrasonic surgical instrument.
Figure 64:
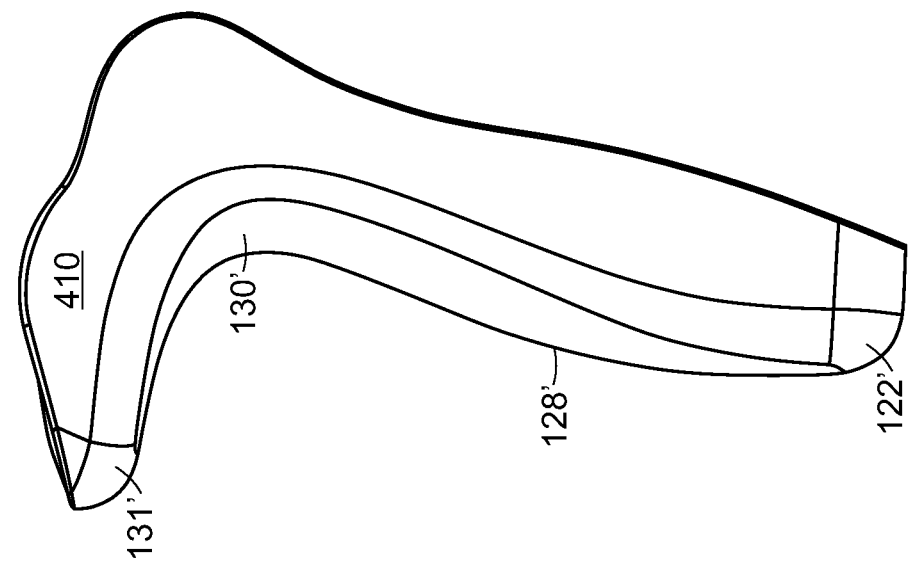
FIG. 64 is right side view of one embodiment of the handle adapter comprising snap-button features shown in FIG. 61.
Figure 63:
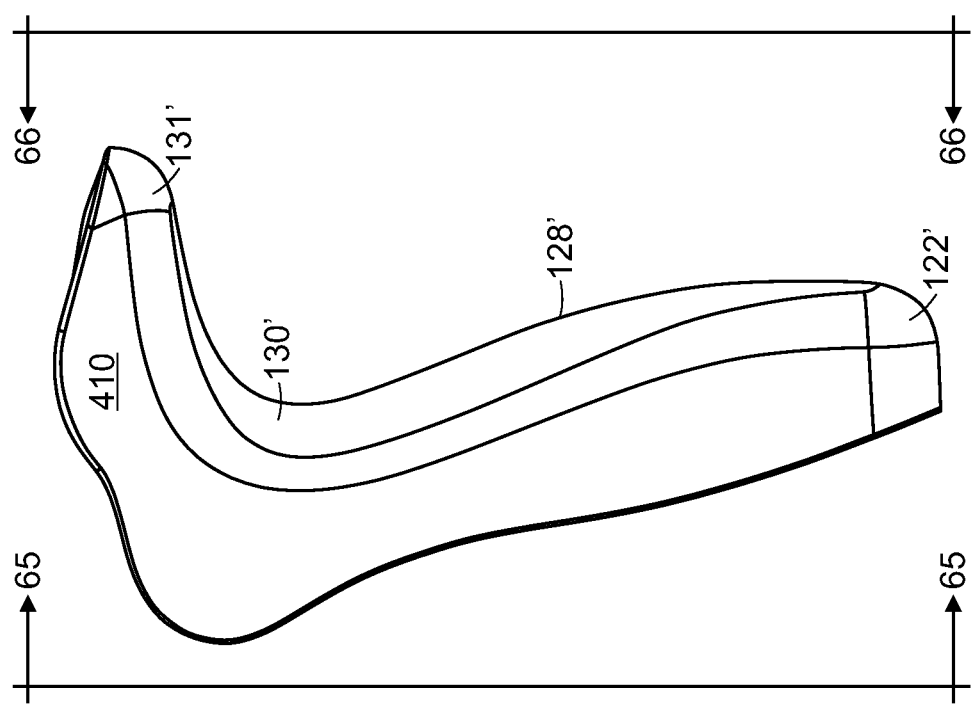
FIG. 63 is a left side view of one embodiment of the handle adapter comprising snap-button features shown in FIG. 62.
Figure 65:
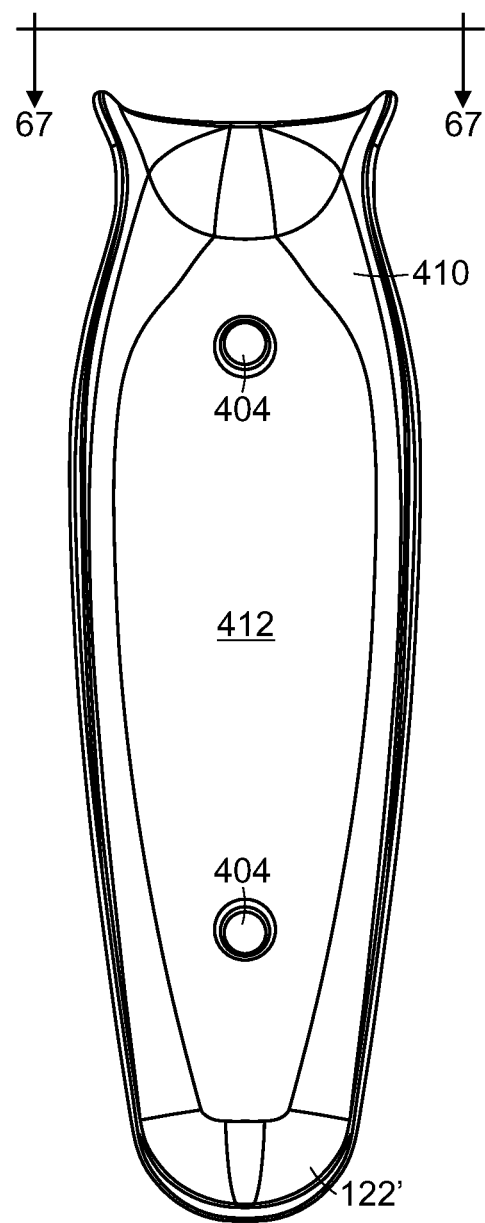
FIG. 65 is a front view of one embodiment of the handle adapter comprising snap-button features shown in FIG. 63 taken along lines 65-65.
Figure 66:
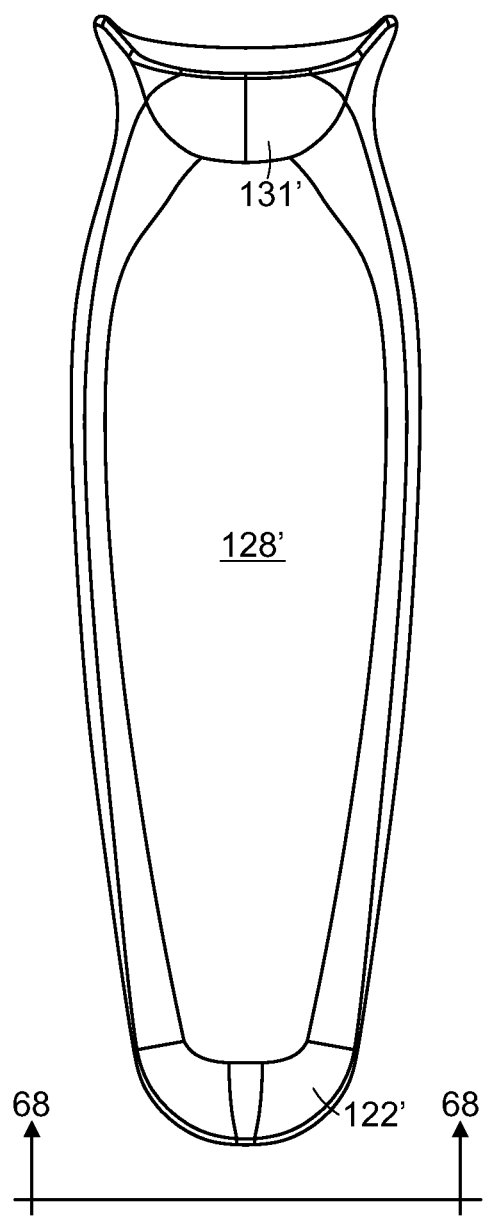
FIG. 66 is a rear view of one embodiment of the handle adapter comprising snap-button features shown in FIG. 63 taken along lines 66-66.
Figure 68:
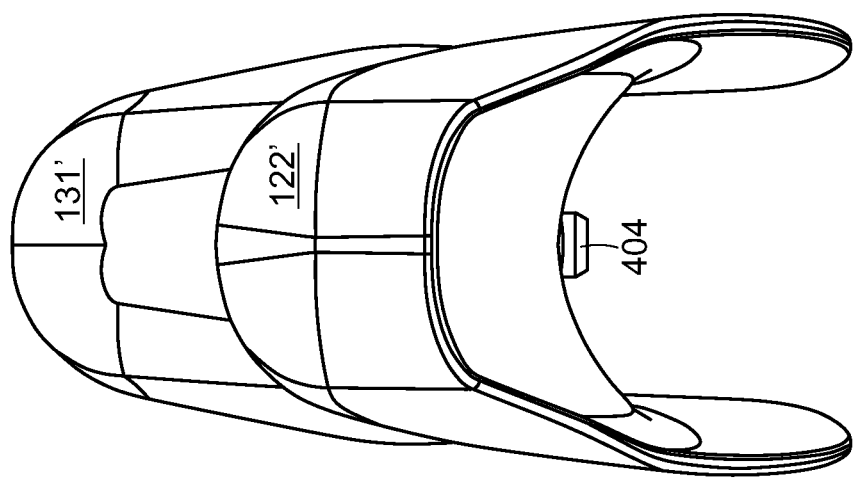
FIG. 68 is a bottom view of one embodiment of the handle adapter comprising snap-button features shown in FIG. 66 taken along lines 68-68.
Figure 67:
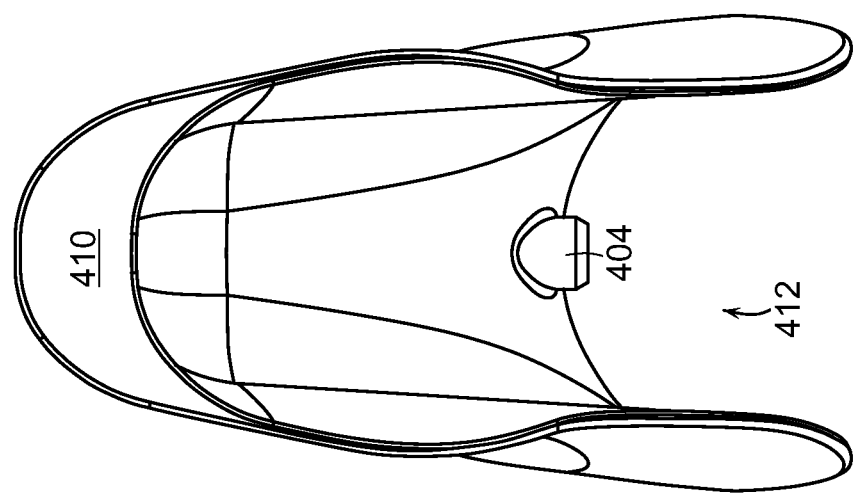
FIG. 67 is a top view of one embodiment of the handle adapter comprising snap-button features shown in FIG. 65 taken along lines 67-67.
Figure 69:
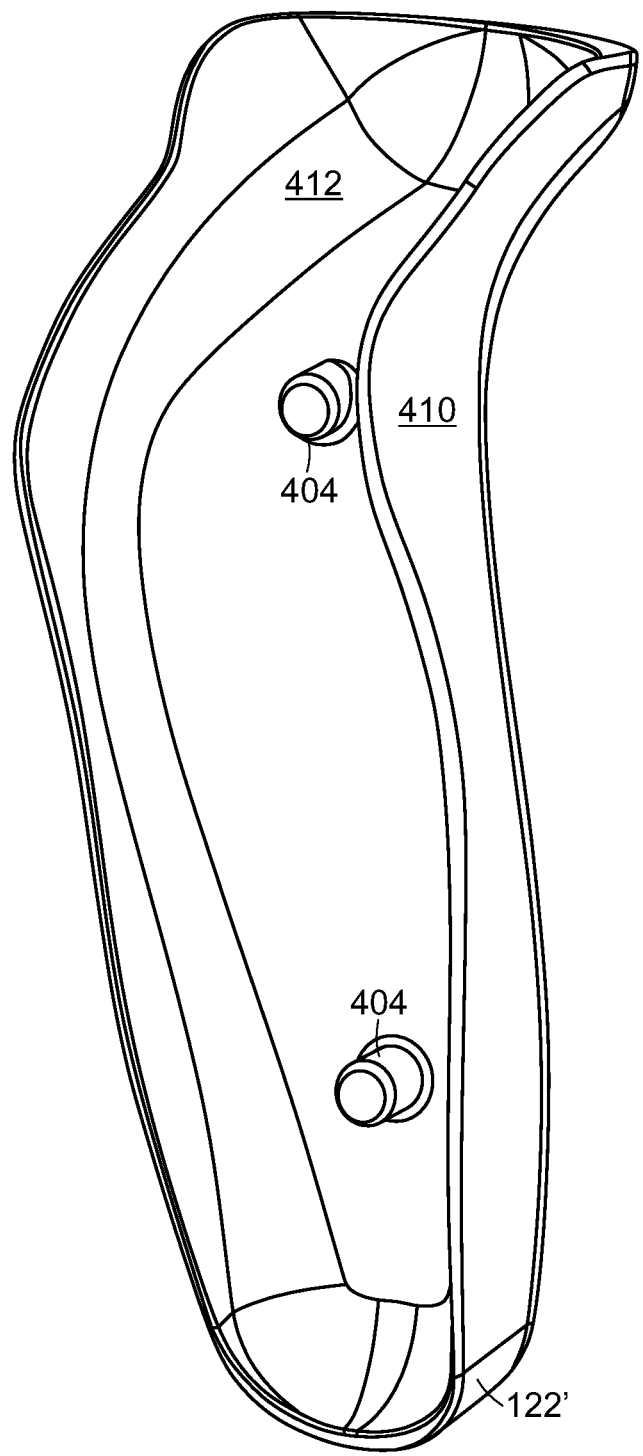
FIG. 69 is a rear perspective view of one embodiment of the handle adapter comprising snap-button features shown in FIG. 61.

FIG. 60 is a right side perspective view of one embodiment of the handle assembly 102 comprising the handle adapter 400 attached thereto. In one embodiment, the handle adaptor 400 may be formed as a press-fit component that fits "like a glove" over the main grip portion of the fixed handle 122. For example, the handle adapter 400 may be configured to extend over at least a portion of a heel/bottom surface of the fixed handle 122 and/or at least a portion of the stabilization tail 131. The handle adapter 400 is frictionally held in place during use. The handle adaptor 400 is easily removable from the handle assembly 102. The handle adaptor 400 may be formed of a variety of materials including a range of elastomers with varying durometers, rigid polymers, and pliable polymers, among others. In one embodiment, the surface area of the adapter may comprise a wide range of texture and grip detailing over the contours of the geometry of the handle adapter 400. In another embodiment, the handle adapter 400 may comprise variable-size feature embedded as part of the main handle—wherein a lock/release control enables the proximal portion of the handle adapter 400 to extend or compress, to allow substantially infinite adjustment for a particular hand size.

FIGS. 61-69 illustrate one embodiment of a handle adapter 410 comprising snap-button features suitable for attaching to a handle assembly of an ultrasonic surgical instrument. The handle adapter 410 defines an opening 412 adapted and configured to receive a fixed handle portion of a handle assembly of a surgical instrument. The handle adapter 410 defines the fixed handle 122', the proximal contact surface 128', the saddle surface 130', and the stabilization tail 131' portions of the handle assembly that are more suitably ergonomically adapted to the hand of the user. Similar to FIG. 60 above, the fixed handle portion 122' of the handle adapter 410 may be configured to extend over at least a portion of a heel/bottom surface of the fixed handle 122 and/or the stabilization tail portion 131' of the handle adapter 410 may be configured to extend over at least a portion of the stabilization tail 131. The handle adapter 410 may be formed of a single-piece component and may be packaged to be used in conjunction with an ultrasonic surgical instrument that may be sized for average-to-smaller hands. The handle adapter 410 may be easily removably attached to the handle assembly 102 (FIGS. 58-60) of the ultrasonic surgical instrument 100, to expand the size of the grip to accommodate larger hands. Prominent graphics may be provided on the package and on the handle adaptor 410 to communicate the intended use of the handle adapter 410. The overall appearance of the handle adaptor 410 makes its function readily understandable.

In one embodiment, the handle adaptor 410 may be formed as a press-fit component that fits "like a glove" over the main grip portion of the fixed handle. The interior portion of the handle adapter 410 comprises snap button features 404 that may be received in corresponding openings (not shown) defined on the fixed handle 122 portion of the handle assembly 102 (FIGS. 58-60). The snap button features 404 mechanically attach the handle adapter 410 to the fixed handle 122 and hold the handle adapter 410 in place during use. The handle adaptor 410 is easily removably attached from the fixed handle 102 of the handle assembly 102. The handle adaptor 410 may be formed of a variety of materials including a range of elastomers with varying durometers, rigid polymers, and pliable polymers, among others. In one embodiment, the surface area of the adapter may comprise a wide range of texture and grip detailing over the contours of the geometry of the handle adapter 410. In another embodiment, the handle adapter 410 may comprise variable-size feature embedded as part of the main handle— wherein a lock/release control enables the proximal portion of the handle adapter 410 to extend or compress, to allow substantially infinite adjustment for a particular hand size.

Turning now to FIGS. 70-87, the multi-function capability of the ultrasonic surgical instrument 100, particularly the laparoscopic ultrasonic surgical instrument 100 may create certain ergonomic challenges for the user to comfortably access and operate the multiple functions and controls of the instrument. These include the ability to comfortably actuate the jaws of the clamping mechanism of the end effector assembly 112 and to activate the hand control buttons such as the toggle switch 132. The user must be able to control the opening motion in direction 148B (FIGS. 3 and 11) of the end effector assembly 112 to facilitate spreading dissection, for example. A spreading dissection using laparoscopic instruments requires a reaction surface to allow the user to manipulate the instrument in multiple directions. Using an outward movement of the thumb to oppose the "anchored" fingers provides for an adequate outward motion to accomplish this task. The ultrasonic surgical instruments previously described include a handle assembly comprising a fixed handle, either integrally formed with the handle assembly or removably attached thereto. The pistol grip incorporates a trigger that may be pushed outward with the index and middle finger while maintaining grip on the handle stock. This outward motion action, however, may create fatigue and hand strain during a spreading or fine dissection procedures. Nevertheless, this outward motion is necessary during spreading or fine dissection laparoscopic procedures. The pistol grip handle, which is preferred by many surgeons for its comfort, ease, and stability of the grip style, may not be optimal for ease of dissection. For dissections, many surgeons prefer a scissor-like loop or ring type grip. Accordingly, various embodiments described below provide an ultrasonic surgical instrument comprising a handle assembly that may be adapted and configured with a scissor-like loop or ring type grip. The scissor-like loop or ring type grip may be formed integrally with the handle assembly or may be implemented in the form of a removably attached loop adapter.

Figure 70:
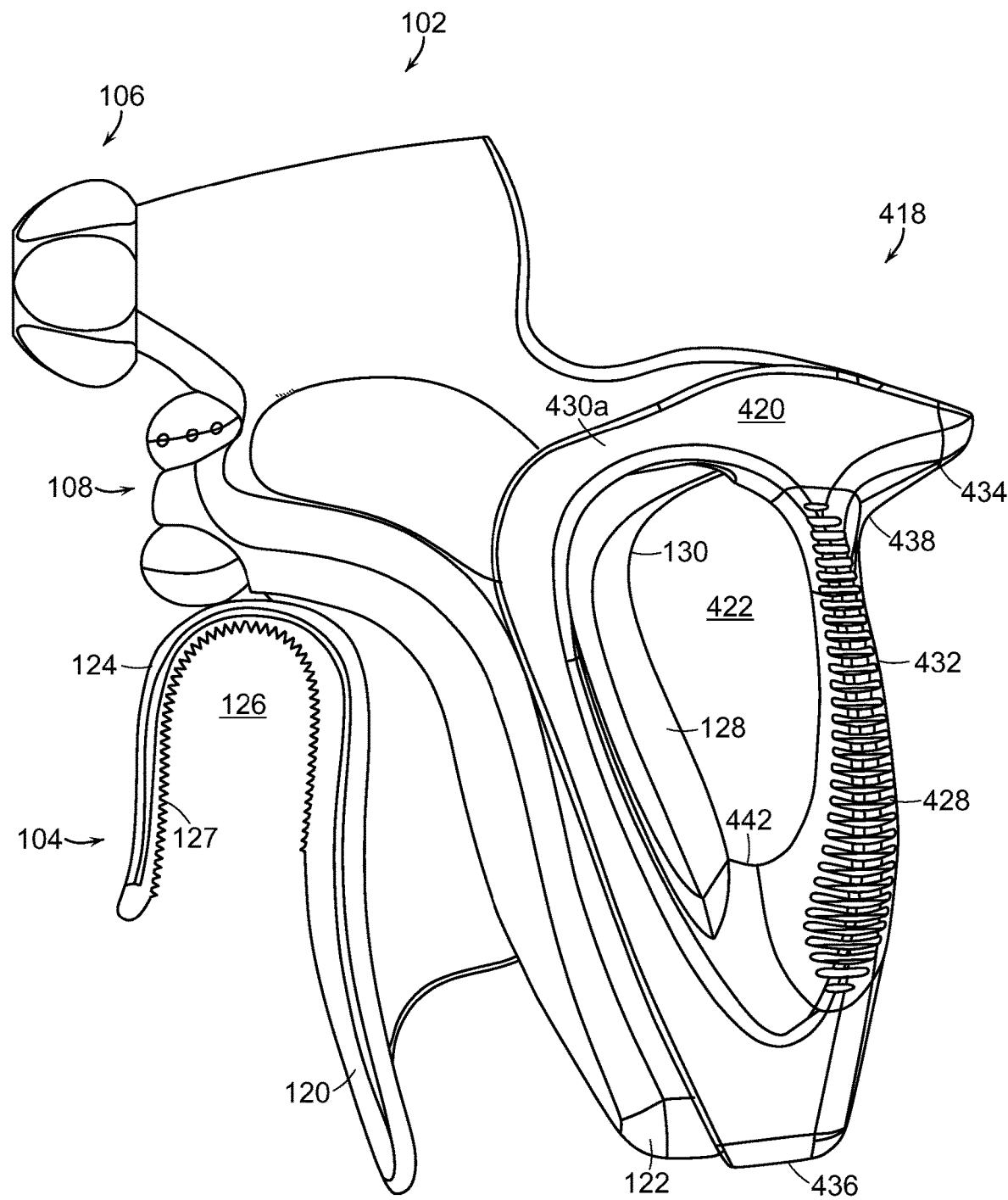
FIG. 70 illustrates one embodiment of a handle assembly of an ultrasonic surgical instrument comprising a loop handle adapter assembly.
Figure 71:
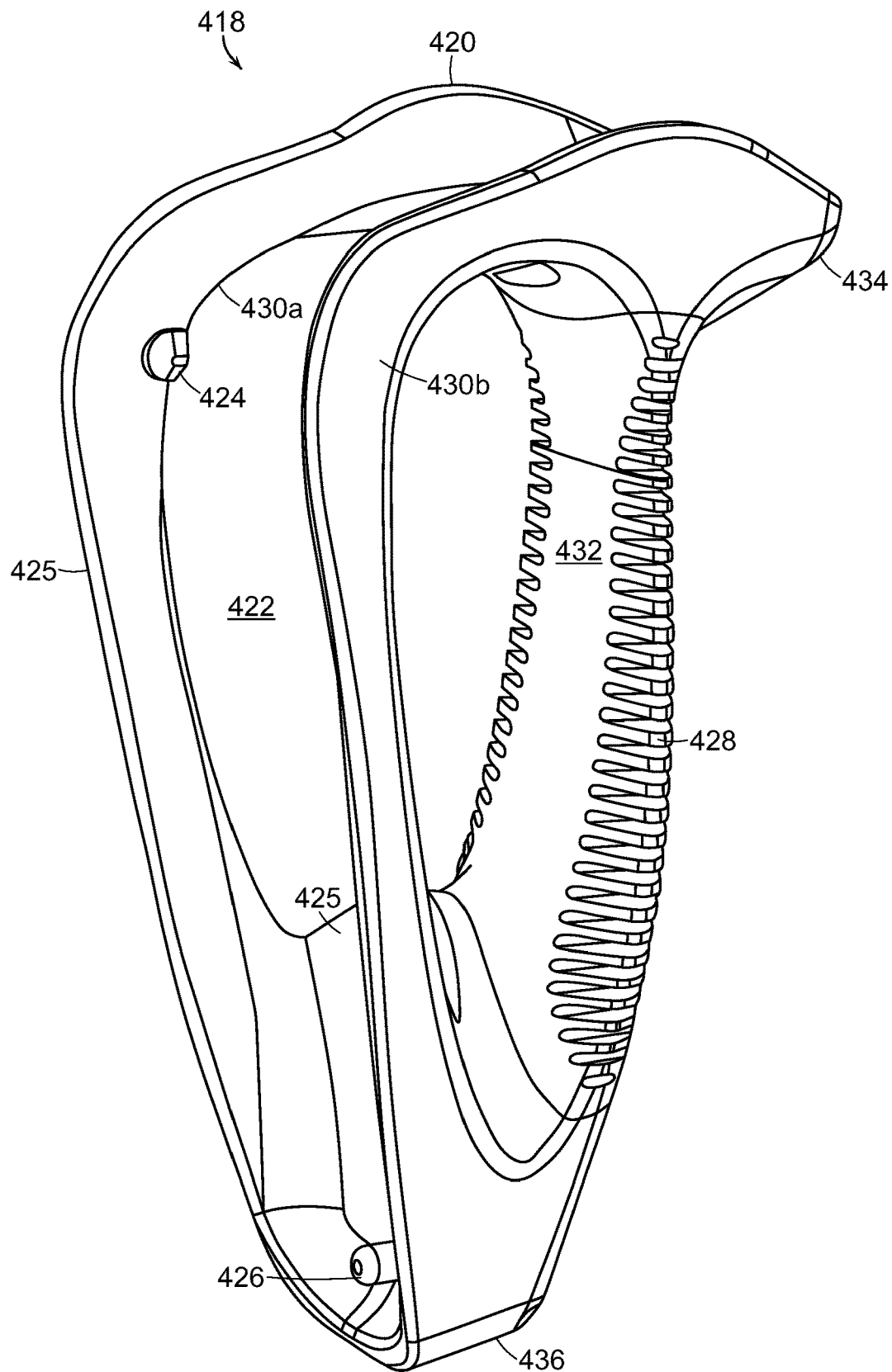
FIG. 71 is a front perspective view of the loop handle adapter assembly shown in FIG. 70
Figure 72:
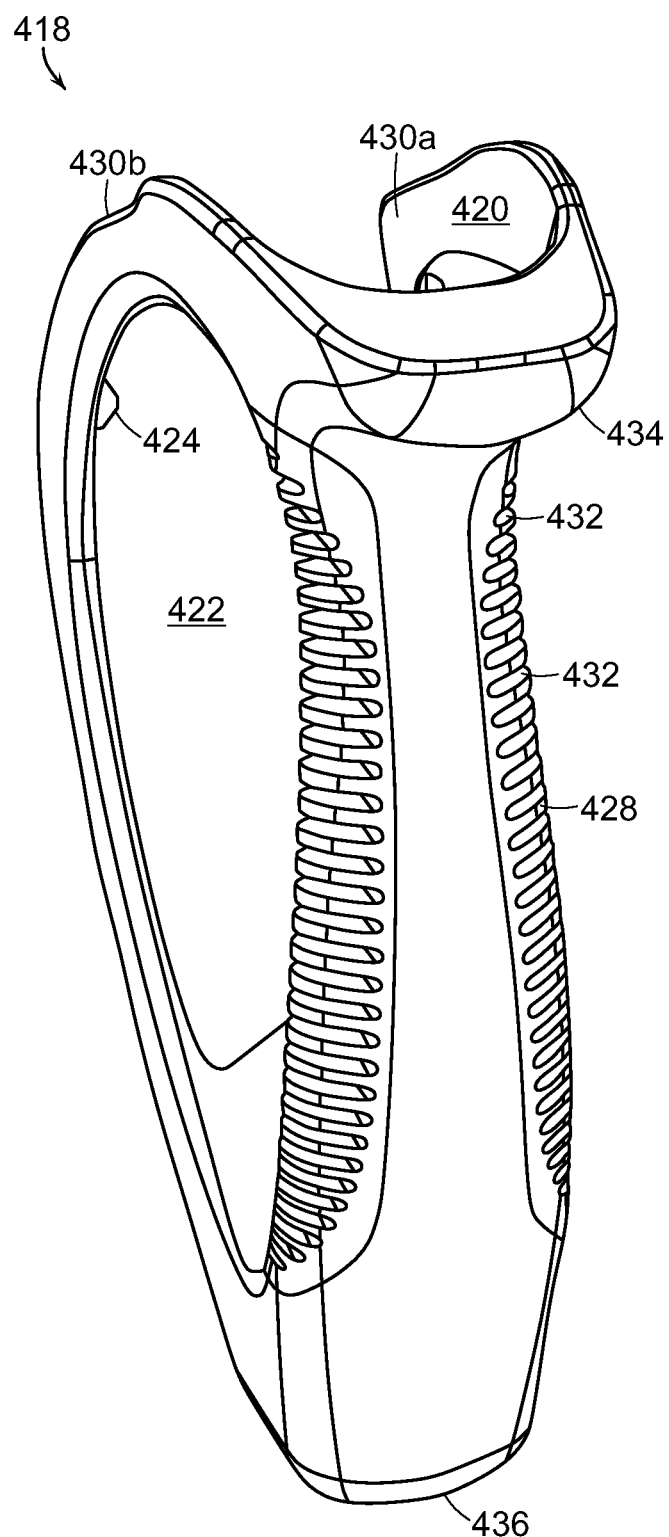
FIG. 72 is a rear perspective view of the loop handle adapter assembly shown in FIG. 71.
Figure 74:
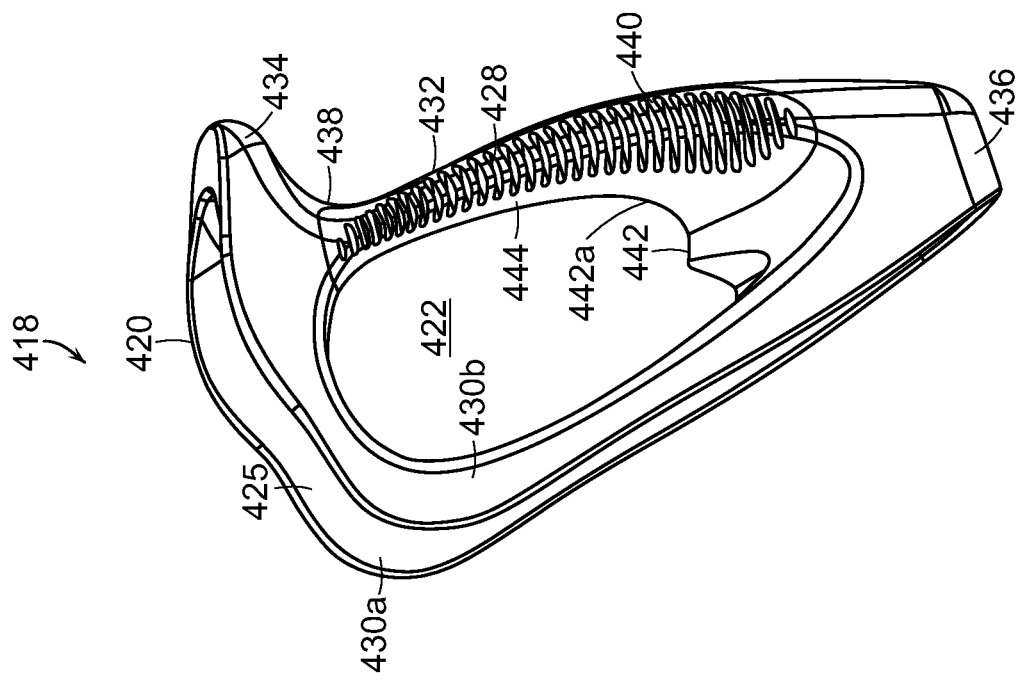
FIG. 74 is a right perspective view of the loop handle adapter assembly shown in FIG. 71.
Figure 73:
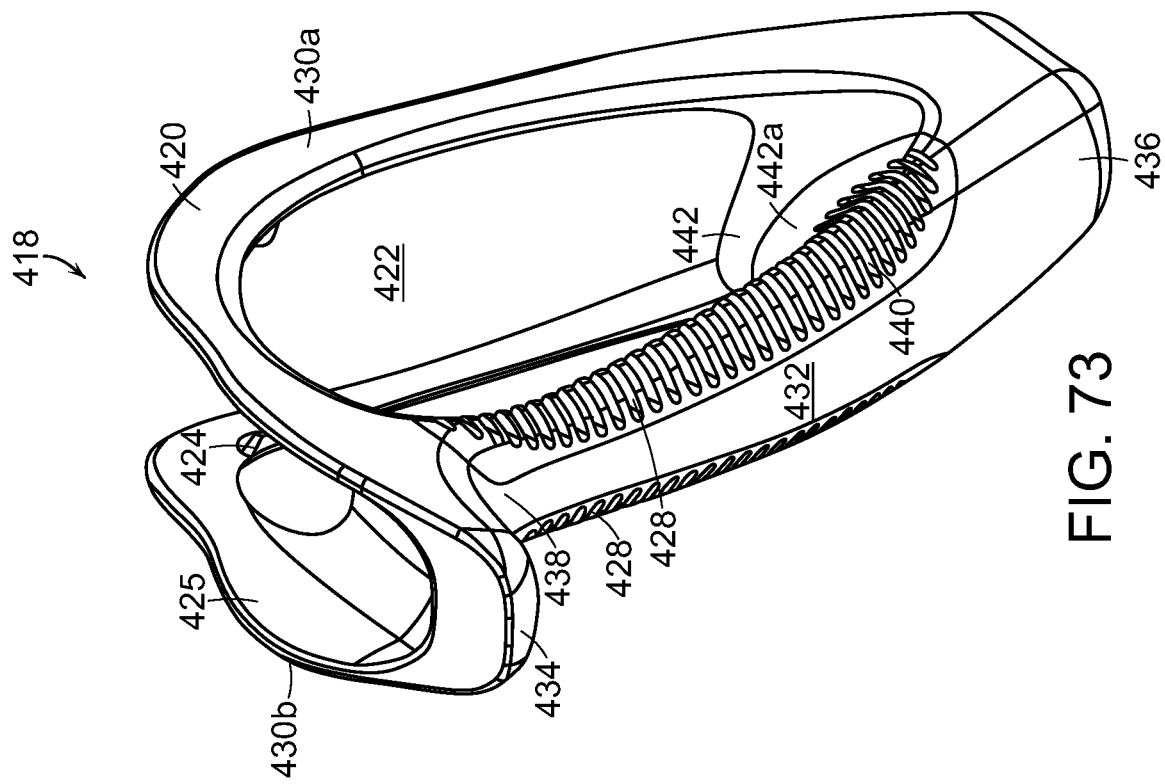
FIG. 73 is a left perspective view of the loop handle adapter assembly shown in FIG. 71.
Figure 76:
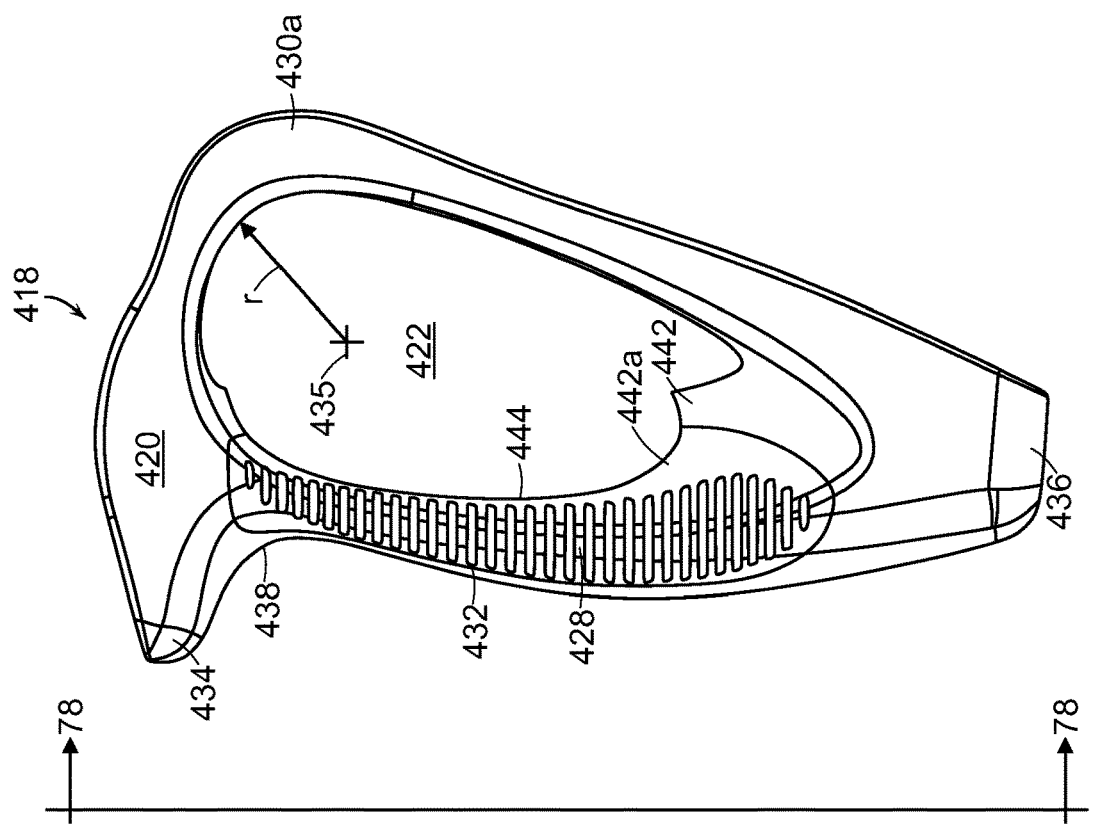
FIG. 76 is a left side view of the loop handle adapter assembly shown in FIG. 71.
Figure 75:
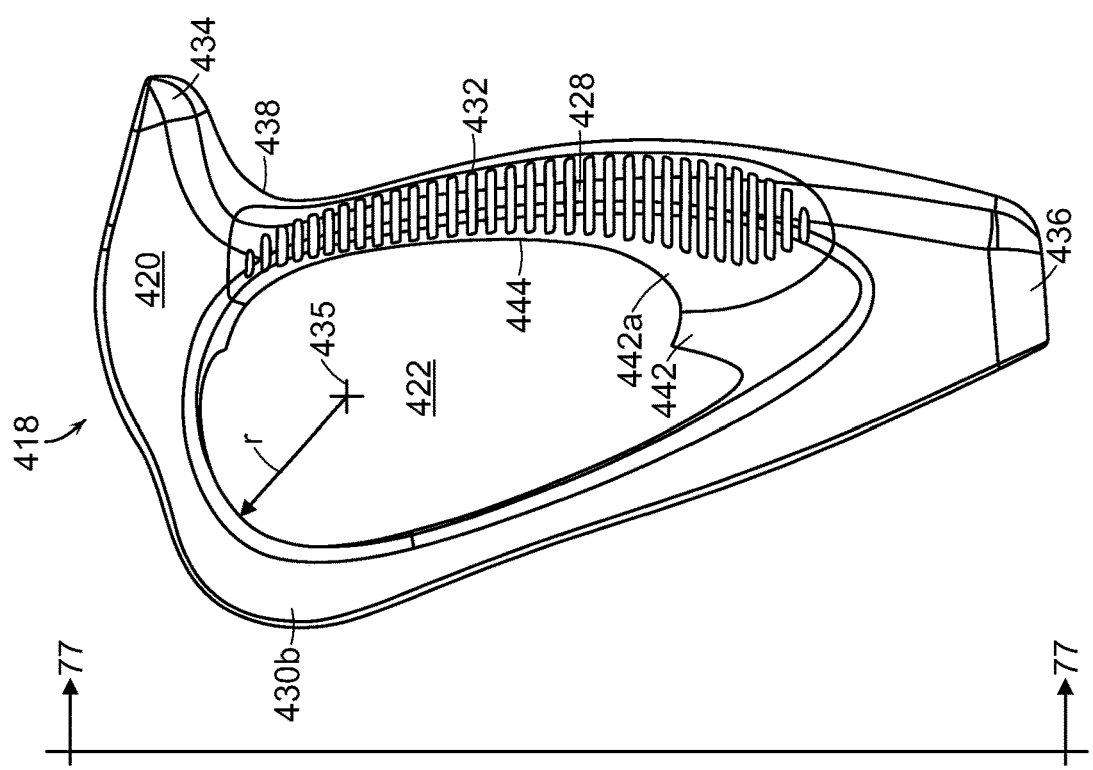
FIG. 75 is a right side view of the loop handle adapter assembly shown in FIG. 71.
Figure 77:
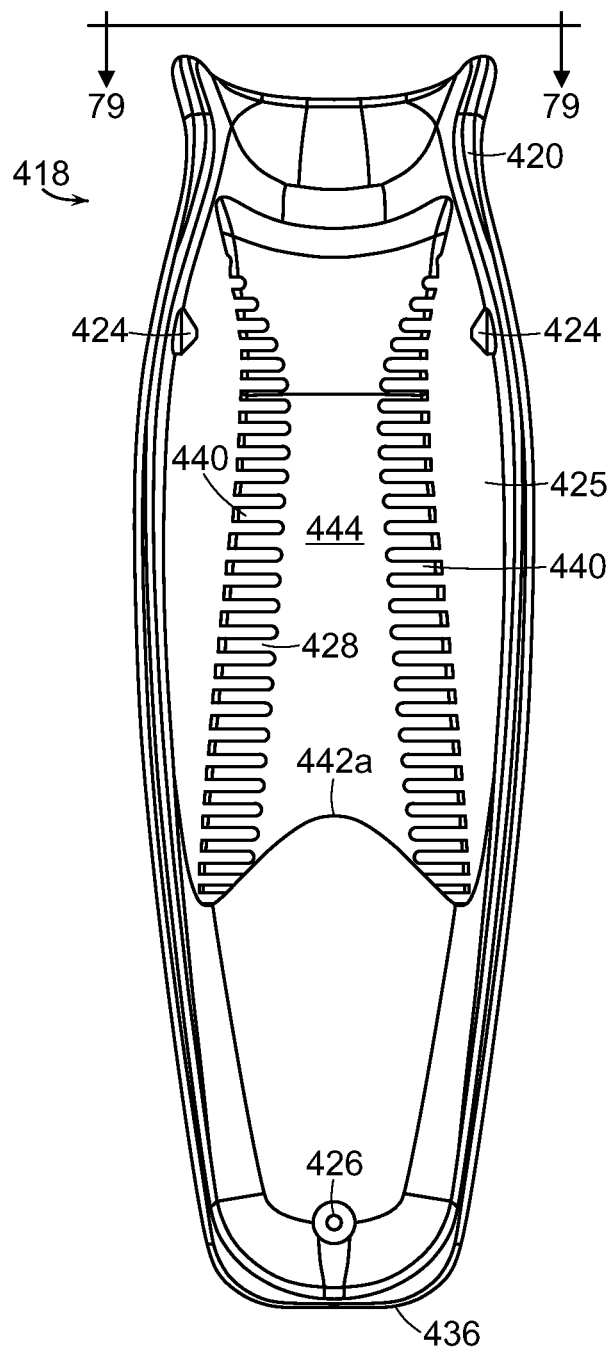
FIG. 77 is a front view of the loop handle adapter assembly shown in FIG. 75 taken along line 77-77.
Figure 78:
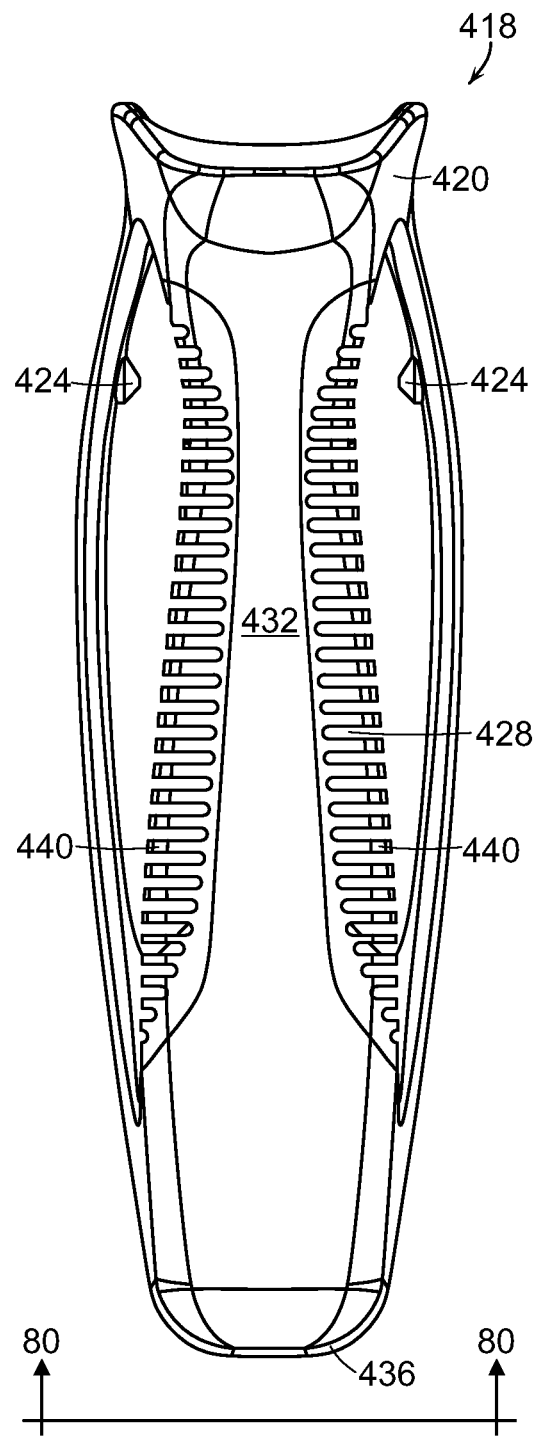
FIG. 78 is a rear view of the loop handle adapter assembly shown in FIG. 76 taken along line 78-78.
Figure 79:
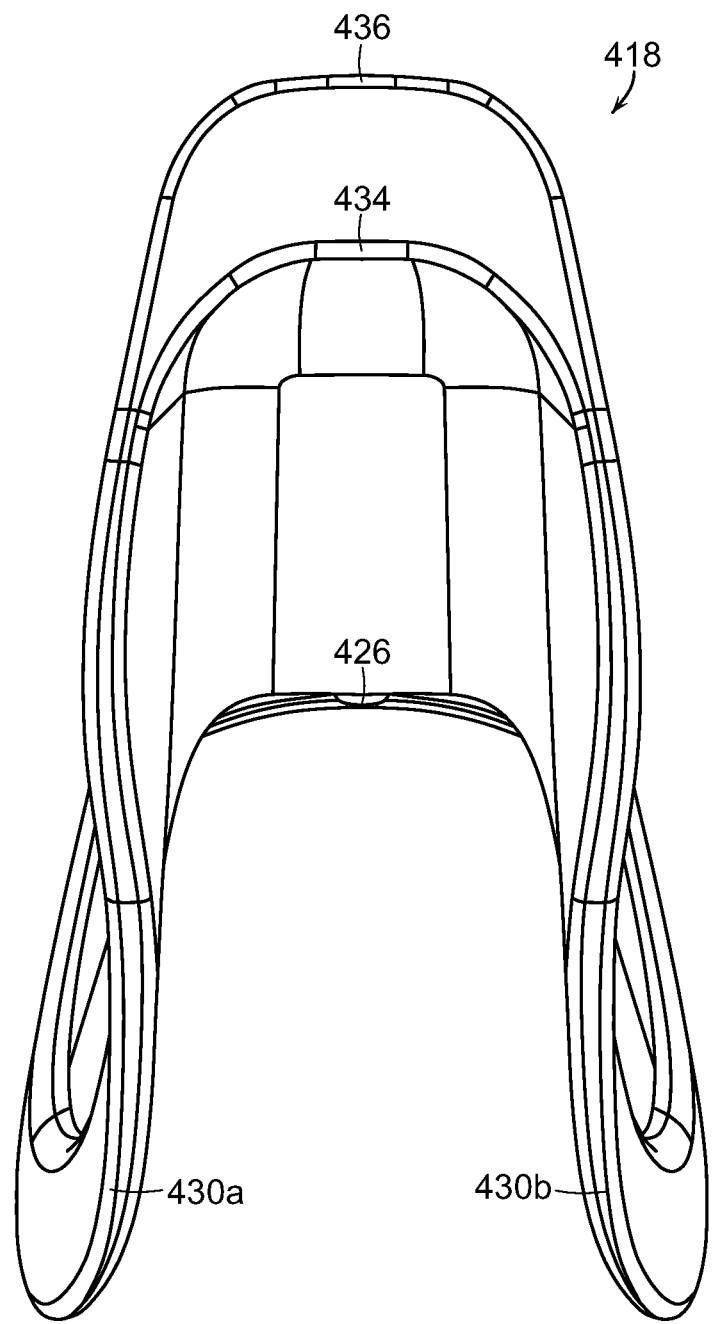
FIG. 79 is a top view of the loop handle adapter assembly shown in FIG. 77 taken along line 79-79.
Figure 80:
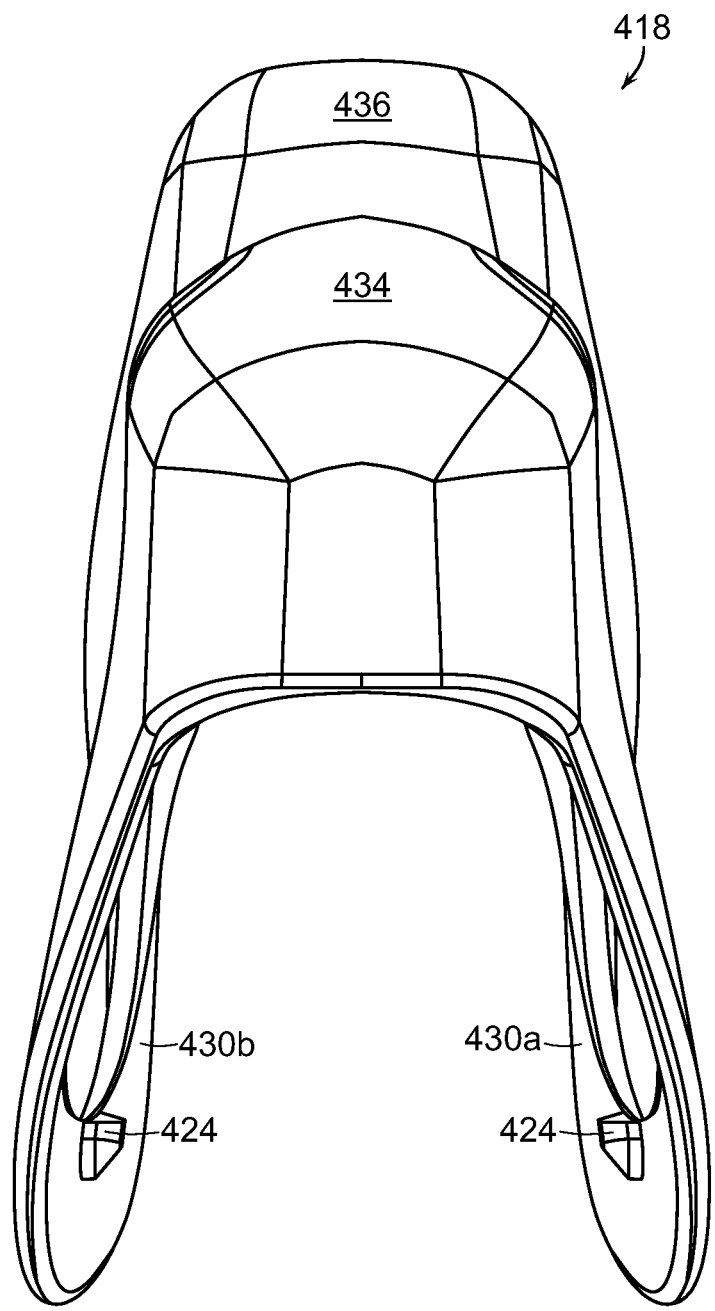
FIG. 80 is a bottom view of the loop handle adapter assembly shown in FIG. 78 taken along line 80-80.

FIG. 70 illustrates one embodiment of a handle assembly 102 of an ultrasonic surgical instrument comprising a loop handle adapter assembly 418. The loop handle adapter assembly 418 comprises a loop handle adapter 420 and a resilient, pliable, and/or flexible element 428 attached thereto. The loop handle adapter 420 adapts or converts the fixed handle 122 portion of the handle assembly 102 from a conventional pistol grip to a scissor-like loop or ring type grip comprising a pair of loops defined by apertures 422. The loop handle adapter 420 facilitates the use of a more controlled manipulation of the handle assembly 102 outward motion during spreading or fine dissection laparoscopic procedures, for example. The loop handle adapter 420 is adapted and configured to removably attach to the fixed handle 122 portion of the handle assembly 102. The loop handle adapter 420 comprises one or more snap features 424 (FIG. 71) and one or more posts 426 (FIGS. 71, 77, 79) formed integrally on an interior surface 425 (FIG. 71) of the loop handle adapter 420. The one or more snap features 424 (FIGS. 71-73, 77-80) removably engage the loop handle adapter 420 to the fixed handle 122 of the handle assembly 102. The one or more posts 426 align the loop handle adapter 420 with the fixed handle 122. In one embodiment, the elongated trigger hook 124 may comprise a plurality of nubs 127 formed of pliable, resilient, flexible polymeric materials including Versaflex® TPE alloys made by GLS Corporation, for example.

The apertures 422 are defined by two curved elements 430*a,b* (430*b* is shown in FIGS. 71-79) and a proximal contact element 432 that are joined at a base portion 436 and at an upper saddle surface 438. The two curved elements 430*a,b* and the proximal contact element 432 also define a stabilization tail 434. The aperture 422 is suitable to receive the thumb of the user therethrough to enable the user to more easily and comfortably manipulate the handle assembly 102 or apply a retracting force. The user may insert the thumb through the aperture 422 and engage the proximal contact surface 128 and the saddle surface 130 of the fixed handle 122, which remains exposed to engage the hand. The loop handle adapter 420 also may be employed as an adapter for larger handed users who wish to use the handle assembly 102 with a conventional pistol grip. The proximal contact element 432, the upper saddle surface 438, and the stabilization tail 434 provide a larger span to accommodate a larger hand to more comfortably reach to controls such as the trigger 120 and the switch assembly 108. The loop handle adapter 420 also defines a lower saddle surface 442 to accommodate the lower base portion of the thumb.

FIGS. 71-80 illustrate one embodiment of the loop handle assembly 418. As illustrated, the loop handle assembly 418 comprises a loop handle adapter 420 coupled to a flexible element 428. The loop handle adapter 420 comprises the two curved elements 430*a,b* that define a radius "r" relative to an axis 435. The two curved elements 430*a,b* join the proximal contact element 432 to define the aperture 422, the upper saddle surface 438, the stabilization tail 434, and the lower saddle surface 442. Functionally, the aperture 422 enables the user to employ the thumb to assist in the manipulation of the handle assembly 102. The upper saddle surface 438 and the stabilization tail 434 perform the same functions as discussed above with reference to FIGS. 25 and 26. The post 426 may be formed near a base portion 436 of the loop handle adapter 420 and the two snap features 424 that snap into corresponding indentations or openings (not shown) formed on the sides of the fixed handle 122 may be formed near the saddle surface 130 region of the handle assembly 102. This allows a quick secure removably mounted connection that can be easily removed if necessary. The flexible element 428 comprises a plurality of ribs 440 to provide resilience and to reduce the pressure to the sides of the thumb. The flexible element 428 also comprises a lower saddle surface 442a to engage the lower saddle surface 442 of the loop handle adapter 420. The loop handle adapter 420 also provides a contact surface 444 to engage the thumb of the user. In one embodiment, the resilient, pliable, flexible element 428 may be attached or molded to the proximal contact element 432 of the loop handle adapter 420. The loop handle adapter 420 may be formed as a single component with the flexible element 428 or they may be formed as separate components. The loop handle adapter 420 may be formed of a durable plastic such as polycarbonate and the flexible element 428 may be formed of softer pliable, resilient, flexible polymeric materials including Versaflex® TPE alloys made by GLS Corporation, for example. The flexible element 428 may be molded over the loop handle adapter 420 or may be formed separately and then attached thereto.

Figure 82:
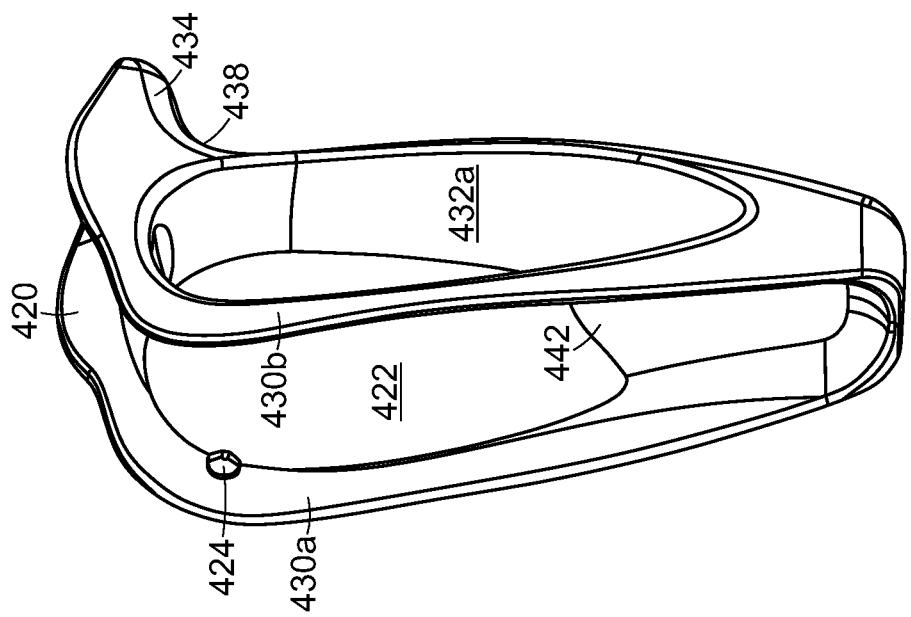
FIG. 82 is a front perspective view of one embodiment of the loop adapter shown in FIGS. 71-80.
Figure 81:
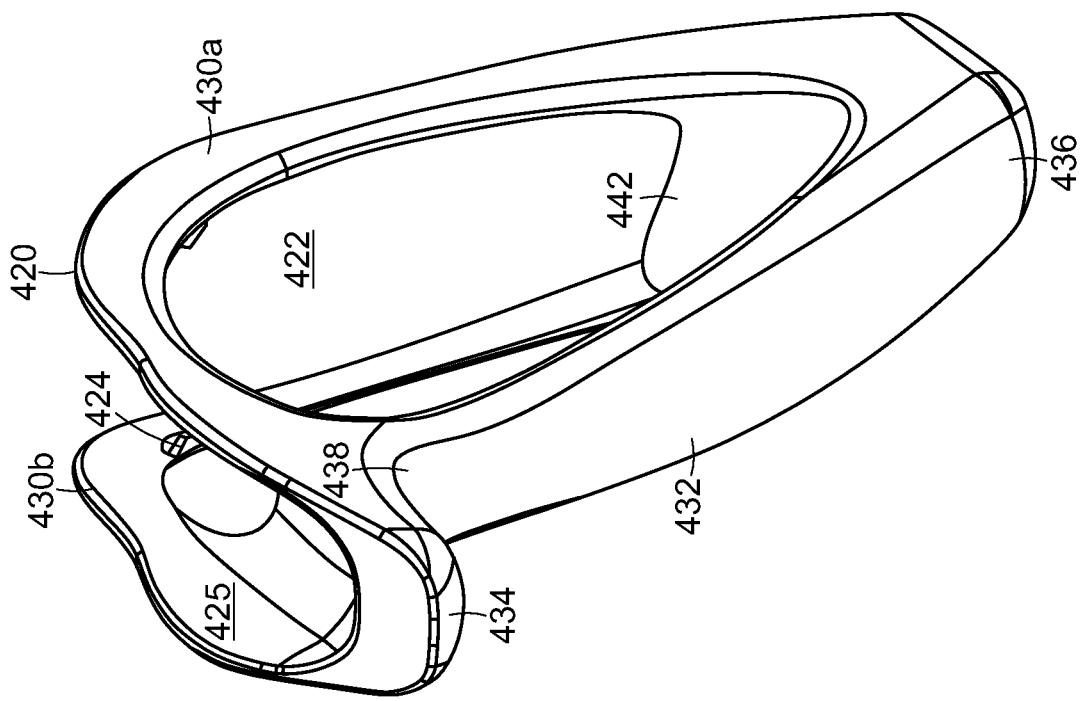
FIG. 81 is a left perspective view of one embodiment of the loop adapter shown in FIGS. 71-80.
Figure 83:
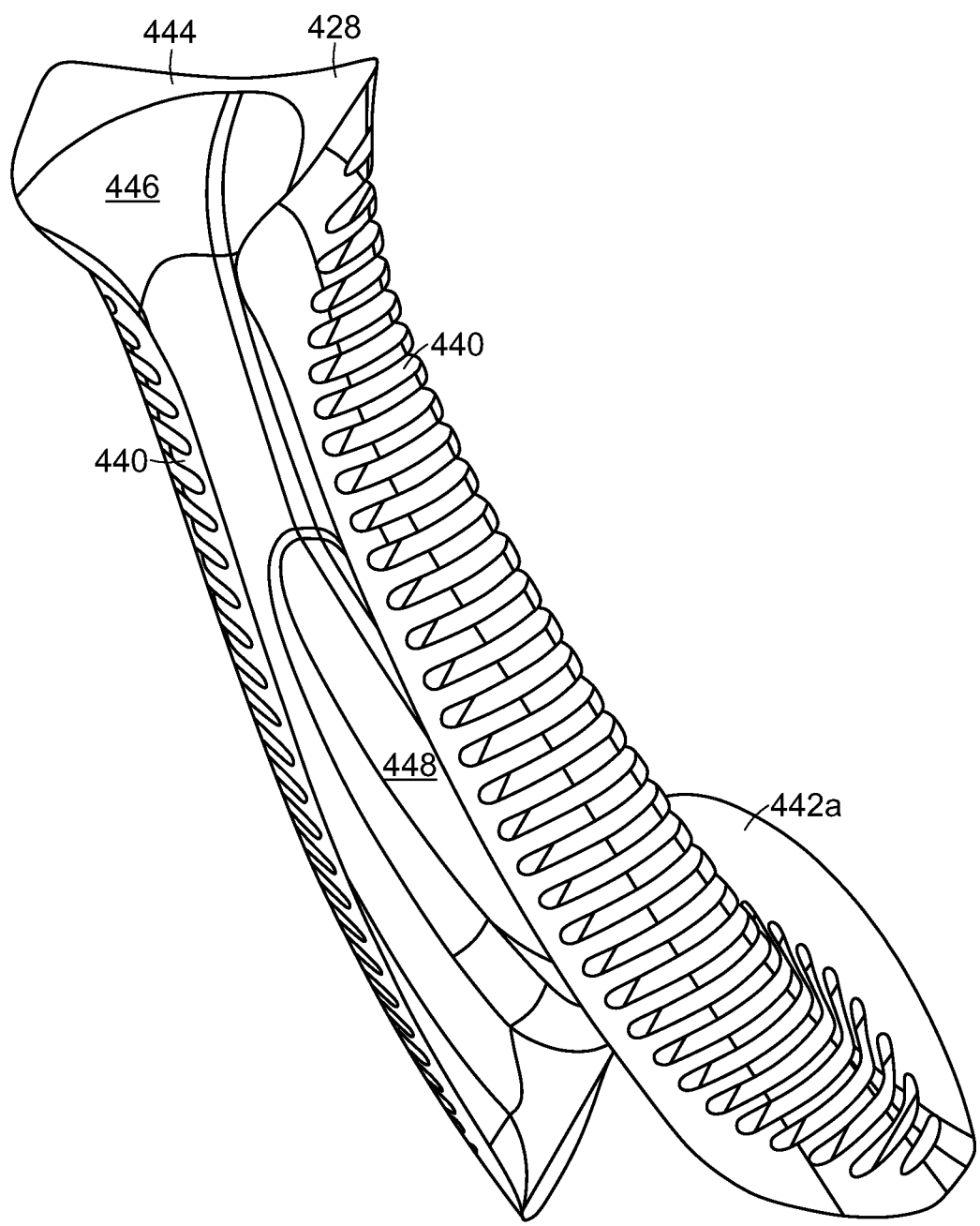
FIG. 83 is a rear perspective view of one embodiment of a flexible element portion of the loop handle assembly shown in FIGS. 71-80.
Figures 84, 85:
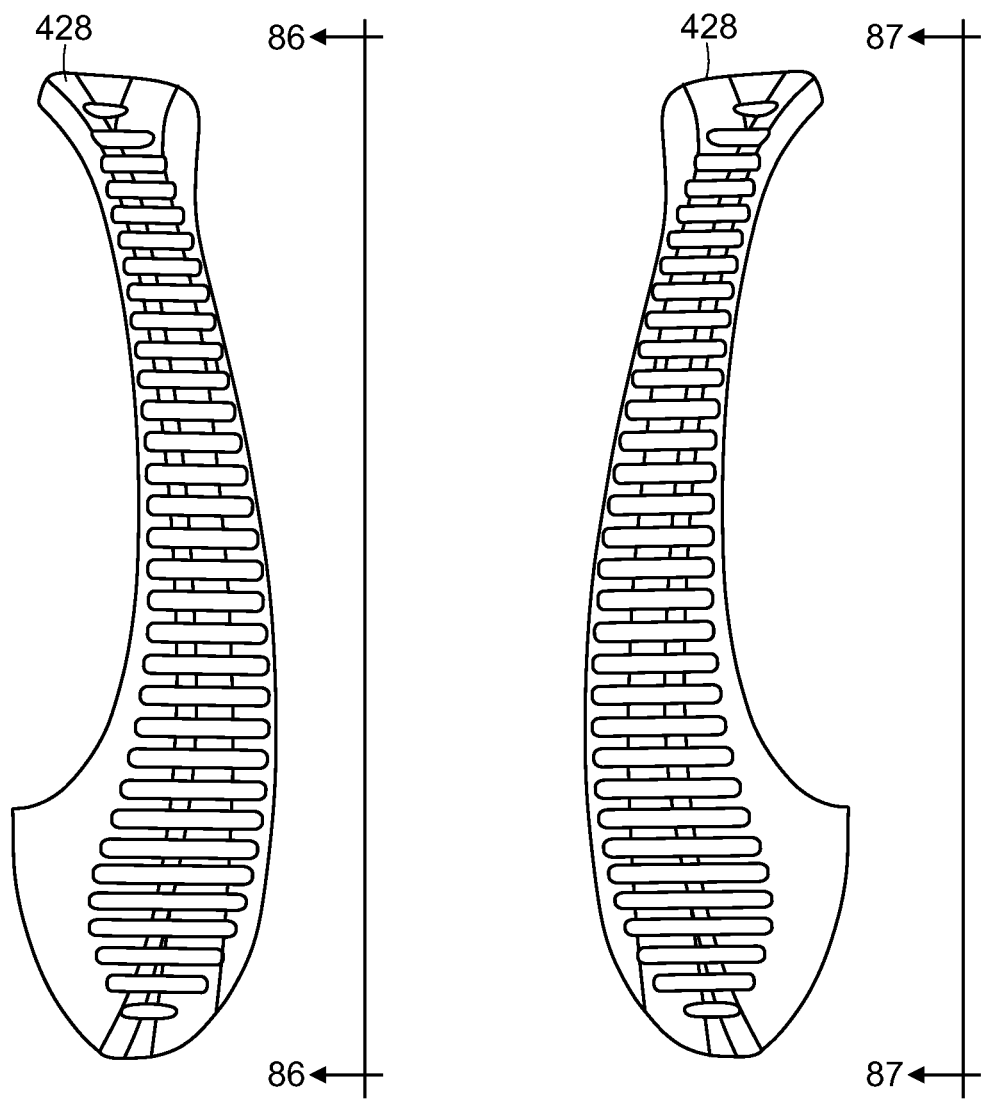
FIG. 84 is a right side view of one embodiment of the flexible element shown in FIG. 83.
FIG. 85 is a left side view of one embodiment of the flexible element shown in FIG. 83.
Figure 86:
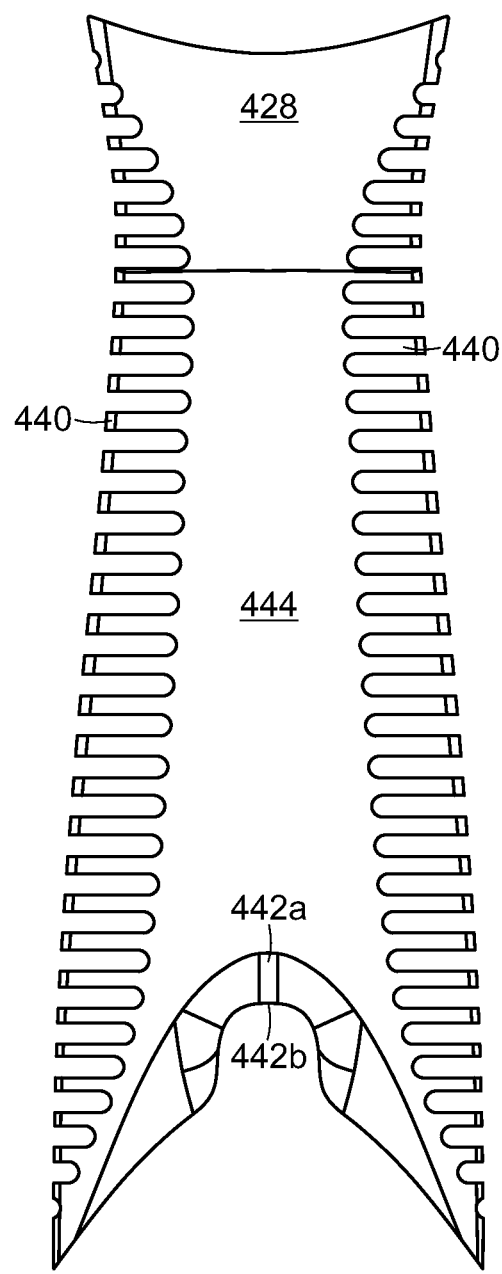
FIG. 86 is a front view of one embodiment of the flexible element shown in FIG. 84 taken along line 86-86.
Figure 87:
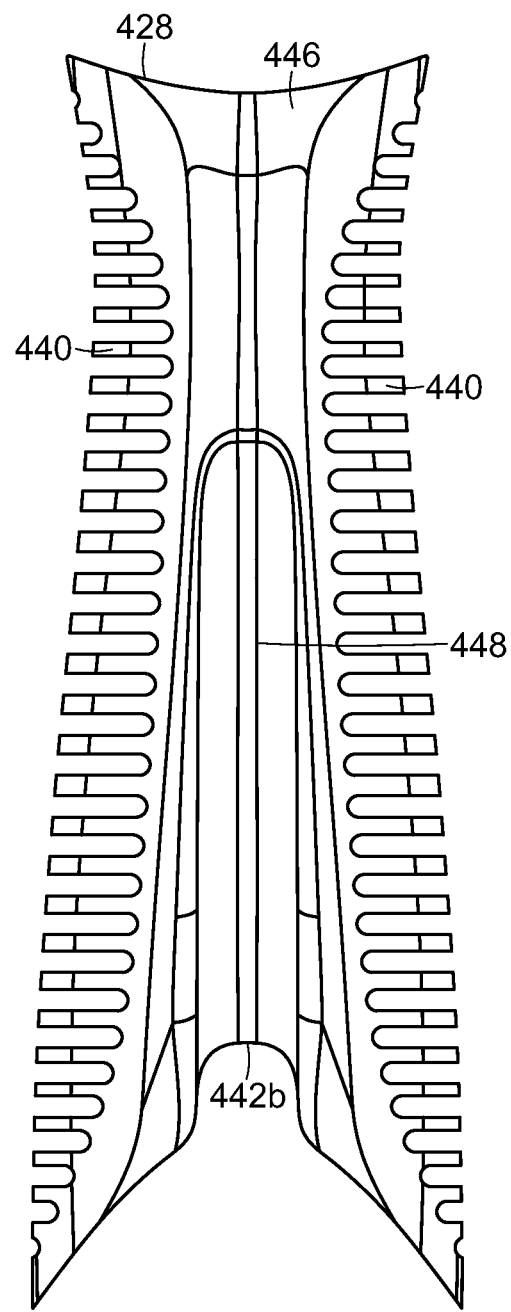
FIG. 87 is a rear view of one embodiment of the flexible element shown in FIG. 85 taken along line 87-87.

FIGS. 81-82 illustrate left and front perspective views of one embodiment of the loop handle adapter 420. FIG. 82 shows an internal body portion 432a of the proximal contact element 432 to receive the flexible element 428.

FIGS. 83-87 illustrate one embodiment of a flexible element 428 portion of the loop handle assembly 418 shown in FIGS. 71-80. The flexible element 428 may be formed of pliable, resilient, flexible polymeric materials including Versaflex® TPE alloys made by GLS Corporation, for example. The flexible element 428 is formed of a single element comprises a contact surface 444, a plurality of ribs 440, and a saddle surface contact surface 442b adapted to engage the lower saddle portion 442 of the loop handle adapter 420 shown in FIGS. 81-82. The saddle surface 442a may be engaged by the thumb or hand of the user. The flexible element 428 also comprises a channel 446 to receive the internal body portion 432a of the proximal contact element 432. As shown, the channel 446 expands to a larger channel 448 to accommodate the lower saddle surface 442 of the of the loop handle adapter 420.

Figure 88:
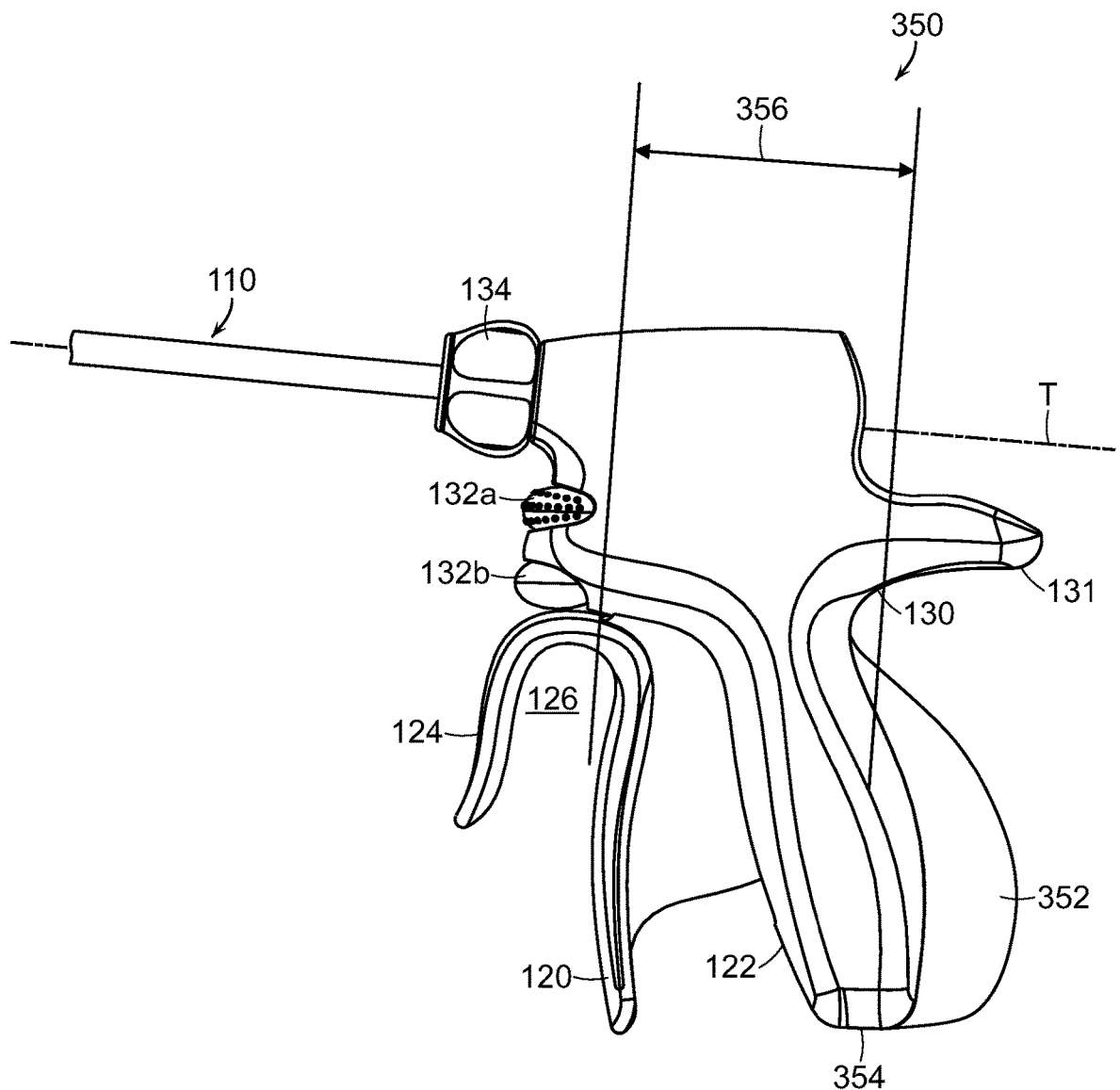
FIG. 88 illustrates one embodiment of a handle assembly for an ultrasonic surgical instrument comprising a curved stability projection formed at the rear or proximal location of a fixed handle.
Figure 89:
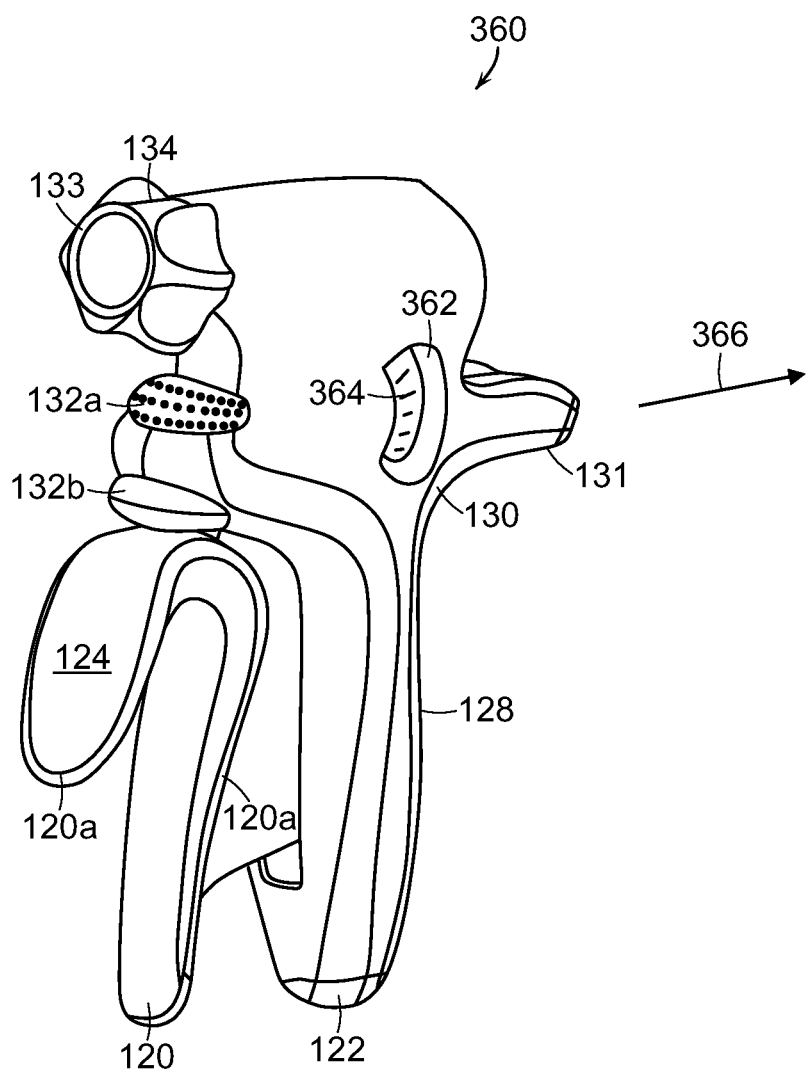
FIG. 89 illustrates one embodiment of a handle assembly for an ultrasonic surgical instrument comprising protrusions formed on both sides of a fixed handle.
Figure 90:
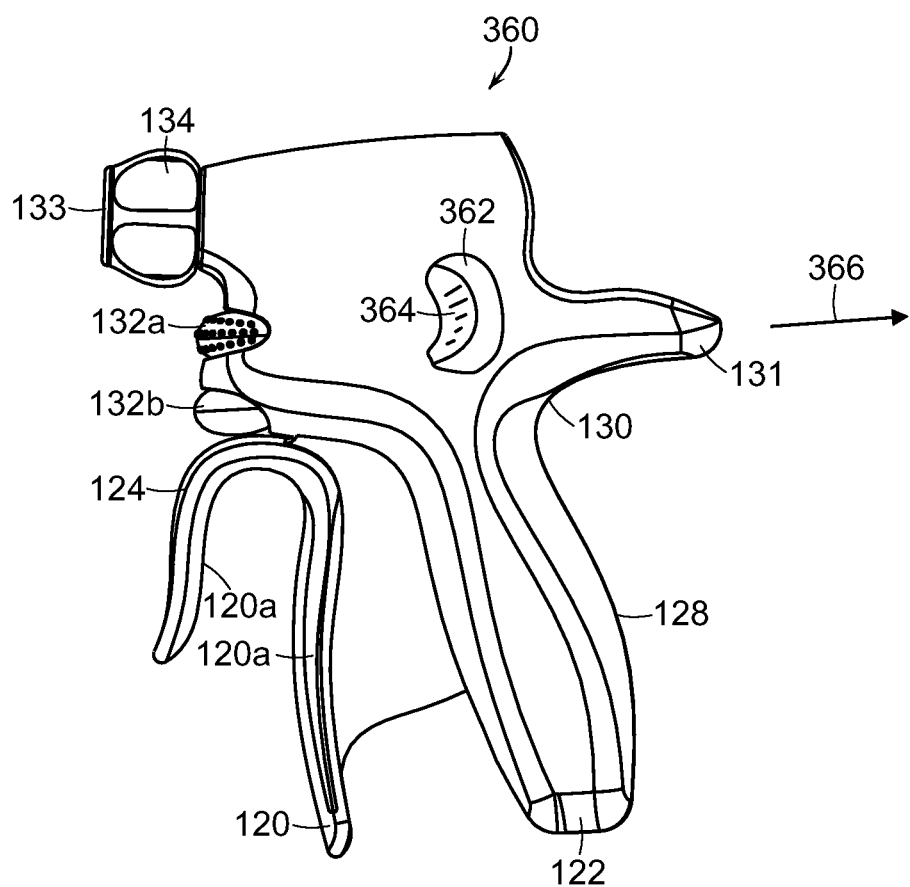
FIG. 90 illustrates one embodiment of a handle assembly for an ultrasonic surgical instrument comprising protrusions formed on both sides of a fixed handle.

Turning now to FIGS. 88-90, several factors can be applied to assess the viability of the ergonomics of a particular design for a medical instrument. Aside from comfort, one objective factor is the ability to control the working end of the handle assembly 102 with a suitable degree of control needed to accomplish a surgical task with ease. To the extent that this control is achieved emanates first from the inherent stability of the handle assembly 102 in the hand of the user, and second from the ease of the finer motions required to manipulate the specific instrument controls. Design efforts include balancing the ability to achieve overall stability in the hand while facilitating appropriate access to the fine controls.

In various embodiments, the handle assembly 102 may be stabilized by adapting a variety of pistol grips. The various embodiments of the pistol grips provide several points of fixation on the hand:

(1) a squeezing force between the thumb and index fingers resting in the web of the joint;
(2) a grasping force between the thumb and index finger; and
(3) a gripping force between the fingers and the palm while activating the trigger 120.

There exists optimal locations between the various controls on the distal end of the handle assembly 102 that may be employed as points of fixation. These include locations between the distal rotation knob 134, the toggle switch 132, the trigger 120, and the saddle surface 130, which rests on the thumb/index web of the joint of the hand. Some embodiments vary the width of the fixed handle 122 portion to accommodate various hand sizes including varying the basic distance between the saddle surface 130 and the front controls. Other embodiments vary the length of the fixed handle 122 to situate the end of the fixed handle 122 against the palm. Still, other embodiments vary the angle of the fixed handle 122.

FIG. 88 illustrates one embodiment of a handle assembly 350 comprising a curved stability projection 352 (e.g., bump) formed at the rear or proximal location of the fixed handle 122. The curved stability projection 352 provides an intimate contact surface between the fixed handle 122 and the length of the palm of the hand to stabilize the handle assembly 350. One point of fixation may be achieved by locating the saddle surface 130 of the handle assembly 350 at the thumb/index finger web of the joint of the hand as described above. A second area of fixation is achieved by locating the curved stability projection 352 at the rear of the fixed handle 122 to achieve contact between the handle assembly 350 and the center of the palm of the hand. In this manner, a large area of contact is achieved in the center of the palm instead of a small area at the base 354 of the fixed handle 122. The saddle surface 130 of the handle assembly 350 is maintained without varying the optimum grip span 356. The contact area may be achieved regardless of hand size because of the broad curve of the curved stability projection 352. Providing two fixation points mechanically prevents the distal tip of the instrument from rotating about the saddle surface 130 with little actual applied hand force, thus freeing up the digits of the hand to actuate the finer controls such as the distal rotation knob 134, the toggle switch 132, and the trigger 120, for example. The curved stability projection 352 may be formed integral to the length of the fixed handle 122 of the handle assembly 352, or may be formed by adding a softer, more conforming material to the fixed handle 122.

FIGS. 89 and 90 illustrate one embodiment of a handle assembly 360 comprising protrusions 362 formed on both sides of the fixed handle 122. The protrusions 362 provide additional fixation points and ergonomic benefits to handle assemblies described herein. In one embodiment, the protrusions 362 enable additional control of the handle assembly 360 during dissection or other types of surgical procedures. Some users may experience fatigue and reduced control when using certain ultrasonic surgical instruments while operating the instrument. One factor that may lead to fatigue and reduced control is pinching the fixed handle 122 between the thumb and index finger of the user while pushing outward on the elongated trigger hook 124 with their other fingers. Accordingly, the ear-like protrusions 362 attached or formed to both sides of the handle assembly 360 provide an edge or surface contact area for the user to engage with the thumb. The protrusions 362 stabilize of the handle assembly 360 during surgical procedures, such as dissecting, and alleviate some of the fatigue due to squeezing the handle assembly 360 between the thumb and index finger. The protrusions 362 may comprise a ridge 364 to allow for the thumb to counteract the extension force in direction 366 with and opposing surface instead of relying on friction and compression from squeezing the thumb and the index finger. The protrusion may be textured or overmolded with a compliant material to improve the grip and feel when the user is wearing surgical gloves. It also may be contoured so as not to create any sharp or uncomfortable edges that the thumb or index finger can rest against.

Various embodiments comprising blades and clamp arm assemblies comprising proximal tissue pad segments, distal tissue pad segments, and tissue pad insert segments have been described. The pivotal movement of the clamp arm assemblies with respect to the blades may be affected by the provision of a pair of pivot points on the clamp arm portion of the clamp arm assembly that interfaces with an ultrasonic surgical instrument via weld pin fastening or other fastening means. The tissue pad segments may be attached to the clamp arm by mechanical means including, for example, rivets, glues, adhesives, epoxies, press fitting or any other fastening means known in the art. Furthermore, the tissue pad segments may be removably attached to the clamp arm by any known means.

In various embodiments, the clamp arm may comprise a T-shaped slot for accepting a T-shaped flange of a proximal tissue pad segment, a distal tissue pad segment and a tissue pad insert segment. In various embodiments, a single unitary tissue pad assembly may comprise the proximal tissue pad segment, the distal tissue pad segment and the tissue pad insert segment, and further comprise a T-shaped flange for reception in a T-shaped slot in the clamp arm assembly. Additional configurations including dove tailed-shaped slots and wedge-shaped flanges are contemplated. As would be appreciated by those skilled in the art, flanges and corresponding slots have alternative shapes and sizes to removably secure the tissue pad segments to the clamp arm.

A method for replacing the proximal tissue pad segment, the distal tissue pad segment and/or the tissue pad insert segment include one or more of the steps of: a) disengaging the clamp arm assembly from the ultrasonic surgical instrument; b) removing at least one of the tissue pad segments from the clamp arm; c) inserting at least one new or reconditioned tissue pad segment into the clamp arm; and d) engaging the clamp arm assembly with the ultrasonic surgical instrument. In this removal and replacement process, the new or reconditioned proximal tissue pad segment, distal tissue pad segment and tissue pad insert segment may be multiple separate segments or of unitary construction.

Another method for replacing the proximal tissue pad segment, the distal tissue pad segment and/or the tissue pad insert segment include one or more of the steps of: a) opening flanges on the clamp arm; b) removing at least one of the tissue pad segments from the clamp arm; c) inserting at least one new or reconditioned tissue pad segment into the clamp arm; and d) closing flanges on the clamp arm. In this removal and replacement process, the new or reconditioned proximal tissue pad segment, distal tissue pad segment and tissue pad insert segment may be multiple separate segments or of unitary construction.

Preferably, the various embodiments described herein will be processed before surgery. First, a new or used instrument is obtained and if necessary cleaned. The instrument can then be sterilized. This can be done by any number of ways known to those skilled in the art including beta or gamma radiation, ethylene oxide sterilization, and/or steam, for example. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons sterilization. The sterilization kills bacteria on the instrument and in the container. The sterilized instrument can then be stored in the sterile container. The sealed container keeps the instrument sterile until it is opened in the medical facility.

Although various embodiments have been described herein, many modifications and variations to those embodiments may be implemented. For example, different types of end effectors may be employed. In addition, combinations of the described embodiments may be used. For example, a concave blade tip may be coated with a hydrophobic material. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

We claim:

1. A handle assembly for a handheld surgical instrument, the handle assembly comprising:
   a body portion extending parallel to a longitudinal axis;
   a fixed handle interfaced with the body portion and extending downwardly from the body portion and away from the longitudinal axis, wherein the fixed handle comprises a stabilization tail extending proximally therefrom, and wherein the fixed handle defines a proximal contact surface; and
   a detachable handle portion, wherein the detachable handle portion defines an internal surface configured to interface with the proximal contact surface of the fixed handle, wherein the detachable handle portion comprises a loop element comprising a tail portion, wherein the tail portion comprises a cavity configured to receive the stabilization tail, and wherein the detachable handle portion comprises at least one attachment feature to removably couple the detachable handle portion to the fixed handle.

2. The handle assembly of claim 1, wherein the at least one attachment feature comprises one or more than one protrusion extending away from the internal surface of the detachable handle portion, and wherein each of the one or more than one protrusion is positioned for receipt in a corresponding aperture defined in the fixed handle to removably couple the detachable handle portion to the fixed handle.

3. The handle assembly of claim 2, wherein the one or more than one protrusion is configured to mechanically fasten the detachable handle portion on the fixed handle.

4. The handle assembly of claim 2, wherein the one or more than one protrusion is configured to frictionally hold the detachable handle portion on the fixed handle.

5. The handle assembly of claim 2, wherein at least one of the one or more than one protrusion is further positioned to align the detachable handle portion on the fixed handle.

6. The handle assembly of claim 1, wherein the at least one attachment feature comprises the internal surface defined by the detachable handle portion.

7. The handle assembly of claim 6, wherein the internal surface defines:
   a distal surface configured to interface with the proximal contact surface of the fixed handle;
   a first lateral surface extending from the distal surface and configured to interface with the fixed handle on a first contoured side of the proximal contact surface; and
   a second lateral surface extending from the distal surface and configured to interface with the fixed handle on a second contoured side of the proximal contact surface, wherein the first lateral surface is opposite the second lateral surface.

8. The handle assembly of claim 7, wherein the distal surface, the first lateral surface, and the second lateral surface are configured to frictionally hold the detachable handle portion on the fixed handle.

9. The handle assembly of claim 7, wherein the first lateral surface is configured to envelop at least a portion of the first contoured side and the second lateral surface is configured to envelop at least a portion of the second contoured side to removably couple the detachable handle portion to the fixed handle.

10. The handle assembly of claim 1, wherein a proximal end of the body portion is configured to receive an ultrasonic transducer.

11. The handle assembly of claim 1, wherein the detachable handle portion further defines an aperture proximal to the internal surface to convert the fixed handle from a pistol grip to a loop grip.

12. The handle assembly of claim 1, further comprising a trigger movably coupled to the handle assembly, wherein the trigger comprises:
   a proximal trigger portion having a first length, wherein the proximal trigger portion comprises a distally-facing surface; and
   a distal trigger hook having a second length shorter than the first length, wherein the distal trigger hook is coupled to the proximal trigger portion, and wherein the distal trigger hook comprises a proximally-facing surface.

13. The handle assembly of claim 12, further comprising:
   a shaft extending distally from the handle assembly along the longitudinal axis;
   an actuation switch positioned upwardly from the trigger; and
   a shaft rotation knob positioned to rotate about the longitudinal axis to rotate the shaft about the longitudinal axis.

14. The handle assembly of claim 1, wherein the proximal contact surface is configured to receive a palm of the hand, and wherein the fixed handle further defines a saddle surface configured to receive a web portion of the hand between a thumb and an index finger of the hand.

15. A handheld surgical instrument, comprising:
   a handle assembly, comprising:
      a body portion;
      a fixed handle coupled to the body portion, wherein the fixed handle comprises a stabilization tail extending proximally therefrom, and wherein the fixed handle defines a proximal contact surface; and
      a detachable handle portion, wherein the detachable handle portion defines an internal surface configured to interface with the proximal contact surface of the fixed handle, wherein the detachable handle portion comprises a loop element comprising a tail portion, wherein the tail portion comprises a cavity configured to receive the stabilization tail, wherein the detachable handle portion comprises at least one attachment feature to removably couple the detachable handle portion to the fixed handle, and wherein the at least one attachment feature comprises the internal surface defined by the detachable handle portion;
   a shaft extending distally from the handle assembly along a longitudinal axis; and
   a trigger movably coupled to the handle assembly.

16. The handheld surgical instrument of claim 15, wherein the internal surface defines:
   a distal surface configured to interface with the proximal contact surface of the fixed handle;
   a first lateral surface extending from the distal surface and configured to interface with the fixed handle on a first contoured side of the proximal contact surface; and
   a second lateral surface extending from the distal surface and configured to interface with the fixed handle on a second contoured side of the proximal contact surface, wherein the first lateral surface is opposite the second lateral surface; and
   wherein the first lateral surface is configured to envelop at least a portion of the first contoured side and the second lateral surface is configured to envelop at least a portion of the second contoured side to removably couple the detachable handle portion to the fixed handle.

17. The handheld surgical instrument of claim 15, wherein the at least one attachment feature further comprises one or more than one protrusion extending away from the internal surface of the detachable handle portion, and wherein each of the one or more than one protrusion is positioned for receipt in a corresponding aperture defined in the fixed handle to removably couple the detachable handle portion to the fixed handle.

* * * * *